US011083725B2

(12) United States Patent
Smallwood et al.

(10) Patent No.: US 11,083,725 B2
(45) Date of Patent: Aug. 10, 2021

(54) COORDINATED METABOLIC REPROGRAMMING IN RESPONSE TO PRODUCTIVE VIRAL INFECTIONS

(71) Applicant: ST. JUDE CHILDREN'S RESEARCH HOSPITAL, Memphis, TN (US)

(72) Inventors: Heather S. Smallwood, Memphis, TN (US); Marie Morfouace, Cambridge (GB); Martine F. Roussel, Memphis, TN (US); Paul G. Thomas, Memphis, TN (US)

(73) Assignee: ST. JUDE CHILDREN'S RESEARCH HOSPITAL, Memphis, TN (US)

( * ) Notice: Subject to any disclaimer, the term of this patent is extended or adjusted under 35 U.S.C. 154(b) by 406 days.

(21) Appl. No.: 15/520,756

(22) PCT Filed: Oct. 16, 2015

(86) PCT No.: PCT/US2015/056036
§ 371 (c)(1),
(2) Date: Apr. 20, 2017

(87) PCT Pub. No.: WO2016/064683
PCT Pub. Date: Apr. 28, 2016

(65) Prior Publication Data
US 2017/0304293 A1 Oct. 26, 2017

Related U.S. Application Data

(60) Provisional application No. 62/068,561, filed on Oct. 24, 2014.

(51) Int. Cl.
| A61K 31/4745 | (2006.01) |
| A61K 31/415 | (2006.01) |
| A61K 31/427 | (2006.01) |
| A61K 31/433 | (2006.01) |
| A61K 31/505 | (2006.01) |
| A61K 31/519 | (2006.01) |
| A61K 31/34 | (2006.01) |
| A61K 31/4164 | (2006.01) |
| A61K 31/454 | (2006.01) |
| A61K 31/277 | (2006.01) |
| A61K 31/352 | (2006.01) |
| A61K 31/365 | (2006.01) |
| A61K 31/416 | (2006.01) |
| A61K 31/4174 | (2006.01) |
| A61K 31/4439 | (2006.01) |
| A61K 31/555 | (2006.01) |
| A61K 31/7004 | (2006.01) |
| A61K 45/06 | (2006.01) |

(52) U.S. Cl.
CPC ........ A61K 31/4745 (2013.01); A61K 31/277 (2013.01); A61K 31/34 (2013.01); A61K 31/352 (2013.01); A61K 31/365 (2013.01); A61K 31/415 (2013.01); A61K 31/416 (2013.01); A61K 31/4164 (2013.01); A61K 31/4174 (2013.01); A61K 31/427 (2013.01); A61K 31/433 (2013.01); A61K 31/4439 (2013.01); A61K 31/454 (2013.01); A61K 31/505 (2013.01); A61K 31/519 (2013.01); A61K 31/555 (2013.01); A61K 31/7004 (2013.01); A61K 45/06 (2013.01)

(58) Field of Classification Search
CPC ............ A61K 2300/00; A61K 31/4745; A61K 31/34; A61K 31/415; A61K 31/4164; A61K 31/427; A61K 31/433; A61K 31/454; A61K 31/505; A61K 31/519; A61K 31/277; A61K 31/352; A61K 31/365; A61K 31/416; A61K 31/4174; A61K 31/4439; A61K 31/555; A61K 31/7004; A61K 45/06; A61P 31/12
See application file for complete search history.

(56) References Cited

U.S. PATENT DOCUMENTS

| 10,004,803 B2 | 6/2018 | Mannick et al. |
| 10,286,069 B2 | 5/2019 | Mannick et al. |
| 2008/0213308 A1 | 9/2008 | Valiante et al. |
| 2012/0114637 A1 | 5/2012 | Nivaggioli et al. |
| 2012/0184519 A1 | 7/2012 | Katsikis et al. |
| 2012/0190686 A1 | 7/2012 | Li et al. |

(Continued)

FOREIGN PATENT DOCUMENTS

| WO | WO-2012/103524 A2 | 8/2012 | |
| WO | WO-2012103524 A2 * | 8/2012 | ........... A61K 31/192 |
| WO | WO-2013135800 A1 * | 9/2013 | ........... A61K 9/1272 |

(Continued)

OTHER PUBLICATIONS

Almarasson, Ö. et al., Crystal Engineering of the Composition of Pharmaceutical Co-Crystals Represent a New Path to Improved Medicines? The Royal Society of Chemistry. 1889-1896 (2004).

(Continued)

Primary Examiner — Jean P Cornet
(74) Attorney, Agent, or Firm — Ballard Spahr LLP

(57) ABSTRACT

The invention generally relates to methods of treating viral infections using known drugs and pharmaceutical compositions comprising same. More specifically, the disclosed methods are useful for the treatment of viral infections that are enveloped viruses. This abstract is intended as a scanning tool for purposes of searching in the particular art and is not intended to be limiting of the present invention.

22 Claims, 49 Drawing Sheets

(56) References Cited

U.S. PATENT DOCUMENTS

2018/0161319 A1   6/2018   Mannick et al.

FOREIGN PATENT DOCUMENTS

| WO | WO-2014/093557 A1 | 6/2014 |
|---|---|---|
| WO | WO-2015/073644 A1 | 5/2015 |
| WO | WO-2016/185443 A1 | 11/2016 |

OTHER PUBLICATIONS

Ansel, H. et al., Pharmaceutical Dosage Forms and Drug Delivery Systems (6th Ed.) pp. 196 and 1456-7 (1995).

Askovich, P.S. et al., Differential Host Response, Rather Than Early Viral Replication Efficiency, Correlates with Pathogenicity Caused by Influenza Viruses. PloS One. 8(9):e74863 (2013).

Brand, K. et al., Glucose and Glutamine Metabolism in Rat Thymocytes. Biochem J. 221(2):471-5 (1984).

Buzzai, M. et al., The Glucose Dependence of Akt-Transformed Cells Can Be Reversed by Pharmacologic Activation of Fatty Acid Beta-Oxidation. Oncogene. 24(26):4165-73 (2005).

Chang, C.H. et al., Posttranscriptional Control of T-Cell Effector Function by Aerobic Glycolysis. Cell. 153(6):1239-51 (2013).

Chen, S.X. et al., Active Constituents Against HIV-1 Protease from *Garcinia mangostana*. Planta Med. 62(4):381-2 (1996).

Cheung, C.Y. et al., H5N1 Virus Causes Significant Perturbations in Host Proteome Very Early in Influenza Virus-Infected Primary Human Monocyte-Derived Macrophages. J Infect Dis. 206(5):640-5 (2012).

Dang, C.V., c-Myc Target Genes Involved in Cell Growth, Apoptosis, and Metabolism. Mol Cell Biol. 19(1):1-11 (1999).

Daniels, J.B. et al., Effect of Glucose on the Growth of Influenza Virus in Deëmbryonated Eggs and Tissue Cultures. J Immunol. 69(3):321-9 (1952).

Das, K. et al., Structures of Influenza A Proteins and Insights into Antiviral Drug Targets. Nat Struct Mol Biol. 17(5):530-8 (2010).

Dennis, G., Jr. et al., DAVID: Database for Annotation, Visualization, and Integrated Discovery. Genome Biol. 4:R60 (2003).

Everts, B. et al., TLR-Driven Early Glycolyticreprogramming via the Kinases TRK1-IKKvarepsilon Supports the Anabolic Demands of Dendritic cell Activation. Nat Immunol. 15(4):323-32 (2014).

Filipp, F. V. et al., Glutamine-Fueled Mitochondrial Metabolism is Decoupled from Glycolysis in Melanoma. Pigment Cell Melanoma Res. 25(6): 732-9 (2012).

Fisher, T.N. and Ginsberg, H.S., The Reaction of Influenza Viruses with Guinea Pig Polymorphonuclear Leucocytes. III. Studies on the Mechanism by Which Influenza Viruses Inhibit Phagocytosis. Virology. 2(5):656-64 (1956).

Gardner, P.R. et al., Superoxide Radical and Iron Modulate Aconitase Activity in Mammalian Cells. J Biol Chem. 270(22):13399-405 (1995).

Henle, G. et al., Studies on Persistent Infections of Tissue Cultures. I. General Aspects of the System. J Exp Med. 108(4):537-60 (1958).

Hue, L. et al., Difference in Glucose Sensitivity of Liver Glycoysis and Glycogen Synthesis. Relationship Between Lactate Prduction and Fructose 2,6-bisphosphate Concentration. Biochem J. 224(3):779-86 (1984).

Intriago, B. et al., Influenza-like Infection Can Result in Diffuse Fluordeoxyglucose Uptake in the Lungs. Clin Nucl Med. 34(10):737-8 (2009).

Isler, J.A. et al., Production of Infectious Human Cytomegalovirus Virions is Inhibited by Drugs that Disrupt Calcium Homeostasis in the Endoplasmic Reticulum. J Virol. 79(24):15388-97 (2005).

Johnson, J.J. et al., α-Mangostin, a Xanthone from Mangosteen Fruit, Promotes Cell Cycle Arrest in Prostate Cancer and Decreases Xenograft Tumor Growth. Carcinogenesis. 33(2):413-9 (2012).

Jonges, M. et al., Influenza Virus Inactivation for Studies of Antigenicity and Phenotypic Neuraminidase Inhibitor Resistance Profiling. J Clin Microbiol. 48(3):928-40 (2010).

Julander, J.G. et al., Use of Plethysmography in Assessing the Efficacy of Antivirals in a Mouse Model of Pandemic Influenza A Virus. Antiviral Res. 92(2):228-36 (2011).

Katz, J. and Wood, H.G., The Use of $C^{14}O_2$ Yields from Glucose-1-and-6-$C^{14}$ for the Evaluation of the Pathways of Glucose Metabolism. J Biol Chem. 238:517-23 (1963).

Legge, K.L. and Braciale, T.J., Accelerated Migration of Respiratory Dendritic Cells to the Regional Lymph Nodes is Limited to the Early Phase of Pulmonary Infection. Immunity. 18(2):265-77 (2003).

Lutz, M.B., An Advanced Culture Method for Generating Large Quantities of Highly Pure Dendritic Cells from Mouse Bone Marrow. J Immunol Methods. 223(1):77-92 (1999).

Monroe, M. et al., MASIC: A Software Program for Fast Quantitation and Flexible Visualization of Chromatographic Profiles from Detected LC-MS(/MS) Features. Comput Biol Chem. 32(3):215-7 (2008).

Moon, A. and Rhead, W.J., Complementation Analysis of Fatty Acid Oxidation Disorders. J Clin Invest. 79(1):59-64 (1987).

Murphy, M.G. et al., Sequestration of Coenzyme A by the Industrial Surfactant, Toximul MP8. A Possible Role in the Inhibition of Fatty-Acid Beta-Oxidation in a Surfactant/Influenza B Virus Mouse Model for Acute Hepatic Encephalopathy. Biochim Biophys Acta. 1361(1):103-13 (1997).

Newsholme et al., Glutamin Metaboliam in Lymphocytes: Its Biochemical, Physiological and Clincal Importance. Q J Exp Physiol. 70(4):473-89 (1985).

Oshansky, C.M. and Thomas, P.G., The Human Side of Influenza. J Leukoc Biol. 92(1):83-96 (2012).

Pearce, E.L. et al., Enhancing CD8 T-Cell memory by Modulating Fatty Acid Metabolism. Nature 460(7251):103-7 (2009).

Pearce, E.L., Metabolism in T Cell Activation and Differentiation. Curr Opin Immunol. 22(3):314-20 (2010).

Peng, X. et al., Integrative Deep Sequencing of the Mouse Lung Transcriptome Reveals Differential Expression of Diverse Classes of Small RNAs in Response to Respiratory Virus Infection. MBio. 2(6). pii:eDD198-11 (2011).

Pommerenke, C. et al., Global Transcriptome Analysis in Influenza-Infected Mouse Lungs Reveals in Kinetics of Innate and Adaptive Host Immune Responses. Plos One. 7:e41169 (2012).

Reed, J. and Muench, H., A Simple Method of Estimating Fifty Per Cent Endpoints. Amer J Hygiene. 27(3):493-7 (1938).

Ritz and Streibig, Functional regression Anaylsis of Fluorescence Curves. Biometrics. 65(2): 609-17 (2009).

Sanders, C.J. et al., Compromised Respiratory Function in Lethal Influenza Infection is Characterized by the Depletion of Type I Alveolar Epithelial Cells Beyond Threshold Levels. Am J Physiol Lung Cell Mol Physiol. 304(7):L481-8 (2013).

Sanders, C.J. et al., Respiratory Ephithelial Cells in Innate Immunity to Influenza Virus Infection. Cell Tissue Res. 343(1):13-21 (2011).

Shaneyfelt, M.E. et al., Natural Products that Reduce Rotavirus Infectivity Identified by a Cell-Based Moderate-Throughput Screening Assay. Virol J. 3:68 (2006).

Smith, G.C. et al., Effects of Acutely Inhibiting PI3K Isoforms and mTOR on regulation of Glucose Metabolism in Vivo. Biochem J. 442(1):161-9 (2012).

Smith, G.C. et al., Extended Treatment with Selective Phosphatidylinositol 3-Kinase and mTOR Inhibitors has Effects on Metabolism, Growth, Behaviour and Bone Strength. FEBS J. 280(21):5337-49 (2013).

Trauner, D.A. et al Inhibition of Fatty Acid Beta Oxidation by Influenza B Virus and Salicylic Acid in Mice: Implications for Reye's Syndrome. Neurology. 38(2): 239-41 (1988).

Vastag, L. et al., Divergent Effects of Human Cytomegalovirus and Herpes Simplex Virus-1 on Cellular Metabolism. PLoS Pathogens. 7(7):e1002124 (2011).

Wilems, H.L. et al., Determination of Pyruvate Oxidation Rate and Citric Acid Cycle Activity in Intact Human Leukocytes and Fibroblasts. Clin Chem. 24(2):200-3 (1978).

Yao, D. et al., Impaired Long-Chain Fatty Acid Metabolism in Mitochondria Causes Brain Vascular Invasion by a Non-Neurotropic Epidemic Influenza A Virus in the Newborn/Suckling

(56) References Cited

OTHER PUBLICATIONS

Period: Implications for Influenza-Associated Encephalopathy. Mol Cell Biochem. 299(1-2):85-92 (2007).

Yu, Y. et al., Viral Affects on Metabolism: Changes in Glucose and Glutamine Utilization During Human Cytomegalovirus Infection. Trends Microbiol. 19(7):360-7 (2011a).

Yu, Y. et al., Viruses and Metabolism: Alterations of Glucose and Glutamine Metabolism Mediated by Human Cytomegalovirus. Adv Virus Res. 80:49-67 (2011b).

International Search Report and Written Opinion dated Dec. 31, 2015 by the International Searching Authority for International Patent Application No. PCT/US2015/056036, which was filed on Oct. 16, 2015 and published as WO 2016/064683 on Apr. 28, 2016 (Inventor—Smallwood et al.; Applicant—St .Jude Children's Research Hosp.) (10 pages).

International Preliminary Report on Patentability dated Apr. 25, 2017 by the International Searching Authority for International Patent Application No. PCT/US2015/056036, which was filed on Oct. 16, 2015 and published as WO 2016/064683 on Apr. 28, 2016 (Inventor—Smallwood et al.; Applicant—St .Jude Children's Research Hosp.) (5 pages).

Mannick, et al. "TORC1 inhibition enhances immune function and reduces infections in the elderly", Sci Transl Med. (2018),10(449). pii: eaaq1564.

\* cited by examiner

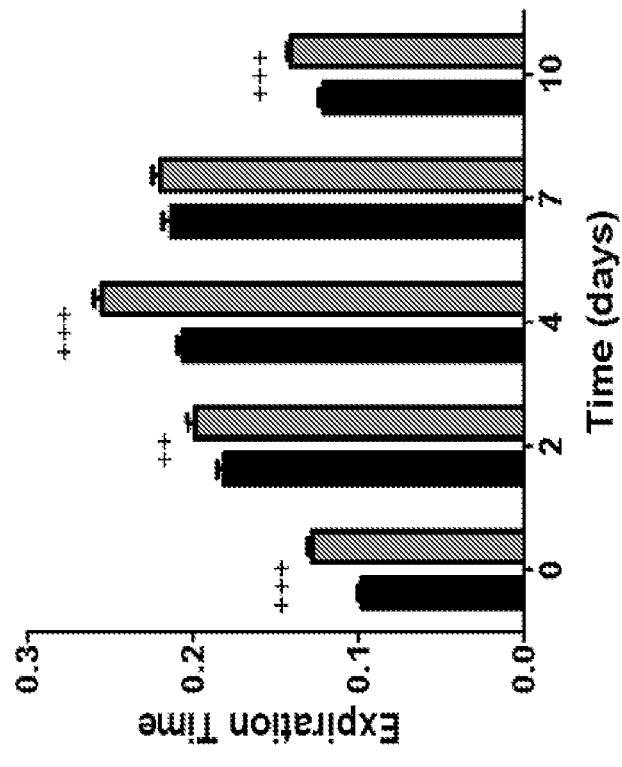
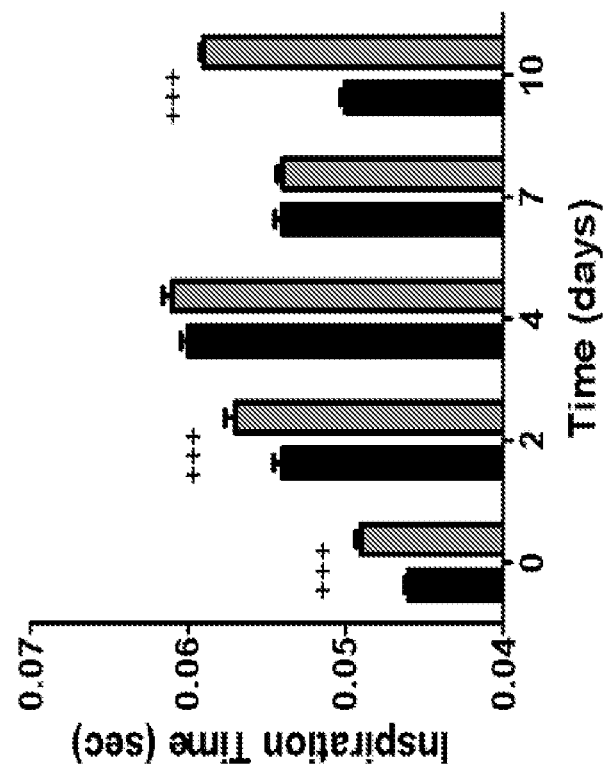
FIG. 10A
FIG. 10B

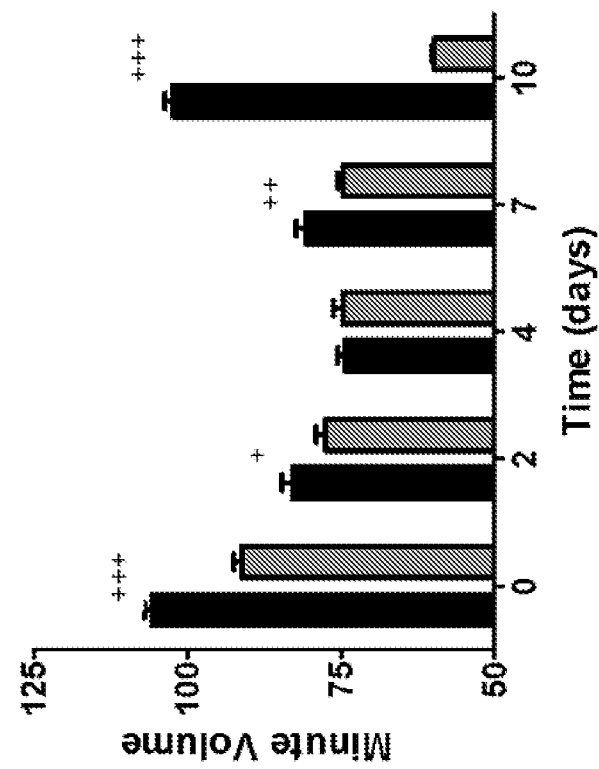
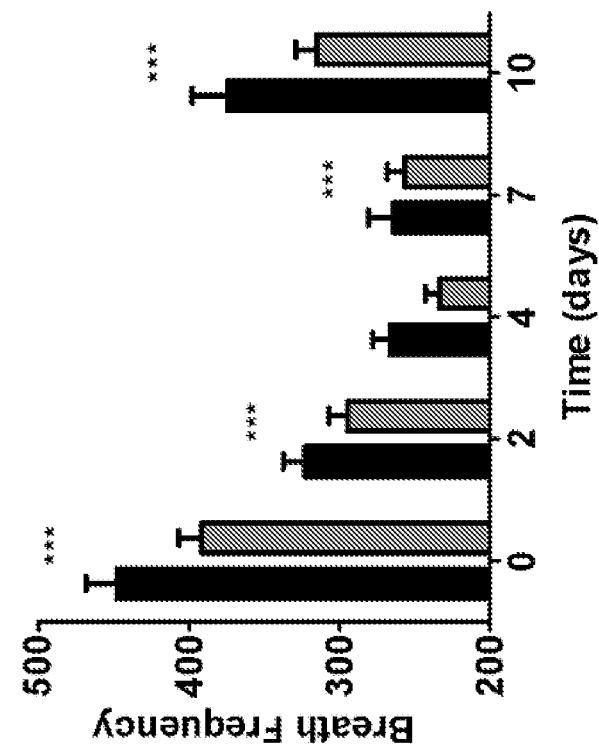
FIG. 10C
FIG. 10D

COORDINATED METABOLIC REPROGRAMMING IN RESPONSE TO PRODUCTIVE VIRAL INFECTIONS

CROSS-REFERENCE TO RELATED APPLICATIONS

This Application is a national stage filing under 35 U.S.C. § 371 of International Application No. PCT/US2015/056036, filed on Oct. 16, 2015, which claims the benefit of U.S. Provisional Application No. 62/068,561, filed on Oct. 24, 2014, the contents of which are incorporated herein by reference in their entireties.

STATEMENT REGARDING FEDERALLY SPONSORED RESEARCH

This invention was made with U.S. Government support under grant number RR 018522 awarded by the National Institute of Health (NIH), grant numbers CA-096832 and Core Grant CA-021765 awarded by the National Cancer Institute, and grant numbers AI091938 and AI077714 awarded by the National Institute of Allergy and Infectious Diseases. The U.S. government has certain rights in the invention.

BACKGROUND

Influenza is a significant health and financial burden worldwide. Influenza A virus has a lipid bilayer envelope with proteins that bind to the host cell-surface, triggering endocytosis and subsequent release of viral RNA segments for transcription and translation. The viral polymerase complex promotes viral mRNA production and blocks host mRNA synthesis. Viral structural proteins are glycosylated and transported to the cell membrane for incorporation into new budding viruses that steal host membrane when released. As a segmented RNA virus, influenza undergoes high rates of antigenic shift and drift requiring new vaccine formulations annually and limiting the efficacy of antiviral therapeutics (Das, K., et al. (2010) *Nature structural & molecular biology* 17, 530-538).

Recent work profiling immune cell transcriptional responses after influenza infection has revealed changes in the host immune response and non-protein-coding RNAs (Askovich, P. S., et al. (2013) *PloS one* 8: e74863; Peng, X., et al. (2011) *mBio* 2(6): e00198-11; Pommerenke, C., et al. (2012) *PloS one* 7: e41169). However, influenza-induced changes in gene expression do not closely correlate with changes in host proteins (Cheung, C. Y., et al. (2012) *The Journal of Infectious Diseases* 206: 640-645; Peng, X., et al. (2011) *mBio* 2(6): e00198-11). Further, influenza replication predominantly occurs in epithelial cells lining the respiratory tract, but virus can also non-productively infect local phagocytes (Legge, K. L. and Braciale, T. J. (2003) *Immunity* 18: 265-277; Oshansky, C. M. and Thomas, P. G. (2012) *Journal of leukocyte biology* 92: 83-96). Infection of these cells causes local pathology and initiates a systemic immune response, which can contribute to poor outcomes. Many studies have characterized key immune cell responses to influenza, but alterations in cells associated with the respiratory tract are less well characterized (Sanders, C. J., et al. (2011) *Cell and tissue research* 343: 13-21).

Despite recent advances in the understanding of immune metabolism, the metabolics of myelid lineage immune cells and airway epithelia in response to viral infection has remained elusive, restricting current treatment methods.

Thus, there remains a need for methods of treating viral infections (i.e., influenza viral infection) via alternative metabolic pathways.

SUMMARY

In accordance with the purpose(s) of the invention, as embodied and broadly described herein, the invention, in one aspect, relates to methods of treating viral infections using known drugs and pharmaceutical compositions comprising same.

Disclosed are methods for treating viral infection, the method comprising the step of administering to the subject an effective amount of at least one compound having a structure selected from:

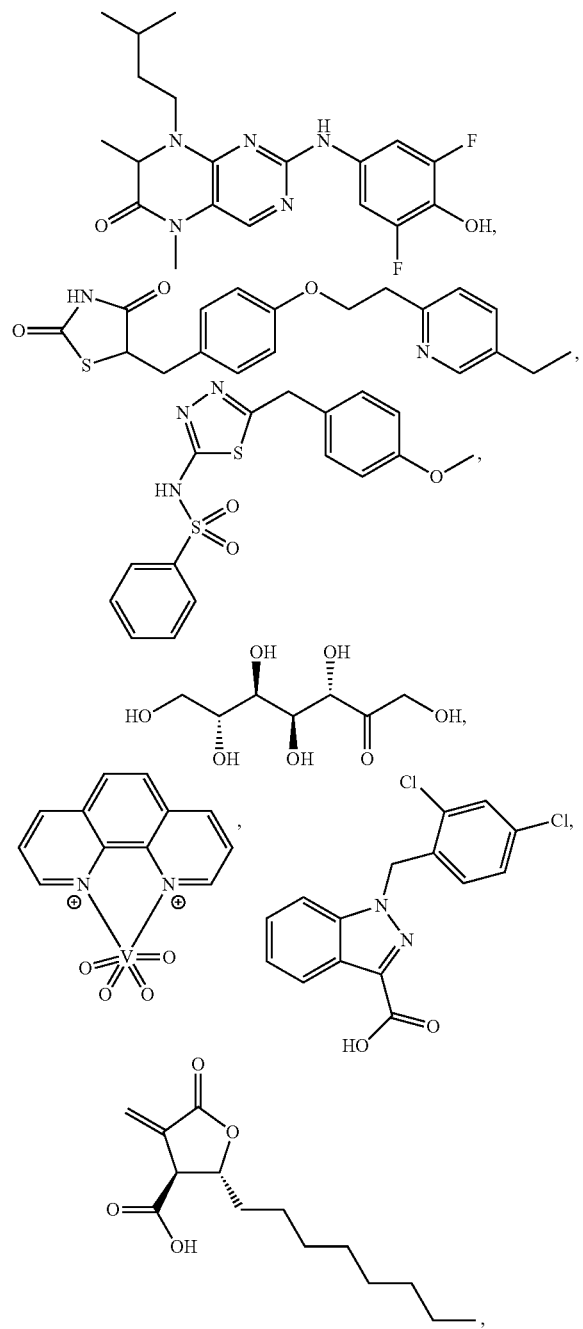

3
-continued
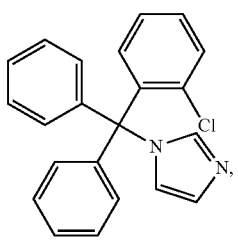
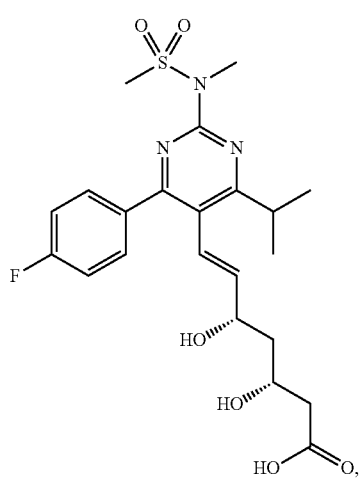
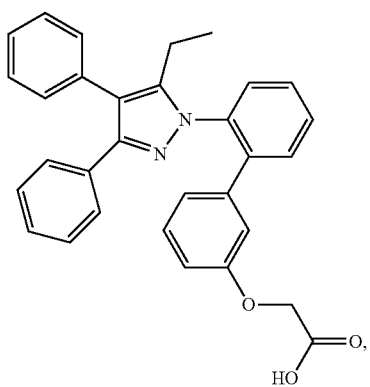
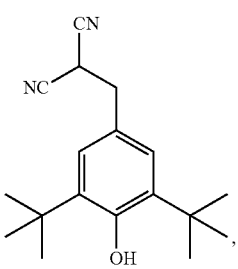
4
-continued
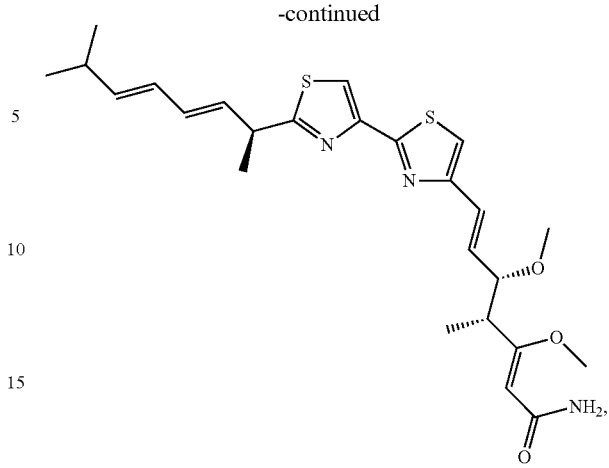
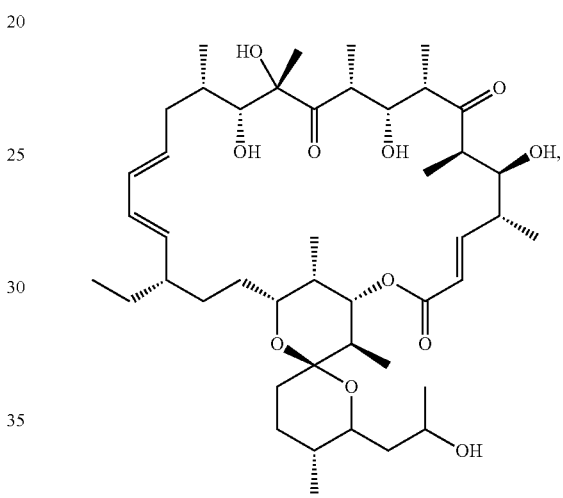
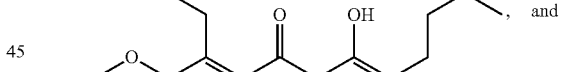
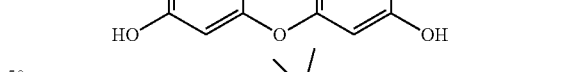
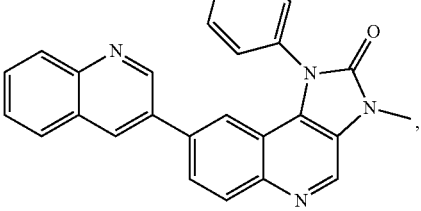
or a pharmaceutically acceptable salt thereof, thereby treating the subject for viral infection.
Also disclosed are pharmaceutical compositions comprising an effective amount of at least one compound having a structure selected from:

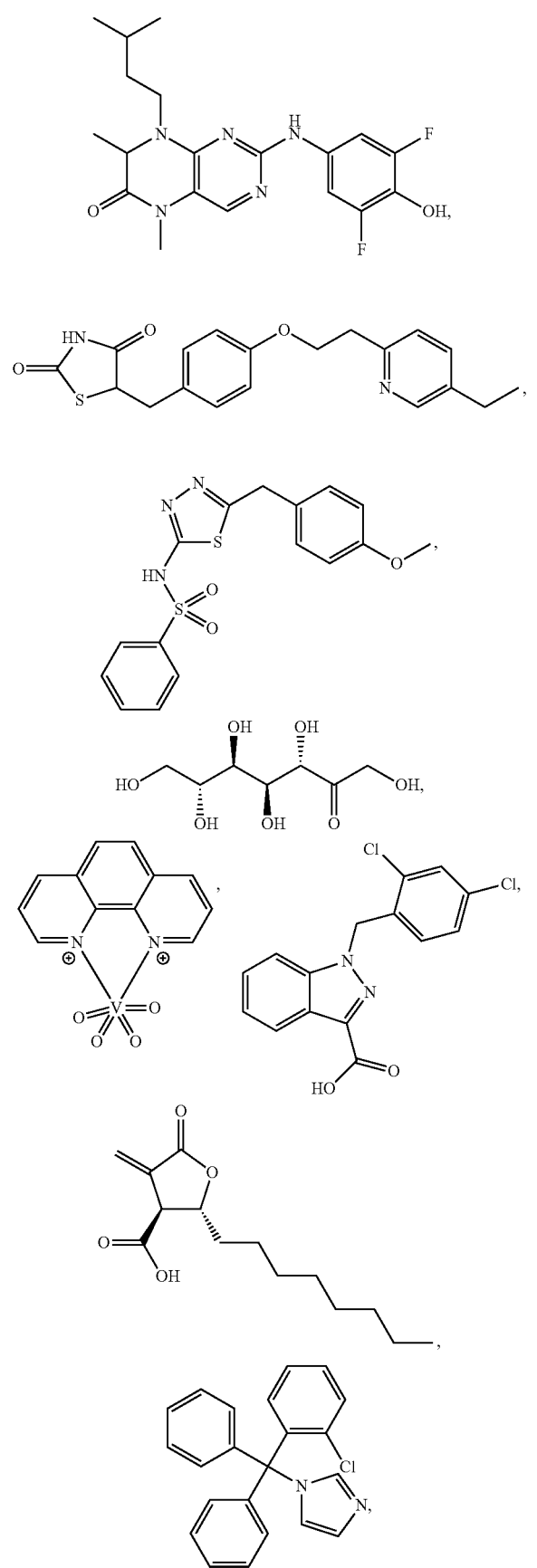
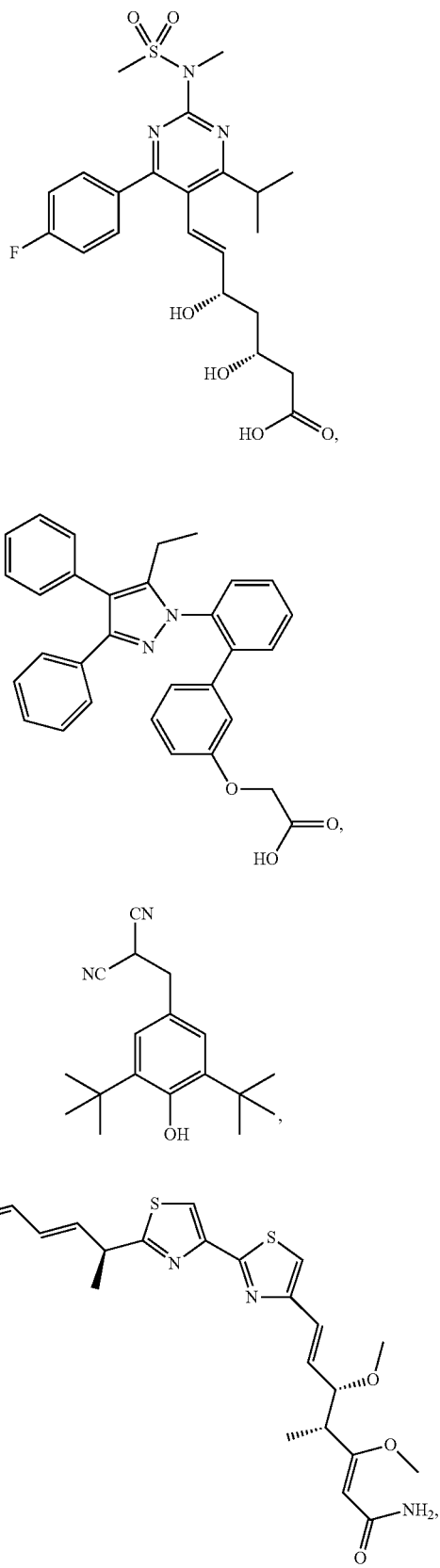

7
-continued

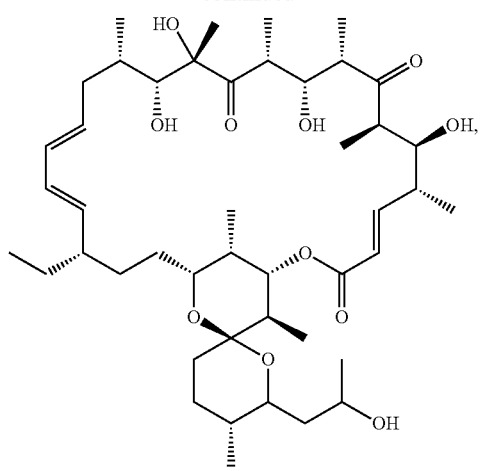

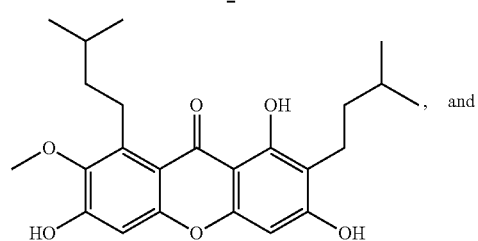

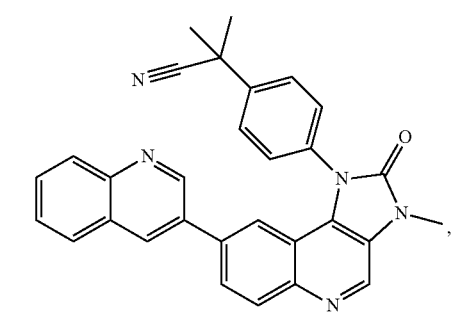 [SMILES: Cn1c(=O)n(-c2ccc(C(C)(C)C#N)cc2)c2c3cc(-c4cnc5ccccc5c4)ccc3ncc21]

or a pharmaceutically acceptable salt thereof; and an effective amount of: (a) at least one antiviral agent or a pharmaceutically acceptable salt thereof; or (b) at least one agent known to weaken the immune system or a pharmaceutically acceptable salt thereof; and a pharmaceutically acceptable carrier.

Also disclosed are kits comprising an effective amount of at least one compound having a structure selected from:

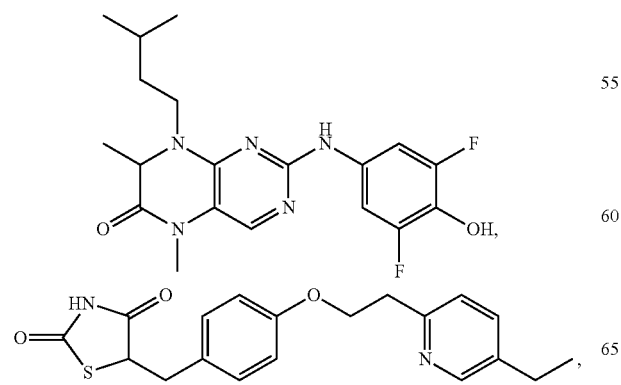

8
-continued

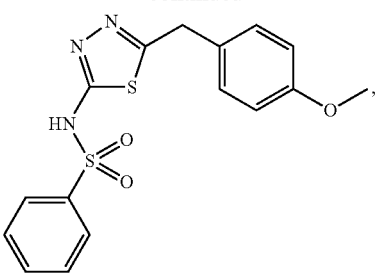

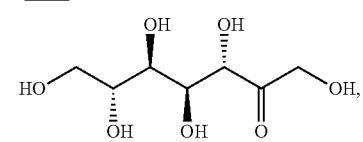

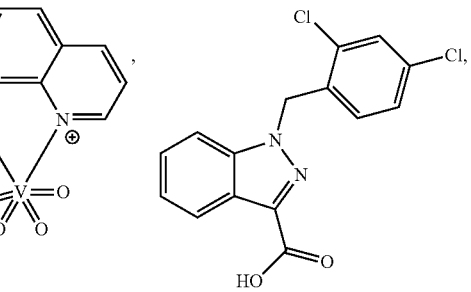

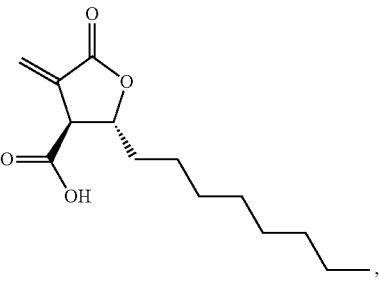

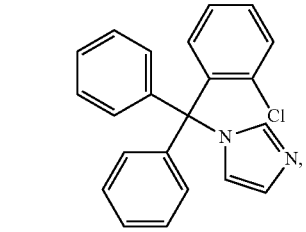

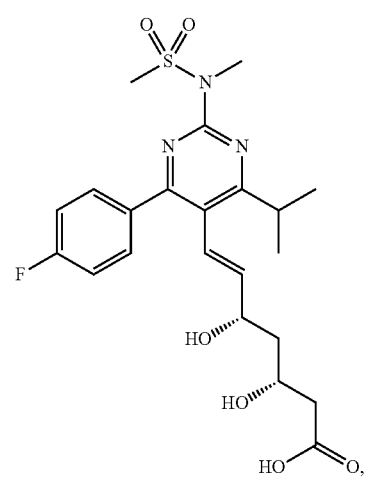

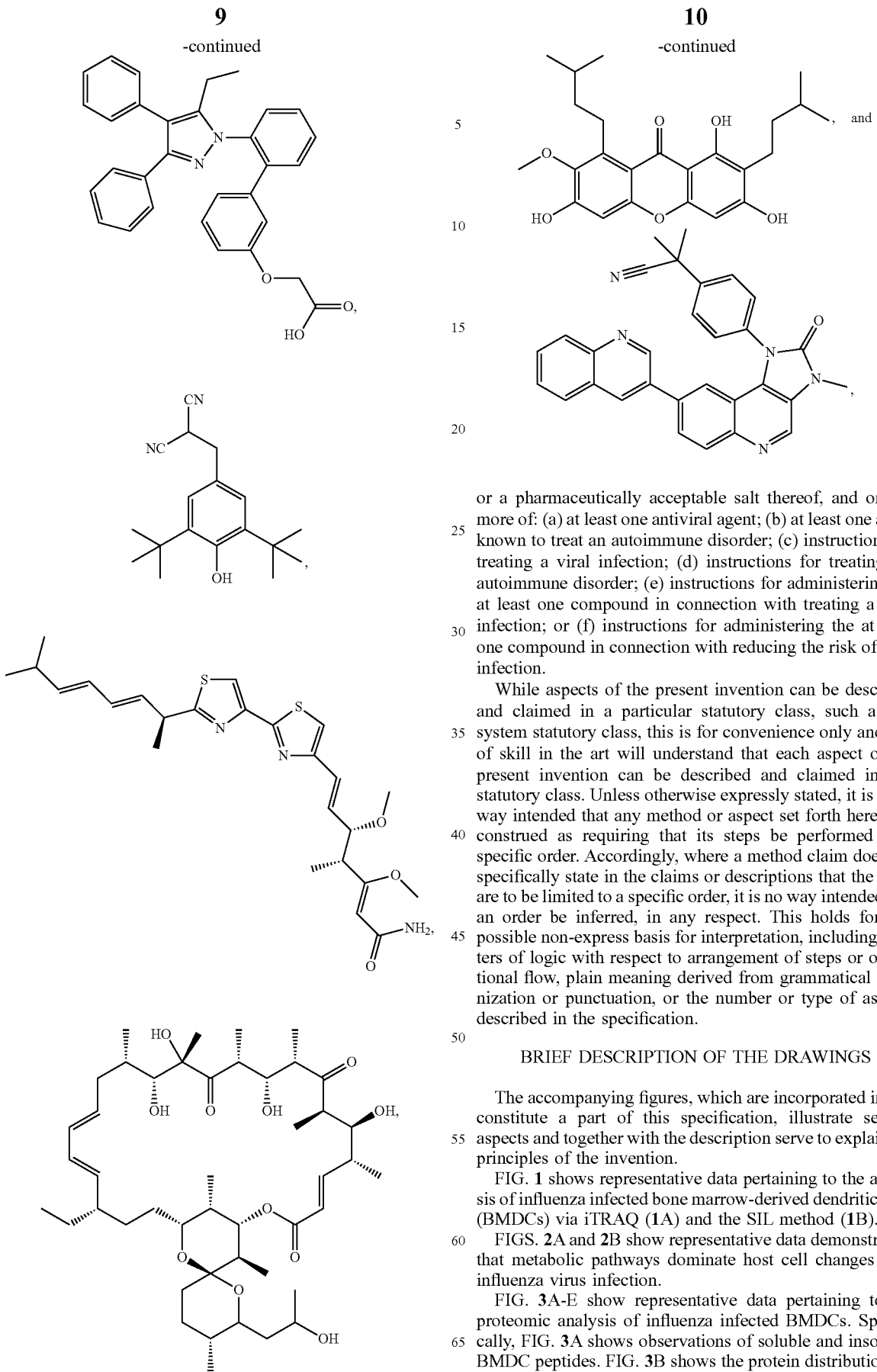

or a pharmaceutically acceptable salt thereof, and one or more of: (a) at least one antiviral agent; (b) at least one agent known to treat an autoimmune disorder; (c) instructions for treating a viral infection; (d) instructions for treating the autoimmune disorder; (e) instructions for administering the at least one compound in connection with treating a viral infection; or (f) instructions for administering the at least one compound in connection with reducing the risk of viral infection.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

FIG. 3A shows observations of soluble and insoluble BMDC peptides. FIG. 3B shows the protein distribution for clusters 1-7. The changes observed in the proteome were validated in cathepsin S, lysozyme, and α-enolase by activity assay (3C), western blot (3D), and/or immunofluorescence (3E).

FIG. 4A shows representative data demonstrating changes in metabolic protein networks via proteomic analysis. These changes were then analyzed using functional metabolic assays including measuring the extracellular acidification rates (ECAR) of virus-infected DCs (4B), the $O_2$ consumption rate (OCR) (4C), and the proton production rate (PPR) (4D). Finally, isotopically labeled substrates indicated the following metabolic pathways: [3-$^3$H]glucose (glycolysis) (4E), [2-$^{14}$C]pyruvate (TCA cycle) (4F), [1-$^{14}$C]glucose (pentose phosphate pathway) (4G), [U-$^{14}$C]glutamine (glutaminolysis) (4H), and [9,10-$^3$H]palmitic acid (fatty acid oxidation) (4J).

FIG. 6D shows representative data pertaining to the observation of metabolic changes that occur in influenza virus-infected primary NHBE cells in vivo.

FIG. 10A-E show representative data pertaining to the effect of NVP-BEZ235 treatment on respiratory parameters in vivo. Specifically, inspiration time (10A), expiration time (10B), breath frequency (10C), volume per minute (10D), and the tidal flow of air at the mid-point of expiration (10E) are shown.

Figure 1A:
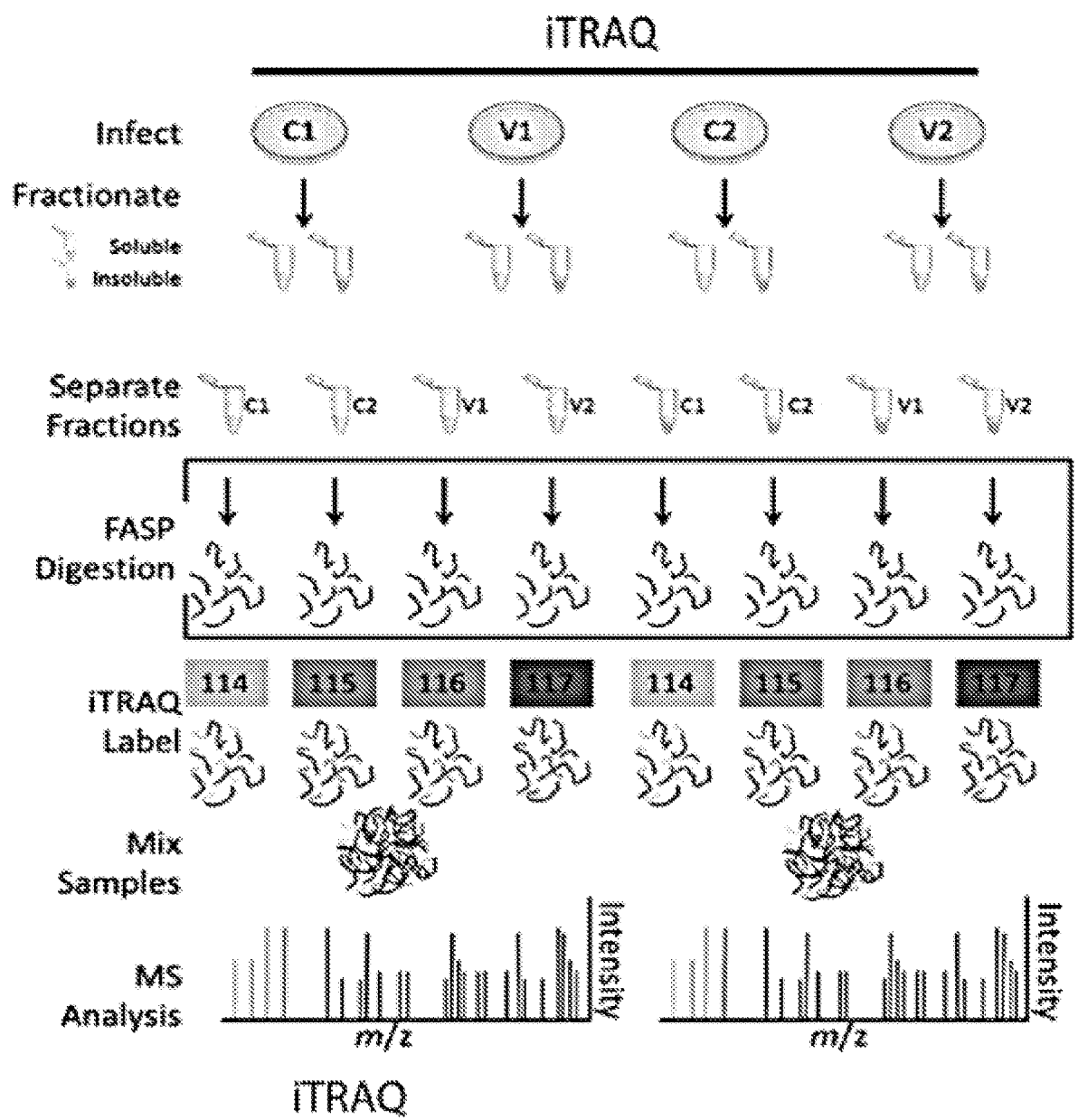
FIG. 1 shows representative data pertaining to the analysis of influenza infected bone marrow-derived dendritic cells (BMDCs) via iTRAQ (1A) and the SIL method (1B).
Figure 1A:
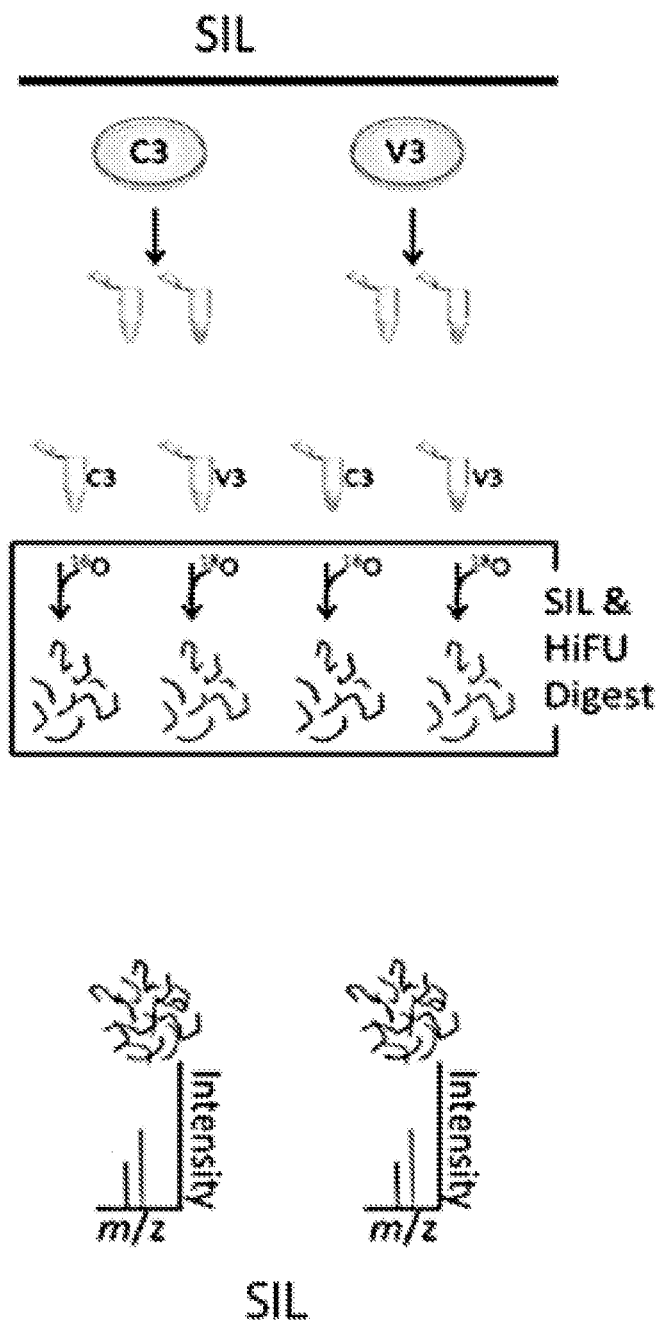

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorders prior to the administering step. In various aspects, the one or more disorders are an influenza viral infection.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a viral infection prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, "$TCID_{50}$," is intended to refer to the concentration of a substance (e.g., a compound or a drug) that is required to produce infection, including a viral infection, in 50% of cell cultures that are inoculated.

As used herein, "$EID_{50}$," is intended to refer to the concentration of a substance (e.g., a compound or a drug) that is required to produce infection, including a viral infection, in 50% of embryonated hen's eggs that are inoculated.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein may comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g., Almarasson, O., et al. (2004) *The Royal Society of Chemistry*, 1889-1896. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. METHODS FOR TREATING VIRAL INFECTION

In one aspect, the invention relates to methods for treating viral infection, the method comprising the step of administering to the subject an effective amount of at least one compound having a structure selected from:

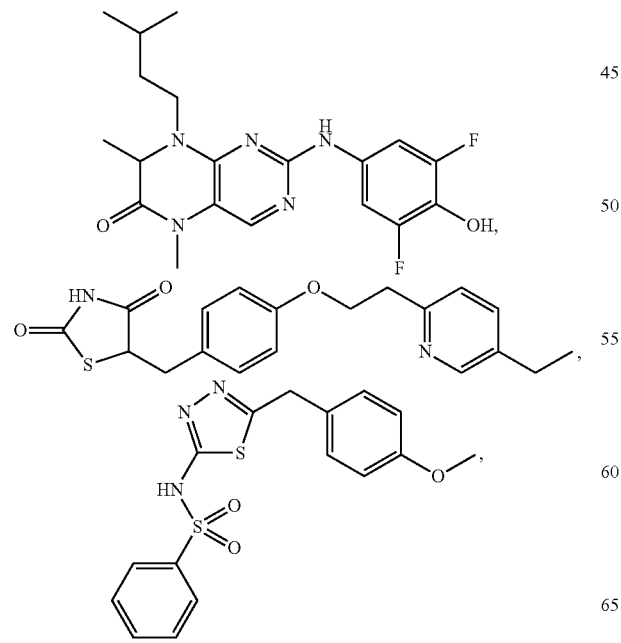

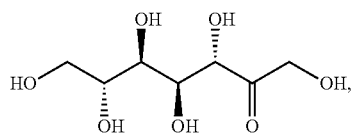

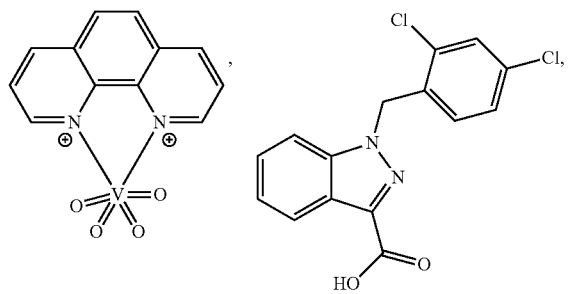

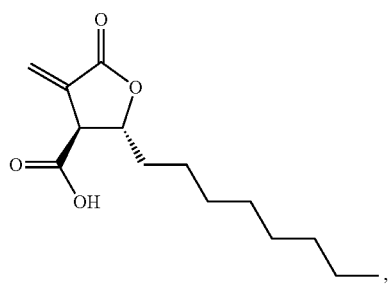

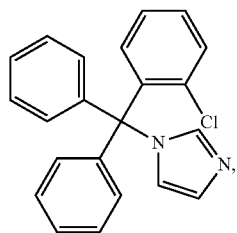

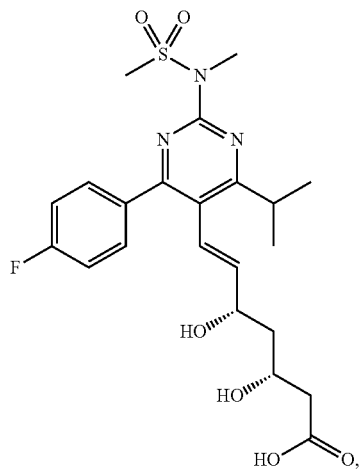

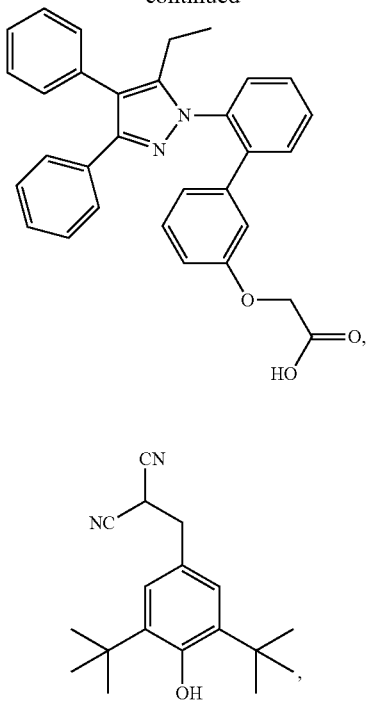

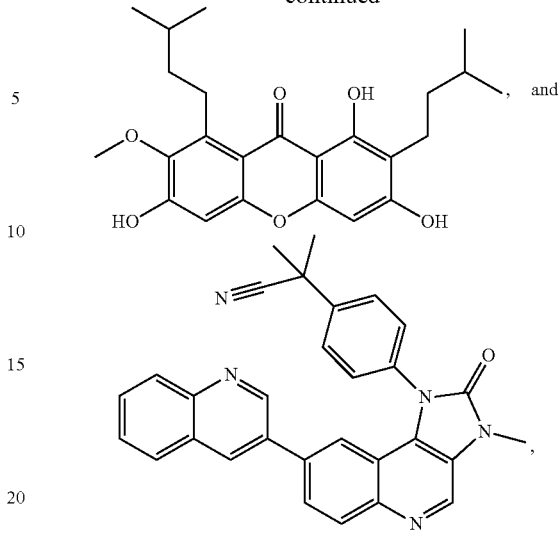

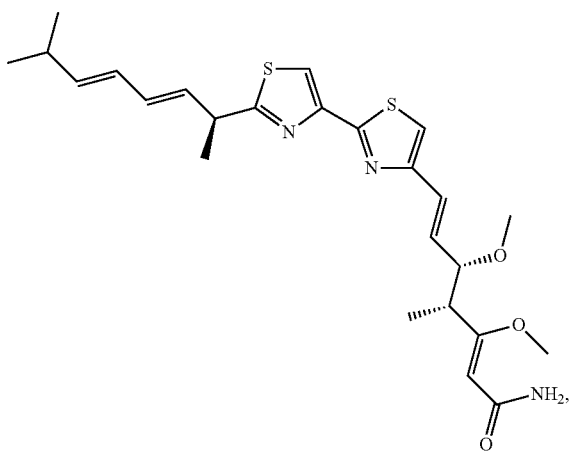

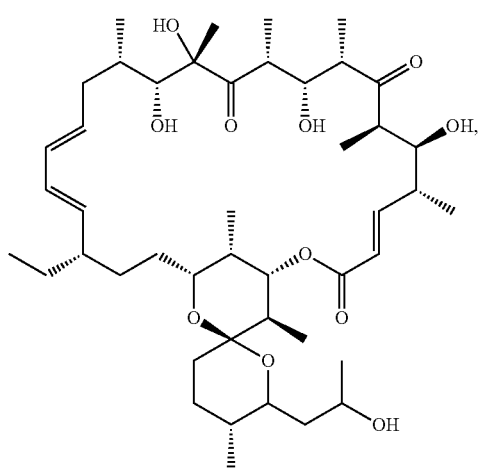

or a pharmaceutically acceptable salt thereof, thereby treating the subject for viral infection. Examples of influenza viral infections for which the compounds and compositions can be useful in treating, include, but are not limited to, human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, and viral pneumonia.

To treat or control the viral infection, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a viral infection, such as influenza virus.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of an infection or condition, such as influenza virus.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

In a further aspect, the at least one compound is:

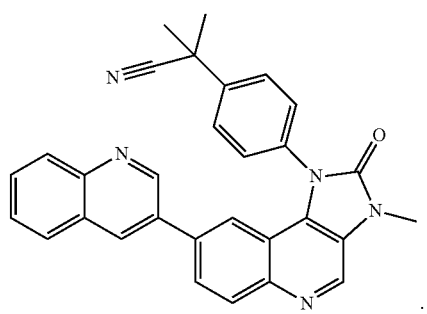 [SMILES: Cn1c(=O)n(-c2ccc(C(C)(C)C#N)cc2)c2c3cc(-c4cnc5ccccc5c4)ccc3ncc21]

In a further aspect, the viral infection is influenza.

In a further aspect, the viral infection is an enveloped virus. In a still further aspect, the enveloped virus is a respiratory virus.

In a further aspect, the subject is a mammal. In a still further aspect, the mammal is a pig. In yet a further aspect, the mammal is a horse. In an even further aspect, the mammal is a human.

In a further aspect, the subject is a bird.

In a further aspect, the subject has been diagnosed with a need for treatment of the viral infection prior to the administering step. In a still further aspect, the method further comprises the step of identifying a subject in need of treatment of the viral infection.

In a further aspect, the effective amount is a therapeutically effective amount. In a still further aspect, the effective amount is a prophylactically effective amount.

C. PHARMACEUTICAL COMPOSITIONS

In one aspect, the invention relates to pharmaceutical compositions comprising an effective amount of at least one compound having a structure selected from:

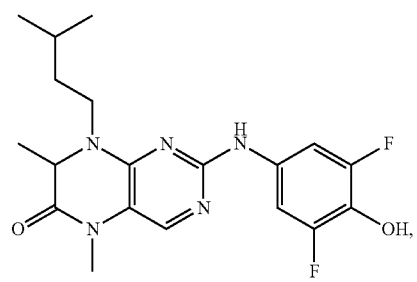

-continued

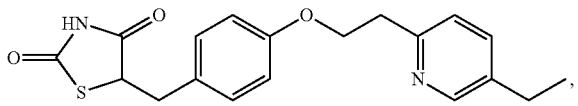

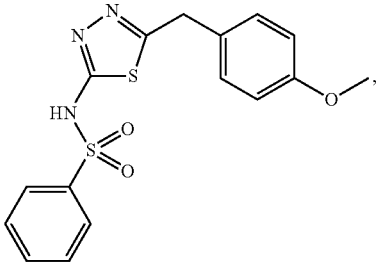

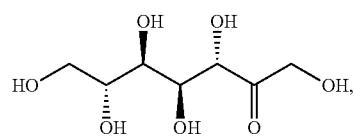

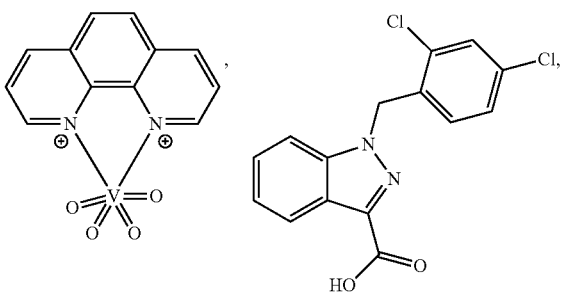

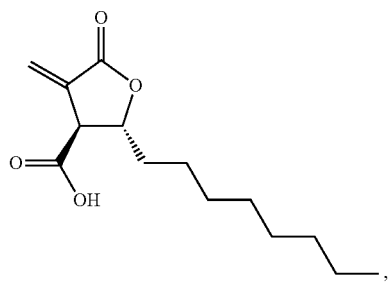

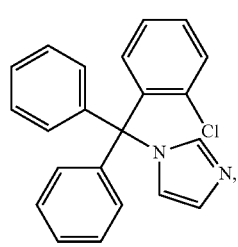

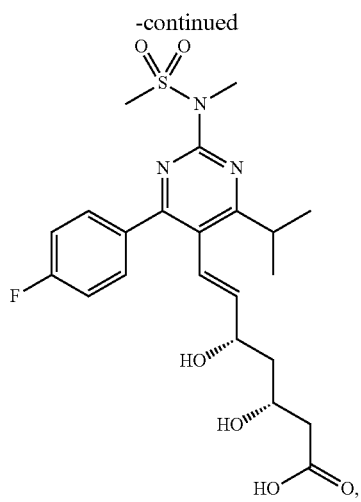

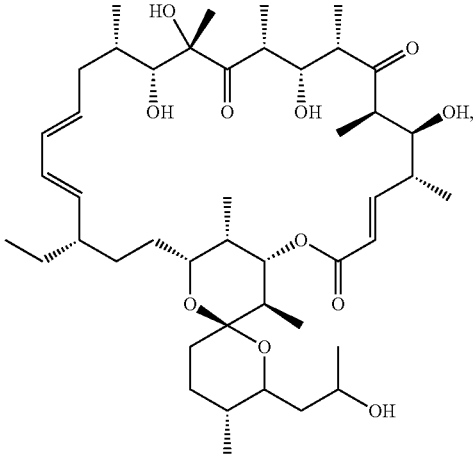

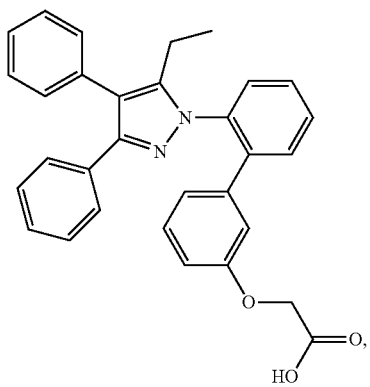

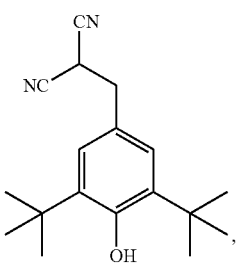

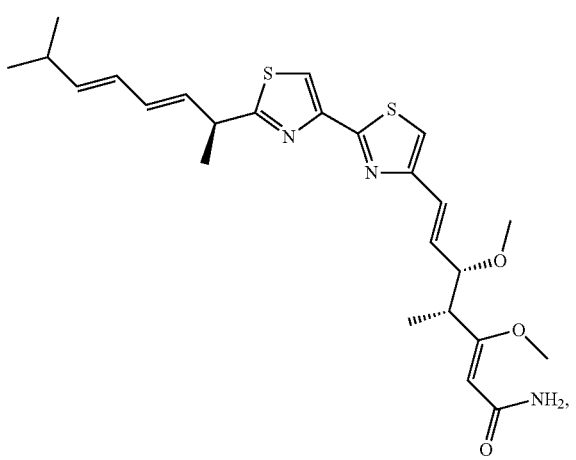

or a pharmaceutically acceptable salt thereof; and an effective amount of: (a) at least one antiviral agent or a pharmaceutically acceptable salt thereof; or (b) at least one agent known to weaken the immune system or a pharmaceutically acceptable salt thereof; and a pharmaceutically acceptable carrier. In a further aspect, the effective amount is a therapeutically effective amount. In a still further aspect, the effective amount is a prophylactically effective amount. In yet a further aspect, the invention relates to pharmaceutical compositions comprising a pharmaceutically acceptable carrier and a compound, wherein the compound is present in an effective amount.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carriers) followed by chilling and shaping in molds.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, the at least one compound is:

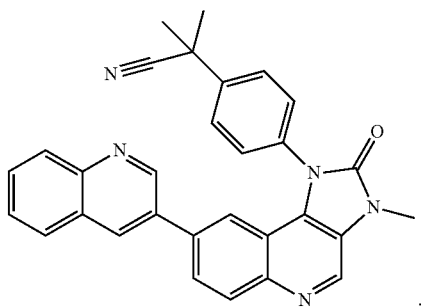 [SMILES: Cn1c(=O)n(-c2ccc(C(C)(C)C#N)cc2)c2c3cc(-c4cnc5ccccc5c4)ccc3ncc21]

In a further aspect, the composition is formulated for parenteral administration. In a still further aspect, the composition is formulated for inhalation. In yet a further aspect, the composition is formulated for oral administration. In an even further aspect, the composition is formulated for topical administration.

In a further aspect, the antiviral agent is selected from oseltamivir, zanamivir, amantadine, and rimantadine.

In a further aspect, the agent known to weaken the immune system is selected from a corticosteroid, a TNF inhibitor, an immunosuppressant, a proton pump inhibitor (PPI), and a selective serotonin reuptake inhibitor (SSRI). In a still further aspect, the corticosteroid is selected from budesonide, cortisone, dexamethasone, hydrocortisone, methylprednisolone, prednisolone, prenisone, triamcinolone, beclomethasone, budesonide, ciclesonide, flunisolide, fluticasone, mometasone, and triamcinolone. In yet a further aspect, the TNF inhibitor is selected from adalimumab, certolizumab, etanercept, golimumab, and infliximab. In an even further aspect, the immunosuppressant is selected from cyclosporine, azathioprine, basiliximab, aclizumab, muromonab, tacrolimus, glatiramer acetate, mycopehnolate, and sirolimus. In a still further aspect, the PPI is selected from esomeprazole, lansoprazole, omeprazole, dexlansoprazole, pantoprazole, raberprazole, and ilaprzole. In yet a further aspect, the SSRI is selected from citzlopram, dapoxetine, escitalopram, fluvoxamine, fluoxetine, indalpine, sertraline, paroxetine, and zimelidine.

It is understood that the disclosed compositions can be prepared from the disclosed compounds. It is also understood that the disclosed compositions can be employed in the disclosed methods of using.

D. KITS

In one aspect, the invention relates to a kit comprising a comprising an effective amount of at least one compound having a structure selected from:

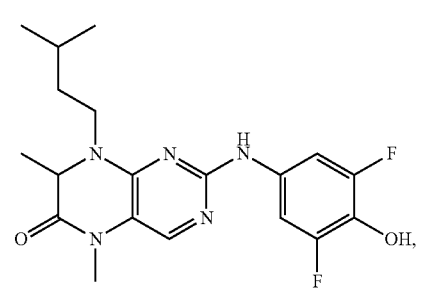

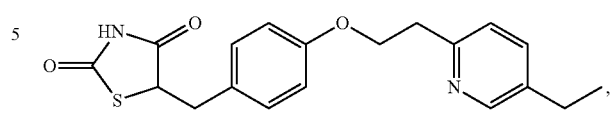

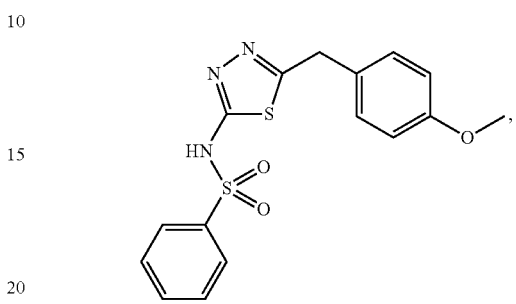

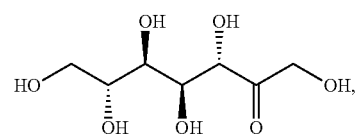

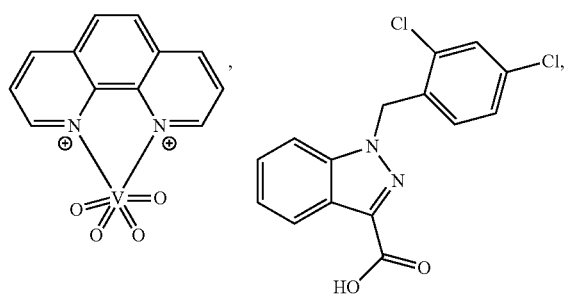

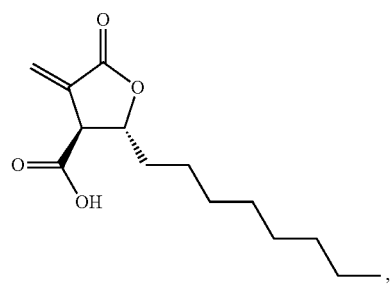

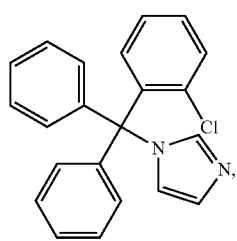

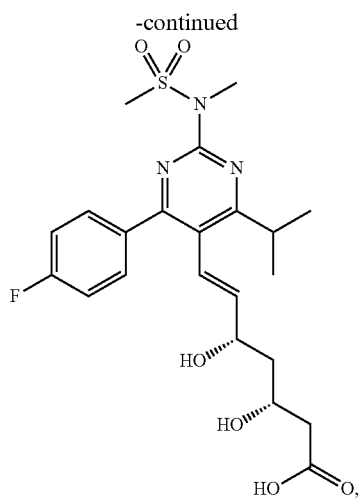

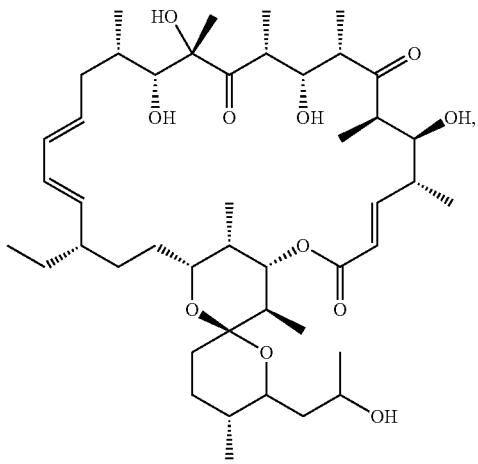

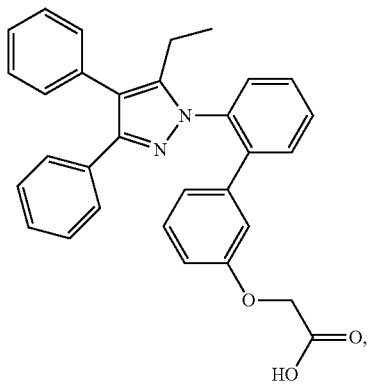

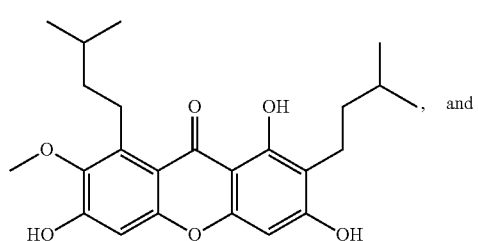

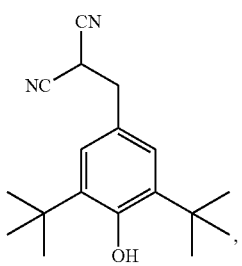

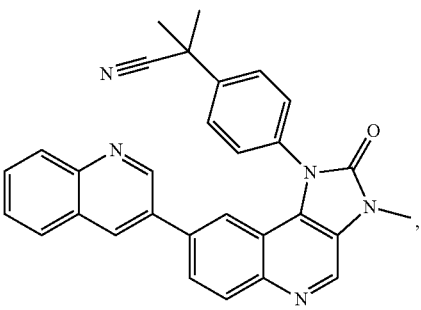

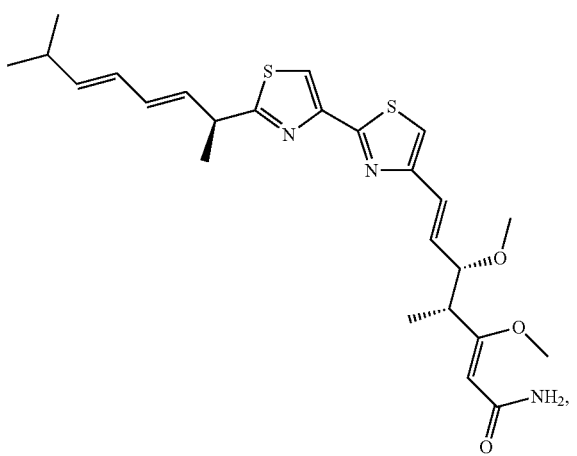

or a pharmaceutically acceptable salt thereof, and one or more of: (a) at least one antiviral agent; (b) at least one agent known to treat an autoimmune disorder; (c) instructions for treating a viral infection; (d) instructions for treating the autoimmune disorder; (e) instructions for administering the at least one compound in connection with treating a viral infection; or (f) instructions for administering the at least one compound in connection with reducing the risk of viral infection. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

In a further aspect, the at least one compound is:

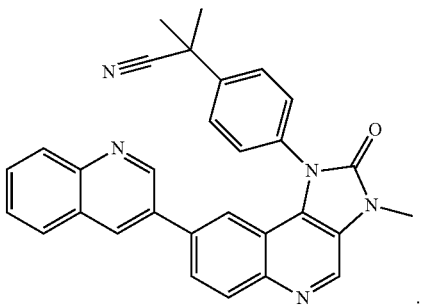

In a further aspect, the at least one compound and the at least one agent are co-packaged. In a still further aspect, the at least one compound and the at least one agent are co-formulated.

In a further aspect, the autoimmune disorder is selected from asthma, rheumatoid arthritis, lupus, inflammatory bowel disease, multiple sclerosis, diabetes, human immunodeficiency virus (HIV), acquired immune deficiency syndrome (AIDS), severe combined immune deficiency (SCID), common variable immune deficiency (CVID), and vasculitis.

In a further aspect, the kit further comprises a plurality of dosage forms, the plurality comprising one or more doses; wherein each dose comprises an effective amount of the at least one compound and the at least one agent. In a still further aspect, the effective amount is a therapeutically effective amount. In yet a further aspect, the effective amount is a prophylactically effective amount.

In a further aspect, each dose of the at least one compound and the at least one agent are co-formulated. In a still further aspect, each dose of the at least one compound and the at least one agent are co-packaged.

In a further aspect, each dose of the at least one compound and the at least one agent are administered sequentially. In a still further aspect, each dose of the at least one compound and the at least one agent are administered simultaneously.

In a further aspect, the dosage forms are formulated for oral administration, inhalation, topical administration, and/or parenteral administration. In a still further aspect, the dosage form for the at least one compound is formulated for oral administration and the dosage form for the at least one agent is formulated for parental administration. In yet a further aspect, the dosage form for the at least one compound is formulated for parental administration and the dosage form for the at least one agent is formulated for oral administration. In an even further aspect, the dosage form for the at least one compound is formulated for topical administration and the dosage form for the at least one agent is formulated for parental administration. In a still further aspect, the dosage form for the at least one compound is formulated for parental administration and the dosage form for the at least one agent is formulated for topical administration. In yet a further aspect, the dosage form for the at least one compound is formulated for oral administration and the dosage form for the at least one agent is formulated for inhalation. In an even further aspect, the dosage form for the at least one compound is formulated for inhalation and the dosage form for the at least one agent is formulated for oral administration. In a still further aspect, the dosage form for the at least one compound is formulated for topical administration and the dosage form for the at least one agent is formulated for inhalation. In a yet further aspect, the dosage form for the at least one compound is formulated for inhalation and the dosage form for the at least one agent is formulated for topical administration.

It is understood that the disclosed kits can be prepared from the disclosed compounds, products, and pharmaceutical compositions. It is also understood that the disclosed kits can be employed in connection with the disclosed methods of using.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. General Experimental Methods a. Proteomics Sample Preparation, Mass Spectrometry, and Data Processing DCs and NHBE cells (Lonza, Walkersville, Md.) were infected for 17 hours with PR8 (MOI 5) or CA09 (MOI 1) followed by lysis, homogenization, and fractionation by centrifugation. DCs were tryptically digested with a FASP Protein Digestion Kit (Protein Discovery, San Diego, Calif.) following the manufacturer's instructions with slight modifications (Supplemental Data), and NHBE cells were desalted by C18 solid-phase extraction (SPE) before isobaric labeling (SUPELCO, Bellefonte, Pa.). Digested samples were then processed according to the manufacturer's directions for iTRAQ 4-plex labeling (ABSciex, Redwood City, Calif.). A separate set of DC samples was processed with trypsin-catalyzed $^{18}O$ labeling. Before fractionating by high-pH reverse-phase fractionation with concatenated pooling, samples were desalted by $C^{18}$ SPE (SUPELCO). All samples were processed with a custom liquid chromatography system using reversed-phase C18 columns. iTRAQ samples were analyzed with a Velos Orbitrap mass spectrometer (Thermo Scientific, San Jose, Calif.), and $^{18}O$-labeled samples were analyzed with an LTQ-Orbitrap mass spectrometer (Thermo Scientific). Both systems were equipped with custom ion funnel-based atmospheric pressure ionization sources and electrospray ionization interfaces.

Raw files were compared with a concatenated NCBI *Mus musculus* database and contaminant database using SEQUEST v.27 (rev. 12). The resulting sequence identifications were rescored using MS-GF and filtered to a 1% false discovery rate using the target-decoy approach and MS-GF-derived spectral probabilities. Reporter ion intensities were quantified using the MASIC tool (Monroe, Matthew et al. (2008) *Computational biology and chemistry* 32.3: 215-217). Missing reporter ion channel results were excluded from analysis. Redundant peptide identification reporter ions were summed across fractions, and median central tendency normalization was used to account for channel bias and then log 2 transformed. Soluble and insoluble fractions were analyzed separately using DanteR software. The analysis of variance model included treatment and peptide effects. The remaining treatment effect and p-value were calculated using Student's *t*test. Benjamin-Hochberg multiple-testing error correction was applied to the results of this hypothesis testing, and proteins with $p<0.05$ were considered significant.

b. Metabolic Assays

OCR and ECAR were measured with the XF-24 Extracellular Flux Analyzer (Seahorse Bioscience, North Billerica, Mass.). Briefly, $2.5\times10^5$ cells/well were seeded with XF media (non-buffered DMEM with 25 mM glucose, 2 mM L-glutamine, and 1 mM sodium pyruvate) in a Cell-Tak (BD Biosciences, San Jose, Calif.)-coated plate 17 hours after infection and 1 hour before loading the plate into the instrument.

Glycolytic flux was determined by measuring the detritiation of [3-3H]glucose (Hue, L., et al. (1984) *The Biochemical Journal* 224: 779-786). Fatty acid beta-oxidation flux was determined by measuring the detritiation of [9,10-3H]-palmitic acid (Buzzai, M., et al. (2005) *Oncogene* 24: 4165-4173; Moon, A. and Rhead, W. J. (1987) *J. Clin. Invest.* 79: 59-64). Glutamine oxidation flux was determined by the rate of $^{14}CO_2$ released from [U-$^{14}$C]-glutamine (Brand, K., et al. (1984) *The Biochemical Journal* 221: 471-475). Pyruvate oxidation flux was determined by the rate of $^{14}CO_2$ released from [2-$^{14}$C]-pyruvate (Willems, H. L., et al., (1978) *Clinical chemistry* 24: 200-203). Glucose oxidation flux through the pentose phosphate pathway (PPP) was determined as previously described with some modifications described in supplemental information (Katz, J. and Wood, H. G. (1963) *J. Biol. Chem.* 238: 517-523).

For the Biolog analysis, NHBE cells were differentiated until day 9 or 10, viability was determined, and the cell suspension was seeded into PM-M1 plates essentially as described by the manufacturer (Biolog). Cells were allowed to uptake carbon and energy sources in the wells for 24-36 hours, and then virus was added at MOI 1. The infection proceeded for 17 hours, and then redox-sensitive dye was added to the wells. Redox energy produced when cells used specific substrates to reduce tetrazolium to formazan caused a color change that was monitored with a spectrophotometer at an absorbance of 590 nm. Interference from background scatter due to precipitate formation was monitored at an absorbance of 750 nm. The kinetics of formazan production from metabolism of substrates were determined from hourly absorbance measurements maintained for 16 hours after dye was added.

c. Viruses, Titers, and Infections (i) Viruses

For mouse studies, A/Puerto Rico/8/34 (PR8) was generated from reverse genetics stock plasmids given by Richard Webby. For human studies, a primary isolate of A/California/4/2009 was used. Both viruses were cultured in specific pathogen free antibiotic treated eggs that were inoculated on day 9 in bulk. Allantoic fluid was harvested 48 hours following inoculation and aliquotted into 50 mL conical tubes and stored at −80° C. Individual bulk viral stocks were then thawed, aliquotted, stored at −80° C. and titers were determined for each stock set. Tissue culture infectious dose at 50% ($TCID_{50}$) were then determined by serial dilution on near confluent Madin-Darby canine kidney (MDCK) cells in the presence of 1 mg/mL trypsin (Sigma Aldrich, St Louis Mo.), verified with 50% egg infectious doses ($EID_{50}$) and calculated according to the Reed and Muench method (Reed et al. (1938) *Journal of Hygiene* 27: 493-497). Virus infectivity and titers from cultures or tissues were assessed by 50% tissue culture infectious dose ($TCID_{50}$).

(ii) Intranasal Infections

Female C57BL/6J (B6) between 4 and 12 months age were anesthetized with intraperitoneal injections of 2,2,2-tribromoethanol ("Avertin") followed by intranasal infections of $1\times10^6$ $EID_{50}$ X31 delivered in 30 μL sterile PBS or controls treated with PBS alone. Mice were monitored until anesthetic effects subsided. B6 mice were euthanized (i.e., $CO_2$ inhalation) at the indicated times following infection (0-17 hr and day 9).

d. Tissue Culture and Mouse Work (i) Dendritic Cells (DC)

Female C57BL/6J (B6) mice purchased from The Jackson Laboratory (Bar Harbor, Me.) and were kept under specific pathogen-free conditions St. Jude Children's Research Hospital animal care facility. Primary bone marrow derived dendritic cells were isolated and differentiated as previously described (Lutz, M. B. (1999) *J. Immunol. Methods* 223:77). Briefly, B6 mice were $CO_2$ sacrificed and femurs and tibias were immediately extracted. Following the removal of the epiphysis bone marrow was flushed out, red blood cells lysed, and cell viability and numbers were determined to facilitate plating 2 million viable precursors per 100 cm$^2$ polystyrene plate in 10 mL RPMI supplemented with Penicillin (100 μg/mL), Streptomycin (100 μg/mL), fetal bovine serum (10% v/v) and 20 ng GM-CSF (R&D systems, Minneapolis, Minn.) per mL medium. On day 3 an additional 20 ng GM-CSF/mL medium was added with 10 mL fresh medium. On days 6 and 8 ten mL of medium was removed from each plate, gently centrifuged, and the cell pellet was resuspended in fresh medium and returned to the original plate. On day 10 DC's were harvested and viability determined. The cells were resuspended in infection medium and seeded $100\times10^6$ per T-75 flask. PR8 virus was added at a multiplicity of infection (MOI) of 5 for 1 hour. Virus laden medium or blank infection medium was then removed and the infection was allowed to proceed for indicated times.

(ii) Normal Human Bronchiolar Epithelial Cells (NHBE)

All NHBE reagents and cells were purchased from Lonza (Walkersville, Md.). Primary tracheal epithelial cells are extracted from healthy 19 year old male tissue donor and cultured as previously described (Oshansky, C. M. and Thomas, P. G. (2012) *Journal of leukocyte biology* 92: 83-96). In brief, cryopreserved NHBE cells all originating from the same donor were expanded for 10 days and treated as follows: NHBE cells were rapid thawed and gently resuspended in BEGM™ medium supplemented with BulletKit™, replacing the retinoic acid with 50 nM fresh retinoic acid and 25 ng/mL Epidermal Growth Factor final concentrations. 1000 cells/cm$^2$ were seeded in T-75 flasks and medium was changed every two days until cells reached <80% confluence. CA virus was added at a multiplicity of infection (MOI) of 0.1, 1, or 5 for 1 hour. Virus laden medium was then removed and the infection was allowed to proceed for 17 hours. Cells were rinsed twice with Hepes Buffered Saline Solution, lifted with trypsin/EDTA (0.25 mg/mL) added to trypsin neutralization solution, centrifuged, and cell viability was determined via trypan blue dye exclusion method with the Vi Cell (Beckman Coulter, Brea Calif.).

e. Pet Scans of Influenza Virus Infected Patients

Patients were given intravenous injections of 5.5 MBq/kg fluorodeoxyglucose (FDG; maximum, 444 MBq) after >4 hours of fasting. Blood glucose was found to be normal before FDG injection. Patients were kept in a quiet, dark room after injection and were told to lie down and relax with their arms at their sides. About 1 hour later, attenuation correction and lesion localization by transmission CT and PET images were acquired with a GE Discovery LS PET/CT system (GE Medical Systems, Waukesha, Wis.). CT parameters were: tube rotation, 0.8 second; slice thickness, 0.5 cm; table speed, 1.5 cm/rotation; pitch, 1.5:1; 120 kV; 90 mA; with dose modulation. PET images were obtained from the top of the skull to the feet for 5 minutes per bed position in 2-dimensional mode. Anesthesia-sedation was used if needed. Scans after July 2011 were acquired on a GE Discovery 690 PET/CT system. Those images were acquired in 3-dimensional mode at 3-5 minutes per bed position. Vendor-supplied software was used for reconstruction. Standardized uptake values were determined by placing regions of interest over areas of normal and abnormal uptake in the lungs.

f. High-Throughput Drug Screening (i) Chemical Library

The St. Jude "metabolic" library consisted of 80 compounds acquired from commercial sources and external academic collaborators. This library consisted on a mix of tool compounds and FDA-approved drugs directed against well know metabolic targets. The screening library was stored at −20° C. in 384-well microtiter plates at a final concentration of 4 µM to 10 mM in 0.1% DMSO. There were up to 32 compounds per plate and columns 21, 22, 23, and 24 were empty and reserved for controls and reference compounds. All compounds were >85% purity at the time of purchase.

The control plate was arranged as such: (a) columns 21 and 23 contained dilution series cycloheximide at 35.5 µM top concentration and 1:3 dilutions from A to P; (b) cycloheximide at 35.5 µM in columns 22 and 24, rows A, B, C, D, I, J, K, and L; (c) DMSO in columns 22 and 24, rows E, F, G, H, M, N, O, and P.

(ii) High-Throughput Assay 2000 cells per well were plated in 384-well plates (Corning) in 30 µL of BEGM using an automated plate filler (Wellmate, Matrix). After 24 hrs, 28 nL of compound was transferred via pin tool resulting in a final drug concentration of approximately 4 nm to 10 µM. On each plate, control rows were "drugged" with 0.1% DMSO only (negative control) or cyclohexamide (single point at 0.5 µM or dose-response from 0.5 µM to 0.01 nM) as positive control for cell killing. After 72 hrs of treatment, the cell number was determined in each well using CellTiter-Glo© reagent (Promega) and the luminescence signal was measured in an automated Envision plate reader (Perkin-Elmer). Luminescence data were normalized by $\log_{10}$ transformation. The percentage of inhibition was calculated using the following equation: 100*(negative control mean−sample result) over (negative control mean−positive control mean). All compounds showing >40% activity in the Group 3 neurosphere tumors in the primary screen were selected to confirm by dose-response. The dose-response assay was performed similarly to the primary screen, except that compounds were diluted 1:3 over 10 points (approximately 4 nM to 10 µM final concentration).

(iii) Data Analysis

High-throughput assay data was analyzed using Robust Interpretation of Screening Experiments (RISE) application written in Pipeline Pilot (Accelrys, v. 8.5) and the R program (R Development Core Team). Unless otherwise noted, dose-response curves were calculated from percent activity values and $\log_{10}$-transformed concentrations. Briefly, nonlinear regression was performed using the R drc package with the four-parameter log-logistic function (LL2.4) (Ritz and Streibig (2009) *Biometrics* 65(2): 609-617). The median value from triplicate experiments for each compound dilution fit three separate times by varying the parameters that were fixed during regression: (1) all parameters free, (2) high response fixed to 100, (3) low response fixed to 0. The best fit from these three nested models was selected using the anova.drc function. 95% confidence intervals were produced based upon this fit.

Curves were considered valid if they satisfied the following criteria: (a) calculated $EC_{50}$ was within the range of concentrations tested, (b) 50%<calculated efficacy<200%, and (c) −0.5<hill slope<8.

g. In Vivo Drug Tests

C57/B6 mice 6 to 8 weeks old were given 0.2 mL oral gavage with NVP-BEZ235 at 25 mg/kg or 0.5 mL intraperitoneal injections of either 120 mg/kg clotrimazole or 8 mg/kg α-mangostin with appropriate vehicle controls daily for 7 days beginning 2 days before infection. Mice were monitored for signs of infection and weight loss daily for 15 days (no significant difference by t-test). On days 0, 2, 4, 7, and 10, after 30 minutes of chamber equilibration time, respiratory parameters were monitored for 5-10 minutes using whole-body plethysmography (Buxco, Wilmington, N.C.). On day 4, a subset of mice was euthanized for arterial blood and lung collection for blood chemistry and complete blood count or titer. Lungs were homogenized and subjected to $TCID_{50}$ with hemagglutination titer readout with significance determined by t-test (p<0.003). Moribund mice were euthanized, and survival percentage differences were calculated with significance determined by Mantel-Cox log rank test (p<0.0001). All procedures were approved by the St. Jude Institutional Animal Care and Use Committee.

2. Influenza Induces Significant Changes in Cellular Metabolic Pathways

Two quantitative labeling strategies were used to determine proteomic changes after influenza virus infection. The mouse-adapted H1N1 influenza strain A/Puerto Rico/68/24 (PR8) was used to infect DCs at multiplicity of infection (MOI) 5 for 17 hours. After harvest, soluble and insoluble fractions were subjected to specialized trypsinization strategies to enhance coverage of proteins with complex tertiary structures (i.e., either filter-aided sample preparation (FASP) digestion for isobaric tags for relative and absolute quantitative (iTRAQ) labeling or several rounds of high-energy and high-pressure trypsinization followed by stable isotope labeling (SIL) (FIG. 1A). iTRAQ allowed four samples to be differentially labeled and mixed, eliminating technical variation between sample runs. Using iTRAQ, approximately 25,000 peptides were detected with corresponding reporter ions; of these 7,556 mapped to National Center for Biotechnology Information (NCBI) reference sequence accession numbers. Of these peptides, 70% had 2 or more peptide hits and were included in the following quantitative analysis: 72% of the proteome did not change while 28% responded to infection with ≥2-fold change in peptide abundance (Table 1). Most dynamic changes occurred in the insoluble fraction, with 654 proteins increasing after infection and 572 decreasing (Table 1).

Referring to FIG. 1A, control uninfected cells or PR8 infected BMDCs (MOI 5 pfu for 17 hours) were separated into soluble and insoluble fractions. The iTRAQ labeled samples were subjected to FASP digestion while the SIL samples received trypsin-catalyzed $^{18}O/^{16}O$ labeling. The samples were desalted with C18 SPE, processed with a custom RPLC system and analyzed with a Velos Orbitrap mass spectrometer or LTQ-Orbitrap for iTRAQ or SIL, respectively.

DCs and NHBE cells were infected for 17 hours with PR8 (MOI 5) or CA09 (MOI 1) respectively followed by lysis, homogenization, and fractionation by centrifugation (i.e., 15 minutes, 12,000 rpm at 4c). For iTRAQ, DCs were tryptically digested with a FASP Protein Digestion Kit, desalted (i.e., C18 solid-phase extraction), isobarically labeled, digested and processed according to the manufacturer's directions for iTRAQ 4-plex labeling. A separate set of DC samples (i.e., SIL) was processed with trypsin-catalyzed $^{18}$O labeling. Before fractionating by high-pH reverse-phase fractionation with concatenated pooling, samples were desalted by C18 SPE (SUPELCO). All samples were processed with a custom liquid chromatography system using reversed-phase C18 columns, then iTRAQ samples were analyzed with a Velos Orbitrap mass spectrometer and $^{18}$O-labeled samples were analyzed with an LTQ-Orbitrap mass spectrometer. Raw files were compared with a concatenated NCBI mouse or human databases using SEQUEST v.27 (rev. 12). The resulting sequence identifications were rescored and filtered to a 1% false discovery rate. For iTRAQ missing reporter ion channel results were excluded from analysis while SIL analysis accounted for both singly and doubly labeled species. Soluble and insoluble fractions were analyzed separately using DanteR software. The analysis of variance model included treatment and peptide effects. The remaining treatment effect and p-value were calculated using Student's Mest. Benjamin-Hochberg multiple-testing error correction was applied to the results of this hypothesis testing, and proteins with p<0.05 were considered significant.

Referring to Table 1, the isobaric tag reporter ion intensities were quantified using the MASIC tool with the exclusion of missing reporter ion channels or SIL ratio for each peptide pair was calculated accounting for singly or doubly labeled species in the $^{16}$O/$^{18}$O ratio and correcting for labeling efficiency. Then the MS/MS data was searched and filtered using 0.5% FDR, peptides passing the filter were quantified. Peptides with multiple hits were combined similar to microarray analysis with redundant gene identifiers combined.

TABLE 1

|  | Up | No Change | Down | Peptide Total |
|---|---|---|---|---|
| SIL Fraction | | | | |
| Insoluble | 263 | 1267 | 97 | 1627 |
| Soluble | 176 | 364 | 97 | 637 |
| Both | 20 | 136 | 2 | 306 |
| iTRAQ Fraction | | | | |
| Insoluble | 654 | 1811 | 572 | 3037 |
| Soluble | 65 | 1819 | 349 | 2233 |
| Both | 29 | 838 | 77 | 1821 |

To validate the iTRAQ results, the well-established SIL method ($^{16}$O/$^{18}$O labeling) was used, with the identical infection protocol. This technique identified more than 20,000 peptides, resulting in about 10,000 unique International Protein Index accession numbers and 2,000 protein identifications. As in the iTRAQ DC proteomes, the vast majority (73%) of DC peptides remained unaltered by PR8 infection, which induced about ≥2-fold abundance change in 27% of DC proteins (Table 1). Similar to the iTRAQ provided expanded coverage of the DC proteome, more than half of all peptides identified with SIL were also present in the iTRAQ data sets with similar trends (FIG. 1B).

Figure 1B:
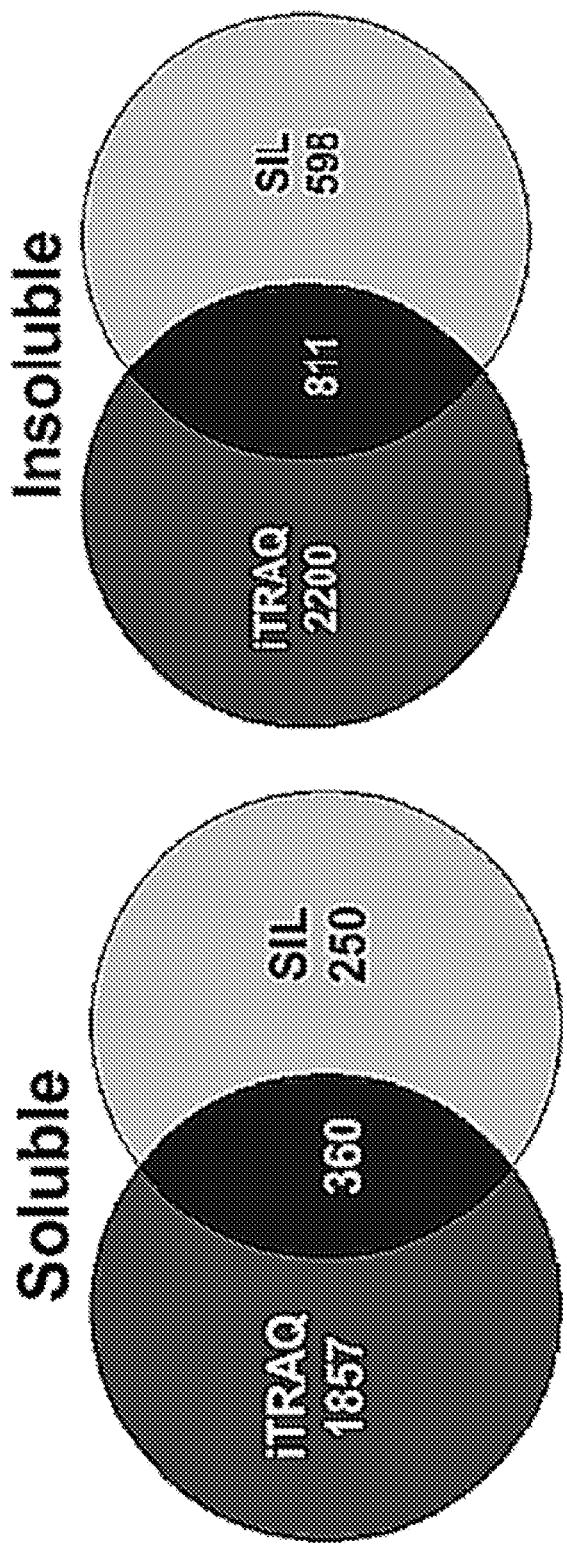

Referring to FIG. 1B, SEQUEST was used for searching against the NCBI *Mus musculus* database and results were refiltered down to 1% FDR, redundancies summed, normalized, and Log 2 transformed. DanteR(3) software suite was used to analyze the fractions and identify significant peptide changes and redundant identifiers were summed Overlap of the resulting peptides from the iTRAQ and SIL were then compared.

Figure 2A:
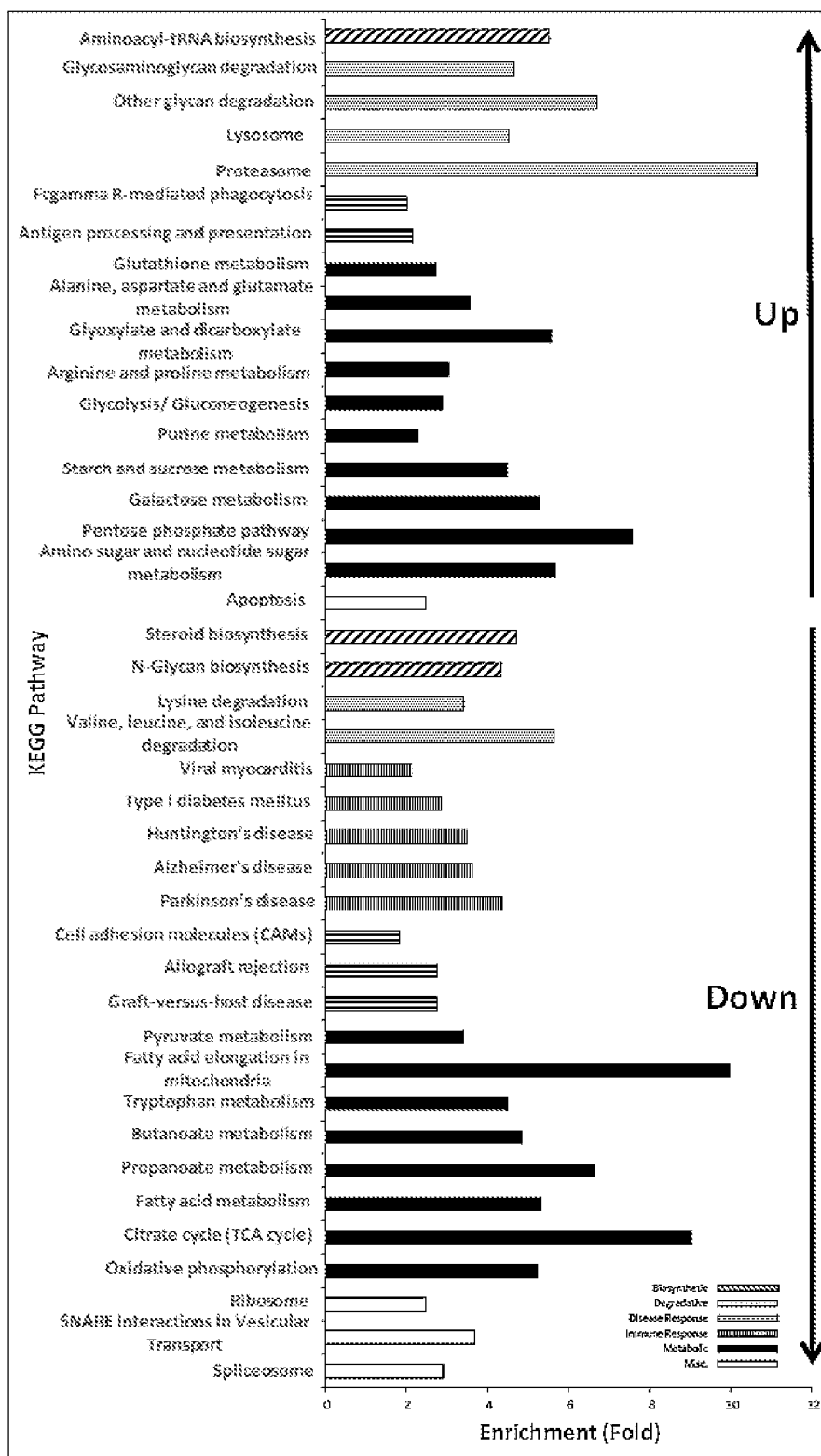
FIGS. 2A and 2B show representative data demonstrating that metabolic pathways dominate host cell changes after influenza virus infection.
Figure 2B:
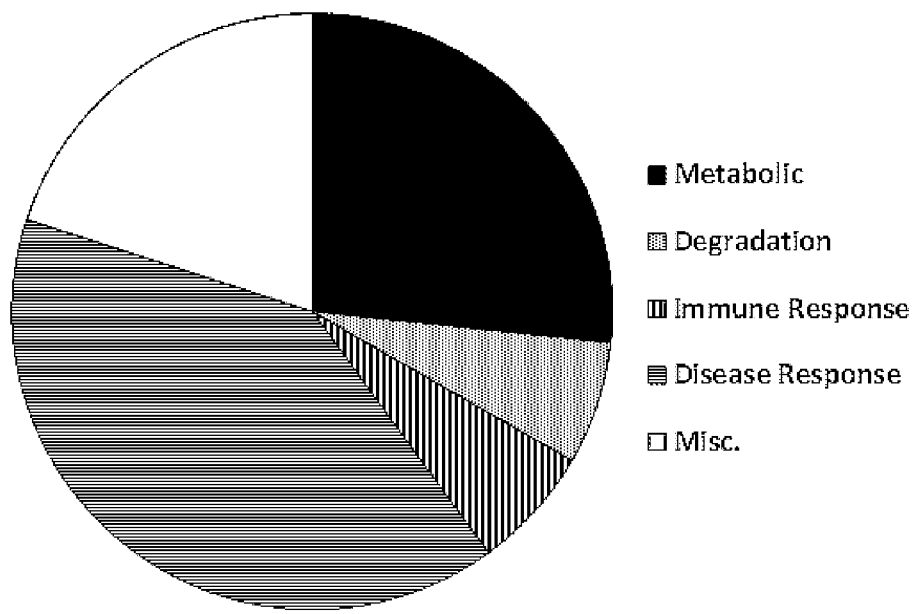

Next, bioinformatics tools were used to identify the major pathways regulated by influenza. Proteomic data were segregated into increasing and decreasing sectors of ≥2-fold change. The lists were submitted to the Database for Annotation, Visualization, and Integrated Discovery (DAVID) v6.7 and queried for enrichment groups (Dennis, G., Jr., et al. (2003) *Genome biology* 4: P3). In the iTRAQ data, biosynthesis, and metabolic pathways dominated the significantly enriched Kyoto Encyclopedia of Genes and Genomes (KEGG) pathways of both increased and decreased proteins, indicating coordinated responses to influenza for these processes (FIGS. 2A and 2B). Within the increased proteome, glycolysis and nucleotide sugar metabolism had high enrichment scores (p=7.3×10$^{-3}$ and 1.2×10$^{-5}$, respectively). In contrast, the decreased iTRAQ proteome contained proteins involved in the tricarboxylic acid cycle (TCA cycle), oxidative phosphorylation, and fatty acid metabolism with high enrichment values and statistical significance (i.e., p values of 8.4×10$^{-11}$, 5×10$^{-15}$, and 2.3×10$^{-7}$ respectively) (FIGS. 2A and 2B).

Referring to FIGS. 2A and 2B, all confidently identified peptides with 2 fold or greater abundance changes were input into DAVID for enrichment analysis with significantly enriched KEGG pathways indicated (i.e., p-value <0.01), grouped by similarity (i.e., biosynthetic, degradative, disease and immune response, metabolic, or miscellaneous) and enumerated by fold enrichment. Legend (2A) indicates subsets of biological processes by color and pie chart (2B) represents the average of both iTRAQ and SIL enrichment subsets.

Figure 3A:
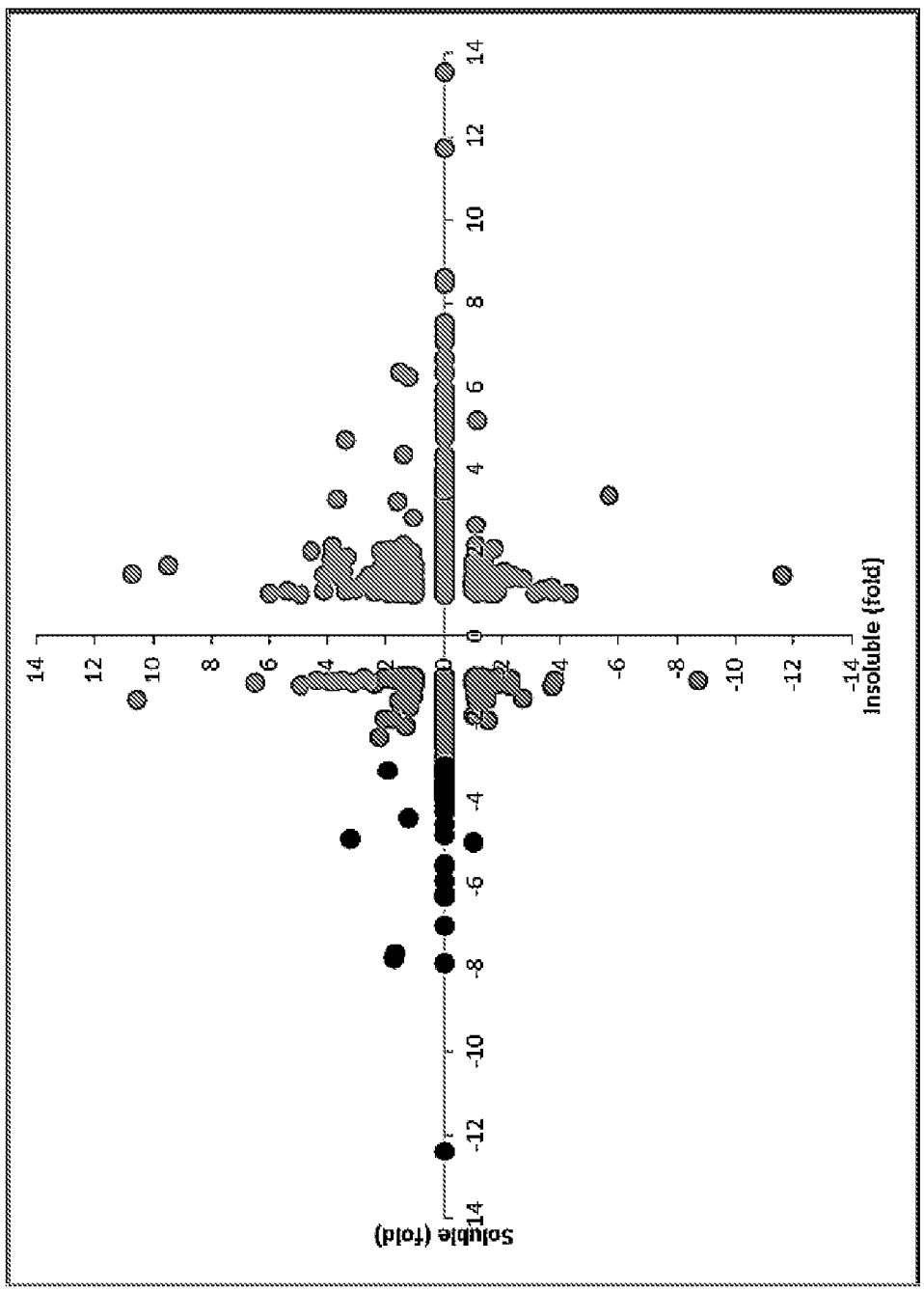
FIG. 3A-E show representative data pertaining to the proteomic analysis of influenza infected BMDCs. Specifically.
Figure 3B:
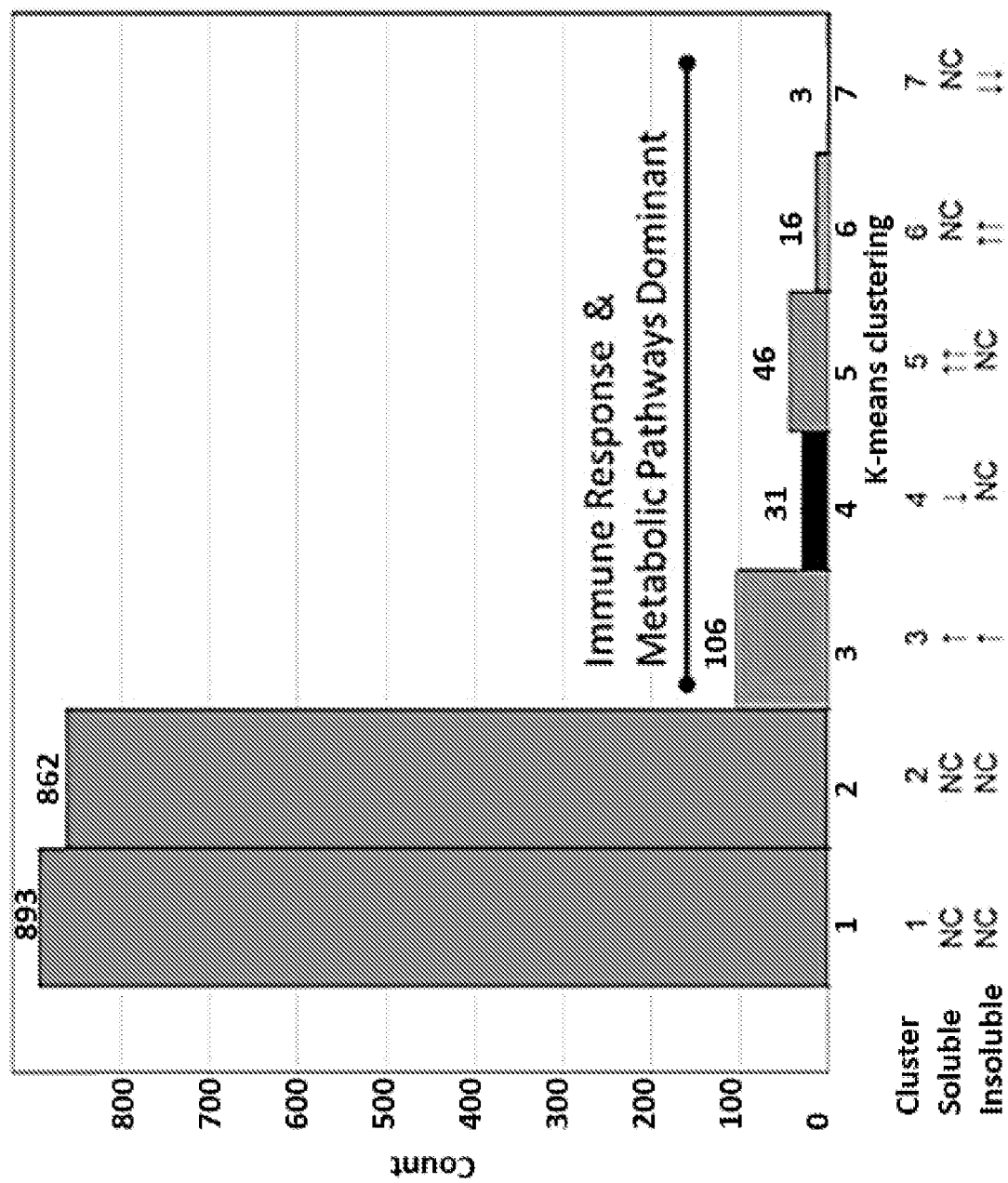

The same analysis applied to the independent SIL proteome produced similar results (FIGS. 2A and 2B). Again, metabolic, biosynthetic, and degradation pathways dominated the KEGG pathways among the increased and decreased protein groups, accounting for 61% of the total identified enriched clusters. Several of the same identical KEGG pathways were enriched in each proteome, including glycolysis (upregulated) and TCA cycle and pyruvate metabolism (downregulated). Thus, the SIL proteome validated the results of the iTRAQ analysis, indicating that host cell metabolism is dramatically altered after influenza infection. Consistent with this, when the entire SIL proteome was subjected to K means cluster analysis, immune response and metabolism dominated the clusters of similarly increasing or decreasing proteins (FIGS. 3A and 3B). Finally, the changes observed in the proteome were validated in cathepsin S, lysozyme, and α-enolase by activity assay, western blot, and/or immunofluorescence; all were consistent with the changes observed in the proteome (FIG. 3C-E).

Referring to FIG. 3A, soluble and insoluble bone marrow-derived DC peptide observations were grouped to the cluster with the nearest mean, colored by K means cluster, and graphed by fold change.

Referring to FIG. 3B, protein distribution for clusters with 3 or more proteins were graphed (i.e., Clusters 1-7). The clusters with the largest abundance changes (i.e., 3-7) were queried for enriched pathways using DAVID.

Figure 3C:
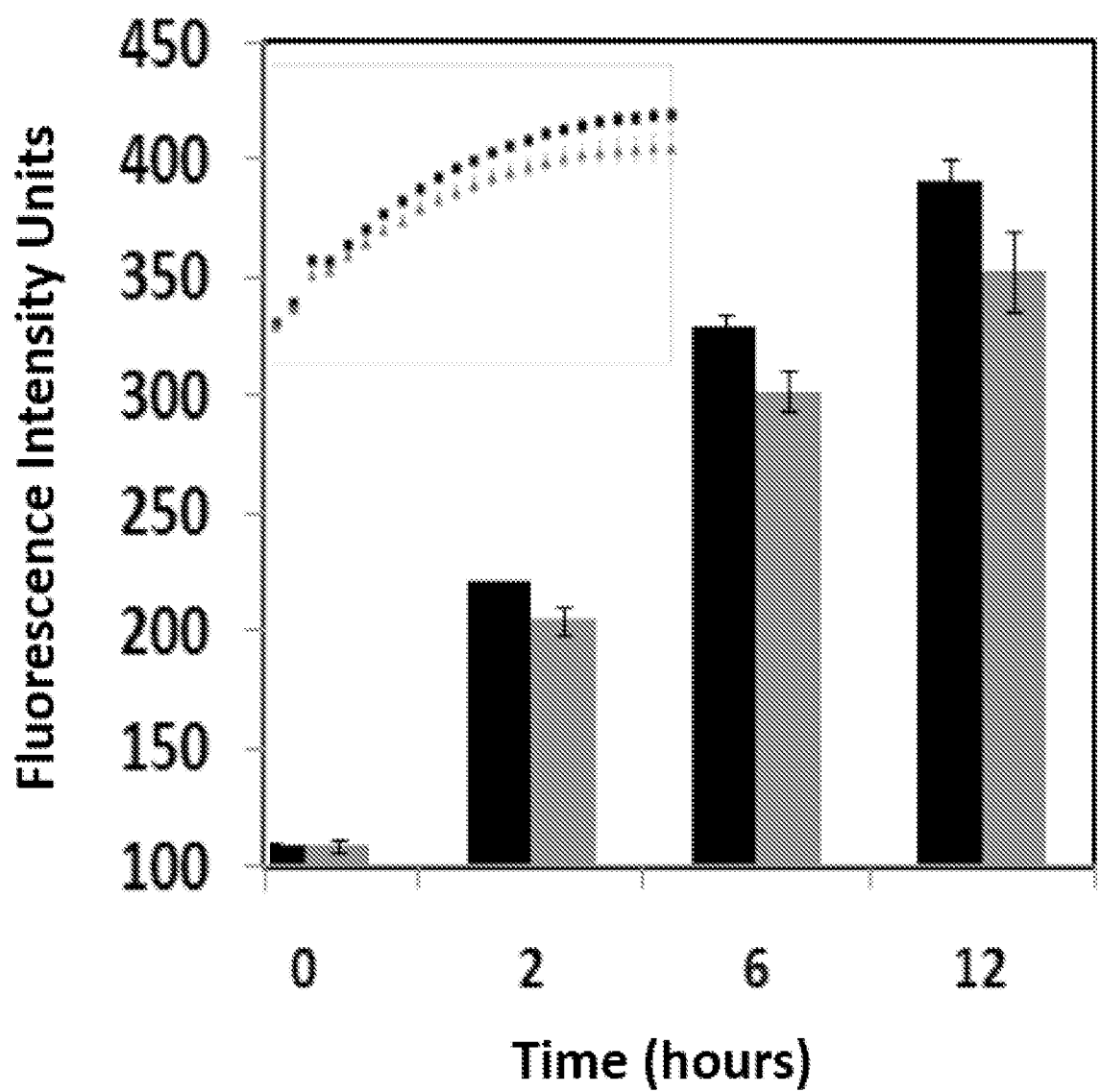
Figure 3C:
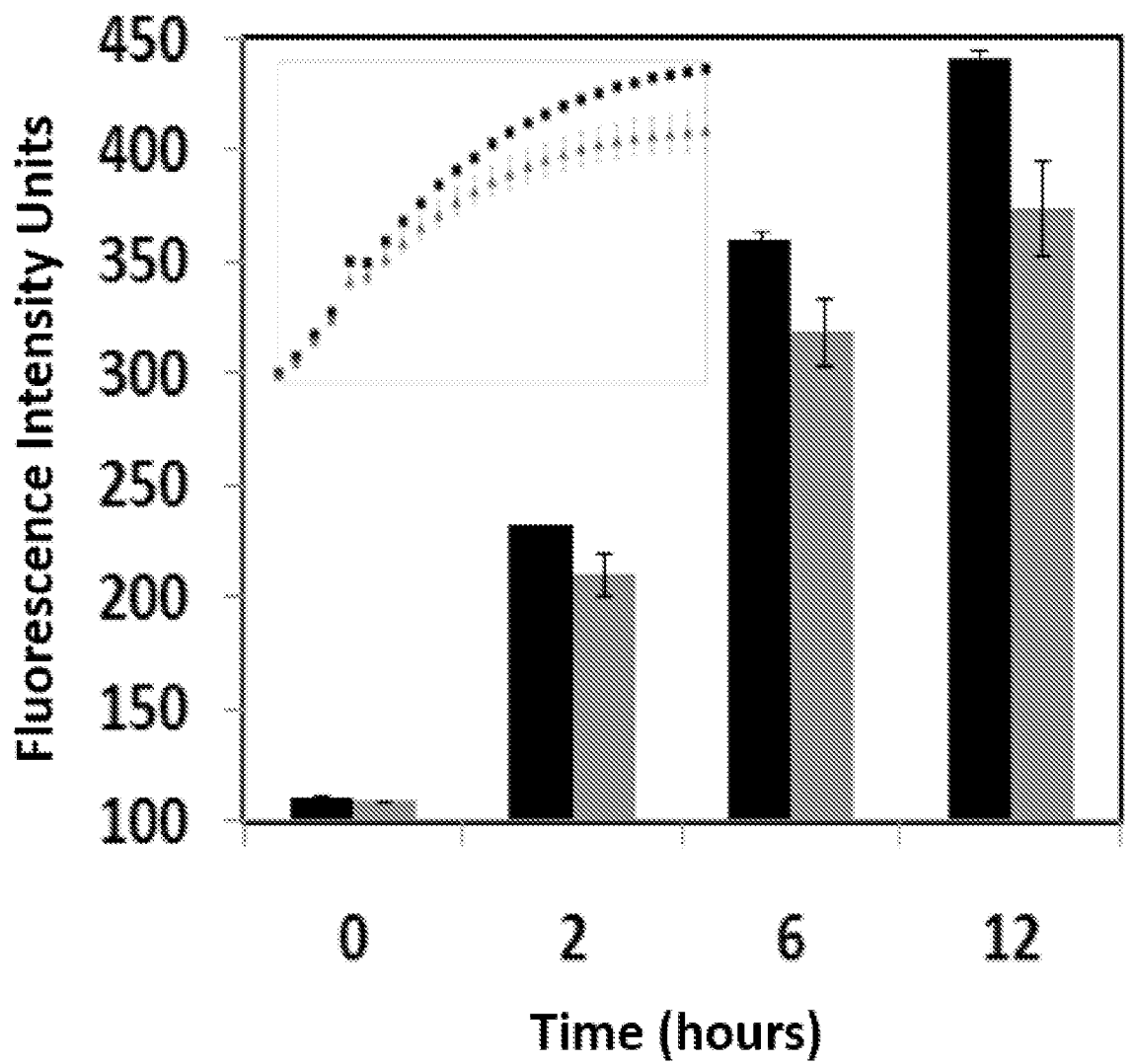
Figure 3D:
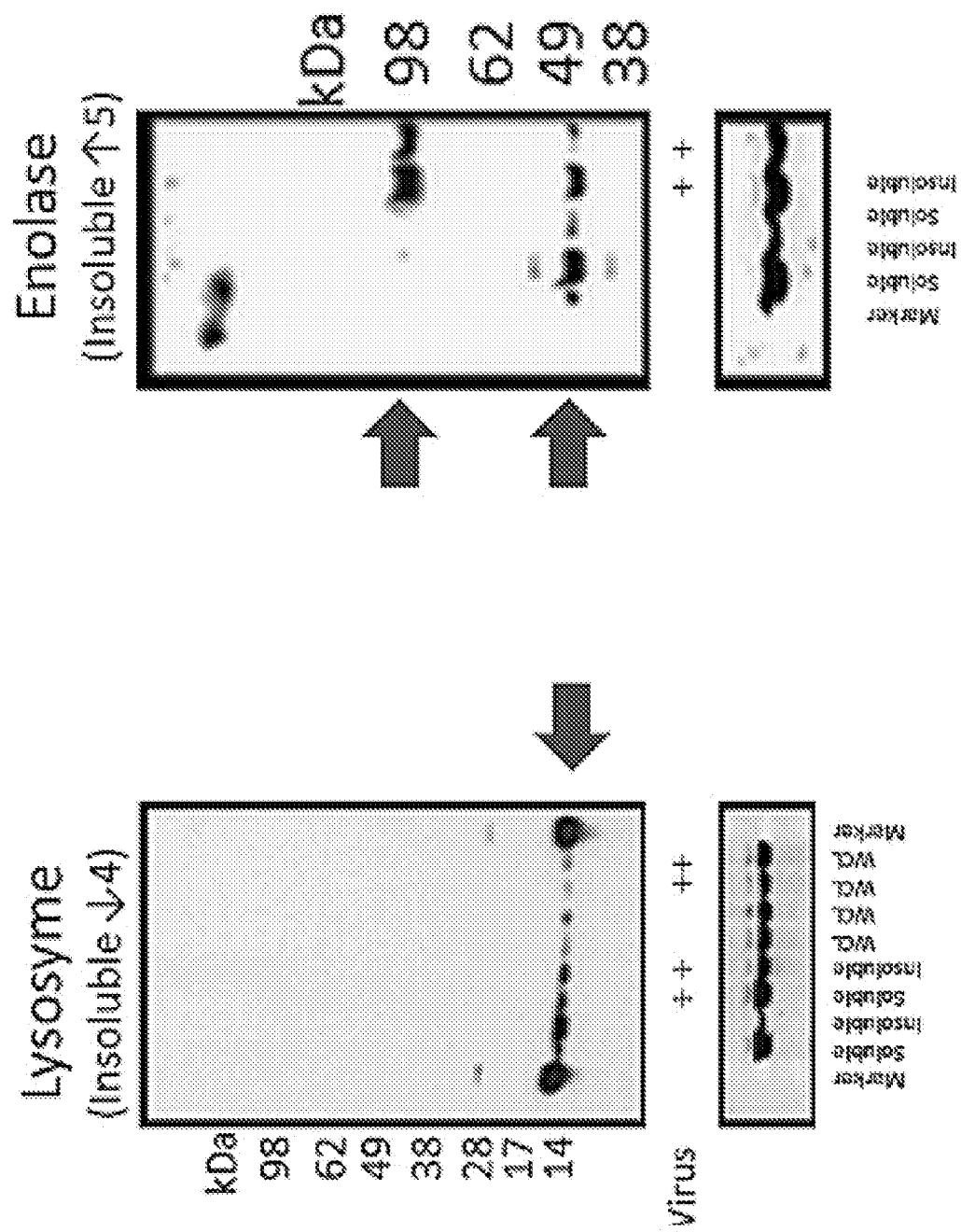
Figure 3E:
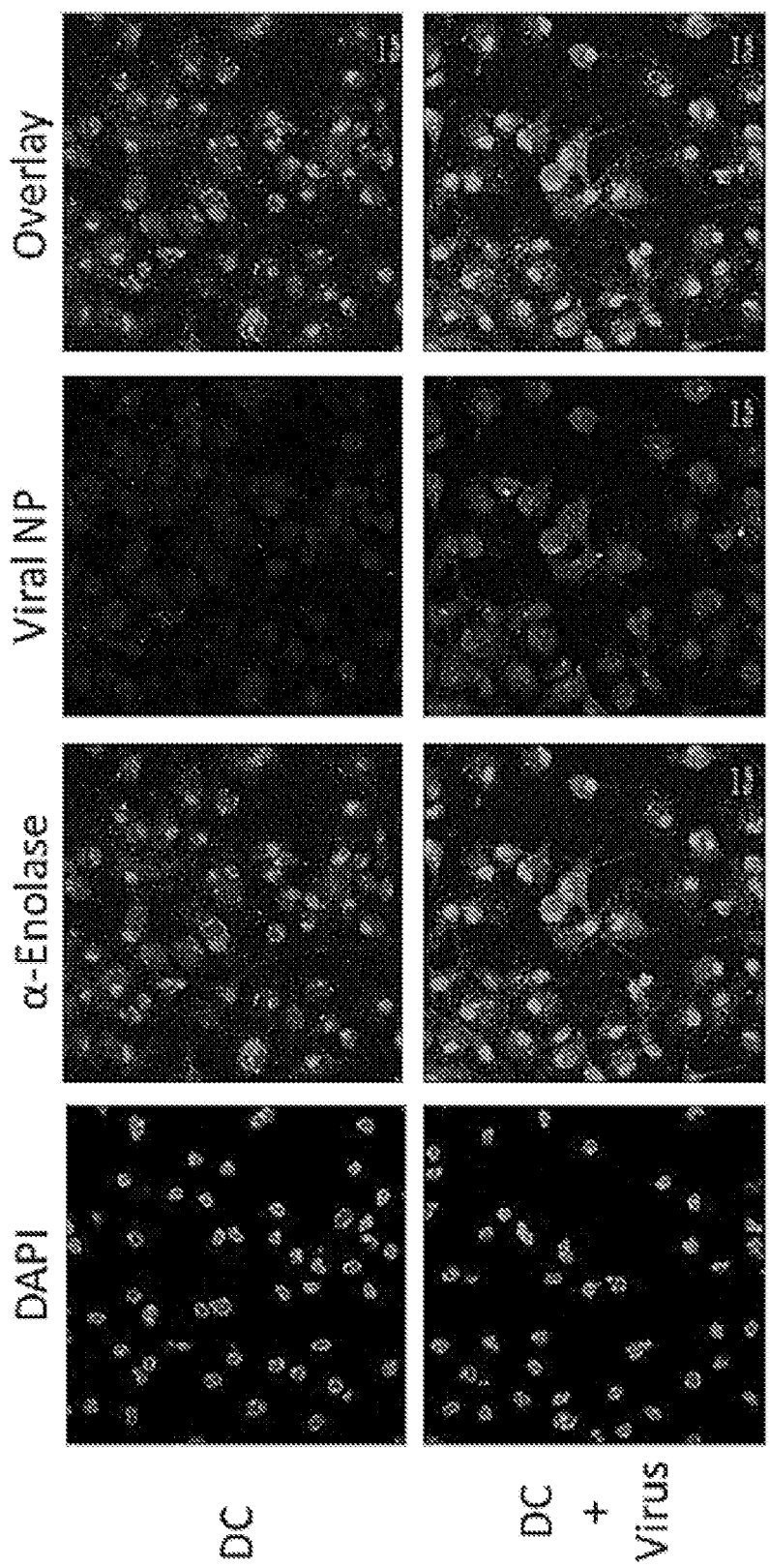

Referring to FIG. 3C, significant decrease (p-value <2.0× $10^{-8}$) in Cathepsin S activity was validated using 10 μM of a specific substrate (i.e., Ac-KQKLR-AMC) that releases a fluorescent product quantifiable at excitation and emission wavelengths of 354 and 442 nm.

Referring to FIG. 3D, dendritic cells +/− infection for 17 hours were either homogenized as whole cell lysates or separated into soluble and insoluble fractions and 15 ng per sample was immunoblotted for the presence of lysozyme or α-enolase.

Referring to FIG. 3E, immunostaining of BMDC +/− PR8 (i.e., MOI 5 for 17 hours) for α-enolase or influenza virus nucleoprotein (NP) was visualized with 60× magnification using LSM META Laser Scanning Ziess Microscope.

To obtain an overview of the metabolic changes indicated from the enrichment analysis, DC proteomes were mapped to the KEGG metabolic atlas. This atlas combines all known KEGG metabolic pathways and proteins into an integrated schematic. Mapping the increased proteome (i.e., ≥2-fold) showed coordinated up regulation in glycolysis, nucleotide synthesis, the first oxidative phase of the TCA cycle, and lipid synthesis with a concomitant break in the link between glycolysis and the TCA cycle. In contrast, mapping proteins that decreased revealed downregulation of lipid oxidation, the urea cycle, and the second oxidative phase of the TCA cycle.

3. Influenza Reprograms DC Metabolism

Due to the increase in α-enolase and the enrichment of glycolysis in the increased pathway analysis, a closer examination of this pathway was explored. Using DAVID to select proteins involved in glycolysis, for which complete coverage was obtained, PPI spider, a tool to determine global protein-protein interaction networks, was used to capture proteins and transcription factors relevant to glycolysis. The DC SIL proteome was mapped to this glycolysis protein network and Cytoscape, an open-source platform for complex network analysis, was used to integrate the absolute changes in protein abundance in the proteome within the glycolysis network (FIG. 4A).

Figure 4A:
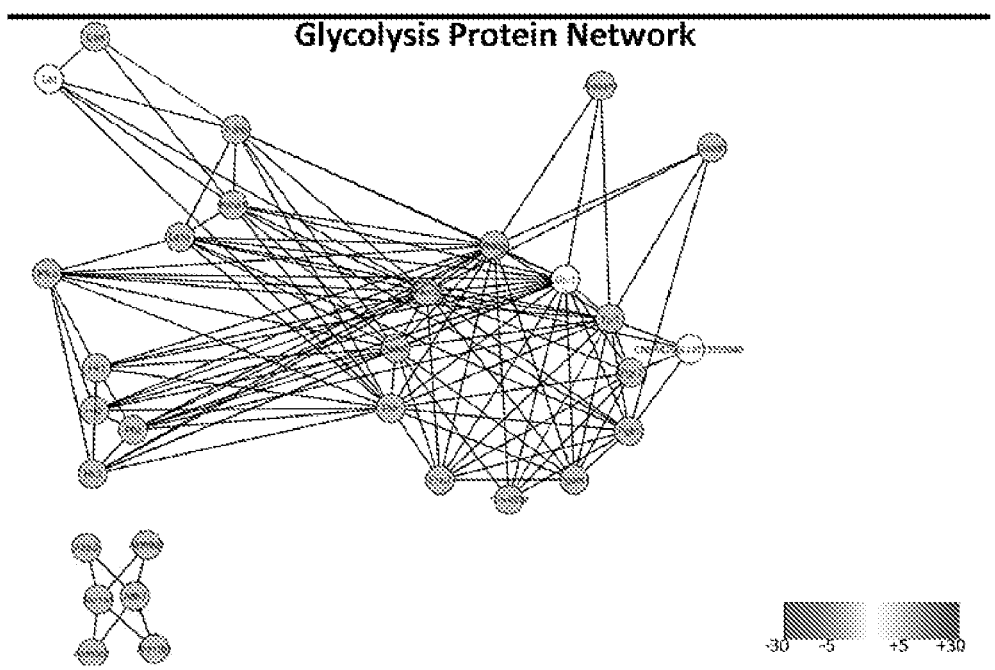
FIG. 4A-J show representative data demonstrating that active viral replication alters metabolite utilization and flux in vitro. Specifically.

Referring to FIG. 4A, DAVID was used to select the glycolysis network from the bone marrow-derived DC (BMDC) proteome, and interactions were identified using MEDUSA and PPI spider with the entire interaction network and then put into Cytoscape with the quantitative data.

Figure 4C:
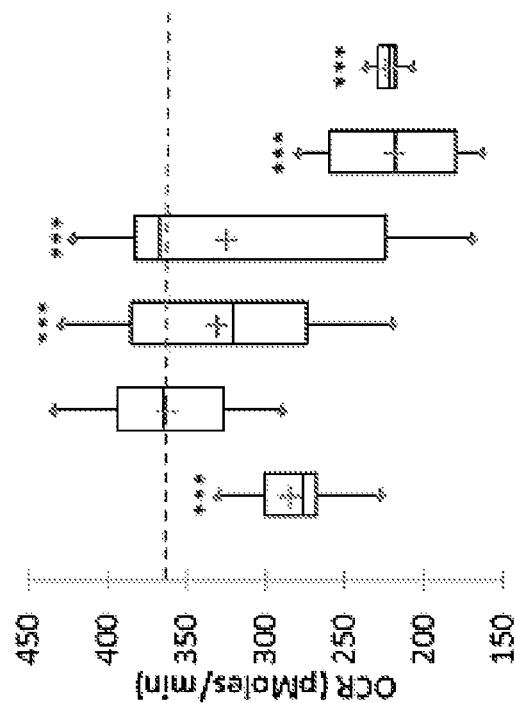
Figure 4B:
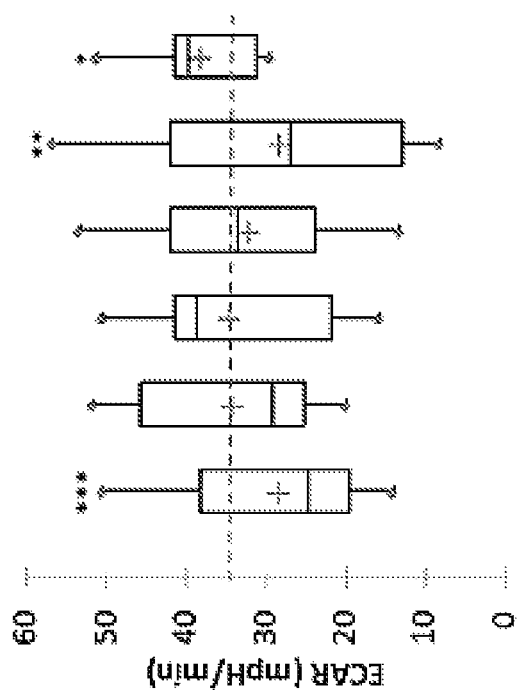
Figure 4D:
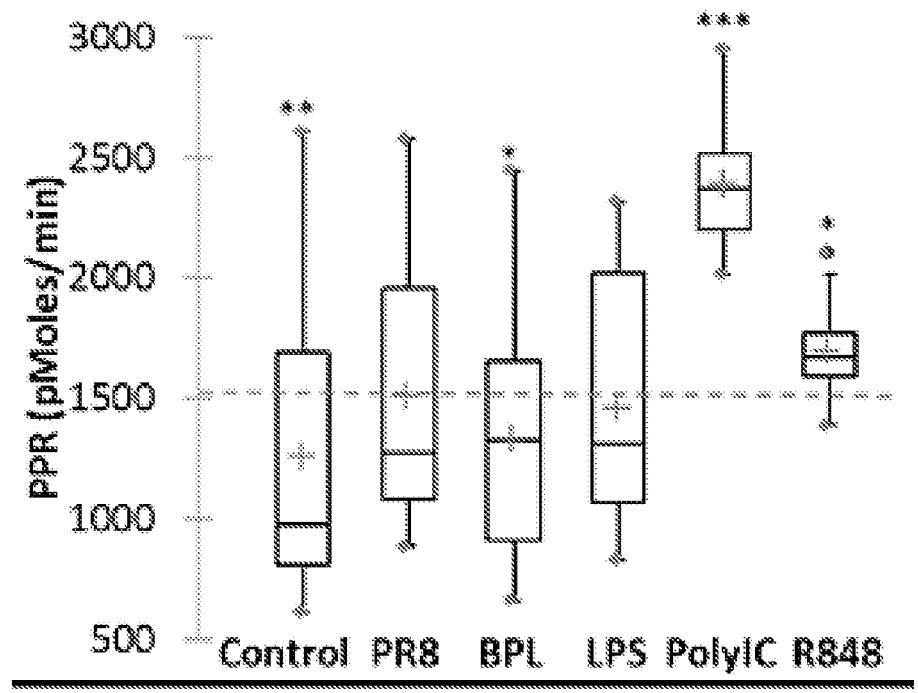

Next, whether changes in metabolic protein networks in the proteomic analysis were reflected in functional metabolic assays was determined. Substrate consumption for ATP production and product efflux vary with cellular metabolism and can be used as proxies to assess metabolic states. Increased extracellular acidification rates (ECAR) of virus-infected DCs (i.e., PR8) were found, indicative of more lactate production via glycolysis over uninfected controls (FIG. 4B). The $O_2$ consumption rate (OCR) and proton production rate (PPR) were also measured, both of which increased with infection (FIGS. 4C and 4D). Without wishing to be bound by theory, the high OCR combined with the high ECAR of infected DCs may indicate aerobic glycolysis. This may also reflect some $O_2$ consumption from the generation of an oxidative burst, a hallmark response to pathogens in innate immune cells.

Figure 4E:
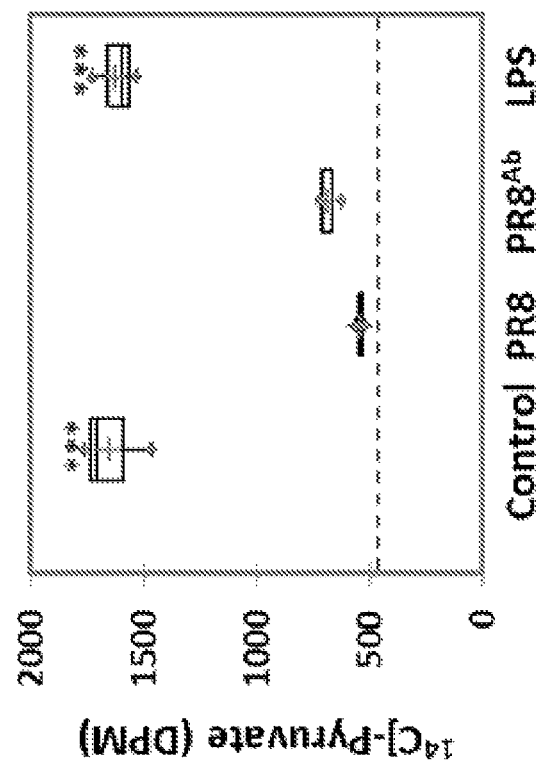
Figure 4F:
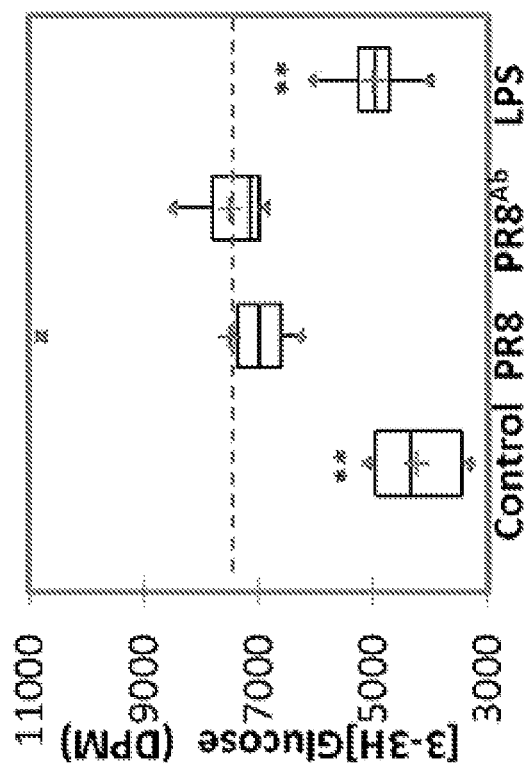
Figure 4H:
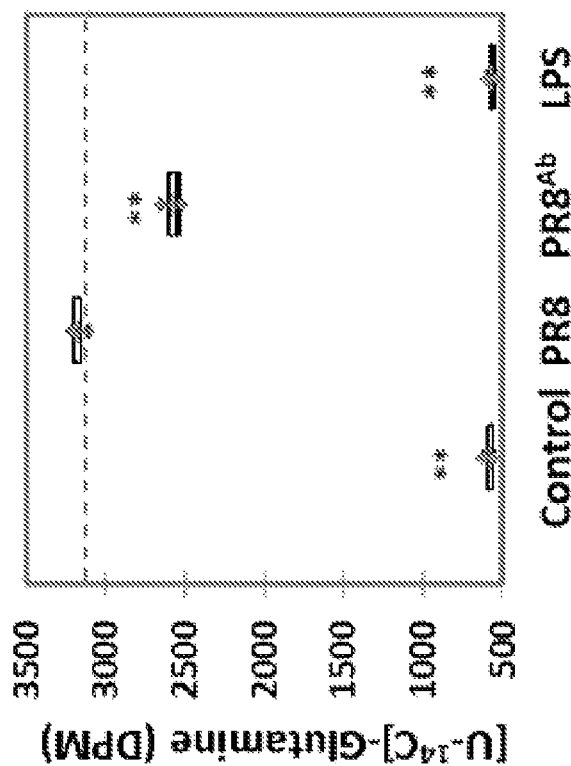
Figure 4G:
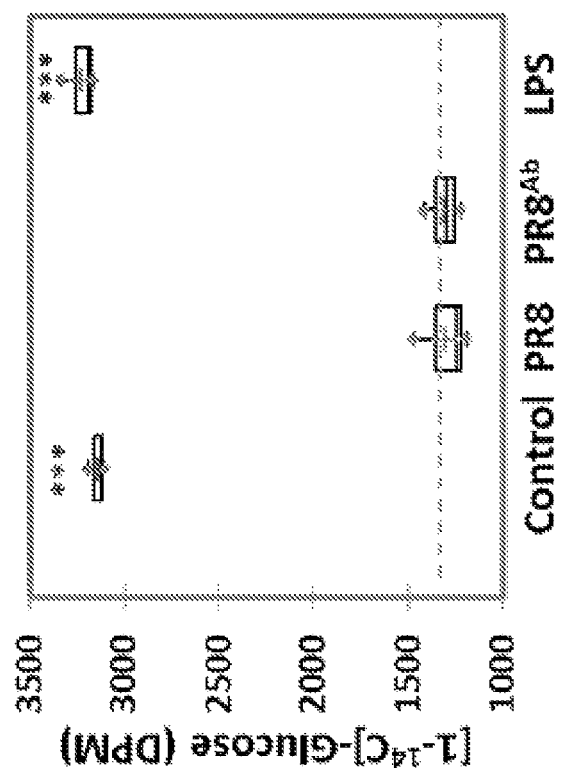

To validate the proteomic and metabolic flux measures and further characterize influenza-induced metabolism, substrate utilization after infection was followed using radio-isotopically labeled metabolites in pulse chase experiments. Isotopically labeled metabolic substrates were used to monitor generation of $^3H_2O$ or $^{14}CO_2$ from glycolysis and fatty acid β-oxidation or from the TCA cycle, pentose phosphate pathway, and glutaminolysis, respectively. Glucose detritiation occurs early in glycolysis as water is produced when phosphofructokinase-1 converts fructose-6-phosphate to fructose-1,6-phosphate. Consistent with the flux analysis, influenza infection significantly increased glucose consumption in glycolysis ([3-$^3H$]glucose detritiaton) (FIG. 4E). Remarkably, while the glycolytic rate doubled after infection, pyruvate consumption in the TCA cycle was reduced by one third (FIG. 4F). This assay captured the aggregate release of $^{14}CO_2$ from [2-$^{14}C$]pyruvate in 3 steps of the TCA cycle. Together, the increase in glycolysis and decrease in TCA cycle utilization is reminiscent of the Warburg effect in some cancers, in which the 2 major metabolic pathways become uncoupled (FIGS. 4E and 4F).

One alternative to glucose oxidation by glycolysis is the pentose phosphate pathway, which is primarily for synthesis of nucleotides and reducing equivalents (e.g., NADPH). A standard method for assessing this pathway is to analyze $CO_2$ release from [1-$^{14}C$]glucose (Katz, J. and Wood, H. G. (1963) *J. Biol. Chem.* 238: 517-523). Using this approach, $CO_2$ release from [1-$^{14}C$]glucose was found to decrease after infection, indicative of diminished glucose entry into the pentose phosphate pathway (FIG. 2G). Given its reduced utilization in the pentose phosphate pathway some [1-$^{14}C$] glucose may have leaked downstream into the TCA cycle. However, without wishing to be bound by theory, considering $^{14}CO_2$ release from both [1-$^{14}C$]glucose and [2-$^{14}C$] pyruvate significantly decreased (i.e., 2- and 3-fold, respectively), it is hypothesized that both pentose phosphate pathway and TCA cycle may decline.

Figures 4I, 4J:
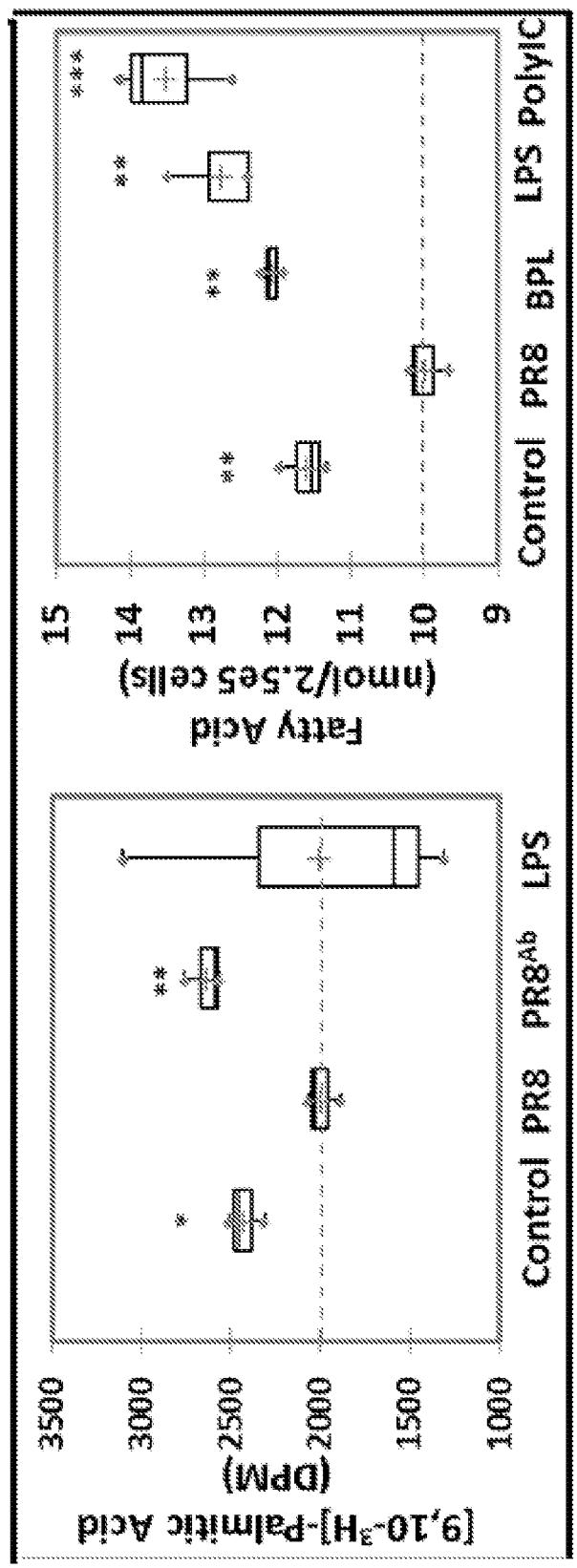

Fatty acid β-oxidation is a catabolic mechanism to feed acetyl CoA into the TCA cycle. Impaired fatty acid β-oxidation after infection in vitro and in humans has been well documented and is implicated in influenza-associated encephalopathy (Murphy, M. G., et al. (1997) *Biochimica et biophysica acta* 1361: 103-113; Trauner, D. A., et al. (1988) *Neurology* 38: 239-241; Yao, D., et al. (2007) *Molecular and cellular biochemistry* 299: 85-92). In DCs, a significant drop in β-oxidation was observed after infection, measured by detritiation of [9,10-$^3H$]palmitic acid (FIG. 4I). This is consistent with reduced need for acetyl CoA, the product of 3-oxidation, which is fed into the TCA cycle. Without wishing to be bound by theory, these findings suggest a host cell metabolic program after infection shifting away from glucose and β-oxidation for energy production and toward carbon commitment for macromolecule synthesis.

Glutamine plays a key role in many macromolecular synthetic pathways. Glutamine use is critical to lymphocyte metabolism and is essential for the immune response (Newsholme, et al. (1985) *Q J Exp Physiol* 70 (4): 473-489). With influenza infection, a 6-fold increase in glutamine oxidation was found by measuring $^{14}CO_2$ release from U-$^{14}C$-glutamine (FIG. 2H). The Warburg phenotype features aerobic metabolism with the same increase in glucose and glutamine consumption and decoupling of the TCA cycle seen in influenza. However, to meet the nucleotide needs of rapidly dividing cancer cells, pentose phosphate pathways also increase. In contrast to proliferating cancer cells, influenza virions need very little nucleotide biomass (i.e., 0.7-1% RNA, 20-30% lipid, and 70-80% protein). Thus, without wishing to be bound by theory, the overall metabolic reprogramming appears directed toward the biomass requirements of viral replication.

4. Influenza Virus-Induced Metabolic Reprogramming is Distinct from TLR Activation and Requires Active Virus The metabolite flux analysis was repeated with TLR agonists to determine if the coordinated metabolic reprogramming of DCs was a result of viral infection or a response to innate immune activation. Metabolite flux in viral infection was compared with stimulation through TLR3, 4, or 7/8 by polyinosinic polycytidylic acid (PolyIC), lipopolysaccharide (LPS), or agonist R848, respectively (FIG. 4B-D). While LPS treatment resulted in metabolic changes that were distinct from untreated controls, viral infection was significantly different from LPS in $O_2$ consumption and all metabolic pulse chase assays except fatty acid oxidation (FIGS. 4C and 4E-J). In the radiolabeled metabolic substrate assays, LPS treatment led to a slight increase in glycolysis, though significantly lower than viral infection, and had little effect on other substrate use measures (FIG. 4E-H).

Referring to FIG. 4B-J, BMDCs were left untreated (control), infected with PR8 for 17 hours at MOI 5 under 3 conditions with viable virus, with β-propiolactone-inactivated virus, or preblocked with α-enolase antibodies and then infected (PR8, BPL, or PR8$^{Ab}$, respectively) or stimulated with TLR agonists lipopolysaccharide, polyinosinic polycytidylic acid, or Resiquimod (LPS, PolyIC, or R848, respectively). After treatment, the extracellular acidification rate (ECAR) (5B), oxygen consumption rate (OCR) (5C), and proton production rate (PPR) (5D) of BMDCs were monitored for 2 hours. Use of isotopically labeled substrates, as indicated on they axis, were used to monitor the generation of traceable products ($^3H_2O$ or $^{14}CO_2$) two hours after BMDC treatments substrates were quenched and allowed to accumulate overnight. Substrates were indicative of the following metabolic pathways: [3-$^3$H]glucose (glycolysis) (5E), [2-$^{14}$C]pyruvate (TCA cycle) (5F), [1-$^{14}$C]glucose (pentose phosphate pathway) (5G), [U-$^{14}$C]glutamine (glutaminolysis) (5H), and [9,10-$^3$H]palmitic acid (fatty acid oxidation) (5I). Referring to FIG. 4J, the concentration of fatty acids (>C8) in BMDCs was determined by a coupled enzyme assay releasing fluorometric product proportional to the fatty acids present and quantifiable with standards after treatments. Error bars represent standard deviation from the mean of triplicate samples, where data represent 2-4 independent experiments.

PolyIC is structurally similar to double-stranded RNA in some viruses and stimulates TLR3. It resulted in extreme drops in all metabolites measured in flux assays, clearly distinct from viral infection (FIGS. 4B-D and 4J). Interestingly, TLR7/8 agonist R848, an imidazoqionoline compound with potent anti-viral activity, resulted in significantly more ECAR and PPR and a lower OCR than viral infection (FIG. 4B-D). Since the influenza virus-induced metabolic program appeared distinct from innate immune activation by single ligands, whether these metabolic changes required viral replicated or were an aggregate response to the virion were investigated. B-Propiolactone (BPL) is commonly used to crosslink viral RNA inactivating influenza or vaccination by preventing active replication (Jonges, M., et al. (2010) *Journal of clinical microbiology* 48: 928-940). Thus, BPL-treated virus was used to distinguish between cell-mediated responses to viral entry and innate recognition and metabolic reprogramming to meet the biomass needs of viral replication. BPL-inactivated virus (BPL) induced an increase in ECAR similar to that of the active virus (FIG. 4B). However, BPL induced much lower OCR and PPR compared to replicating virus (FIGS. 4C and 4D). Importantly, BPL induced significantly more free long-chain fatty acid accumulation than the replicating virus (FIG. 4J). This is consistent with a significant investment by cellular metabolism in fatty acids directed toward membrane generation for new virus.

In keeping with the metabolite flux analysis, decoupling of glycolysis was found in the proteome and the TCA cycle was observed with downregulation of pyruvate dehydrogenase, which converts pyruvate to acetyl CoA by pyruvate decarboxylation. While the disparity between increased glycolysis, pyruvate dehydrogenase downregulation, and the truncated TCA cycle was once thought to be a mitochondria defect, it has recently been postulated to produce a more robust and flexible metabolic program (Filipp, F. V., et al. (2012) *Pigment cell & melanoma research* 25: 732-739). A possible protein underpinning these concerted metabolic changes is c-Myc, a transcription factor instrumental in similar metabolic patterns in cancer (Dang, C. V. (1999) *Mol. Cell Biol.* 19: 1-11). Indeed, when probed, infected DCs showed a marked increase in this master regulator (FIG. 5).

Figure 5:
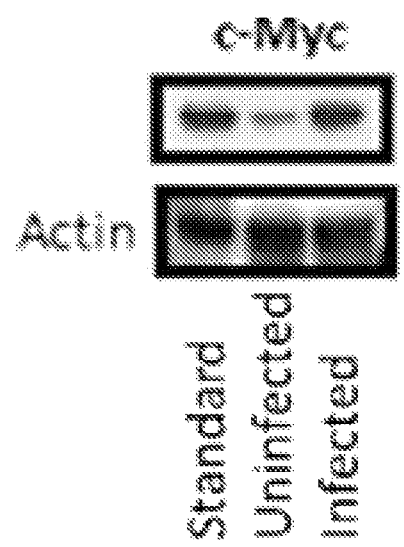
FIG. 5 shows representative data pertaining to the expression of c-Myc in infected DCs.

Referring to FIG. 5, 15 μg of DC whole cell lysate (i.e., infected and uninfected) was separated with SDS PAGE, transferred to nitrocellulose and immunoblot probed for the presence of cMyc in the presence of a cMyc loading standard.

5. Influenza Virus Reprograms Human Respiratory Cell Metabolism

Mice are not a natural host for influenza virus, and therefore to determine if this influenza virus-induced metabolic shift was specific to DCs, primary normal human bronchial epithelial (NHBE) cells were used. The metabolic response from 2 healthy young male donors was assessed. This required a switch to a more relevant human virus, the H1N1 strain A/CA/04/2009 representative of the 2009 pandemic (CA09). When infected with CA09, NHBE cells responded similarly to the mouse DCs, with proteomic changes dominated by immune response and metabolism.

Figure 6A:
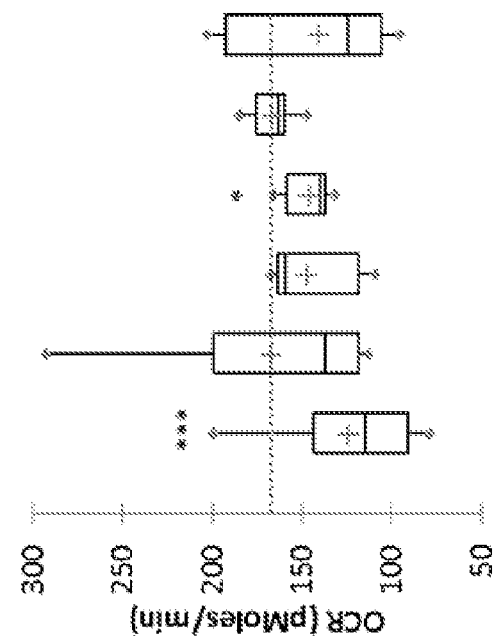
FIG. 6A-D show representative data pertaining to the metabolic changes that occur in primary human epithelial cells after influenza infection. Specifically, several functional assays were performed including measuring the ECAR of virus-infected normal human bronchial epithelial (NHBE) cells (6A), the OCR (6B), and the PPR (6C).

To understand changes in energy metabolism in human primary cells as a result of influenza virus, with cell number restrictions limiting the ability to perform radiologic tracking experiments, the use of many substrates was monitored simultaneously to give a balanced view of energy changes. Thus, the Biolog metabolic array was used to monitor changes in use of more than 80 substrates, some of which are not used by human cells (e.g., plant and bacteria metabolites) (Table 2). Indeed, many of the substrates were not metabolized regardless of infection (Table 3 cluster 5 and FIG. 6A). However, organizing substrate data by K means clusters revealed different patterns in the use of some substrates after infection (FIG. 6A). In keeping with the increased glycolytic rate of influenza virus-infected DCs, glucose use increased dramatically in NHBE cells after infection (Table 3 and FIG. 6A). Similar to DCs, entry into the TCA cycle was impaired such that pyruvic acid metabolism decreased after NHBE cell infection (Table 3). The heat map of metabolite use kinetics highlighted highly orchestrated metabolic changes in response to infection that were distinct from the untreated metabolic profile (Table 2).

Referring to Table 2, NHBE cells were seeded in 96-well plates coated with individual metabolites (Biolog PMM2) with metabolite-restricted medium and allowed to rest for 24 hours followed by CA09 infection for 17 hours at MOI 1. Substrate use led to a quantifiable colorimetric change by the reduction of tetrazolium to formazan, characterized by maximal absorbance at 590 nm, which was monitored hourly and plotted in a heat map with increasing values in green. Use kinetics of each substrate were K means clustered to identify similarly behaving groups and cluster metabolic pathway enrichment.

Referring to Table 3, NHBE cells were seeded in 96-well plates coated with individual metabolites (Biolog PMM2)

with metabolite-restricted medium and allowed to rest for 24 hours followed by CA09 infection for 17 hours at MOI 1. Substrate use led to a quantifiable colorimetric change by the reduction of tetrazolium to formazan, characterized by maximal absorbance at 590 nm, which was monitored hourly and plotted in a heat map with increasing values in green. Use kinetics of each substrate were K-means clustered to identify similarly behaving groups and cluster metabolic pathway enrichment. 590 nm absorbance readings were normalized to zero hour hourly according to the manufacturer's suggestion. Statistical significance was determined with an f-test, and p-values were as indicated. Substrates are organized by K-means clusters, as in Table 2, with each metabolic substrate and pathway indicated.

TABLE 2

| Metabolite | 0 hr | 1 hr | 2 hr | 3 hr | 4 hr | 5 hr | 6 hr | 7 hr | 8 hr | 9 hr | 10 hr | 11 hr | K-Means Cluster |
|---|---|---|---|---|---|---|---|---|---|---|---|---|---|
| Control | | | | | | | | | | | | | |
| D-(+)-Glucose | 1.00 | 1.12 | 1.19 | 1.21 | 1.13 | 1.56 | 0.67 | 1.43 | 1.37 | 1.59 | 1.64 | 1.74 | 9 |
| D-(+)-Glucose | 1.00 | 1.51 | 1.74 | 1.86 | 2.09 | 2.68 | 1.68 | 2.70 | 2.95 | 3.08 | 3.38 | 3.79 | |
| Maltose | 1.00 | 1.07 | 1.04 | 1.27 | 1.22 | 1.53 | 1.72 | 1.53 | 1.68 | 1.97 | 1.93 | 2.37 | 4 |
| D-Glucose-6-Phosphate | 1.00 | 1.14 | 1.18 | 3.24 | 1.30 | 1.48 | 0.74 | 2.93 | 1.28 | 1.38 | 2.69 | 1.87 | |
| D-Glucose-1-Phosphate | 1.00 | 1.01 | 1.31 | 1.24 | 1.16 | 1.12 | 0.33 | 1.10 | 1.03 | 1.09 | 1.06 | 0.93 | |
| b-Methyl-D-Glucoside | 1.00 | 1.32 | 1.80 | 1.84 | 2.02 | 2.32 | 1.04 | 2.85 | 3.05 | 3.33 | 3.70 | 4.24 | |
| D,L-a-Glycerol Phosphate | 1.00 | 0.34 | 0.48 | 0.56 | 0.60 | 0.70 | 0.71 | 0.79 | 0.83 | 0.91 | 0.91 | 1.05 | |
| Glycerol | 1.00 | 1.36 | 1.42 | 1.19 | 1.18 | 1.27 | 0.68 | 1.06 | 1.04 | 1.08 | 1.04 | 1.04 | |
| Xylitol | 1.00 | 1.02 | 1.53 | 1.57 | 1.01 | 1.51 | 0.40 | 1.01 | 1.49 | 1.02 | 0.97 | 0.97 | |
| N-Acetyl-D-Glucosamine | 1.00 | 0.19 | 0.27 | 0.32 | 0.34 | 0.40 | 0.32 | 0.46 | 0.48 | 0.50 | 0.45 | 0.44 | |
| a-Methyl-D-Glucoside | 1.00 | 1.18 | 1.07 | 1.02 | 0.58 | 0.76 | 0.90 | 0.68 | 0.74 | 0.79 | 0.83 | 0.93 | 2 |
| Salicin | 1.00 | 1.17 | 0.93 | 0.96 | 0.83 | 0.78 | 0.43 | 0.69 | 0.67 | 0.66 | 0.62 | 0.62 | |
| D-Glucosaminic Acid | 1.00 | 0.86 | 0.94 | 0.90 | 1.21 | 1.22 | 0.36 | 0.95 | 0.97 | 0.98 | 0.97 | 0.39 | |
| Butyric Acid | 1.00 | 0.95 | 0.15 | 0.14 | 0.15 | 0.16 | 0.05 | 0.15 | 0.15 | 0.16 | 0.16 | 0.17 | |
| D-Glucuronic Acid | 1.00 | 1.13 | 1.37 | 1.29 | 1.42 | 1.57 | 0.86 | 1.71 | 1.83 | 1.90 | 2.04 | 2.34 | |
| N-Acetyl-D-Mannosamine | 1.00 | 0.90 | 0.77 | 0.71 | 0.68 | 0.68 | 0.65 | 0.61 | 0.63 | 0.58 | 0.67 | 0.66 | |
| Lactitol | 1.00 | 0.19 | 0.26 | 0.31 | 0.33 | 0.39 | 0.40 | 0.44 | 0.47 | 0.50 | 0.55 | 0.62 | |
| Melibionic Acid | 1.00 | 0.20 | 0.76 | 0.58 | 0.66 | 0.48 | 0.40 | 0.47 | 0.51 | 0.53 | 0.57 | 0.60 | |
| D-Melibiose | 1.00 | 0.88 | 1.14 | 1.40 | 1.44 | 1.69 | 1.81 | 1.88 | 1.80 | 2.05 | 2.19 | 1.80 | |
| D-Galactose | 1.00 | 0.95 | 1.46 | 1.73 | 1.56 | 1.88 | 1.78 | 2.03 | 2.22 | 2.53 | 2.67 | 2.53 | |
| n-acetyl-neuraminic acid | 1.00 | 0.19 | 0.21 | 0.19 | 0.20 | 0.23 | 0.36 | 0.26 | 0.27 | 0.29 | 0.32 | 0.25 | |
| Succinamic Acid | 1.00 | 1.11 | 0.37 | 0.42 | 0.42 | 0.45 | 0.44 | 0.50 | 0.51 | 0.54 | 0.56 | 0.61 | |
| Succinic Acid | 1.00 | 1.02 | 1.06 | 1.08 | 1.06 | 1.04 | 0.39 | 1.00 | 0.96 | 0.94 | 0.87 | 0.81 | |
| Mono Methyl Succinate | 1.00 | 1.07 | 1.14 | 1.10 | 1.10 | 1.13 | 0.53 | 1.07 | 1.09 | 1.11 | 1.11 | 1.11 | |
| L-Malic Acid | 1.00 | 1.11 | 1.27 | 1.37 | 1.35 | 1.41 | 0.72 | 1.33 | 1.35 | 1.39 | 1.37 | 1.43 | |
| g-Amino Butyric Acid | 1.00 | 1.25 | 1.36 | 1.42 | 1.47 | 1.52 | 3.94 | 1.05 | 1.09 | 2.20 | 1.13 | 2.55 | |
| Thymidine | 1.00 | 1.65 | 1.61 | 1.67 | 1.64 | 1.75 | 0.92 | 0.61 | 0.62 | 1.52 | 1.43 | 0.81 | |
| 1,2-Propanediol | 1.00 | 1.28 | 1.41 | 1.17 | 1.19 | 1.27 | 0.68 | 1.17 | 1.12 | 1.22 | 1.15 | 1.18 | |
| 2-Aminoethanol | 1.00 | 1.30 | 1.35 | 1.12 | 1.15 | 1.24 | 0.46 | 1.07 | 1.06 | 1.03 | 1.05 | 1.07 | |
| Citric Acid | 1.00 | 1.40 | 1.41 | 1.16 | 1.15 | 1.22 | 1.07 | 1.04 | 1.05 | 1.05 | 1.05 | 1.04 | |
| Methyl D-Lactate | 1.00 | 1.36 | 1.52 | 2.08 | 2.04 | 2.26 | 1.34 | 2.14 | 2.16 | 2.39 | 2.41 | 2.99 | |
| Methyl Pyruvate | 1.00 | 1.32 | 1.57 | 1.25 | 1.36 | 1.59 | 0.77 | 1.51 | 1.65 | 1.74 | 1.79 | 1.76 | |
| D,L-a-Hydroxy-Butyric Acid | 1.00 | 0.92 | 1.05 | 0.99 | 1.01 | 1.18 | 0.56 | 1.41 | 0.72 | 1.79 | 0.74 | 2.19 | |
| Negative Control | 1.00 | 1.56 | 2.13 | 2.71 | 2.92 | 3.57 | 2.68 | 4.37 | 4.81 | 5.55 | 5.73 | 5.57 | 5 |
| Negative Control | 1.00 | 1.52 | 2.01 | 2.58 | 2.80 | 3.49 | 4.38 | 4.14 | 4.64 | 5.28 | 4.79 | 5.61 | |
| a-Cyclo-dextrin | 1.00 | 1.89 | 2.66 | 3.24 | 3.50 | 4.31 | 4.31 | 4.96 | 5.25 | 5.99 | 6.37 | 5.86 | |
| Glycogen | 1.00 | 1.61 | 2.16 | 2.58 | 2.80 | 3.46 | 4.32 | 4.20 | 4.85 | 4.87 | 4.50 | 5.01 | |
| D-Trehalose | 1.00 | 1.68 | 2.24 | 2.70 | 2.88 | 3.48 | 3.69 | 4.20 | 4.74 | 5.11 | 4.09 | 4.60 | |
| D-Cellobiose | 1.00 | 1.74 | 2.30 | 2.69 | 2.91 | 3.55 | 4.52 | 4.26 | 4.59 | 5.13 | 5.20 | 5.51 | |

TABLE 2-continued

| Metabolite | 0 hr | 1 hr | 2 hr | 3 hr | 4 hr | 5 hr | 6 hr | 7 hr | 8 hr | 9 hr | 10 hr | 11 hr | K-Means Cluster |
|---|---|---|---|---|---|---|---|---|---|---|---|---|---|
| D-Sorbitol | 1.00 | 2.10 | 2.97 | 3.57 | 3.84 | 4.59 | 4.81 | 5.29 | 5.56 | 6.08 | 6.47 | 6.92 | |
| D-Melezitose | 1.00 | 1.47 | 1.93 | 2.23 | 2.39 | 2.80 | 3.85 | 3.32 | 3.55 | 3.84 | 4.31 | 3.97 | |
| Sucrose | 1.00 | 1.67 | 2.16 | 2.42 | 2.66 | 3.05 | 4.49 | 3.46 | 3.62 | 4.04 | 4.20 | 4.72 | |
| Lactulose | 1.00 | 1.71 | 2.30 | 2.70 | 2.88 | 3.40 | 3.78 | 3.82 | 4.04 | 4.27 | 4.46 | 5.14 | |
| Uridine | 1.00 | 3.24 | 3.24 | 3.69 | 3.63 | 4.05 | 1.96 | 4.21 | 3.98 | 4.22 | 4.18 | 4.29 | |
| Inosine | 1.00 | 3.56 | 5.67 | 2.78 | 4.11 | 4.02 | 2.23 | 6.19 | 4.46 | 6.41 | 6.92 | 5.14 | |
| L-Arabinose | 1.00 | 1.72 | 2.30 | 2.99 | 3.04 | 3.33 | 2.95 | 3.87 | 3.74 | 4.05 | 4.01 | 4.09 | |
| b-Methyl-D-Xyloside | 1.00 | 1.53 | 6.40 | 1.59 | 1.73 | 2.08 | 1.14 | 4.46 | 4.02 | 2.33 | 2.61 | 3.03 | |
| L-Lactic Acid (DL) | 1.00 | 1.56 | 2.01 | 2.57 | 2.66 | 3.09 | 1.75 | 2.97 | 3.21 | 3.56 | 3.63 | 4.70 | |
| b-Hydroxy-Butyric Acid | 1.00 | 1.65 | 2.08 | 2.16 | 2.31 | 2.75 | 2.37 | 2.49 | 2.68 | 2.90 | 3.02 | 7.04 | |
| Dextrin | 1.00 | 2.16 | 3.19 | 4.01 | 4.49 | 6.14 | 4.79 | 7.35 | 8.34 | 9.71 | 8.28 | 8.41 | 8 |
| Malto-triose | 1.00 | 2.27 | 3.36 | 4.16 | 4.58 | 6.09 | 5.62 | 7.39 | 7.97 | 7.32 | 6.88 | 8.46 | |
| D-Mannose | 1.00 | 2.20 | 3.33 | 4.33 | 4.90 | 6.64 | 6.50 | 8.62 | 8.13 | 9.60 | 10.60 | 12.47 | |
| D-(+)-Glucose | 1.00 | 3.18 | 4.97 | 6.38 | 7.18 | 9.83 | 6.95 | 12.24 | 13.49 | 15.07 | 16.97 | 19.38 | 10 |
| Negative Control | 1.00 | 1.46 | 1.90 | 2.36 | 2.57 | 3.10 | 2.45 | 3.63 | 3.96 | 4.34 | 4.77 | 5.85 | 6 |
| Stachyose | 1.00 | 8.51 | 8.20 | 7.94 | 8.00 | 3.55 | 3.45 | 6.99 | 3.67 | 3.90 | 9.13 | 4.47 | 7 |
| a-Methyl-D-Galactoside | 1.00 | 1.13 | 0.68 | 0.80 | 0.84 | 1.01 | 1.20 | 1.15 | 1.15 | 1.29 | 1.42 | 1.06 | 1 |
| Pectin | 1.00 | 3.40 | 1.82 | 1.76 | 1.72 | 1.45 | 2.65 | 1.44 | 0.95 | 1.44 | 1.37 | 0.91 | |
| Acetoacetic Acid | 1.00 | 1.24 | 1.37 | 2.22 | 2.13 | 2.15 | 0.39 | 1.53 | 1.52 | 1.66 | 1.49 | 2.20 | |
| Mannan | 1.00 | 1.03 | 0.89 | 1.03 | 1.06 | 1.14 | 1.80 | 1.15 | 1.08 | 1.09 | 1.11 | 1.27 | |
| Propionic Acid | 1.00 | 1.39 | 1.55 | 1.71 | 1.74 | 1.91 | 0.17 | 1.75 | 1.84 | 1.99 | 1.15 | 1.23 | |
| D-Arabinose | 1.00 | 1.59 | 1.50 | 0.77 | 1.35 | 0.99 | 0.39 | 1.04 | 1.00 | 1.14 | 0.96 | 1.35 | |
| Pyruvic Acid | 1.00 | 1.34 | 1.40 | 1.54 | 1.61 | 1.70 | 1.39 | 1.52 | 1.57 | 1.71 | 1.81 | 2.49 | |
| b-Methyl-D-Galactoside | 1.00 | 0.52 | 0.68 | 0.78 | 0.87 | 1.05 | 1.28 | 1.17 | 1.24 | 1.36 | 1.54 | 1.61 | |
| D-Fructose-6-Phosphate | 1.00 | 1.03 | 0.90 | 0.59 | 0.97 | 0.54 | 0.23 | 1.00 | 0.49 | 0.97 | 0.92 | 0.64 | |
| Sedoheptulosan | 1.00 | 0.31 | 0.41 | 0.44 | 0.49 | 0.61 | 0.56 | 0.71 | 0.71 | 0.82 | 0.89 | 1.46 | |
| D-Raffinose | 1.00 | 1.09 | 1.11 | 1.37 | 1.53 | 1.75 | 0.75 | 1.71 | 1.82 | 1.82 | 2.00 | 2.15 | |
| D-Mannitol | 1.00 | 0.96 | 0.94 | 1.00 | 0.99 | 0.91 | 0.34 | 0.81 | 0.74 | 0.79 | 0.74 | 0.64 | |
| Turanose | 1.00 | 0.23 | 0.31 | 0.36 | 0.40 | 0.55 | 0.49 | 0.44 | 0.51 | 0.57 | 0.57 | 0.60 | |
| D-Tagatose | 1.00 | 1.07 | 1.01 | 0.88 | 0.28 | 0.29 | 0.49 | 0.32 | 0.34 | 0.36 | 0.37 | 0.39 | |
| L-Fucose | 1.00 | 0.10 | 0.20 | 0.18 | 0.18 | 0.22 | 0.26 | 0.25 | 0.27 | 0.26 | 0.24 | 0.26 | |
| a-D-Lactose | 1.00 | 0.44 | 0.58 | 0.65 | 0.69 | 0.82 | 0.63 | 0.88 | 0.94 | 1.01 | 1.02 | 0.92 | |
| Tricarballylic Acid | 1.00 | 1.07 | 1.03 | 0.79 | 1.20 | 0.72 | 0.35 | 0.89 | 0.54 | 0.83 | 0.74 | 0.59 | |
| Adonitol | 1.00 | 0.57 | 0.78 | 0.93 | 0.98 | 1.16 | 1.35 | 1.28 | 1.40 | 1.55 | 1.43 | 1.46 | |
| L-Rhamnose | 1.00 | 1.28 | 1.52 | 1.49 | 1.66 | 2.12 | 2.53 | 1.91 | 2.01 | 2.71 | 2.22 | 2.36 | |
| a-Keto-Glutaric Acid | 1.00 | 1.29 | 1.54 | 1.40 | 1.45 | 1.52 | 1.98 | 1.61 | 1.69 | 1.80 | 1.93 | 2.00 | |
| a-Keto-Butyric Acid | 1.00 | 1.10 | 1.17 | 1.24 | 1.25 | 1.28 | 1.49 | 1.33 | 1.34 | 1.36 | 1.37 | 1.39 | |
| g-Hydroxy-Butyric Acid | 1.00 | 1.24 | 1.38 | 1.92 | 1.86 | 1.71 | 0.79 | 1.88 | 1.94 | 2.09 | 2.05 | 2.76 | |
| 2,3-Butanediol | 1.00 | 1.23 | 1.54 | 1.61 | 1.58 | 1.83 | 0.83 | 1.84 | 1.93 | 2.09 | 2.19 | 2.33 | |
| Palatinose | 1.00 | 1.31 | 1.79 | 1.68 | 1.81 | 2.10 | 2.44 | 2.18 | 2.16 | 2.14 | 1.94 | 1.44 | |
| 3-Methyl Glucose | 1.00 | 1.48 | 1.54 | 1.58 | 1.60 | 1.97 | 2.15 | 2.30 | 1.94 | 2.13 | 2.45 | 2.35 | |
| m-Tartaric Acid | 1.00 | 1.39 | 1.72 | 2.14 | 2.16 | 2.42 | 3.24 | 2.70 | 2.82 | 2.95 | 2.65 | 2.75 | 3 |
| Chondroitin Sulfate C | 1.00 | 1.60 | 1.94 | 2.10 | 2.19 | 2.50 | 3.28 | 2.63 | 2.56 | 2.92 | 3.00 | 2.49 | |
| Maltitol | 1.00 | 1.76 | 2.36 | 2.82 | 3.07 | 3.80 | 3.52 | 4.49 | 4.77 | 5.77 | 5.24 | 5.98 | |
| 3-Hydroxy 2-Butanone | 1.00 | 1.49 | 1.75 | 1.64 | 1.71 | 2.01 | 0.48 | 1.80 | 1.86 | 7.44 | 7.39 | 2.14 | |
| Adenosine | 1.00 | 2.85 | 1.34 | 1.67 | 1.86 | 2.21 | 2.50 | 2.97 | 3.10 | 3.78 | 3.46 | 3.32 | |
| D-Malic Acid | 1.00 | 1.49 | 2.03 | 2.06 | 2.25 | 2.63 | 2.19 | 2.87 | 3.00 | 3.06 | 3.20 | 3.52 | |
| Gentio-biose | 1.00 | 1.71 | 2.34 | 2.83 | 3.01 | 3.72 | 4.46 | 4.35 | 4.57 | 5.20 | 5.59 | 5.94 | |
| a-Methyl-D-Mannoside | 1.00 | 1.26 | 1.58 | 1.74 | 1.89 | 2.33 | 2.77 | 2.46 | 2.13 | 2.16 | 2.95 | 2.58 | |
| D-Fructose | 1.00 | 2.31 | 2.22 | 1.77 | 2.00 | 2.59 | 1.51 | 3.18 | 3.38 | 4.01 | 3.99 | 4.24 | |
| L-Glucose | 1.00 | 1.65 | 2.20 | 2.64 | 2.83 | 3.52 | 3.82 | 3.51 | 3.55 | 3.76 | 3.89 | 4.25 | |
| m-Inositol | 1.00 | 1.63 | 2.13 | 3.87 | 3.78 | 3.07 | 3.01 | 3.55 | 3.42 | 3.81 | 3.89 | 4.22 | |
| i-Erythritol | 1.00 | 1.76 | 2.33 | 2.67 | 2.83 | 3.31 | 5.19 | 3.78 | 3.84 | 4.30 | 4.08 | | |
| Acetic Acid | 1.00 | 2.02 | 2.71 | 3.02 | 3.24 | 3.75 | 3.33 | 4.10 | 4.32 | 4.64 | 3.99 | 4.58 | |

TABLE 2-continued

| Metabolite | 0 hr | 1 hr | 2 hr | 3 hr | 4 hr | 5 hr | 6 hr | 7 hr | 8 hr | 9 hr | 10 hr | 11 hr | K-Means Cluster |
|---|---|---|---|---|---|---|---|---|---|---|---|---|---|
| Hexanoic Acid | 1.00 | 1.35 | 1.47 | 2.74 | 2.80 | 1.18 | 1.04 | 4.15 | 4.11 | 4.10 | 4.13 | 3.16 | |
| L-Sorbose | 1.00 | 1.57 | 2.05 | 2.28 | 2.38 | 2.79 | 4.12 | 2.84 | 2.81 | 2.80 | 3.02 | 2.98 | |
| D-Fucose | 1.00 | 1.61 | 1.96 | 2.02 | 2.15 | 2.65 | 2.11 | 2.19 | 2.49 | 2.69 | 2.78 | 2.97 | |
| Virus | | | | | | | | | | | | | |
| D-(+)-Glucose | 1.00 | 2.25 | 3.59 | 4.41 | 4.97 | 6.52 | 7.36 | 8.16 | 9.07 | 10.76 | 11.26 | 13.34 | 9 |
| D-(+)-Glucose | 1.00 | 2.54 | 4.07 | 5.25 | 5.97 | 7.91 | 9.03 | 10.04 | 11.13 | 13.31 | 13.75 | 14.88 | |
| Maltose | 1.00 | 2.29 | 3.23 | 3.88 | 4.21 | 5.22 | 5.86 | 6.41 | 7.01 | 8.07 | 8.77 | 8.43 | 4 |
| D-Glucose-6-Phosphate | 1.00 | 2.01 | 3.00 | 3.61 | 4.04 | 4.92 | 5.47 | 5.87 | 6.35 | 7.41 | 7.21 | 5.87 | |
| D-Glucose-1-Phosphate | 1.00 | 1.74 | 2.39 | 2.86 | 3.20 | 3.94 | 4.34 | 4.56 | 4.91 | 5.77 | 5.49 | 6.50 | |
| b-Methyl-D-Glucoside | 1.00 | 2.00 | 2.80 | 3.24 | 3.45 | 3.99 | 4.32 | 4.57 | 4.86 | 5.41 | 5.67 | 6.22 | |
| D,L-a-Glycerol Phosphate | 1.00 | 2.01 | 2.64 | 3.07 | 3.24 | 3.72 | 3.99 | 4.18 | 4.43 | 4.93 | 5.12 | 5.62 | |
| Glycerol | 1.04 | 1.04 | 1.04 | 1.04 | 1.04 | 3.55 | 3.71 | 3.91 | 4.11 | 4.51 | 4.63 | 5.09 | |
| Xylitol | 1.00 | 1.69 | 2.39 | 3.14 | 3.34 | 3.95 | 4.25 | 4.50 | 4.55 | 5.13 | 4.85 | 5.48 | |
| N-Acetyl-D-Glucosamine | 1.00 | 2.25 | 3.27 | 3.85 | 4.12 | 4.99 | 5.27 | 5.67 | 6.03 | 6.65 | 6.45 | 5.53 | |
| a-Methyl-D-Glucoside | 1.00 | 1.29 | 1.66 | 1.87 | 1.99 | 2.31 | 2.50 | 2.67 | 2.77 | 3.14 | 3.10 | 3.31 | 2 |
| Salicin | 1.00 | 0.77 | 1.06 | 1.26 | 1.36 | 1.64 | 1.76 | 1.87 | 2.01 | 2.26 | 2.38 | 2.62 | |
| D-Glucosaminic Acid | 1.00 | 1.69 | 2.21 | 2.51 | 2.69 | 3.09 | 3.31 | 3.47 | 3.57 | 3.89 | 3.88 | 3.32 | |
| Butyric Acid | 1.00 | 1.82 | 2.27 | 2.61 | 2.66 | 2.95 | 2.88 | 2.62 | 2.60 | 2.89 | 3.02 | 3.20 | |
| D-Glucuronic Acid | 1.00 | 1.44 | 1.90 | 2.18 | 2.37 | 2.79 | 2.96 | 3.14 | 3.24 | 3.62 | 3.66 | 3.99 | |
| N-Acetyl-D-Mannosamine | 1.00 | 1.40 | 1.88 | 2.13 | 2.22 | 2.60 | 2.70 | 2.89 | 3.09 | 3.29 | 3.34 | 3.55 | |
| Lactitol | 1.00 | 1.61 | 2.20 | 2.54 | 2.73 | 3.16 | 3.38 | 3.55 | 3.76 | 4.11 | 4.31 | 4.66 | |
| Melibionic Acid | 1.00 | 3.52 | 3.58 | 3.59 | 3.66 | 3.34 | 3.22 | 3.05 | 2.89 | 2.67 | 1.66 | 2.18 | |
| D-Melibiose | 1.00 | 3.65 | 3.76 | 3.77 | 3.78 | 3.62 | 3.58 | 3.59 | 3.20 | 1.54 | 1.54 | 1.63 | |
| D-Galactose | 1.00 | 0.91 | 1.21 | 1.47 | 1.60 | 1.89 | 2.03 | 2.16 | 2.29 | 2.54 | 2.63 | 2.86 | |
| n-acetyl-neuraminic acid | 1.00 | 4.77 | 3.35 | 3.95 | 3.57 | 1.43 | 2.71 | 1.58 | 1.60 | 1.61 | 1.82 | 2.21 | |
| Succinamic Acid | 1.00 | 1.45 | 1.65 | 1.88 | 1.85 | 2.03 | 2.14 | 2.22 | 2.30 | 2.41 | 2.37 | 2.51 | |
| Succinic Acid | 1.00 | 1.69 | 2.01 | 2.37 | 2.37 | 2.54 | 2.73 | 2.78 | 2.85 | 3.06 | 2.98 | 3.12 | |
| Mono Methyl Succinate | 1.00 | 1.44 | 1.71 | 1.97 | 2.04 | 2.16 | 2.33 | 2.40 | 2.45 | 2.58 | 2.55 | 2.67 | |
| L-Malic Acid | 1.00 | 1.48 | 1.19 | 1.27 | 3.32 | 1.59 | 1.42 | 2.93 | 3.48 | 1.72 | 2.20 | 2.05 | |
| g-Amino Butyric Acid | 1.00 | 1.68 | 2.39 | 2.83 | 2.96 | 3.40 | 3.56 | 3.70 | 3.84 | 3.99 | 3.94 | 3.74 | |
| Thymidine | 1.00 | 1.52 | 2.29 | 2.27 | 2.32 | 2.34 | 2.33 | 2.34 | 2.26 | 2.28 | 0.94 | 2.21 | |
| 1,2-Propanediol | 1.00 | 1.95 | 2.44 | 2.83 | 2.94 | 3.29 | 3.55 | 3.75 | 3.87 | 4.24 | 4.34 | 4.75 | |
| 2-Aminoethanol | 1.00 | 1.65 | 2.01 | 2.38 | 2.50 | 2.74 | 2.88 | 3.01 | 3.12 | 3.41 | 3.22 | 3.78 | |
| Citric Acid | 1.00 | 1.54 | 1.94 | 2.21 | 2.31 | 2.64 | 2.74 | 2.85 | 2.95 | 3.10 | 2.94 | 2.81 | |
| Methyl D-Lactate | 1.00 | 2.10 | 2.49 | 2.89 | 2.64 | 2.75 | 2.94 | 3.10 | 3.20 | 3.46 | 3.46 | 3.61 | |
| Methyl Pyruvate | 1.00 | 1.93 | 2.20 | 2.60 | 2.51 | 2.66 | 2.87 | 2.99 | 3.03 | 3.24 | 3.21 | 3.04 | |
| D,L-a-Hydroxy-Butyric Acid | 1.00 | 1.29 | 1.58 | 1.74 | 1.84 | 2.00 | 2.10 | 2.18 | 2.26 | 2.35 | 2.39 | 2.21 | |
| Negative Control | 1.00 | 1.47 | 1.91 | 2.21 | 2.43 | 3.01 | 3.39 | 3.73 | 4.08 | 4.89 | 5.22 | 4.13 | 5 |
| Negative Control | 1.00 | 1.87 | 2.11 | 2.55 | 2.70 | 3.09 | 3.30 | 3.46 | 3.64 | 3.96 | 4.11 | 3.26 | |
| a-Cyclo-dextrin | 1.00 | 1.86 | 2.62 | 2.99 | 3.18 | 3.75 | 4.06 | 4.29 | 4.56 | 4.96 | 5.19 | 4.09 | |
| Glycogen | 1.00 | 1.68 | 2.26 | 2.71 | 2.92 | 3.70 | 4.21 | 4.74 | 5.48 | 3.99 | 4.33 | 4.63 | |
| D-Trehalose | 1.00 | 1.66 | 2.04 | 2.20 | 2.27 | 2.52 | 2.66 | 2.79 | 2.93 | 3.11 | 3.25 | 3.07 | |
| D-Cellobiose | 1.00 | 1.58 | 2.09 | 2.38 | 2.49 | 2.81 | 3.00 | 3.14 | 3.31 | 3.54 | 3.69 | 4.06 | |
| D-Sorbitol | 1.00 | 1.80 | 2.63 | 3.10 | 3.35 | 4.00 | 4.37 | 4.63 | 4.94 | 5.39 | 5.64 | 6.18 | |
| D-Melezitose | 1.00 | 1.67 | 2.39 | 2.73 | 2.88 | 3.35 | 3.57 | 3.77 | 3.98 | 4.49 | 4.69 | 5.01 | |
| Sucrose | 1.00 | 1.64 | 2.25 | 2.51 | 2.58 | 2.99 | 3.11 | 3.22 | 3.41 | 3.83 | 3.87 | 4.04 | |
| Lactulose | 1.00 | 1.68 | 2.24 | 2.56 | 2.71 | 3.13 | 3.31 | 3.50 | 3.70 | 4.05 | 4.25 | 4.63 | |
| Uridine | 1.00 | 0.99 | 1.55 | 1.96 | 2.18 | 2.78 | 3.02 | 3.29 | 3.58 | 4.12 | 4.35 | 4.93 | |
| Inosine | 1.00 | 1.16 | 1.78 | 2.23 | 2.45 | 3.06 | 3.30 | 3.54 | 3.88 | 4.33 | 3.83 | 4.20 | |
| L-Arabinose | 1.00 | 1.79 | 2.45 | 3.01 | 3.10 | 3.49 | 3.66 | 3.82 | 4.01 | 4.41 | 4.50 | 4.78 | |
| b-Methyl-D-Xyloside | 1.00 | 1.92 | 2.38 | 2.79 | 2.82 | 3.12 | 3.28 | 3.39 | 3.52 | 3.77 | 3.87 | 4.01 | |

TABLE 2-continued

| Metabolite | 0 hr | 1 hr | 2 hr | 3 hr | 4 hr | 5 hr | 6 hr | 7 hr | 8 hr | 9 hr | 10 hr | 11 hr | K-Means Cluster |
|---|---|---|---|---|---|---|---|---|---|---|---|---|---|
| L-Lactic Acid (DL) | 1.00 | 1.33 | 1.66 | 2.04 | 2.11 | 2.48 | 2.68 | 2.86 | 3.04 | 3.36 | 3.49 | 3.91 | |
| b-Hydroxy-Butyric Acid | 1.00 | 1.78 | 2.31 | 2.61 | 2.77 | 3.16 | 3.34 | 3.47 | 3.62 | 3.79 | 3.87 | 3.29 | |
| Dextrin | 1.00 | 2.14 | 2.79 | 3.43 | 3.84 | 4.91 | 5.56 | 6.11 | 6.72 | 7.89 | 8.23 | 6.40 | 8 |
| Malto-triose | 1.00 | 2.01 | 3.05 | 3.70 | 4.08 | 5.20 | 5.81 | 6.29 | 6.78 | 7.44 | 6.04 | 6.50 | |
| D-Mannose | 1.00 | 1.49 | 2.09 | 2.68 | 3.06 | 4.10 | 4.57 | 4.94 | 5.47 | 6.51 | 6.80 | 7.75 | |
| D-(+)-Glucose | 1.00 | 0.82 | 1.44 | 1.76 | 1.96 | 2.64 | 2.91 | 3.23 | 3.59 | 4.21 | 4.43 | 5.05 | 10 |
| Negative Control | 1.00 | 9.15 | 2.47 | 9.51 | 8.01 | 3.75 | 9.68 | 3.53 | 3.69 | 3.94 | 4.08 | 6.12 | 6 |
| Stachyose | 1.00 | 1.42 | 1.76 | 1.96 | 2.07 | 4.65 | 5.10 | 3.71 | 3.40 | 3.17 | 2.89 | 4.13 | 7 |
| a-Methyl-D-Galactoside | 1.00 | 2.91 | 1.88 | 1.16 | 1.24 | 1.43 | 1.51 | 1.59 | 1.67 | 1.83 | 1.89 | 2.05 | 1 |
| Pectin | 1.00 | 3.25 | 2.85 | 0.75 | 0.80 | 0.91 | 0.95 | 1.00 | 1.05 | 1.15 | 1.17 | 1.27 | |
| Acetoacetic Acid | 1.00 | 1.26 | 1.40 | 1.48 | 1.54 | 1.64 | 1.67 | 1.71 | 1.74 | 1.81 | 1.74 | 1.81 | |
| Mannan | 1.00 | 1.03 | 1.25 | 1.28 | 1.35 | 1.41 | 1.44 | 1.49 | 1.49 | 1.61 | 1.64 | 1.76 | |
| Propionic Acid | 1.00 | 1.23 | 0.70 | 0.83 | 0.93 | 1.08 | 1.15 | 1.17 | 1.18 | 1.32 | 1.11 | 1.26 | |
| D-Arabinose | 1.00 | 0.65 | 0.90 | 1.03 | 1.07 | 1.22 | 1.29 | 1.37 | 1.33 | 1.34 | 1.38 | 1.58 | |
| Pyruvic Acid | 1.00 | 1.27 | 0.82 | 0.94 | 1.20 | 1.10 | 1.09 | 1.06 | 0.67 | 0.65 | 0.75 | 0.61 | |
| b-Methyl-D-Galactoside | 1.00 | 0.74 | 0.95 | 1.11 | 1.18 | 1.36 | 1.45 | 1.52 | 1.60 | 1.76 | 1.81 | 1.96 | |
| D-Fructose-6-Phosphate | 1.00 | 0.59 | 0.75 | 0.87 | 0.94 | 1.11 | 1.18 | 1.27 | 1.35 | 1.49 | 1.55 | 1.65 | |
| Sedoheptulosan | 1.00 | 1.49 | 1.48 | 1.46 | 1.43 | 1.30 | 1.36 | 1.39 | 1.49 | 1.58 | 1.48 | 1.65 | |
| D-Raffinose | 1.00 | 0.68 | 0.59 | 0.55 | 0.49 | 1.98 | 0.54 | 1.92 | 1.77 | 1.74 | 1.15 | 1.53 | |
| D-Mannitol | 1.00 | 0.20 | 0.27 | 0.32 | 0.34 | 0.40 | 0.42 | 0.44 | 0.47 | 0.52 | 0.53 | 0.57 | |
| Turanose | 1.00 | 0.20 | 0.28 | 0.34 | 0.36 | 0.44 | 0.48 | 0.51 | 0.56 | 0.61 | 0.60 | 0.55 | |
| D-Tagatose | 1.00 | 0.17 | 0.24 | 0.28 | 0.30 | 0.36 | 0.39 | 0.42 | 0.44 | 0.49 | 0.51 | 0.48 | |
| L-Fucose | 1.00 | 0.21 | 0.28 | 0.33 | 0.35 | 0.42 | 0.45 | 0.47 | 0.50 | 0.54 | 0.57 | 0.61 | |
| a-D-Lactose | 1.00 | 0.17 | 0.22 | 0.26 | 0.28 | 0.33 | 0.35 | 0.37 | 0.39 | 0.42 | 0.41 | 0.39 | |
| Tricarballylic Acid | 1.00 | 0.20 | 0.25 | 0.29 | 0.29 | 0.32 | 0.34 | 0.36 | 0.36 | 0.39 | 0.40 | 0.38 | |
| Adonitol | 1.00 | 0.21 | 0.26 | 0.29 | 0.31 | 0.34 | 0.36 | 0.38 | 0.39 | 0.42 | 0.44 | 0.43 | |
| L-Rhamnose | 1.00 | 0.16 | 0.22 | 0.25 | 0.28 | 0.32 | 0.34 | 0.36 | 0.38 | 0.41 | 0.43 | 0.46 | |
| a-Keto-Glutaric Acid | 1.00 | 0.28 | 0.37 | 0.45 | 0.46 | 0.51 | 0.54 | 0.56 | 0.58 | 0.64 | 0.64 | 0.69 | |
| a-Keto-Butyric Acid | 1.00 | 0.28 | 0.29 | 0.30 | 0.31 | 0.32 | 0.32 | 0.33 | 0.33 | 0.34 | 0.34 | 0.34 | |
| g-Hydroxy-Butyric Acid | 1.00 | 0.53 | 0.53 | 0.41 | 0.44 | 0.50 | 0.54 | 0.56 | 0.59 | 0.62 | 0.63 | 0.53 | |
| 2,3-Butanediol | 1.00 | 1.66 | 1.65 | 0.31 | 0.33 | 0.38 | 0.40 | 0.42 | 0.43 | 0.45 | 0.42 | 0.39 | |
| Palatinose | 1.00 | 0.18 | 0.24 | 0.28 | 0.29 | 0.34 | 0.36 | 0.38 | 0.41 | 0.45 | 0.46 | 0.50 | |
| 3-Methyl Glucose | 1.00 | 0.15 | 0.21 | 0.25 | 0.27 | 0.32 | 0.35 | 0.37 | 0.39 | 0.44 | 0.45 | 0.50 | |
| m-Tartaric Acid | 1.00 | 1.50 | 1.66 | 1.90 | 1.96 | 2.05 | 2.17 | 2.23 | 2.28 | 2.43 | 2.40 | 2.41 | 3 |
| Chondroitin Sulfate C | 1.00 | 1.22 | 1.41 | 1.45 | 1.55 | 1.62 | 1.61 | 1.63 | 1.65 | 1.72 | 1.69 | 1.75 | |
| Maltitol | 1.00 | 1.05 | 1.03 | 1.37 | 0.98 | 0.88 | 0.89 | 0.92 | 0.96 | 1.01 | 1.08 | 1.16 | |
| 3-Hydroxy 2-Butanone | 1.00 | 1.24 | 1.65 | 2.42 | 2.37 | 2.39 | 2.28 | 2.37 | 2.01 | 2.18 | 2.16 | 2.35 | |
| Adenosine | 1.00 | 1.39 | 1.23 | 1.60 | 1.77 | 1.96 | 2.16 | 2.38 | 2.56 | 2.88 | 2.56 | 2.60 | |
| D-Malic Acid | 1.00 | 2.26 | 2.49 | 2.54 | 2.71 | 2.61 | 1.75 | 1.82 | 1.98 | 1.95 | 2.27 | 2.21 | |
| Gentio-biose | 1.00 | 1.23 | 1.38 | 1.44 | 1.47 | 1.55 | 1.62 | 1.66 | 1.72 | 1.79 | 1.85 | 1.99 | |
| a-Methyl-D-Mannoside | 1.00 | 0.38 | 0.54 | 0.64 | 0.69 | 0.83 | 0.89 | 0.93 | 0.99 | 1.10 | 1.14 | 1.24 | |
| D-Fructose | 1.00 | 0.44 | 0.58 | 0.71 | 0.79 | 1.00 | 1.09 | 1.17 | 1.26 | 1.43 | 1.52 | 1.70 | |
| L-Glucose | 1.00 | 0.29 | 0.39 | 0.45 | 0.49 | 0.57 | 0.61 | 0.64 | 0.68 | 0.76 | 0.76 | 0.86 | |
| m-Inositol | 1.00 | 0.51 | 0.66 | 0.77 | 0.81 | 0.94 | 0.99 | 1.04 | 1.10 | 1.20 | 1.24 | 1.34 | |
| i-Erythritol | 1.00 | 0.23 | 0.29 | 0.32 | 0.34 | 0.39 | 0.41 | 0.43 | 0.45 | 0.49 | 0.50 | 0.53 | |
| Acetic Acid | 1.00 | 0.21 | 0.28 | 0.32 | 0.34 | 0.38 | 0.41 | 0.40 | 0.41 | 0.40 | 0.40 | 0.46 | |
| Hexanoic Acid | 1.00 | 0.25 | 0.28 | 0.31 | 0.33 | 0.36 | 0.37 | 0.37 | 0.38 | 0.36 | 0.40 | 0.41 | |
| L-Sorbose | 1.00 | 0.18 | 0.23 | 0.26 | 0.28 | 0.32 | 0.34 | 0.37 | 0.38 | 0.41 | 0.41 | 0.48 | |
| D-Fucose | 1.00 | 0.66 | 0.33 | 0.67 | 0.64 | 0.62 | 0.65 | 0.65 | 0.60 | 0.52 | 0.57 | 0.61 | |

TABLE 3

| Metabolite | 0 hr | 1 hr | 2 hr | 3 hr | 4 hr | 5 hr | 6 hr | 7 hr | 8 hr | 9 hr | 10 hr | 11 hr | K-Means Cluster |
|---|---|---|---|---|---|---|---|---|---|---|---|---|---|
| | | | | | | Control | | | | | | | |
| D-(+)-Glucose | 1.00 | 1.12 | 1.19 | 1.21 | 1.13 | 1.56 | 0.67 | 1.43 | 1.37 | 1.59 | 1.64 | 1.74 | 9 |
| D-(+)-Glucose | 1.00 | 1.51 | 1.74 | 1.86 | 2.09 | 2.68 | 1.68 | 2.70 | 2.95 | 3.08 | 3.38 | 3.79 | |
| Maltose | 1.00 | 1.07 | 1.04 | 1.27 | 1.22 | 1.53 | 1.72 | 1.53 | 1.68 | 1.97 | 1.93 | 2.37 | 4 |
| D-Glucose-6-Phosphate | 1.00 | 1.14 | 1.18 | 3.24 | 1.30 | 1.48 | 0.74 | 2.93 | 1.28 | 1.38 | 2.69 | 1.87 | |
| D-Glucose-1-Phosphate | 1.00 | 1.01 | 1.31 | 1.24 | 1.16 | 1.12 | 0.33 | 1.10 | 1.03 | 1.09 | 1.06 | 0.93 | |
| b-Methyl-D-Glucoside | 1.00 | 1.32 | 1.80 | 1.84 | 2.02 | 2.32 | 1.04 | 2.85 | 3.05 | 3.33 | 3.70 | 4.24 | |
| D,L-a-Glycerol Phosphate | 1.00 | 0.34 | 0.48 | 0.56 | 0.60 | 0.70 | 0.71 | 0.79 | 0.83 | 0.91 | 0.91 | 1.05 | |
| Glycerol | 1.00 | 1.36 | 1.42 | 1.19 | 1.18 | 1.27 | 0.68 | 1.06 | 1.04 | 1.08 | 1.04 | 1.08 | |
| Xylitol | 1.00 | 1.02 | 1.53 | 1.57 | 1.01 | 1.51 | 0.40 | 1.01 | 1.49 | 1.02 | 0.97 | 0.97 | |
| N-Acetyl-D-Glucosamine | 1.00 | 0.19 | 0.27 | 0.32 | 0.34 | 0.40 | 0.32 | 0.46 | 0.48 | 0.50 | 0.45 | 0.44 | |
| a-Methyl-D-Glucoside | 1.00 | 1.18 | 1.07 | 1.02 | 0.58 | 0.76 | 0.90 | 0.68 | 0.74 | 0.79 | 0.83 | 0.93 | 2 |
| Salicin | 1.00 | 1.17 | 0.93 | 0.96 | 0.83 | 0.78 | 0.43 | 0.69 | 0.67 | 0.66 | 0.62 | 0.62 | |
| D-Glucosaminic Acid | 1.00 | 0.86 | 0.94 | 0.90 | 1.21 | 1.22 | 0.36 | 0.95 | 0.97 | 0.98 | 0.97 | 0.39 | |
| Butyric Acid | 1.00 | 0.95 | 0.15 | 0.14 | 0.15 | 0.16 | 0.05 | 0.15 | 0.15 | 0.16 | 0.16 | 0.17 | |
| D-Glucuronic Acid | 1.00 | 1.13 | 1.37 | 1.29 | 1.42 | 1.57 | 0.86 | 1.71 | 1.83 | 1.90 | 2.04 | 2.34 | |
| N-Acetyl-D-Mannosamine | 1.00 | 0.90 | 0.77 | 0.71 | 0.68 | 0.68 | 0.65 | 0.61 | 0.63 | 0.58 | 0.67 | 0.66 | |
| Lactitol | 1.00 | 0.19 | 0.26 | 0.31 | 0.33 | 0.39 | 0.40 | 0.44 | 0.47 | 0.50 | 0.55 | 0.62 | |
| Melibionic Acid | 1.00 | 0.20 | 0.76 | 0.58 | 0.66 | 0.48 | 0.40 | 0.47 | 0.51 | 0.53 | 0.57 | 0.60 | |
| D-Melibiose | 1.00 | 0.88 | 1.14 | 1.40 | 1.44 | 1.69 | 1.81 | 1.88 | 1.80 | 2.05 | 2.19 | 1.80 | |
| D-Galactose | 1.00 | 0.95 | 1.46 | 1.73 | 1.56 | 1.88 | 1.78 | 2.03 | 2.22 | 2.53 | 2.67 | 2.53 | |
| n-acetyl-neuraminic acid | 1.00 | 0.19 | 0.21 | 0.19 | 0.20 | 0.23 | 0.36 | 0.26 | 0.27 | 0.29 | 0.32 | 0.25 | |
| Succinamic Acid | 1.00 | 1.11 | 0.37 | 0.42 | 0.42 | 0.45 | 0.44 | 0.50 | 0.51 | 0.54 | 0.56 | 0.61 | |
| Succinic Acid | 1.00 | 1.02 | 1.06 | 1.08 | 1.06 | 1.04 | 0.39 | 1.00 | 0.96 | 0.94 | 0.87 | 0.81 | |
| Mono Methyl Succinate | 1.00 | 1.07 | 1.14 | 1.10 | 1.10 | 1.13 | 0.53 | 1.07 | 1.09 | 1.11 | 1.11 | 1.11 | |
| L-Malic Acid | 1.00 | 1.11 | 1.27 | 1.37 | 1.35 | 1.41 | 0.72 | 1.33 | 1.35 | 1.39 | 1.37 | 1.43 | |
| g-Amino Butyric Acid | 1.00 | 1.25 | 1.36 | 1.42 | 1.47 | 1.52 | 3.94 | 1.05 | 1.09 | 2.20 | 1.13 | 2.55 | |
| Thymidine | 1.00 | 1.65 | 1.61 | 1.67 | 1.64 | 1.75 | 0.92 | 0.61 | 0.62 | 1.52 | 1.43 | 0.81 | |
| 1,2-Propanediol | 1.00 | 1.28 | 1.41 | 1.17 | 1.19 | 1.27 | 0.68 | 1.17 | 1.12 | 1.22 | 1.15 | 1.18 | |
| 2-Aminoethanol | 1.00 | 1.30 | 1.35 | 1.12 | 1.15 | 1.24 | 0.46 | 1.07 | 1.06 | 1.03 | 1.05 | 1.07 | |
| Citric Acid | 1.00 | 1.40 | 1.41 | 1.16 | 1.15 | 1.22 | 1.07 | 1.04 | 1.05 | 1.05 | 1.05 | 1.04 | |
| Methyl D-Lactate | 1.00 | 1.36 | 1.52 | 2.08 | 2.04 | 2.26 | 1.34 | 2.14 | 2.16 | 2.39 | 2.41 | 2.99 | |
| Methyl Pyruvate | 1.00 | 1.32 | 1.57 | 1.25 | 1.36 | 1.59 | 0.77 | 1.51 | 1.65 | 1.74 | 1.79 | 1.76 | |
| D,L-a-Hydroxy-Butyric Acid | 1.00 | 0.92 | 1.05 | 0.99 | 1.01 | 1.18 | 0.56 | 1.41 | 0.72 | 1.79 | 0.74 | 2.19 | |
| Negative Control | 1.00 | 1.56 | 2.13 | 2.71 | 2.92 | 3.57 | 2.68 | 4.37 | 4.81 | 5.55 | 5.73 | 5.57 | 5 |
| Negative Control | 1.00 | 1.52 | 2.01 | 2.58 | 2.80 | 3.49 | 4.38 | 4.14 | 4.64 | 5.28 | 4.79 | 5.61 | |
| a-Cyclodextrin | 1.00 | 1.89 | 2.66 | 3.24 | 3.50 | 4.31 | 4.31 | 4.96 | 5.25 | 5.99 | 6.37 | 5.86 | |
| Glycogen | 1.00 | 1.61 | 2.16 | 2.58 | 2.80 | 3.46 | 4.32 | 4.20 | 4.85 | 4.87 | 4.50 | 5.01 | |
| D-Trehalose | 1.00 | 1.68 | 2.24 | 2.70 | 2.88 | 3.48 | 3.69 | 4.20 | 4.74 | 5.11 | 4.09 | 4.60 | |
| D-Cellobiose | 1.00 | 1.74 | 2.30 | 2.69 | 2.91 | 3.55 | 4.52 | 4.26 | 4.59 | 5.13 | 5.51 | 5.51 | |
| D-Sorbitol | 1.00 | 2.10 | 2.97 | 3.57 | 3.84 | 4.59 | 4.81 | 5.29 | 5.56 | 6.08 | 6.47 | 6.92 | |
| D-Melezitose | 1.00 | 1.47 | 1.93 | 2.23 | 2.39 | 2.80 | 3.85 | 3.32 | 3.55 | 3.84 | 4.31 | 3.97 | |
| Sucrose | 1.00 | 1.67 | 2.16 | 2.42 | 2.66 | 3.05 | 4.49 | 3.46 | 3.62 | 4.04 | 4.20 | 4.72 | |
| Lactulose | 1.00 | 1.71 | 2.30 | 2.70 | 2.88 | 3.40 | 3.78 | 3.82 | 4.04 | 4.27 | 4.46 | 5.14 | |
| Uridine | 1.00 | 3.24 | 3.24 | 3.69 | 3.63 | 4.05 | 1.96 | 4.21 | 3.98 | 4.22 | 4.18 | 4.29 | |
| Inosine | 1.00 | 3.56 | 5.67 | 2.78 | 4.11 | 4.02 | 2.23 | 6.19 | 4.46 | 6.41 | 6.92 | 5.14 | |
| L-Arabinose | 1.00 | 1.72 | 2.30 | 2.99 | 3.04 | 3.33 | 2.95 | 3.87 | 3.74 | 4.05 | 4.01 | 4.09 | |
| b-Methyl-D-Xyloside | 1.00 | 1.53 | 6.40 | 1.59 | 1.73 | 2.08 | 1.14 | 4.46 | 4.02 | 2.33 | 2.61 | 3.03 | |

TABLE 3-continued

| | | | | | | | | | | | | | |
|---|---|---|---|---|---|---|---|---|---|---|---|---|---|
| L-Lactic Acid (DL) | 1.00 | 1.56 | 2.01 | 2.57 | 2.66 | 3.09 | 1.75 | 2.97 | 3.21 | 3.56 | 3.63 | 4.70 | |
| b-Hydroxy-Butyric Acid | 1.00 | 1.65 | 2.08 | 2.16 | 2.31 | 2.75 | 2.37 | 2.49 | 2.68 | 2.90 | 3.02 | 7.04 | |
| Dextrin | 1.00 | 2.16 | 3.19 | 4.01 | 4.49 | 6.14 | 4.79 | 7.35 | 8.34 | 9.71 | 8.28 | 8.41 | 8 |
| Malto-triose | 1.00 | 2.27 | 3.36 | 4.16 | 4.58 | 6.09 | 5.62 | 7.39 | 7.97 | 7.32 | 6.88 | 8.46 | |
| D-Mannose | 1.00 | 2.20 | 3.33 | 4.33 | 4.90 | 6.64 | 6.50 | 8.62 | 8.13 | 9.60 | 10.60 | 12.47 | |
| D-(+)-Glucose | 1.00 | 3.18 | 4.97 | 6.38 | 7.18 | 9.83 | 6.95 | 12.24 | 13.49 | 15.07 | 16.97 | 19.38 | 10 |
| Negative Control | 1.00 | 1.46 | 1.90 | 2.36 | 2.57 | 3.10 | 2.45 | 3.63 | 3.96 | 4.34 | 4.77 | 5.85 | 6 |
| Stachyose | 1.00 | 8.51 | 8.20 | 7.94 | 8.00 | 3.55 | 3.45 | 6.99 | 3.67 | 3.90 | 9.13 | 4.47 | 7 |
| a-Methyl-D-Galactoside | 1.00 | 1.13 | 0.68 | 0.80 | 0.84 | 1.01 | 1.20 | 1.15 | 1.15 | 1.29 | 1.42 | 1.06 | 1 |
| Pectin | 1.00 | 3.40 | 1.82 | 1.76 | 1.72 | 1.45 | 2.65 | 1.44 | 0.95 | 1.44 | 1.37 | 0.91 | |
| Acetoacetic Acid | 1.00 | 1.24 | 1.37 | 2.22 | 2.13 | 2.15 | 0.39 | 1.53 | 1.52 | 1.66 | 1.49 | 2.20 | |
| Mannan | 1.00 | 1.03 | 0.89 | 1.03 | 1.06 | 1.14 | 1.80 | 1.15 | 1.08 | 1.09 | 1.11 | 1.27 | |
| Propionic Acid | 1.00 | 1.39 | 1.55 | 1.71 | 1.74 | 1.91 | 0.17 | 1.75 | 1.84 | 1.99 | 1.15 | 1.23 | |
| D-Arabinose | 1.00 | 1.59 | 1.50 | 0.77 | 1.35 | 0.99 | 0.39 | 1.04 | 1.00 | 1.14 | 0.96 | 1.35 | |
| Pyruvic Acid | 1.00 | 1.34 | 1.40 | 1.54 | 1.61 | 1.70 | 1.39 | 1.52 | 1.57 | 1.71 | 1.81 | 2.49 | |
| b-Methyl-D-Galactoside | 1.00 | 0.52 | 0.68 | 0.78 | 0.87 | 1.05 | 1.28 | 1.17 | 1.24 | 1.36 | 1.54 | 1.61 | |
| D-Fructose-6-Phosphate | 1.00 | 1.03 | 0.90 | 0.59 | 0.97 | 0.54 | 0.23 | 1.00 | 0.49 | 0.97 | 0.92 | 0.64 | |
| Sedoheptulosan | 1.00 | 0.31 | 0.41 | 0.44 | 0.49 | 0.61 | 0.56 | 0.71 | 0.71 | 0.82 | 0.89 | 1.46 | |
| D-Raffinose | 1.00 | 1.09 | 1.11 | 1.37 | 1.53 | 1.75 | 0.75 | 1.71 | 1.82 | 1.82 | 2.00 | 2.15 | |
| D-Mannitol | 1.00 | 0.96 | 0.94 | 1.00 | 0.99 | 0.91 | 0.34 | 0.81 | 0.74 | 0.79 | 0.74 | 0.64 | |
| Turanose | 1.00 | 0.23 | 0.31 | 0.36 | 0.40 | 0.55 | 0.49 | 0.44 | 0.51 | 0.57 | 0.57 | 0.60 | |
| D-Tagatose | 1.00 | 1.07 | 1.01 | 0.88 | 0.28 | 0.29 | 0.49 | 0.32 | 0.34 | 0.36 | 0.37 | 0.39 | |
| L-Fucose | 1.00 | 0.10 | 0.20 | 0.18 | 0.18 | 0.22 | 0.26 | 0.25 | 0.27 | 0.26 | 0.24 | 0.26 | |
| a-D-Lactose | 1.00 | 0.44 | 0.58 | 0.65 | 0.69 | 0.82 | 0.63 | 0.88 | 0.94 | 1.01 | 1.02 | 0.92 | |
| Tricarballylic Acid | 1.00 | 1.07 | 1.03 | 0.79 | 1.20 | 0.72 | 0.35 | 0.89 | 0.54 | 0.83 | 0.74 | 0.59 | |
| Adonitol | 1.00 | 0.57 | 0.78 | 0.93 | 0.98 | 1.16 | 1.35 | 1.28 | 1.40 | 1.55 | 1.43 | 1.46 | |
| L-Rhamnose | 1.00 | 1.28 | 1.52 | 1.49 | 1.66 | 2.12 | 2.53 | 1.91 | 2.01 | 2.71 | 2.22 | 2.36 | |
| a-Keto-Glutaric Acid | 1.00 | 1.29 | 1.54 | 1.40 | 1.45 | 1.52 | 1.98 | 1.61 | 1.69 | 1.80 | 1.93 | 2.00 | |
| a-Keto-Butyric Acid | 1.00 | 1.10 | 1.17 | 1.24 | 1.25 | 1.28 | 1.49 | 1.33 | 1.34 | 1.36 | 1.37 | 1.39 | |
| g-Hydroxy-Butyric Acid | 1.00 | 1.24 | 1.38 | 1.92 | 1.86 | 1.71 | 0.79 | 1.88 | 1.94 | 2.09 | 2.05 | 2.76 | |
| 2,3-Butanediol | 1.00 | 1.23 | 1.54 | 1.61 | 1.58 | 1.83 | 0.83 | 1.84 | 1.93 | 2.09 | 2.19 | 2.33 | |
| Palatinose | 1.00 | 1.31 | 1.79 | 1.68 | 1.81 | 2.10 | 2.44 | 2.18 | 2.16 | 2.14 | 1.94 | 1.44 | |
| 3-Methyl Glucose | 1.00 | 1.48 | 1.54 | 1.58 | 1.60 | 1.97 | 2.15 | 2.30 | 1.94 | 2.13 | 2.45 | 2.35 | |
| m-Tartaric Acid | 1.00 | 1.39 | 1.72 | 2.14 | 2.16 | 2.42 | 3.24 | 2.70 | 2.82 | 2.95 | 2.65 | 2.75 | 3 |
| Chondroitin Sulfate C | 1.00 | 1.60 | 1.94 | 2.10 | 2.19 | 2.50 | 3.28 | 2.63 | 2.56 | 2.92 | 3.00 | 2.49 | |
| Maltitol | 1.00 | 1.76 | 2.36 | 2.82 | 3.07 | 3.80 | 3.52 | 4.49 | 4.77 | 5.77 | 5.24 | 5.98 | |
| 3-Hydroxy 2-Butanone | 1.00 | 1.49 | 1.75 | 1.64 | 1.71 | 2.01 | 0.48 | 1.80 | 1.86 | 7.44 | 7.39 | 2.14 | |
| Adenosine | 1.00 | 2.85 | 1.34 | 1.67 | 1.86 | 2.21 | 2.50 | 2.97 | 3.10 | 3.78 | 3.46 | 3.32 | |
| D-Malic Acid | 1.00 | 1.49 | 2.03 | 2.06 | 2.25 | 2.63 | 2.19 | 2.87 | 3.00 | 3.06 | 3.20 | 3.52 | |
| Gentio-biose | 1.00 | 1.71 | 2.34 | 2.83 | 3.01 | 3.72 | 4.46 | 4.35 | 4.57 | 5.20 | 5.59 | 5.94 | |
| a-Methyl-D-Mannoside | 1.00 | 1.26 | 1.58 | 1.74 | 1.89 | 2.33 | 2.77 | 2.46 | 2.13 | 2.16 | 2.95 | 2.58 | |
| D-Fructose | 1.00 | 2.31 | 2.22 | 1.77 | 2.00 | 2.59 | 1.51 | 3.18 | 3.38 | 4.01 | 3.99 | 4.24 | |
| L-Glucose | 1.00 | 1.65 | 2.20 | 2.64 | 2.83 | 3.52 | 3.82 | 3.51 | 3.55 | 3.76 | 3.89 | 4.25 | |
| m-Inositol | 1.00 | 1.63 | 2.13 | 3.87 | 3.78 | 3.07 | 3.01 | 3.55 | 3.42 | 3.81 | 3.89 | 3.64 | |
| i-Erythritol | 1.00 | 1.76 | 2.33 | 2.67 | 2.83 | 3.31 | 5.19 | 3.78 | 3.84 | 4.30 | 4.08 | 4.22 | |
| Acetic Acid | 1.00 | 2.02 | 2.71 | 3.02 | 3.24 | 3.75 | 3.33 | 4.10 | 4.32 | 4.64 | 3.99 | 4.58 | |
| Hexanoic Acid | 1.00 | 1.35 | 1.47 | 2.74 | 2.80 | 1.18 | 1.04 | 4.15 | 4.11 | 4.10 | 4.13 | 3.16 | |
| L-Sorbose | 1.00 | 1.57 | 2.05 | 2.28 | 2.38 | 2.79 | 4.12 | 2.84 | 2.81 | 2.80 | 3.02 | 2.98 | |
| D-Fucose | 1.00 | 1.61 | 1.96 | 2.02 | 2.15 | 2.65 | 2.11 | 2.19 | 2.49 | 2.69 | 2.78 | 2.97 | |
| Virus | | | | | | | | | | | | | |
| D-(+)-Glucose | 1.00 | 2.25 | 3.59 | 4.41 | 4.97 | 6.52 | 7.36 | 8.16 | 9.07 | 10.76 | 11.26 | 13.34 | 9 |
| D-(+)-Glucose | 1.00 | 2.54 | 4.07 | 5.25 | 5.97 | 7.91 | 9.03 | 10.04 | 11.13 | 13.31 | 13.75 | 14.88 | |
| Maltose | 1.00 | 2.29 | 3.23 | 3.88 | 4.21 | 5.22 | 5.86 | 6.41 | 7.01 | 8.07 | 8.77 | 8.43 | 4 |
| D-Glucose-6-Phosphate | 1.00 | 2.01 | 3.00 | 3.61 | 4.04 | 4.92 | 5.47 | 5.87 | 6.35 | 7.41 | 7.21 | 5.87 | |
| D-Glucose-1-Phosphate | 1.00 | 1.74 | 2.39 | 2.86 | 3.20 | 3.94 | 4.34 | 4.56 | 4.91 | 5.77 | 5.49 | 6.50 | |
| b-Methyl-D-Glucoside | 1.00 | 2.00 | 2.80 | 3.24 | 3.45 | 3.99 | 4.32 | 4.57 | 4.86 | 5.41 | 5.67 | 6.22 | |

TABLE 3-continued

| | | | | | | | | | | | | | |
|---|---|---|---|---|---|---|---|---|---|---|---|---|---|
| D,L-a-Glycerol Phosphate | 1.00 | 2.01 | 2.64 | 3.07 | 3.24 | 3.72 | 3.99 | 4.18 | 4.43 | 4.93 | 5.12 | 5.62 | |
| Glycerol | 1.00 | 2.05 | 2.67 | 3.09 | 3.24 | 3.55 | 3.71 | 3.91 | 4.11 | 4.51 | 4.63 | 5.09 | |
| Xylitol | 1.00 | 1.69 | 2.39 | 3.14 | 3.34 | 3.95 | 4.25 | 4.50 | 4.55 | 5.13 | 4.85 | 5.48 | |
| N-Acetyl-D-Glucosamine | 1.00 | 2.25 | 3.27 | 3.85 | 4.12 | 4.99 | 5.27 | 5.67 | 6.03 | 6.65 | 6.45 | 5.53 | |
| a-Methyl-D-Glucoside | 1.00 | 1.29 | 1.66 | 1.87 | 1.99 | 2.31 | 2.50 | 2.67 | 2.77 | 3.14 | 3.10 | 3.31 | 2 |
| Salicin | 1.00 | 0.77 | 1.06 | 1.26 | 1.36 | 1.64 | 1.76 | 1.87 | 2.01 | 2.26 | 2.38 | 2.62 | |
| D-Glucosaminic Acid | 1.00 | 1.69 | 2.21 | 2.51 | 2.69 | 3.09 | 3.31 | 3.47 | 3.57 | 3.89 | 3.88 | 3.32 | |
| Butyric Acid | 1.00 | 1.82 | 2.27 | 2.61 | 2.66 | 2.95 | 2.88 | 2.62 | 2.60 | 2.89 | 3.02 | 3.20 | |
| D-Glucuronic Acid | 1.00 | 1.44 | 1.90 | 2.18 | 2.37 | 2.79 | 2.96 | 3.14 | 3.24 | 3.62 | 3.66 | 3.99 | |
| N-Acetyl-D-Mannosamine | 1.00 | 1.40 | 1.88 | 2.13 | 2.22 | 2.60 | 2.70 | 2.89 | 3.09 | 3.29 | 3.34 | 3.55 | |
| Lactitol | 1.00 | 1.61 | 2.20 | 2.54 | 2.73 | 3.16 | 3.38 | 3.55 | 3.76 | 4.11 | 4.31 | 4.66 | |
| Melibionic Acid | 1.00 | 3.52 | 3.58 | 3.59 | 3.66 | 3.34 | 3.22 | 3.05 | 2.89 | 2.67 | 1.66 | 2.18 | |
| D-Melibiose | 1.00 | 3.65 | 3.76 | 3.77 | 3.78 | 3.62 | 3.58 | 3.59 | 3.20 | 1.54 | 1.54 | 1.63 | |
| D-Galactose | 1.00 | 0.91 | 1.21 | 1.47 | 1.60 | 1.89 | 2.03 | 2.16 | 2.29 | 2.54 | 2.63 | 2.86 | |
| n-acetyl-neuraminic acid | 1.00 | 4.77 | 3.35 | 3.95 | 3.57 | 1.43 | 2.71 | 1.58 | 1.60 | 1.61 | 1.82 | 2.21 | |
| Succinamic Acid | 1.00 | 1.45 | 1.65 | 1.88 | 1.85 | 2.03 | 2.14 | 2.22 | 2.30 | 2.41 | 2.37 | 2.51 | |
| Succinic Acid | 1.00 | 1.69 | 2.01 | 2.37 | 2.37 | 2.54 | 2.73 | 2.78 | 2.85 | 3.06 | 2.98 | 3.12 | |
| Mono Methyl Succinate | 1.00 | 1.44 | 1.71 | 1.97 | 2.04 | 2.16 | 2.33 | 2.40 | 2.45 | 2.58 | 2.55 | 2.67 | |
| L-Malic Acid | 1.00 | 1.48 | 1.19 | 1.27 | 3.32 | 1.59 | 1.42 | 2.93 | 3.48 | 1.72 | 2.20 | 2.05 | |
| g-Amino Butyric Acid | 1.00 | 1.68 | 2.39 | 2.83 | 2.96 | 3.40 | 3.56 | 3.70 | 3.84 | 3.99 | 3.94 | 3.74 | |
| Thymidine | 1.00 | 1.52 | 2.29 | 2.27 | 2.32 | 2.34 | 2.33 | 2.34 | 2.26 | 2.28 | 0.94 | 2.21 | |
| 1,2-Propanediol | 1.00 | 1.95 | 2.44 | 2.83 | 2.94 | 3.29 | 3.55 | 3.75 | 3.87 | 4.24 | 4.34 | 4.75 | |
| 2-Aminoethanol | 1.00 | 1.65 | 2.01 | 2.38 | 2.50 | 2.74 | 2.88 | 3.01 | 3.12 | 3.41 | 3.22 | 3.78 | |
| Citric Acid | 1.00 | 1.54 | 1.94 | 2.21 | 2.31 | 2.64 | 2.74 | 2.85 | 2.95 | 3.10 | 2.94 | 2.81 | |
| Methyl D-Lactate | 1.00 | 2.10 | 2.49 | 2.89 | 2.64 | 2.75 | 2.94 | 3.10 | 3.20 | 3.46 | 3.46 | 3.61 | |
| Methyl Pyruvate | 1.00 | 1.93 | 2.20 | 2.60 | 2.51 | 2.66 | 2.87 | 2.99 | 3.03 | 3.24 | 3.21 | 3.04 | |
| D,L-a-Hydroxy-Butyric Acid | 1.00 | 1.29 | 1.58 | 1.74 | 1.84 | 2.00 | 2.10 | 2.18 | 2.26 | 2.35 | 2.39 | 2.21 | |
| Negative Control | 1.00 | 1.47 | 1.91 | 2.21 | 2.43 | 3.01 | 3.39 | 3.73 | 4.08 | 4.89 | 5.22 | 4.13 | 5 |
| Negative Control | 1.00 | 1.87 | 2.11 | 2.55 | 2.70 | 3.09 | 3.30 | 3.46 | 3.64 | 3.96 | 4.11 | 3.26 | |
| a-Cyclo-dextrin | 1.00 | 1.86 | 2.62 | 2.99 | 3.18 | 3.75 | 4.06 | 4.29 | 4.56 | 4.96 | 5.19 | 4.09 | |
| Glycogen | 1.00 | 1.68 | 2.26 | 2.71 | 2.92 | 3.70 | 4.21 | 4.74 | 5.48 | 3.99 | 4.33 | 4.63 | |
| D-Trehalose | 1.00 | 1.66 | 2.04 | 2.20 | 2.27 | 2.52 | 2.66 | 2.79 | 2.93 | 3.11 | 3.25 | 3.07 | |
| D-Cellobiose | 1.00 | 1.58 | 2.09 | 2.38 | 2.49 | 2.81 | 3.00 | 3.14 | 3.31 | 3.54 | 3.69 | 4.06 | |
| D-Sorbitol | 1.00 | 1.80 | 2.63 | 3.10 | 3.35 | 4.00 | 4.37 | 4.63 | 4.94 | 5.39 | 5.64 | 6.18 | |
| D-Melezitose | 1.00 | 1.67 | 2.39 | 2.73 | 2.88 | 3.35 | 3.57 | 3.77 | 3.98 | 4.49 | 4.69 | 5.01 | |
| Sucrose | 1.00 | 1.64 | 2.25 | 2.51 | 2.58 | 2.99 | 3.11 | 3.22 | 3.41 | 3.83 | 3.87 | 4.04 | |
| Lactulose | 1.00 | 1.68 | 2.24 | 2.56 | 2.71 | 3.13 | 3.31 | 3.50 | 3.70 | 4.05 | 4.25 | 4.63 | |
| Uridine | 1.00 | 0.99 | 1.55 | 1.96 | 2.18 | 2.78 | 3.02 | 3.29 | 3.58 | 4.12 | 4.35 | 4.93 | |
| Inosine | 1.00 | 1.16 | 1.78 | 2.23 | 2.45 | 3.06 | 3.30 | 3.54 | 3.88 | 4.33 | 3.83 | 4.20 | |
| L-Arabinose | 1.00 | 1.79 | 2.45 | 3.01 | 3.10 | 3.49 | 3.66 | 3.82 | 4.01 | 4.41 | 4.50 | 4.78 | |
| b-Methyl-D-Xyloside | 1.00 | 1.92 | 2.38 | 2.79 | 2.82 | 3.12 | 3.28 | 3.39 | 3.52 | 3.77 | 3.87 | 4.01 | |
| L-Lactic Acid (DL) | 1.00 | 1.33 | 1.66 | 2.04 | 2.11 | 2.48 | 2.68 | 2.86 | 3.04 | 3.36 | 3.49 | 3.91 | |
| b-Hydroxy-Butyric Acid | 1.00 | 1.78 | 2.31 | 2.61 | 2.77 | 3.16 | 3.34 | 3.47 | 3.62 | 3.79 | 3.87 | 3.29 | |
| Dextrin | 1.00 | 2.14 | 2.79 | 3.43 | 3.84 | 4.91 | 5.56 | 6.11 | 6.72 | 7.89 | 8.23 | 6.40 | 8 |
| Malto-triose | 1.00 | 2.01 | 3.05 | 3.70 | 4.08 | 5.20 | 5.81 | 6.29 | 6.78 | 7.44 | 6.04 | 6.50 | |
| D-Mannose | 1.00 | 1.49 | 2.09 | 2.68 | 3.06 | 4.10 | 4.57 | 4.94 | 5.47 | 6.51 | 6.80 | 7.75 | |
| D-(+)-Glucose | 1.00 | 0.82 | 1.44 | 1.76 | 1.96 | 2.64 | 2.91 | 3.23 | 3.59 | 4.21 | 4.43 | 5.05 | 10 |
| Negative Control | 1.00 | 9.15 | 2.47 | 9.51 | 8.01 | 3.75 | 9.68 | 3.53 | 3.69 | 3.94 | 4.08 | 6.12 | 6 |
| Stachyose | 1.00 | 1.42 | 1.76 | 1.96 | 2.07 | 4.65 | 5.10 | 3.71 | 3.40 | 3.17 | 2.89 | 4.13 | 7 |
| a-Methyl-D-Galactoside | 1.00 | 2.91 | 1.88 | 1.16 | 1.24 | 1.43 | 1.51 | 1.59 | 1.67 | 1.83 | 1.89 | 2.05 | 1 |
| Pectin | 1.00 | 3.25 | 2.85 | 0.75 | 0.80 | 0.91 | 0.95 | 1.00 | 1.05 | 1.15 | 1.17 | 1.27 | |

TABLE 3-continued

| | | | | | | | | | | | | | |
|---|---|---|---|---|---|---|---|---|---|---|---|---|---|
| Acetoacetic Acid | 1.00 | 1.26 | 1.40 | 1.48 | 1.54 | 1.64 | 1.67 | 1.71 | 1.74 | 1.81 | 1.74 | 1.81 | |
| Mannan | 1.00 | 1.03 | 1.25 | 1.28 | 1.35 | 1.41 | 1.44 | 1.49 | 1.49 | 1.61 | 1.64 | 1.76 | |
| Propionic Acid | 1.00 | 1.23 | 0.70 | 0.83 | 0.93 | 1.08 | 1.15 | 1.17 | 1.18 | 1.32 | 1.11 | 1.26 | |
| D-Arabinose | 1.00 | 0.65 | 0.90 | 1.03 | 1.07 | 1.22 | 1.29 | 1.37 | 1.33 | 1.34 | 1.38 | 1.58 | |
| Pyruvic Acid | 1.00 | 1.27 | 0.82 | 0.94 | 1.20 | 1.10 | 1.09 | 1.06 | 0.67 | 0.65 | 0.75 | 0.61 | |
| b-Methyl-D-Galactoside | 1.00 | 0.74 | 0.95 | 1.11 | 1.18 | 1.36 | 1.45 | 1.52 | 1.60 | 1.76 | 1.81 | 1.96 | |
| D-Fructose-6-Phosphate | 1.00 | 0.59 | 0.75 | 0.87 | 0.94 | 1.11 | 1.18 | 1.27 | 1.35 | 1.49 | 1.55 | 1.65 | |
| Sedoheptulosan | 1.00 | 1.49 | 1.48 | 1.46 | 1.43 | 1.30 | 1.36 | 1.39 | 1.49 | 1.58 | 1.48 | 1.65 | |
| D-Raffinose | 1.00 | 0.68 | 0.59 | 0.55 | 0.49 | 1.98 | 0.54 | 1.92 | 1.77 | 1.74 | 1.15 | 1.53 | |
| D-Mannitol | 1.00 | 0.20 | 0.27 | 0.32 | 0.34 | 0.40 | 0.42 | 0.44 | 0.47 | 0.52 | 0.53 | 0.57 | |
| Turanose | 1.00 | 0.20 | 0.28 | 0.34 | 0.36 | 0.44 | 0.48 | 0.51 | 0.56 | 0.61 | 0.60 | 0.55 | |
| D-Tagatose | 1.00 | 0.17 | 0.24 | 0.28 | 0.30 | 0.36 | 0.39 | 0.42 | 0.44 | 0.49 | 0.51 | 0.48 | |
| L-Fucose | 1.00 | 0.21 | 0.28 | 0.33 | 0.35 | 0.42 | 0.45 | 0.47 | 0.50 | 0.54 | 0.57 | 0.61 | |
| a-D-Lactose | 1.00 | 0.17 | 0.22 | 0.26 | 0.28 | 0.33 | 0.35 | 0.37 | 0.39 | 0.42 | 0.41 | 0.39 | |
| Tricarballylic Acid | 1.00 | 0.20 | 0.25 | 0.29 | 0.29 | 0.32 | 0.34 | 0.36 | 0.36 | 0.39 | 0.40 | 0.38 | |
| Adonitol | 1.00 | 0.21 | 0.26 | 0.29 | 0.31 | 0.34 | 0.36 | 0.38 | 0.39 | 0.42 | 0.44 | 0.43 | |
| L-Rhamnose | 1.00 | 0.16 | 0.22 | 0.25 | 0.28 | 0.32 | 0.34 | 0.36 | 0.38 | 0.41 | 0.43 | 0.46 | |
| a-Keto-Glutaric Acid | 1.00 | 0.28 | 0.37 | 0.45 | 0.46 | 0.51 | 0.54 | 0.56 | 0.58 | 0.64 | 0.64 | 0.69 | |
| a-Keto-Butyric Acid | 1.00 | 0.28 | 0.29 | 0.30 | 0.31 | 0.32 | 0.32 | 0.33 | 0.33 | 0.34 | 0.34 | 0.34 | |
| g-Hydroxy-Butyric Acid | 1.00 | 0.53 | 0.53 | 0.41 | 0.44 | 0.50 | 0.54 | 0.56 | 0.59 | 0.62 | 0.63 | 0.53 | |
| 2,3-Butanediol | 1.00 | 1.66 | 1.65 | 0.31 | 0.33 | 0.38 | 0.40 | 0.42 | 0.43 | 0.45 | 0.42 | 0.39 | |
| Palatinose | 1.00 | 0.18 | 0.24 | 0.28 | 0.29 | 0.34 | 0.36 | 0.38 | 0.41 | 0.45 | 0.46 | 0.50 | |
| 3-Methyl Glucose | 1.00 | 0.15 | 0.21 | 0.25 | 0.27 | 0.32 | 0.35 | 0.37 | 0.39 | 0.44 | 0.45 | 0.50 | |
| m-Tartaric Acid | 1.00 | 1.50 | 1.66 | 1.90 | 1.96 | 2.05 | 2.17 | 2.23 | 2.28 | 2.43 | 2.40 | 2.41 | 3 |
| Chondroitin Sulfate C | 1.00 | 1.22 | 1.41 | 1.45 | 1.55 | 1.62 | 1.61 | 1.63 | 1.65 | 1.72 | 1.69 | 1.75 | |
| Maltitol | 1.00 | 1.05 | 1.03 | 1.37 | 0.98 | 0.88 | 0.89 | 0.92 | 0.96 | 1.01 | 1.08 | 1.16 | |
| 3-Hydroxy 2-Butanone | 1.00 | 1.24 | 1.65 | 2.42 | 2.37 | 2.39 | 2.28 | 2.37 | 2.01 | 2.18 | 2.16 | 2.35 | |
| Adenosine | 1.00 | 1.39 | 1.23 | 1.60 | 1.77 | 1.96 | 2.16 | 2.38 | 2.56 | 2.88 | 2.56 | 2.60 | |
| D-Malic Acid | 1.00 | 2.26 | 2.49 | 2.54 | 2.71 | 2.61 | 1.75 | 1.82 | 1.98 | 1.95 | 2.27 | 2.21 | |
| Gentio-biose | 1.00 | 1.23 | 1.38 | 1.44 | 1.47 | 1.55 | 1.62 | 1.66 | 1.72 | 1.79 | 1.85 | 1.99 | |
| a-Methyl-D-Mannoside | 1.00 | 0.38 | 0.54 | 0.64 | 0.69 | 0.83 | 0.89 | 0.93 | 0.99 | 1.10 | 1.14 | 1.24 | |
| D-Fructose | 1.00 | 0.44 | 0.58 | 0.71 | 0.79 | 1.00 | 1.09 | 1.17 | 1.26 | 1.43 | 1.52 | 1.70 | |
| L-Glucose | 1.00 | 0.29 | 0.39 | 0.45 | 0.49 | 0.57 | 0.61 | 0.64 | 0.68 | 0.76 | 0.76 | 0.86 | |
| m-Inositol | 1.00 | 0.51 | 0.66 | 0.77 | 0.81 | 0.94 | 0.99 | 1.04 | 1.10 | 1.20 | 1.24 | 1.34 | |
| i-Erythritol | 1.00 | 0.23 | 0.29 | 0.32 | 0.34 | 0.39 | 0.41 | 0.43 | 0.45 | 0.49 | 0.50 | 0.53 | |
| Acetic Acid | 1.00 | 0.21 | 0.28 | 0.32 | 0.34 | 0.38 | 0.41 | 0.40 | 0.41 | 0.40 | 0.40 | 0.46 | |
| Hexanoic Acid | 1.00 | 0.25 | 0.28 | 0.31 | 0.33 | 0.36 | 0.37 | 0.37 | 0.38 | 0.36 | 0.40 | 0.41 | |
| L-Sorbose | 1.00 | 0.18 | 0.23 | 0.26 | 0.28 | 0.32 | 0.34 | 0.37 | 0.38 | 0.41 | 0.41 | 0.48 | |
| D-Fucose | 1.00 | 0.66 | 0.33 | 0.67 | 0.64 | 0.62 | 0.65 | 0.65 | 0.60 | 0.52 | 0.57 | 0.61 | |

| Metabolite | p-value (Two-tailed) | K-means cluster | Pathway |
|---|---|---|---|
| D-(+)-Glucose | <0.0001 | 9 | Glycolysis |
| D-(+)-Glucose | <0.0003 | | Glycolysis |
| Maltose | <0.0001 | 4 | Carbohydrate Metabolism |
| D-Glucose-6-Phosphate | <0.0001 | | Glycolysis And Pentose phosphate pathway |
| D-Glucose-1-Phosphate | <0.0001 | | Glycolysis And Pentose phosphate pathway |
| b-Methyl-D-Glucoside | <0.008 | | Glucose Monosaccharide (Microbial Metabolite) |
| D,L-a-Glycerol Phosphate | <0.0001 | | Glycolysis |
| Glycerol | <0.0001 | | Galactose Metabolism Glycerolipid Metabolism |
| Xylitol | <0.0001 | | Sugar Alcohol (Plant Metabolite) |
| N-Acetyl-D-Glucosamine | <0.0001 | | Monosaccharide derivative of glucose (Microbial Metabolite) |
| a-Methyl-D-Glucoside | <0.0001 | 2 | Monosaccharide from Glucose (Microbial Metabolite) |
| Salicin | <0.0001 | | β-glucoside alcohol (Plant Metabolite) |
| D-Glucosaminic Acid | <0.0001 | | Pentose phosphate pathway (Microbial Metabolite) |
| Butyric Acid | <0.0001 | | Fatty Acid (Microbial Metabolite) |

TABLE 3-continued

| | | | |
|---|---|---|---|
| D-Glucuronic Acid | <0.0008 | | Xenobiotic metabolism (Microbial Metabolite) |
| N-Acetyl-D-Mannosamine | <0.0001 | | Amino Sugar Metabolism |
| Lactitol | <0.0001 | | Sugar Alcohol (Microbial Metabolite) |
| Melibionic Acid | <0.0001 | | Carbohydrate (Microbial Metabolite) |
| D-Melibiose | <0.0008 | | Disaccharide (Microbial Metabolite) |
| D-Galactose | NS | | Galactose Metabolism Lactose Degradation Nucleotide Sugars Metabolism |
| n-acetyl-neuraminic acid | <0.0001 | | Aminosugars metabolism |
| Succinamic Acid | <0.0001 | | TCA cycle (Plant Metabolite) |
| Succinic Acid | <0.0001 | | Citric Acid Cycle |
| Mono Methyl Succinate | <0.0001 | | Citric Acid Cycle |
| L-Malic Acid | 0.01 | | Citric Acid Cycle |
| g-Amino Butyric Acid | 0.001 | | Glutamate Metabolism |
| Thymidine | 0.001 | | Pyrimidine Metabolism |
| 1,2-Propanediol | <0.0001 | | Pyruvate Metabolism |
| 2-Aminoethanol | <0.0001 | | Phospholipid metabolism |
| Citric Acid | <0.0001 | | Citric Acid Cycle |
| Methyl D-Lactate | <0.005 | | Pyruvate Metabolism |
| Methyl Pyruvate | <0.0001 | | Glycine, Serine & Methionine Metabolism |
| D,L-a-Hydroxy-Butyric Acid | <0.0004 | | Ketone Body Metabolism & glutathione synthesis |
| Negative Control | NS | 5 | Negative Control |
| Negative Control | NS | | Negative Control |
| a-Cyclo-dextrin | NS | | Dietary fiber (Microbial Metabolite) |
| Glycogen | NS | | Starch and Sucrose Metabolism |
| D-Trehalose | NS | | Starch and Sucrose metabolism (Microbial Metabolite) |
| D-Cellobiose | NS | | Starch and Sucrose metabolism (Microbial Metabolite) |
| D-Sorbitol | NS | | Fructose and Mannose metabolism (Microbial Metabolite) |
| D-Melezitose | NS | | Fermentation (Plant Metabolite) |
| Sucrose | NS | | Galactose Metabolism Starch and Sucrose Metabolism |
| Lactulose | NS | | Non-digestible Sugar (Microbial Metabolite) |
| Uridine | NS | | Pyrimidine Metabolism |
| Inosine | 0.025 | | Purine Metabolism |
| L-Arabinose | NS | | Pentose and Glucuronate Interconversions (Microbial Metabolite) |
| b-Methyl-D-Xyloside | NS | | Fermentation (Plant Metabolite) |
| L-Lactic Acid (DL) | NS | | Pyruvate Metabolism |
| b-Hydroxy-Butyric Acid | NS | | Ketone Body Metabolism |
| Dextrin | NS | 8 | Starch and Sucrose metabolism (Microbial Metabolite) |
| Malto-triose | NS | | Starch and Sucrose metabolism (Microbial Metabolite) |
| D-Mannose | NS | | Fructose and Mannose Degradation Galactose Metabolism |
| D-(+)-Glucose | <0.0005 | 10 | Glycolysis |
| Negative Control | 0.025 | 6 | Negative Control |
| Stachyose | <0.005 | 7 | Galactose Metabolism |
| a-Methyl-D-Galactoside | <0.001 | 1 | Fermentation (Microbial Metabolite) |
| Pectin | NS | | Dietary Fiber (Microbial Metabolite) |
| Acetoacetic Acid | NS | | Butyrate Metabolism |
| Mannan | 0.011 | | Mannan-binding Lectin Pathway (Plant Metabolite) |
| Propionic Acid | <0.03 | | Propanoate Metabolism (Microbial Metabolite) |
| D-Arabinose | NS | | Lipopolysaccharide biosynthesis (Microbial Metabolite) |
| Pyruvic Acid | <0.0001 | | Citric Acid Cycle |
| b-Methyl-D-Galactoside | NS | | Fermentation (Microbial Metabolite) |
| D-Fructose-6-Phosphate | <0.006 | | Carbohydrate Metabolism |
| Sedoheptulosan | <0.0001 | | Fermentation (Plant Metabolite) |
| D-Raffinose | NS | | Fermentation (Plant Metabolite) |
| D-Mannitol | <0.0002 | | Sugar Alcohol (Plant Metabolite) |

TABLE 3-continued

| | | | |
|---|---|---|---|
| Turanose | NS | | Starch and Sucrose metabolism (Microbial Metabolite) |
| D-Tagatose | NS | | Component of Galactose, Glycerolipid and Glycosphingolipid metabolism |
| L-Fucose | <0.04 | | Fructose and Mannose Metbolism |
| a-D-Lactose | <0.0001 | | Sugar (Microbial Metabolite) |
| Tricarballylic Acid | <0.0002 | | Citric Acid Cycle Inhibitor (Microbial Metabolite) |
| Adonitol | <0.0001 | | Starch and Sucrose Metabolism |
| L-Rhamnose | <0.0001 | | Deoxy Sugar (Plant Metabolite) |
| a-Keto-Glutaric Acid | <0.0001 | | Citric Acid Cycle |
| a-Keto-Butyric Acid | <0.0001 | | Glycine, Serine & Methionine Metabolism |
| g-Hydroxy-Butyric Acid | <0.0001 | | Fermentation (Microbial Metabolite) |
| 2,3-Butanediol | <0.0001 | | Fermentation (Microbial Metabolite) |
| Palatinose | <0.0001 | | Fermentation (Microbial Metabolite) |
| 3-Methyl Glucose | <0.0001 | | Non-metabolizable Glucose Analogue (Microbial Metabolite) |
| m-Tartaric Acid | NS | 3 | Food Additive |
| Chondroitin Sulfate C | <0.0003 | | Mucopolysaccharide |
| Maltitol | <0.0001 | | Starch and Sucrose metabolism (Microbial Metabolite) |
| 3-Hydroxy 2-Butanone | NS | | Fermentation (Plant Metabolite) |
| Adenosine | NS | | Purine Metabolism |
| D-Malic Acid | NS | | Citric Acid Cycle |
| Gentio-biose | <0.0002 | | Carbohydrate Catabolism (Microbial Metabolite) |
| a-Methyl-D-Mannoside | <0.0001 | | Mannose Metabolism Inhibitor (Microbial Metabolite) |
| D-Fructose | <0.0001 | | Carbohydrate Metabolism |
| L-Glucose | <0.0001 | | Glycolysis Inhibitor (Microbial Metabolite) |
| m-Inositol | <0.0001 | | Inositol Phosphate Metabolism |
| i-Erythritol | <0.0001 | | Sugar Alcohol (Microbial Metabolite) |
| Acetic Acid | <0.0001 | | Pyruvate Metabolism |
| Hexanoic Acid | <0.0001 | | Beta Oxidation of Fatty Acids |
| L-Sorbose | <0.0001 | | Carbohydrate Metablosim (Microbial Metabolite) |
| D-Fucose | <0.0001 | | Glycan Production |

Figure 6B:
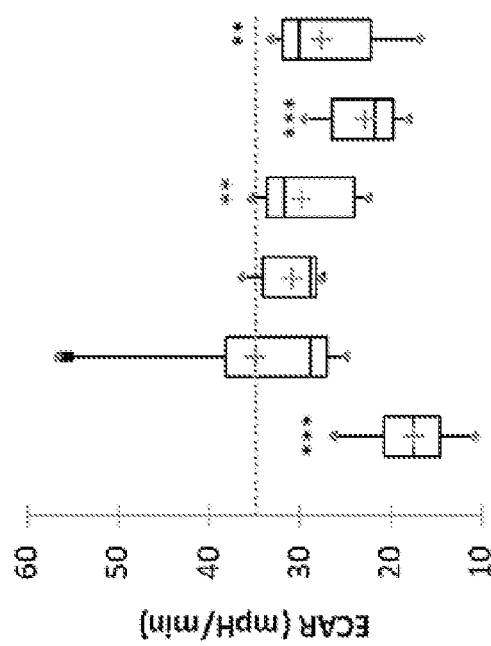
Figure 6C:
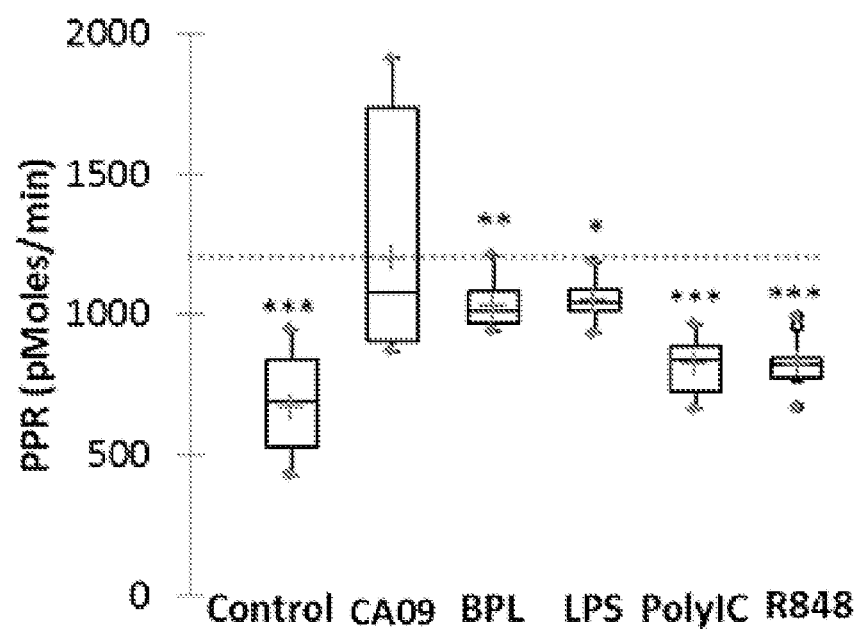

Next, we returned to monitoring metabolite use and product efflux (FIG. 6A). NHBE cells responded to influenza virus with higher ECAR, significantly higher than uninfected cells and more pronounced than DCs (FIG. 6A). OCR and PPR were also higher in infected NHBE cells (FIGS. 6B and 6C). Thus, the coordinated metabolic changes in murine DCs with PR8 infection were replicated in NHBE cells infected with CA09. This led to the conclusion that these metabolic changes may represent a conserved response to mammalian influenza virus infection. Indeed, as with DCs, a clear difference was observed between TLR agonists and viral infection in NHBE cells (FIGS. 4B-D and 6A-C). TLR agonists produced less extracellular acidification, presumably via lactic acid production in glycolysis, than infected cells (FIG. 6A). OCR in infected NHBEs was also higher than in uninfected and LPS-stimulated cells (FIG. 6B). PPR was lower across the panel of agonists than with influenza virus (FIG. 6C). Similar to DCs, TLR agonists produced a metabolic program distinct from viral infection with less magnitude (FIGS. 4B-D and 6A-C). However, while metabolic changes in response to the virus were similar for DCs and NHBE cells, it is noteworthy that the NHBE cell metabolic response to TLR agonists did not mirror the DC response exactly (i.e., PolyIC PPR and R848 ECAR and OCAR). DCs are innate immune cells; thus, without wishing to be bound by theory, their response to innate agonists is likely to be distinct from that of terminally differentiated NHBE cells.

Referring to FIG. 6A-C, NHBE cells were grown and differentiated in 24-well Seahorse plates and left untreated (control), infected for 17 hours at MOI 1 with either viable virus or a p-propiolactone-inactivated virus (CA09 or BPL, respectively) or stimulated with TLR agonists lipopolysaccharide (LPS), polyinosinic polycytidylic acid (PolyIC), or Resiquimod (R848). After treatment, the extracellular acidification rate (ECAR) (6A), oxygen consumption rate (OCR) (6B), and proton production rate (PPR) (6C) of NHBE cells were monitored for 2 hours. Error bars represent standard deviation from the mean of triplicate samples, where data represent 3 independent experiments.

Finally, the NHBE cell response to BPL inactivated CA09 in less extracellular acidification and $O_2$ consumption was explored (FIGS. 6A and 6B). Furthermore, the proton production rate for BPL-inactivated CA09 was significantly lower than with replicating virus and was in keeping with the difference seen in infection with PR8$^{BPL}$ in DCs (FIGS. 6A and 6C). Thus, without wishing to be bound by theory, influenza-induced metabolic reprogramming of DCs with PR8 and NHBE cells with CA09 may require active viral replication.

6. Glucose Utilization in Influenza Virus-Infected Patients

Figure 6D:
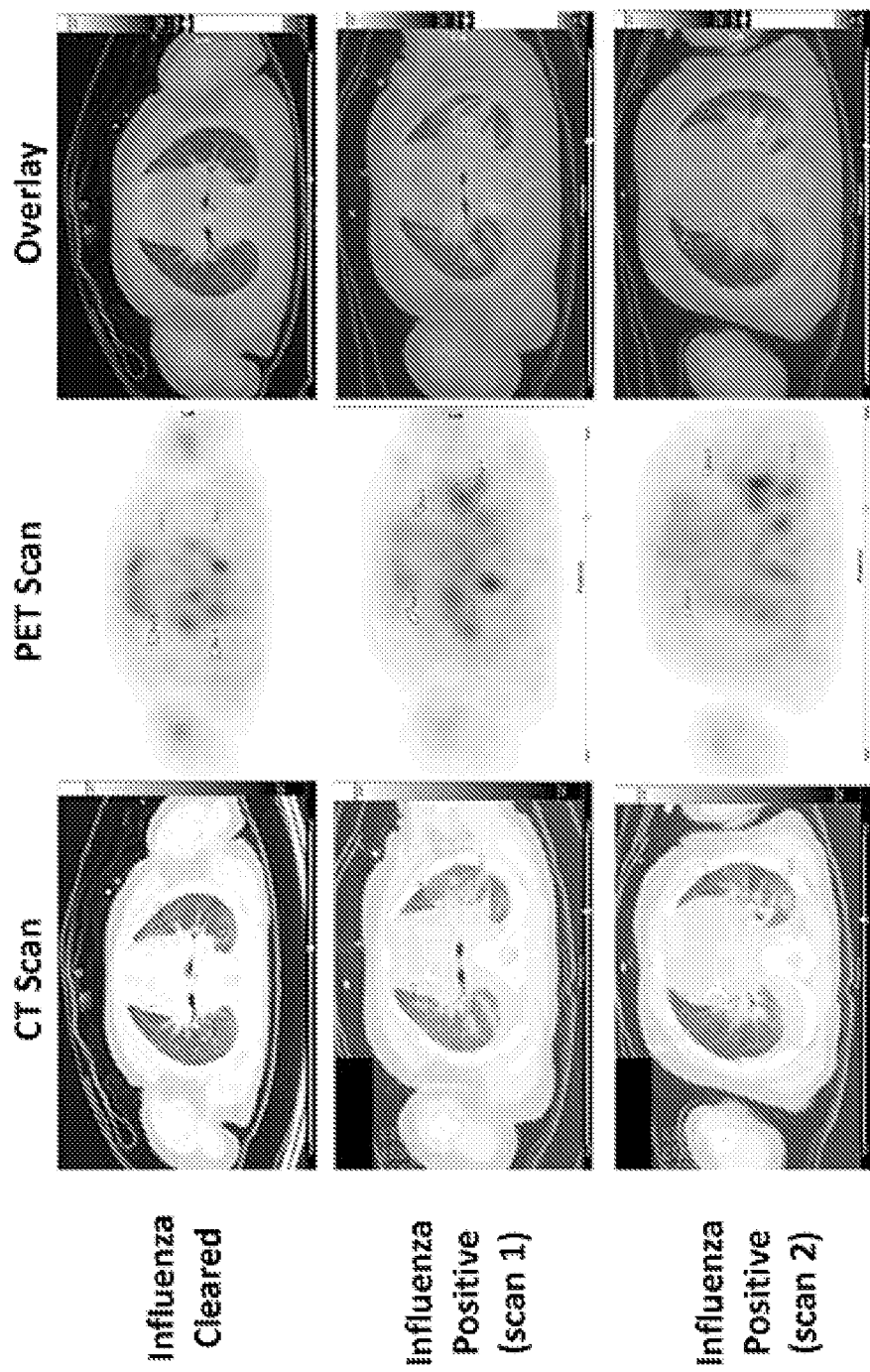

The increase in glucose consumption and other metabolic changes in influenza virus-infected primary NHBE cells led to the investigation of whether this phenomenon could be seen directly in vivo. Diffuse fluordeoxyglucose (FDG)

uptake in the lung of a 32-year-old man with mediastinal bulky non-Hodgkin lymphoma and an influenza-like infection was reported, but the findings were inconclusive as it was based on a single positron emission tomography (PET) scan (Intriago, B., et al. (2009) Clinical nuclear medicine 34: 737-738). Thus, pediatric patients who had PET scans in tandem with 3-dimensional imaging by computed tomography (CT) shortly after influenza A infection was diagnosed by PCR were identified and followed 2 months after clearance of the infection. One patient was a 4-year-old female admitted for chemotherapy to treat neuroblastoma in the pelvic region. The top row of images shows healthy dark lung tissue surrounding the white area corresponding to the heart in the CT scan, while the PET scan has normal FDG uptake in the heart (i.e., grey circle in center of scan) and minimal background in the surrounding lungs (FIG. 6D). In contrast, the middle and bottom row of infected patient images has visible white patches of lung inflammation in the CT scans while the PET scan shows dark puncta as well as diffuse FDG uptake in the influenza positive lungs (FIG. 6D). Colorizing the PET scan and merging these images covers the FDG uptake in the heart and reveals bright red and yellow areas of dense FDG uptake at the site of infection in the lungs (FIG. 6D, overlay). This provides in vivo confirmation of increased glucose use and glycolysis in humans, analogous to the findings in infected NHBE cells (see Table 2 and FIG. 6A). Densitometry of glucose uptake in the influenza virus-infected patient's lungs was significantly higher (p=0.03) than in the influenza cleared follow up scan 8 weeks later (Table 4).

Referring to FIG. 6D, a female patient 4 years old had symptoms and was found positive for influenza A by PCR. She underwent CT/PET scanning 24 hours later and 2 months later (influenza-positive and cleared, respectively).

Referring to Table 4, regions of interest (ROIs) were selected from the influenza positive (+) or cleared (−) PET scans, and densitometry was analyzed. Mean, minimum, maximum, and median densities are indicated with ROI sizes. The Mann-Whitney U test showed that the density values of the influenza-positive areas were significantly larger than the cleared areas, p=0.037 for mean ROI and p=0.03 for median ROI.

TABLE 4

| Influenza | ROI | Intensity of ROI | | | | Diameter (mm) | Area (cm$^2$) |
|---|---|---|---|---|---|---|---|
| | | Mean | Min. | Max. | Median | | |
| − | 1 | 0.8 | 0.76 | 0.85 | 0.80 (±0.03) | 10 | 0.27 |
| − | 2 | 0.74 | 0.72 | 0.79 | 0.73 (±0.03) | 11 | 0.53 |
| − | 3 | 0.76 | 0.72 | 0.79 | 0.79 (±0.04) | 12 | 0.53 |
| − | 4 | 0.88 | 0.85 | 0.91 | 0.89 (±0.03) | 12 | 0.40 |
| + | 1 | 2.04 | 1.42 | 2.78 | 2.05 (±0.33) | 32 | 4.65 |
| + | 2 | 1.86 | 1.39 | 2.3 | 1.86 (±0.26) | 22 | 2.13 |
| + | 3 | 0.95 | 0.93 | 0.96 | 0.95 (±0.01) | 14 | 0.40 |
| + | 4 | 0.93 | 0.87 | 0.98 | 0.97 (±0.05) | 10 | 0.27 |
| + | 5 | 1.98 | 1.04 | 3.38 | 1.96 (±0.62) | 41 | 6.11 |
| + | 6 | 0.81 | 0.81 | 0.82 | 0.82 (±<0.00) | 8 | 0.13 |
| + | 7 | 0.8 | 0.76 | 0.84 | 0.84 (±<0.00) | 8 | 0.13 |

Chemotherapy before imaging was 5 days of cyclophosphamide and topotecan, which depleted the patient's innate and adaptive immune cells. The complete blood count was low, with white blood cell (WBC) counts, hemoglobin, hematocrit percent, and platelet counts nearing critical levels, requiring aggressive treatment or transfusion (Table 5). Likewise, WBC morphology and red blood cell mean corpuscular volume were low. Virtually all blood cell subtypes' absolute values were low or absent (Table 5). Of note was the absence of band cells, which one would expect to increase in an infected patient in the absence of chemotherapy. The drop in immune cell counts was noteworthy because it suggested that the increased glucose uptake was not a result of local immune cell infiltration or proliferation. Together, these data suggest influenza virus-induced glucose uptake in vivo in human lungs (FIG. 6D, Table 5).

Referring to Table 5, complete blood count and parameters of the patient were taken the day of the CT/PET scan and 48 hours prior. Values considered abnormal are indicated as low (L), high (H), or critical (*). Absolute values of blood cell subtypes are indicated with the changing trend indicated by percent difference from the prior measurement.

TABLE 5

| | Patient Values | Normal Range |
|---|---|---|
| Complete Blood Count (CBC) | | |
| White Blood Cell (mm$^3$) | 2.4 (L) | 4.8-10 |
| Hemoglobin (g/dl) | 8.2 (L)* | 10.6-15.2 |
| Hematocrit (%) | 24.6 (L)* | 32-42 |
| Platelet Count | 44,000 (L) | >150,000 |
| Absolute Neutrophil Count (ANC) | 1,800 | 3,000-5,000 |
| Blood Cell Quality | | |
| White Blood Cell Morphology | Abnormal | Normal |
| Mean Corpuscular Volume (MCV) | 83.9 (L)* | 79-102 |
| Mean Corpuscular Weight of Hemoglobin (MCH) | 28 | 24-30 |
| Mean Corpuscular Hemoglobin Concentration (MCHC) | 33.4 | 30-37 |
| Subtype Percentages | | |
| Segmented Mature Neutrophils (Segs) | 68 (H) | 54-62 |
| Immature Neutrophils (Bands) | 0 | 3-5 |
| Lymphocyte | 27 | 25-33 |
| Monocyte | 5 | 3-7 |
| Eosinophil | 0 (L) | 1-3 |
| Basophil | 0 | 0-0.75 |
| Subtype Absolute Values | | |
| Segmented Mature Neutrophils (Segs) | 1,632 | −57.9 |
| Immature Neutrophils (Bands) | 0 | −100.0 |
| Lymphocyte | 648 (L) | −9.2 |
| Monocyte | 120 (L) | 17.6 |
| Eosinophil | 0 (L) | NC |
| Basophil | 0 (L) | NC |

Figure 7A:
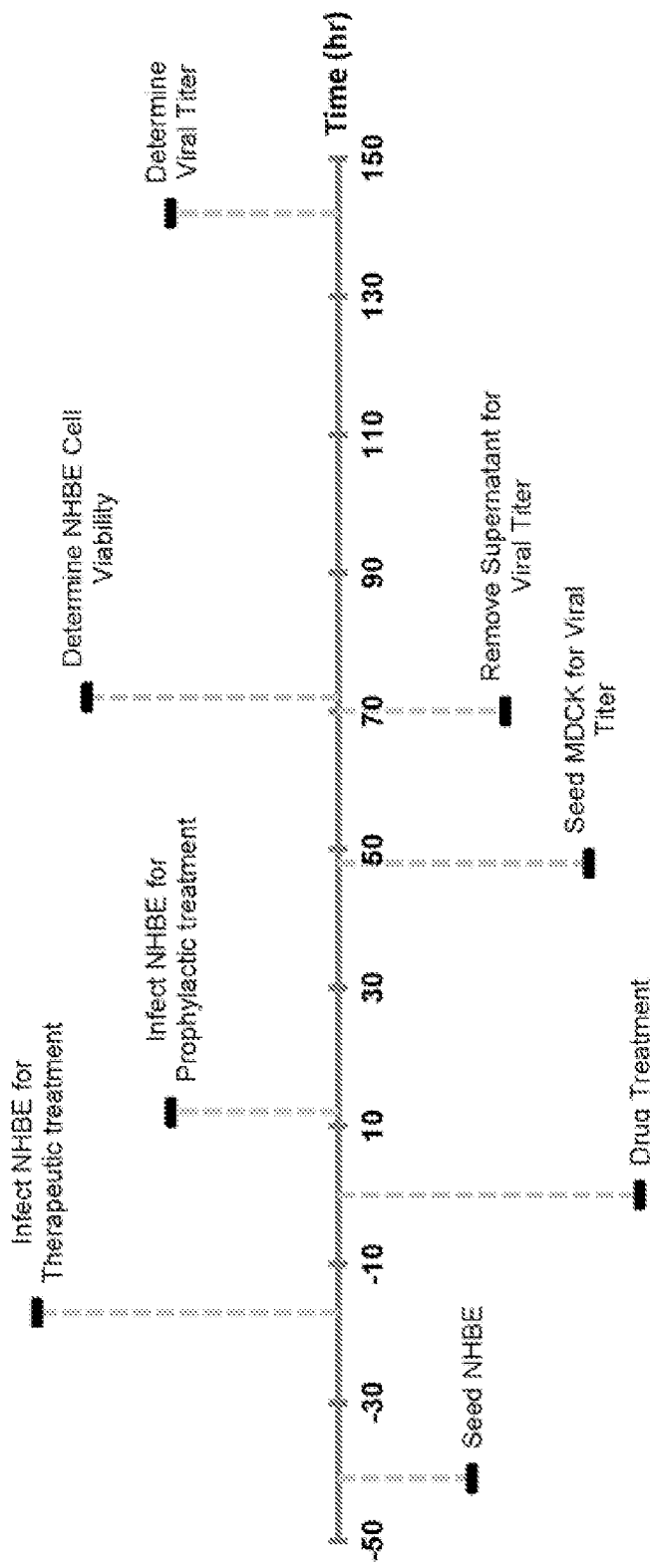
FIGS. 7A and 7B show representative data pertaining to the effects of metabolic pathway inhibitors on influenza infected NHBE cells. Specifically, the experimental timeline of the high-throughput drug screen (7A) and the relative proportion of the mode of action of drugs that altered viability with infection or reduced titer (7B) are shown.

Key: Low (L), High (H);
*Indicates nearing critical values for blood transfusion 7. High-Throughput Screening Reveals Mechanistic and Therapeutic Determinants To determine pathways and proteins critical in the metabolic response to influenza virus, 80 drugs targeting metabolic processes were screened with prophylactic versus therapeutic treatment modalities (i.e., 12 hours prior to versus 17 hours following infection). After either treatment, two endpoints were evaluated: NHBE cell death and viral titer (FIG. 7A). Compounds were considered a hit if they showed significantly increased levels of cell death in either control or virus-infected cells (but not both) or reduced viral titer (Tables 6 and 7). The compounds were clustered based on the pathways of their putative targets and found statistically significant bias in the compounds that had an effect compared to the entire screened set. In particular, PI3K and hexokinase inhibitors were over-represented, while several pathway targets produced no hits (FIG. 7B).

Referring to FIG. 7A, an experimental timeline of the high-throughput drug screening centered on the time of drug treatment is shown.

Figure 7B:
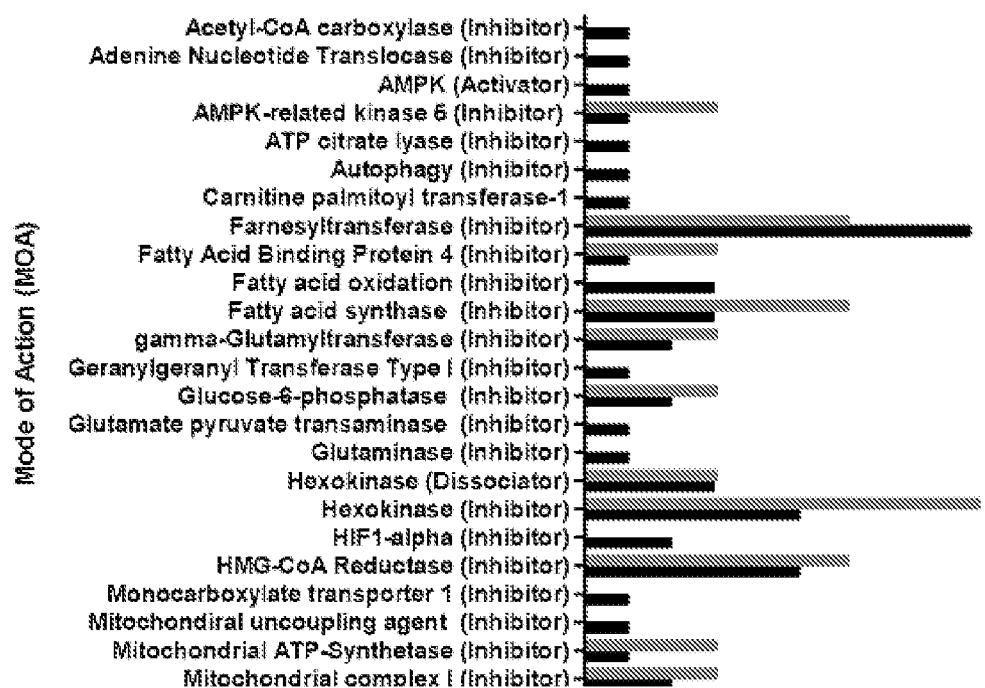
Figure 7B:
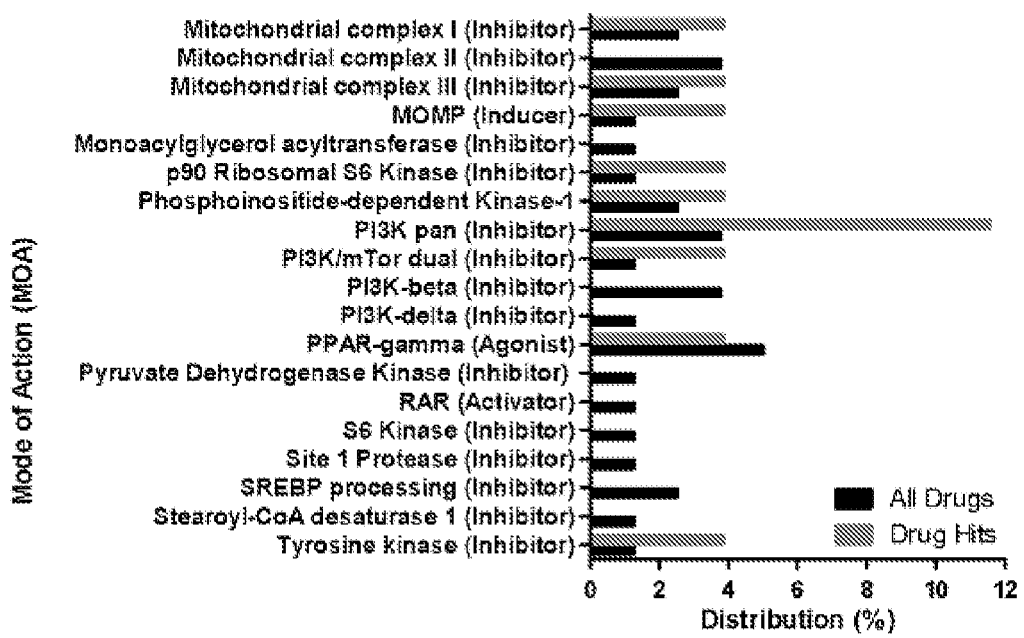

Referring to FIG. 7B, the mode of action of all drugs in the high throughout screen were given relative proportions (black). Then the relative proportions of the mode of action of drugs that altered viability with infection or reduced titer were calculated (red) and their percent distribution plotted.

Referring to Table 6, drugs with differential effects on cell death or titers were selected and drug targets organized by drug target. All drugs that reduced titer in the high throughput titer are listed, with the results of the follow up validation titer indicated ("NC" for no statistical change or "reduced" when titers were statistically lowered by drug treatment).

TABLE 6

| Drug Name | Cell Death | | Viral Titer | |
|---|---|---|---|---|
| | Prophy-lactic | Therapeutic | Prophy-lactic | Therapeutic |
| Betulinic Acid | C > V | C = V | NC | |
| BI-D1870 | C > V | | Reduced | |
| Lonafarnib | C > V | | NC | |
| Tipifarnib | C = V | | NC | |
| BP/(PHEN) | V > C | | | NC |
| OU749 | | | | Reduced |
| 2-deoxyglucose | | | | Reduced |
| D-mannoheptulose | | | | NC |
| Lonidamine | | | | NC |
| C75 | C > V | C = V | | |
| Clotrimazole | C > V | | Reduced | |
| FABP4 Inhibitor | V > C | | Reduced | |
| Pioglitazone | C > V | | NC | |
| Fluvastatin | | | | NC |
| Rosuvastatin | | | | Reduced |
| Trypophostin A 9 | V > C | | | |
| Myxothiazol | C = V | C > V | | NC |
| Oligomycin A | C > V | C > V | | Reduced |
| Rotenone | C > V | C > V | | NC |
| A-Mangostin | C > V | C > V | Reduced | |
| Antimycin A | | | | NC |
| BX-912 | | | | Reduced |
| GDC-0941 | C = V | C = V | | |
| NVP-BEZ235 | C = V | C > V | Reduced | |
| NVP-BKM120 | C = V | C = V | | NC |
| PKI-402 | C = V | C = V | | |
| Imidazolo-oxindole C 16 | | V > C | NC | |

| Drug Name | Drug Target | |
|---|---|---|
| | General | Specific |
| Betulinic Acid | Cell Cycle | Topoisomerase |
| BI-D1870 | Cell Cycle | p90 ribosomal S6 kinase (RSK1, 2, 3 & 4) |
| Lonafarnib | Cell Cycle | Farnesyl-OH-transferase |
| Tipifarnib | Cell Cycle | Farnesyl-OH-transferase |

TABLE 6-continued

| BP/(PHEN) | Glucose Metabolism | Insulin Mimetic |
|---|---|---|
| OU749 | Glutathione Metabolism | Gamma-glutamyl transpeptidase |
| 2-deoxyglucose | Glycolysis | Hexokinase |
| D-mannoheptulose | Glycolysis | Hexokinase |
| Lonidamine | Glycolysis | Hexokinase |
| C75 | Lipid Metabolism | Fatty acid synthase |
| Clotrimazole | Lipid Metabolism | Sterol Synthesis (Fungus) |
| FABP4 Inhibitor | Lipid Metabolism | Fatty Acid Binding Protein |
| Pioglitazone | Lipid Metabolism | PPAR-$\alpha$, $\gamma_1$ & $\gamma_2$ ligand |
| Fluvastatin | Mevalonate Pathway | Hydroxymethylglutaryl-coenzyme A Reductase |
| Rosuvastatin | Mevalonate Pathway | Hydroxymethylglutaryl-coenzyme A Reductase |
| Trypophostin A 9 | Mitochondria | Tyrosine kinase |
| Myxothiazol | Mitochondria Oxidative Phosphorylation | Unbiquinol/bc1 Complex |
| Oligomycin A | Mitochondria Oxidative Phosphorylation | ATP synthase/proton channel F0 |
| Rotenone | Mitochondria Oxidative Phosphorylation | e$^-$ transfer to Ubiquinone |
| A-Mangostin | Mitochondria Oxidative Phosphorylation | Respiratory Complex IV |
| Antimycin A | Mitochondria Oxidative Phosphorylation | Cytochrome C Reductase |
| BX-912 | PI3K/Akt/mTOR Signaling Pathway | 3-Phosphoinositide-dependent Kinase-1 |
| GDC-0941 | PI3K/Akt/mTOR Signaling Pathway | Phosphatidylinositol 3 kinase (p100$\alpha$ & p100$\delta$) |
| NVP-BEZ235 | PI3K/Akt/mTOR Signaling Pathway | PI3K & mTOR (Dual inhibitor) |
| NVP-BKM120 | PI3K/Akt/mTOR Signaling Pathway | PI3K & mTOR (Dual inhibitor) |
| PKI-402 | PI3K/Akt/mTOR Signaling Pathway | Phosphoinositide 3-kinase I, II, III & IV |
| Imidazolo-oxindole C 16 | PI3K/Eif2ak2 Signaling Pathway | RNA-dependent Protein Kinases |

Fifteen compounds differentially affected the viability of infected NHBE cells (Tables 6, 7 and 8). Inhibition of glucose metabolism using 2-Deoxyglucose either reduced viral titers or preferentially killed infected cells, in keeping with the findings that influenza infection increased glycolysis compared to uninfected control cells (Tables 6 and 9). Reduced cell death in infected cells compared to control cells was also observed in several instances including putative mitochondrial inhibitors of ATP-Synthetase, Mitochondrial Complex I and II as well as a MOMP inducer. Without wishing to be bound by theory, this may indicate that the targets of these compounds are either not expressed or not essential for the infected cell compared to a control cell (FIG. 7B and Table 9). Interestingly, the fatty acid synthase and fatty acid binding protein 4 inhibitors reduced titer and altered infected cell survival, while the fatty acid oxidation inhibitors had no effect (FIG. 7B and Table 9).

TABLE 7

| Drug Name | Structure |
|---|---|
| BI-D1870 | 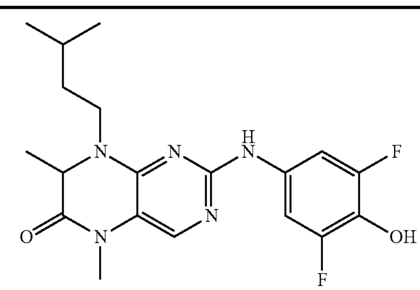 |

TABLE 7-continued
| Drug Name | Structure |
|---|---|
| BP/(PHEN) | 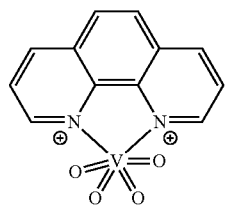 |
| OU749 | 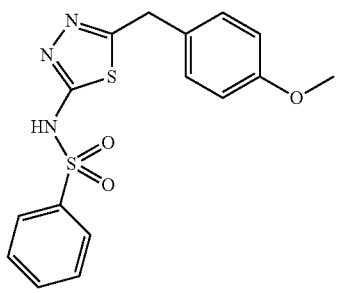 [SMILES: COc1ccc(Cc2nnc(NS(=O)(=O)c3ccccc3)s2)cc1] |
| D-mannoheptulose | 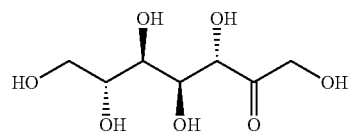 [SMILES: O=C(CO)[C@@H](O)[C@@H](O)[C@H](O)[C@H](O)CO] |
| Lonidamine | 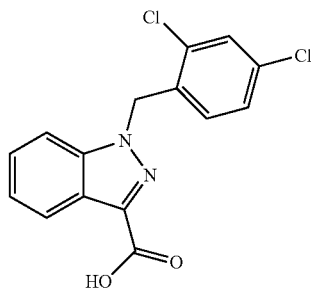 [SMILES: O=C(O)c1nn(Cc2ccc(Cl)cc2Cl)c2ccccc12] |
| C75 | 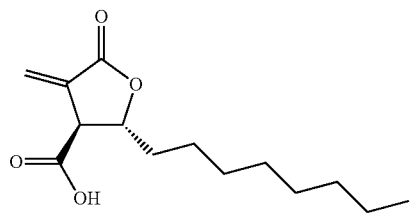 [SMILES: C=C1C(=O)O[C@H](CCCCCCCC)[C@H]1C(=O)O] |
| Clotrimazole | 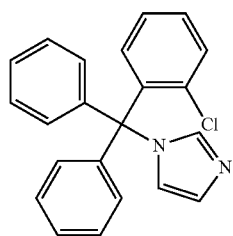 [SMILES: Clc1ccccc1C(c1ccccc1)(c1ccccc1)n1ccnc1] |

TABLE 7-continued
| Drug Name | Structure |
|---|---|
| FABP4 Inhibitor | 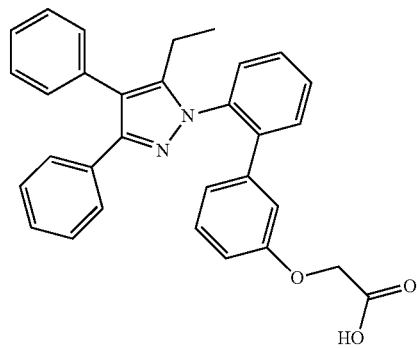 [SMILES: CCc1c(-c2ccccc2)c(-c2ccccc2)nn1-c1ccccc1-c1cccc(OCC(=O)O)c1] |
| Pioglitazone | 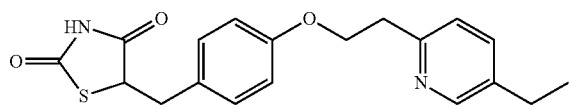 [SMILES: CCc1ccc(CCOc2ccc(CC3SC(=O)NC3=O)cc2)nc1] |
| Rosuvastatin | 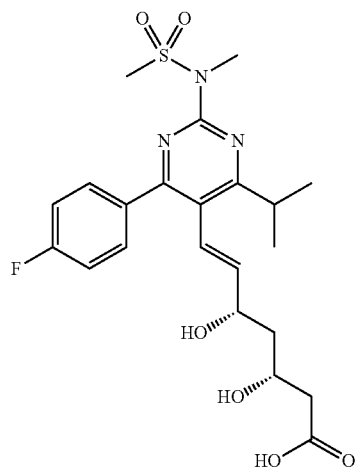 [SMILES: CC(C)c1nc(N(C)S(C)(=O)=O)nc(-c2ccc(F)cc2)c1/C=C/[C@@H](O)C[C@@H](O)CC(=O)O] |
| Trypophostin A 9 | 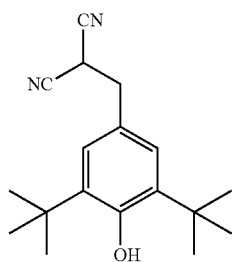 [SMILES: CC(C)(C)c1cc(CC(C#N)C#N)cc(C(C)(C)C)c1O] |

TABLE 7-continued

| Drug Name | Structure |
|---|---|
| Myxothiazol | 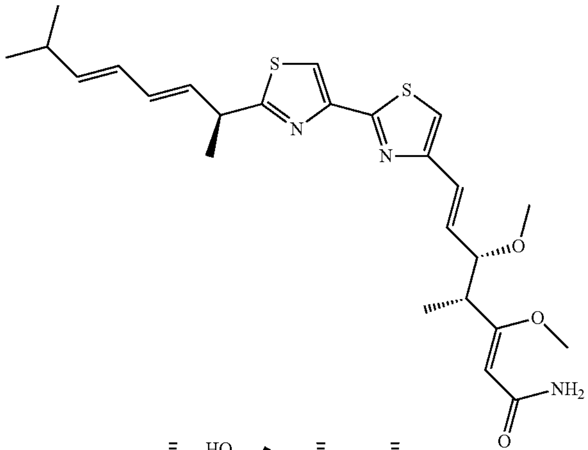 [SMILES: CO/C(=C\C(N)=O)[C@H](C)[C@H](/C=C/c1csc(-c2csc([C@@H](C)/C=C/C=C/C(C)C)n2)n1)OC] |
| Oligomycin A | 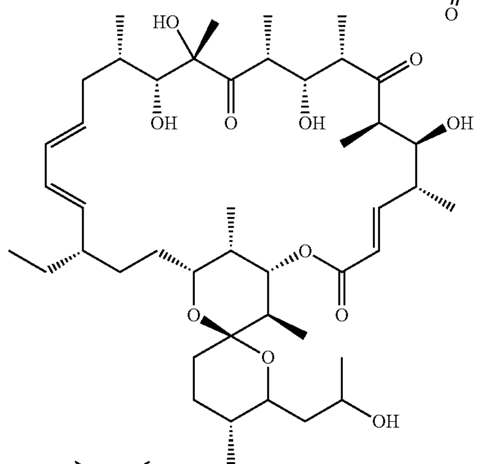 |
| α-Mangostin | 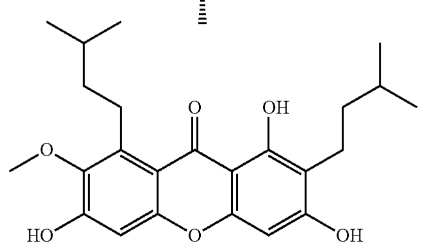 |
| BVP-BEZ235 | 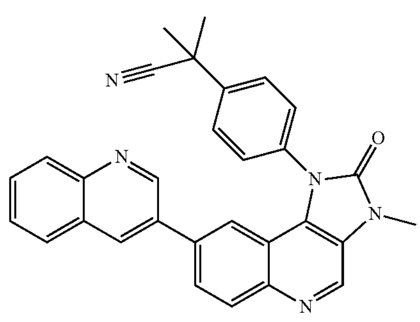 |

Referring to Table 8, NHBE cells were treated 8 hours before infection with CA09 at MOI 1 (prophylactic) or 17 hours after (therapeutic), and infection proceeded for 6 days (similar to in the high-throughput screening). $TCID_{50}$ was determined for each dose by determining the cytopathic effects on MDCK cultures after 72 hours. The $TCID_{50}$ was determined in triplicate cultures of serial dilutions of each drug dose of the virus supernatant and calculated by the Reed-Muench method. The $TCID_{50}$ for DMSO controls was then subtracted from the drug values with the log change indicated for each drug concentration. T-test p-values specify statistical differences between drug and virus-only controls in "n" experiments with the average $TCID_{50}$ of the virus-only control samples indicated.

TABLE 8

| | Prophylactic Drug Treatment | | | | | |
|---|---|---|---|---|---|---|
| | Tipifarnib | | FABP4 Inhibitor | | NVP-BEZ235 | |
| Drug Dose | Change in Titer (+/−) | TCID$_{50}$ (per mL) | Change in Titer (+/−) | TCID$_{50}$ (μM) | Change in Titer (+/−) | TCID$_{50}$ (per mL) |
| 100 μM | + | 0.00 | + | −0.10 | − | −0.91 |
| 10 μM | −− | −1.40 | − | −0.90 | −− | −0.97 |
| 1 μM | −− | −1.04 | −− | −1.34 | − | −0.51 |
| 100 nM | ++ | 0.16 | ++ | 0.07 | + | −0.29 |
| 10 nM | − | −0.60 | − | −0.64 | − | −0.53 |
| 1 nM | −− | −1.04 | − | −0.90 | − | −0.50 |
| 100 pM | − | −0.73 | −− | −1.40 | + | −0.42 |
| 10 pM | + | −0.02 | −− | −1.09 | − | −0.75 |

| | Tipifarnib | FABP4 Inhibitor | NVP-BEZ235 |
|---|---|---|---|
| P value | NS (0.0925) | 0.027 | 0.023 |
| N | 2 | 2 | 9 |
| Control | 2.7 | 2.7 | 5.1 |

| | Prophylactic Drug Treatment | | | | | |
|---|---|---|---|---|---|---|
| | Clotrimazole | | α-Mangostin | | BI-D1870 | |
| Drug Dose | Change in Titer (+/−) | TCID$_{50}$ (per mL) | Change in Titer (+/−) | TCID$_{50}$ (per mL) | Change in Titer (+/−) | TCID$_{50}$ (per mL) |
| 100 μM | −− | −1.07 | − | −0.85 | − | −0.65 |
| 10 μM | − | −0.90 | −− | −1.20 | − | −0.60 |
| 1 μM | −− | −0.95 | − | −0.71 | − | −0.84 |
| 100 nM | − | −0.48 | − | −0.84 | −− | −0.99 |
| 10 nM | − | −0.70 | − | −0.65 | + | −0.20 |
| 1 nM | − | −0.84 | − | −0.54 | − | −0.78 |
| 100 pM | − | −0.85 | − | −0.69 | ++ | −1.18 |
| 10 pM | − | −0.71 | − | −0.74 | − | −0.28 |

| | Clotrimazole | α-Mangostin | BI-D1870 |
|---|---|---|---|
| P value | 0.007 | 0.003 | 0.015 |
| N | 9 | 8 | 2 |
| Control | 5.1 | 4.8 | 2.7 |

| | Prophylactic Drug Treatment | | | | | | | |
|---|---|---|---|---|---|---|---|---|
| | Betulinic Acid | | Imidazole | | Lonafarnib | | Pioglitazone | |
| Drug Dose | Change in Titer (+/−) | TCID$_{50}$ (per mL) | Change in Titer (+/−) | TCID$_{50}$ (per mL) | Change in Titer (+/−) | TCID$_{50}$ (per mL) | Change in Titer (+/−) | TCID$_{50}$ (per mL) |
| 100 μM | − | −0.59 | ++ | 0.56 | −− | −1.25 | + | −0.23 |
| 10 μM | − | −0.61 | − | −0.60 | + | −0.28 | − | −0.73 |
| 1 μM | −− | −0.96 | − | −0.51 | −− | −1.16 | − | −0.49 |
| 100 nM | + | −0.31 | + | −0.31 | + | −0.30 | ++ | 0.10 |
| 10 nM | − | −0.55 | + | −0.42 | + | 0.06 | − | −0.47 |
| 1 nM | − | −0.51 | + | −0.33 | − | −0.56 | − | −0.66 |
| 100 pM | − | −0.63 | −− | −0.92 | + | −0.15 | − | −0.80 |
| 10 pM | + | −0.37 | − | −0.51 | + | −0.04 | + | −0.22 |

| | Betulinic Acid | Imidazole | Lonafarnib | Pioglitazone |
|---|---|---|---|---|
| P value | NS (0.051) | NS (0.062) | NS (0.281) | NS (0.331) |
| N | 5 | 6 | 2 | 5 |
| Control | 3.3 | 5.8 | 2.7 | 3.3 |

| | Therapeutic Drug Treatment | | | | | |
|---|---|---|---|---|---|---|
| | Fluvostatin | | Rotenone | | Myxothiazol | |
| Drug Dose | Change in Titer (+/−) | TCID$_{50}$ (per mL) | Change in Titer (+/−) | TCID$_{50}$ (per mL) | Change in Titer (+/−) | TCID$_{50}$ (per mL) |
| 100 μM | ++ | 0.33 | ++ | 0.05 | ++ | 0.10 |
| 10 μM | − | −0.75 | −− | −1.14 | −− | −1.08 |
| 1 μM | − | −0.51 | − | −0.50 | − | −0.84 |

TABLE 8-continued

| Drug Dose | | | | | | |
|---|---|---|---|---|---|---|
| 100 nM | + | −0.15 | + | −0.07 | −− | −0.88 |
| 10 nM | + | −0.34 | + | −0.04 | − | −0.56 |
| 1 nM | + | −0.18 | −− | −0.90 | − | −0.46 |
| 100 pM | − | −0.50 | + | −0.15 | − | −0.55 |
| 10 pM | + | −0.16 | + | −0.09 | − | −0.65 |

| | Fluvostatin | Rotenone | Myxothiazol |
|---|---|---|---|
| P value | NS (0.501) | NS (0.339) | NS (0.195) |
| n | 6 | 2 | 5 |
| Control | 5.8 | 2.7 | 3.3 |

Therapeutic Drug Treatment

| | Oligomycin | | Rosuvastatin | | 2-deoxyglucose | |
|---|---|---|---|---|---|---|
| Drug Dose | Change in Titer (+/−) | $TCID_{50}$ (per mL) | Change in Titer (+/−) | $TCID_{50}$ (per mL) | Change in Titer (+/−) | $TCID_{50}$ (per mL) |
| 100 μM | + | −0.28 | − | −0.64 | − | −0.85 |
| 10 μM | − | −0.66 | − | −0.79 | −− | −1.01 |
| 1 μM | − | −0.77 | −− | −1.00 | − | −0.87 |
| 100 nM | + | −0.38 | + | −0.41 | + | −0.28 |
| 10 nM | − | −0.60 | − | −0.66 | + | −0.43 |
| 1 nM | − | −0.51 | − | −0.76 | − | −0.48 |
| 100 pM | + | −0.23 | + | −0.15 | + | −0.35 |
| 10 pM | −− | −0.92 | −− | 0.00 | −− | −0.94 |

| | Oligomycin | Rosuvastatin | 2-deoxyglucose |
|---|---|---|---|
| P value | 0.034 | 0.016 | 0.021 |
| n | 8 | 2 | 5 |
| Control | 4.8 | 2.7 | 3.3 |

Therapeutic Drug Treatment

| | OU749 | | BX-912 | | D-mannoheptulose | |
|---|---|---|---|---|---|---|
| Drug Dose | Change in Titer (+/−) | $TCID_{50}$ (per mL) | Change in Titer (+/−) | $TCID_{50}$ (per mL) | Change in Titer (+/−) | $TCID_{50}$ (per mL) |
| 100 μM | + | −0.05 | − | −0.68 | ++ | 0.03 |
| 10 μM | − | −0.46 | −− | −1.31 | + | −0.40 |
| 1 μM | −− | −1.31 | − | −0.78 | −− | −0.88 |
| 100 nM | + | −0.33 | − | −0.50 | + | −0.25 |
| 10 nM | + | −0.35 | + | −0.10 | ++ | 0.00 |
| 1 nM | − | −0.56 | − | −0.56 | − | −0.56 |
| 100 pM | − | −0.65 | − | −0.56 | − | −0.76 |
| 10 pM | ++ | 0.00 | ++ | 0.00 | ++ | 0.00 |

| | OU749 | BX-912 | D-mannoheptulose |
|---|---|---|---|
| P value | 0.047 | 0.036 | NS (0.084) |
| N | 2 | 2 | 2 |
| Control | 2.7 | 2.7 | 2.7 |

Therapeutic Drug Treatment

| | Lonidamine | | bpv-Phen | | BKM-120 | | OU749 | |
|---|---|---|---|---|---|---|---|---|
| Drug Dose | Change in Titer (+/−) | $TCID_{50}$ (per mL) | Change in Titer (+/−) | $TCID_{50}$ (per mL) | Change in Titer (+/−) | $TCID_{50}$ (per mL) | Change in Titer (+/−) | $TCID_{50}$ (per mL) |
| 100 μM | − | −0.65 | + | −0.18 | ++ | 0.37 | ++ | 0.13 |
| 10 μM | + | −0.18 | + | −0.10 | + | −0.07 | + | −0.27 |
| 1 μM | + | −0.24 | + | −0.32 | ++ | 0.08 | + | −0.44 |
| 100 nM | + | −0.24 | + | −0.13 | + | −0.29 | ++ | 0.43 |
| 10 nM | − | −0.67 | − | −0.74 | ++ | 0.00 | + | −0.21 |
| 1 nM | + | −0.54 | + | −0.44 | − | −0.76 | + | −0.25 |
| 100 pM | − | −0.54 | − | −0.54 | + | −0.40 | − | −0.65 |
| 10 pM | −− | −0.94 | − | −0.50 | ++ | 0.00 | ++ | 0.00 |

TABLE 8-continued

|  | Lonidamine | bpv-Phen | BKM-120 | OU749 |
|---|---|---|---|---|
| P value | NS (0.148) | NS (0.228) | NS (0.169) | NS (0.294) |
| N | 5 | 5 | 2 | 2 |
| Control | 3.3 | 3.3 | 2.7 | 2.7 |

Referring to Table 9, the drug library included 80 compounds (FDA-approved drugs and tool compounds directed at well-known metabolic targets) that were screened on NHBE cells. The dose response of each drug was determined (4 nM to 10 μM) as a prophylactic treatment 8 hours before infection or as a therapeutic treatment 17 hours after CA09 infection at MOI 1. After 72 hours, supernatant was removed for viral titer and cell viability determination by ATP production with CellTiter-Glo (Promega, Fitchburg, Wis.). Raw data were $log_{10}$-transformed, and the percentage of inhibition was estimated in relation to previously and empirically determined controls (negative DMSO controls for 0% cell death and positive cycloheximide controls for 100% cell death). The half maximal inhibitory concentration ($IC_{50}$) of each compound is listed with calculated efficacy and hill slope. To determine the viral titer from these cultures, virus-laden supernatant from the drug screen was removed from the NHBE plates, prior to the addition of CellTiter-Glo, and added to confluent MDCK cells. Each drug treatment was titrated to 8 serial dilutions or 3 serial dilutions for uninfected controls (3 384-well plates per drug in triplicate for 3 conditions). After 72 hours, the cytopathic effect was determined with the CellTiter-Glo viability assay. Data processing for the titer (171 384-well plates) was done by determining the area under the curve (AUC) for each titer resulting in the selection of 23 compounds for validation by traditional $TCID_{50}$.

TABLE 9

|  | Prophylactic Treatment | | | | Therapeutic Treatment | | | |
|---|---|---|---|---|---|---|---|---|
|  | Viral Infected | | Control | | Viral Infected | | Control | |
| Drug Name(s) | $IC_{50}$ | Grade | $IC_{50}$ | Grade | $IC_{50}$ | Grade | $IC_{50}$ | Grade |
| 2-METHOXYESTRADIOL\|2-METHOXYESTRADIOL\|2-ME\|2-MEOE2\|2ME2\|NSC-659853\|\|2-METHOXYESTRADIOL\|PANZEM\|PULMOLAR\|2-ME\|2-MEOE2\|2ME2\|NSC-659853\| | $1 \times 10^5$ | D555 | $1 \times 10^5$ | C555 | $1 \times 10^5$ | D555 | $1 \times 10^5$ | D555 |
| TYRPHOSTIN A9\|TYRPHOSTIN A9\|MALONOBEN\|AG-17\|GCP-5126\|NSC-242557\|RG-50872\|SF-6847\|\|TYRPHOSTIN 9\|TRRPHOSTIN A9\|MALONOBEN\|AG-17\|GCP-5126\|NSC-242557\|RG-50872\|SF-6847\| | $1 \times 10^5$ | D555 | $1 \times 10^5$ | D555 | $1 \times 10^5$ | D555 | $1 \times 10^5$ | C555 |
| TOFA\|AC-8632\|RMI-14514\| | $1 \times 10^5$ | C555 | 4 | C555 | $1 \times 10^5$ | D555 | $1 \times 10^5$ | C555 |
| CERULENIN | $1 \times 10^5$ | D555 | $1 \times 10^5$ | D555 | $1 \times 10^5$ | D555 | $1 \times 10^5$ | D555 |
| CLOTRIMAZOLE\|CLOTRIMAZOLE\|AES-210\|BAY-5097\|EVP-3546\|EVPK-0003546\| | $1 \times 10^5$ | C555 | $1 \times 10^5$ | C555 | $1 \times 10^5$ | D555 | $1 \times 10^5$ | D555 |
| BETULIN\|BETULIN\|NSC-4644\|BETULINIC ALCOHOL\|BETULINOL\|TROCHOL\| | $1 \times 10^5$ | D555 | $1 \times 10^5$ | D555 | $1 \times 10^5$ | D555 | $1 \times 10^5$ | D555 |
| RADICICOL\|NSC-294404\|MONORDEN\| | $1 \times 10^5$ | D555 | $1 \times 10^5$ | D555 | $1 \times 10^5$ | D555 | $1 \times 10^5$ | D555 |
| JZL 184 | $1 \times 10^5$ | D555 | $1 \times 10^5$ | D555 | $1 \times 10^5$ | D555 | $1 \times 10^5$ | D555 |
| OU749\| | $1 \times 10^5$ | D555 | $1 \times 10^5$ | D555 | $1 \times 10^5$ | D555 | $1 \times 10^5$ | D555 |
| METFORMIN HYDROCHLORIDE\|METFORMIN HYDROCHLORIDE\|ADX-155\|LA-6023\|SMP-862\| | $1 \times 10^5$ | D555 | $1 \times 10^5$ | D555 | $1 \times 10^5$ | D555 | $1 \times 10^5$ | D555 |
| THENOYLTRIFLUOROACETONE | $1 \times 10^5$ | D555 | $1 \times 10^5$ | D555 | $1 \times 10^5$ | D555 | $1 \times 10^5$ | D555 |
| ALPHA-CYANO-4-HYDROXYCINNAMIC ACID\|ACCA\|CHC\|CHCA\| | $1 \times 10^5$ | C555 | 3 | B314 | $1 \times 10^5$ | D555 | $1 \times 10^5$ | C555 |

TABLE 9-continued

| | Prophylactic Treatment | | | | Therapeutic Treatment | | | |
| | Viral Infected | | Control | | Viral Infected | | Control | |
| Drug Name(s) | $IC_{50}$ | Grade | $IC_{50}$ | Grade | $IC_{50}$ | Grade | $IC_{50}$ | Grade |
|---|---|---|---|---|---|---|---|---|
| 3-BROMOPYRUVATE\|BROMOPYRUVIC ACID | $1 \times 10^5$ | D555 | $1 \times 10^5$ | D555 | $1 \times 10^5$ | D555 | $1 \times 10^5$ | D555 |
| LONAFARNIB\|SCH-066336\|SCH-66336\| | 1.3 | B312 | 1.9 | B312 | $1 \times 10^5$ | D555 | $1 \times 10^5$ | D555 |
| PX-478 | $1 \times 10^5$ | D555 | $1 \times 10^5$ | D555 | $1 \times 10^5$ | D555 | $1 \times 10^5$ | D555 |
| BPV(PHEN) | $1 \times 10^5$ | D555 | $1 \times 10^5$ | D555 | $1 \times 10^5$ | D555 | $5 \times 10^{-3}$ | A141 |
| O-(CARBOXYMETHYL)HYDROXYLAMINE HEMIHYDROCHLORIDE\|AMINOOXYACETATIC ACID | 10 | B314 | 5 | B314 | $1 \times 10^5$ | D555 | $1 \times 10^5$ | C555 |
| C75\|C 75 | $1 \times 10^5$ | D555 | $1 \times 10^5$ | D555 | $1 \times 10^5$ | D555 | $1 \times 10^5$ | C555 |
| PF 429242 | 6 | B314 | $1 \times 10^5$ | C555 | $1 \times 10^5$ | D555 | $1 \times 10^5$ | C555 |
| FABP4 INHIBITOR\|FABP4 INHIBITOR\|ADIPOCYTE FATTY-ACID-BINDING PROTEIN INHIBITOR\| | $1 \times 10^5$ | D555 | $1 \times 10^5$ | C555 | $1 \times 10^5$ | D555 | 4 | B341 |
| FATOSTATIN\|125B11\|FATOSTATIN A\| | $1 \times 10^5$ | D555 | $1 \times 10^5$ | D555 | $1 \times 10^5$ | D555 | $1 \times 10^5$ | D555 |
| FPT INHIBITOR III\|FPT III\| | $1 \times 10^5$ | D555 | $1 \times 10^5$ | D555 | $1 \times 10^5$ | D555 | $1 \times 10^5$ | D555 |
| FTI-2628 | $1 \times 10^5$ | D555 | $1 \times 10^5$ | D555 | $1 \times 10^5$ | D555 | $1 \times 10^5$ | D555 |
| GGTI-2147 | $1 \times 10^5$ | D555 | $1 \times 10^5$ | D555 | $1 \times 10^5$ | D555 | $1 \times 10^5$ | D555 |
| SODIUM DICHLORACETATE\|SODIUM DICHLOROACETATE\|DICHLOROACETIC ACID SODIUM SALT | $1 \times 10^5$ | C555 | $1 \times 10^5$ | C555 | $1 \times 10^5$ | D555 | $1 \times 10^5$ | D555 |
| BENZYL ISOTHIOCYANATE\|BENZYL ISOTHIOCYANATE\|BITC\| | $1 \times 10^5$ | D555 | $1 \times 10^5$ | D555 | $1 \times 10^5$ | D555 | $1 \times 10^5$ | C555 |
| GSK2334470 | $1 \times 10^5$ | D555 | $1 \times 10^5$ | NC555 | $1 \times 10^5$ | D555 | $1 \times 10^5$ | D555 |
| LB 42708 | $1 \times 10^5$ | C555 | $1 \times 10^5$ | B110 | $1 \times 10^5$ | C555 | $4.5 \times 10^{-3}$ | B113 |
| OLIGOMYCIN (A SHOWN)\|OLIGOMYCIN\|OLIGOMYCIN\|\|OLIGOMYCIN A | $1 \times 10^5$ | C555 | $1 \times 10^5$ | C555 | $4 \times 10^{-3}$ | C555 | 1 | NC555 |
| TRETINON\|RETINOIC ACID\|ISOTRETINOIN\|ISOTRETINON\|13-CIS-RETINOIC ACID\|ACCUTANE\|TRETINOIN\|RETINOIC ACID, ALL-TRANS\|9-CIS RETINOIC ACID | $1 \times 10^5$ | D555 | $1 \times 10^5$ | C555 | $1 \times 10^5$ | D555 | $1 \times 10^5$ | C555 |
| METHYL JASMONATE\|JASMONIC ACID METHYL ESTER | $1 \times 10^5$ | D555 | $1 \times 10^5$ | C555 | $1 \times 10^5$ | D555 | $1 \times 10^5$ | D555 |
| TELMISARTAN\|BAY-68-9291\|BIBR-277\|BIBR-277-SE\|YM-086\| | $1 \times 10^5$ | D555 | $1 \times 10^5$ | D555 | $1 \times 10^5$ | D555 | $1 \times 10^5$ | D555 |
| LONIDAMINE\|SJ000287991\|LONIDAMINE\|AF-1890\|KN-228\|TH-070\|DICLONDAZOLIC ACID\|\|LONIDAMINE\| | $1 \times 10^5$ | D555 | $1 \times 10^5$ | D555 | $1 \times 10^5$ | D555 | $1 \times 10^5$ | D555 |
| BI-D1870 | $1 \times 10^5$ | D555 | $1 \times 10^5$ | C555 | $1 \times 10^5$ | D555 | $1 \times 10^5$ | D555 |
| CURCUMIN\|NSC-32982\|CURCUMIN 1\|DIFERULOYLMETHANE\| | $1 \times 10^5$ | D555 | $1 \times 10^{-3}$ | C555 | $1 \times 10^5$ | D555 | $1 \times 10^5$ | D555 |
| 944396-07-0\|NVP-BKM120\|BKM-120\|\|NVP-BKM120\|BKM-120\|BUPARLISIB\| | $1 \times 10^5$ | D555 | $1 \times 10^5$ | NC555 | $1 \times 10^5$ | D555 | $1 \times 10^5$ | D555 |
| CAL-101\|GS-1101\|\|CAL-101\|GS-1101\|IDELALISIB\| | $1 \times 10^5$ | C555 | $1 \times 10^5$ | C555 | $1 \times 10^5$ | C555 | $1 \times 10^5$ | C555 |
| GSK-2636771 | $1 \times 10^5$ | D555 | $1 \times 10^5$ | D555 | $1 \times 10^5$ | D555 | $1 \times 10^5$ | D555 |
| 6-DIAZO-5-OXO-L-NORLEUCINE | $1 \times 10^5$ | D555 | $1 \times 10^5$ | D555 | $1 \times 10^5$ | D555 | $1 \times 10^5$ | D555 |
| 2-DEOXY-D-GLUCOSE\|2-DEOXY-D-GALACTOSE\|2-DEOXY- | $1 \times 10^5$ | D555 | $1 \times 10^5$ | D555 | $1 \times 10^5$ | D555 | $1 \times 10^5$ | D555 |

TABLE 9-continued

| | Prophylactic Treatment | | | | Therapeutic Treatment | | | |
| | Viral Infected | | Control | | Viral Infected | | Control | |
| Drug Name(s) | IC$_{50}$ | Grade | IC$_{50}$ | Grade | IC$_{50}$ | Grade | IC$_{50}$ | Grade |
|---|---|---|---|---|---|---|---|---|
| D-GLUCOSE\|2-DG\|2-DEOXYGLUCOSE\|2-DEOXY-D-GLUCOSE\|ETOMOXIR\|B-877-44\| | $1 \times 10^5$ | D555 | $1 \times 10^5$ | D555 | $1 \times 10^5$ | D555 | $1 \times 10^5$ | D555 |
| FTI-277 TTRIFLUOROACETATE | $1 \times 10^5$ | D555 | $1 \times 10^5$ | D555 | $1 \times 10^5$ | D555 | $1 \times 10^5$ | D555 |
| GDC-0941\|RG-7321\|PICTILISIB\|PICTRELISIB\|GDC-0941\|RG-7321\|PICTILISIB\| | $1 \times 10^5$ | C555 | $1 \times 10^5$ | D555 | $1 \times 10^5$ | D555 | $1 \times 10^5$ | D555 |
| H-CYS-4-ABZ-MET-OH\|FTASE INHIBITOR II | $1 \times 10^5$ | C555 | $1 \times 10^5$ | C555 | $1 \times 10^5$ | C555 | $1 \times 10^5$ | C555 |
| H-CYS-VAL-2-NAL-MET-OH\|FTASE INHIBITOR III | $1 \times 10^5$ | D555 | $1 \times 10^5$ | D555 | $1 \times 10^5$ | D555 | $1 \times 10^5$ | D555 |
| HYDROXYCHLOROQUINE SULFATE | $1 \times 10^5$ | D555 | $1 \times 10^5$ | D555 | $1 \times 10^5$ | D555 | $1 \times 10^5$ | D555 |
| IMIDAZOLO-OXINDOLE PKR INHIBITOR C16 | $1 \times 10^5$ | D555 | $1 \times 10^5$ | C555 | $1 \times 10^5$ | D555 | $7 \times 10^{-2}$ | A141 |
| 5-THIO-D-GLUCOSE | $1 \times 10^5$ | D555 | $1 \times 10^5$ | D555 | $1 \times 10^5$ | D555 | $1 \times 10^5$ | D555 |
| ORLISTAT\|ORLISTAT\|R-212\|RO-18-0647\|RO-18-0647/002\|ORLIPASTAT\|TETRAHYDROLIPSTATIN\| | $1 \times 10^5$ | D555 | $1 \times 10^5$ | D555 | $1 \times 10^5$ | D555 | $1 \times 10^5$ | D555 |
| DISODIUM DL-MALATE HYDRATE\|malic acid | $1 \times 10^5$ | C555 | $3 \times 10^{-2}$ | NC555 | 7 | B314 | $1 \times 10^5$ | C555 |
| D-MANNOHEPTULOSE\|NSC 226836\|D-MANNO-HEPTULOSE\| | $1 \times 10^5$ | D555 | $1 \times 10^5$ | D555 | $1 \times 10^5$ | D555 | $1 \times 10^5$ | D555 |
| ALPHA-MANGOSTIN\|ALPHA MANGO STIN | $1 \times 10^5$ | NC555 | $1 \times 10^5$ | D555 | $1 \times 10^5$ | D555 | 0 | C555 |
| MIDRONATE DIHYDRATE | $1 \times 10^5$ | D555 | $1 \times 10^5$ | D555 | $1 \times 10^5$ | D555 | $1 \times 10^5$ | D555 |
| 915019-65-7\|NVP-BEZ235\|BEZ-235\|NVP-BEZ235\|BEZ-235\|DACTOLISIB\| | $1 \times 10^5$ | D555 | $1 \times 10^5$ | D555 | $1 \times 10^5$ | D555 | $1 \times 10^5$ | D555 |
| PIOGLITAZONE HYDROCHLORIDE\|PIOGLITAZONE HCL\|PIOGLITAZONE 2-IMINE\|AD-4833\|U-72107\| | $1 \times 10^5$ | D555 | $1 \times 10^5$ | D555 | $1 \times 10^5$ | D555 | $1 \times 10^5$ | D555 |
| MK-8245 | $1 \times 10^5$ | C555 | 5 | B313 | $1 \times 10^5$ | D555 | $1 \times 10^5$ | C555 |
| TGX-221 | $1 \times 10^5$ | D555 | $1 \times 10^5$ | D555 | $1 \times 10^5$ | D555 | $1 \times 10^5$ | D555 |
| BX-912 | $1 \times 10^5$ | D555 | $1 \times 10^5$ | D555 | $1 \times 10^5$ | D555 | $1 \times 10^5$ | D555 |
| TIPIFARNIB\|NSC-702818\|R-115777\| | $1 \times 10^5$ | C555 | $1.2 \times 10^{-2}$ | B111 | $3.3 \times 10^{-2}$ | A132 | $1.3 \times 10^{-2}$ | A131 |
| AZD-6482\|PI3-KINASE BETA INHIBITOR\|\|AZD6482 | $1 \times 10^5$ | D555 | 5 | B333 | $1 \times 10^5$ | D555 | $1 \times 10^5$ | D555 |
| PKI-402 | 3 | NB321 | $1 \times 10^5$ | D555 | $1 \times 10^5$ | D555 | $2 \times 10^{-3}$ | C555 |
| BETULINIC ACID\|BETULINIC ACID\|ALS-357\|\|BETA-BETULINIC ACID\|ALPHA-BETULINIC ACID | 2 | NC555 | $1 \times 10^5$ | D555 | $1 \times 10^5$ | D555 | $1 \times 10^5$ | D555 |
| ALPHA TOCOPHERYL SUCCINATE\|D-ALPHA-TOCOPHERYL SUCCINATE | $1 \times 10^5$ | C555 | $1 \times 10^5$ | C555 | $1 \times 10^5$ | D555 | $1 \times 10^5$ | C555 |
| ANTIMYCIN A\|ANTIMYCIN A\| | $1 \times 10^5$ | D555 | $1 \times 10^5$ | D555 | $1 \times 10^5$ | D555 | $1 \times 10^5$ | D555 |
| BEZAFIBRATE\|BEZAFIBRATE\|BM-15075\| | $1 \times 10^5$ | C555 | 7.2 | B312 | $1 \times 10^5$ | D555 | $1 \times 10^5$ | C555 |
| BIFONAZOLE\|BIFONAZOLE\|BAY-H-4502\| | $1 \times 10^5$ | C555 | $1 \times 10^5$ | D555 | $1 \times 10^5$ | D555 | $1 \times 10^5$ | D555 |
| FTASE INHIBITOR I | $1 \times 10^5$ | C555 | $1 \times 10^5$ | C555 | 0.2 | B231 | $9 \times 10^{-2}$ | A131 |
| MT-21 | $1 \times 10^5$ | D555 | $1 \times 10^5$ | D555 | $1 \times 10^5$ | D555 | $1 \times 10^5$ | C555 |
| 2,4-DINITROPHENOL\|2,4-DINITROPHENOL\|DNP\|NSC-1532\| | $1 \times 10^5$ | D555 | 0.38 | C555 | 4 | B314 | 8 | B314 |

TABLE 9-continued

| | Prophylactic Treatment | | | | Therapeutic Treatment | | | |
| | Viral Infected | | Control | | Viral Infected | | Control | |
| Drug Name(s) | $IC_{50}$ | Grade | $IC_{50}$ | Grade | $IC_{50}$ | Grade | $IC_{50}$ | Grade |
|---|---|---|---|---|---|---|---|---|
| ALDIFEN\|DINOFAN\|NITROFEN\|NITROPHENE\|OXFENICINE\|4 HYDROXY-L-PHENYLGLYCINE\|UK-25842\| | $1 \times 10^5$ | D555 | $1 \times 10^5$ | D555 | $1 \times 10^5$ | D555 | $1 \times 10^5$ | D555 |
| PF 4708671 | $1 \times 10^5$ | C555 | $1 \times 10^5$ | C555 | $1 \times 10^5$ | D555 | $1 \times 10^5$ | C555 |
| MYXOTHIAZOL | $1 \times 10^5$ | B110 | $1 \times 10^5$ | B110 | $1 \times 10^5$ | B110 | $1 \times 10^5$ | NB110 |
| ACIVICIN\|ACIVICIN\|ACIA\|AT-125\|NSC-163501\|U-42126\|\|ACIVICIN\|(2R)-2-AMINO-2-[(5S)-3-CHLORO-4,5-DIHYDRO-1,2-OXAZOL-5-YL]ACETIC ACID | $1 \times 10^5$ | D555 | $1 \times 10^5$ | D555 | $1 \times 10^5$ | D555 | $1 \times 10^5$ | D555 |
| ROSIGLITAZONE\|ROSIGLITAZONE MALEATE\|AVANDIA\|ROSIGLITAZONE MALEATE\|BRL-49653C\| | $1 \times 10^5$ | D555 | $1 \times 10^5$ | D555 | $1 \times 10^5$ | D555 | $1 \times 10^5$ | D555 |
| ROTENONE\|ROTENONE\| | $1 \times 10^5$ | D555 | $1 \times 10^5$ | D555 | $1 \times 10^5$ | D555 | $1 \times 10^5$ | D555 |
| FLUVASTATIN SODIUM SALT\|FLUVASTATIN SODIUM\|SRI-62320\|XU-62-320\|XU-620\|FLUVASTATIN SODIUM\|SRI-62320\|XU-62-320\|XU-620\|FLUINDOSTATIN SODIUM\| | $1 \times 10^5$ | D555 | $1 \times 10^5$ | D555 | $1 \times 10^5$ | D555 | $1 \times 10^5$ | D555 |
| ATORVASTATIN CALCIUM\|LIPITOR\|ATORVASTATIN CALCIUM\|CI-981\|YM-548\| | 3 | B314 | 3 | C555 | $1 \times 10^5$ | D555 | $1 \times 10^5$ | D555 |
| LOVASTATIN\|LOVASTATIN\|MEVINOLIN\|MONAKOLIN K\|L-154803\|MK-803\|\|MEVACOR\|LOVASTATIN\|L-154803\|MK-803\|MEVINOLIN\|MONAKOLIN K\| | $1 \times 10^5$ | D555 | $1 \times 10^5$ | D555 | $1 \times 10^5$ | D555 | $1 \times 10^5$ | D555 |
| ROSUVASTATIN\|ROSUVASTATIN CALCIUM SALT\|ROSUVASTATIN CALCIUM\|ROSUVASTATIN CALCIUM SALT\|AZD-4522\|S-4522\|ZD-4522\| | $1 \times 10^5$ | C555 | $1 \times 10^5$ | C555 | $1 \times 10^5$ | D555 | $1 \times 10^5$ | C555 |
| SIMVASTATIN\|MK-733\|SYNVINOLIN\|SIMVASTATIN\|MK-733\|SYNVINOLIN\| | $1 \times 10^5$ | C555 | $1 \times 10^5$ | B110 | $1 \times 10^5$ | C555 | $5 \times 10^{-3}$ | B113 |

Each well of the dose-response curves from the drug screening were subjected to high-throughput titration on Madin-Darby canine kidney (MDCK) cells to determine viral titers. To process these results, the area under the curve of each titer was plotted and examined for an increase in MDCK cell death due to virus (Table 9). Twenty-three drugs reduced viral titers in this high-throughput modified $TCID_{50}$ assay and were selected for classical low-throughput viral tittering (Tables 8 and 9). Putative inhibitors of hexose kinase, glucose metabolism, and lipid metabolism all reduced titers in the high-throughput screening, and some significantly reduced viral load in the follow-up $TCID_{50}$ (FIG. 7B, Table 8). Among the PI3K/mTOR pathway inhibitors, GDC-0941, NVP-BKM120, and PKI-402 had no effect on NHBE cell survival, while BX-912, BNP-BEZ235, and imidazole-oxindole C16 reduced viral titers.

8. In Vivo Drug Trials Enhance Survival and Respiratory Parameters

Figure 8A:
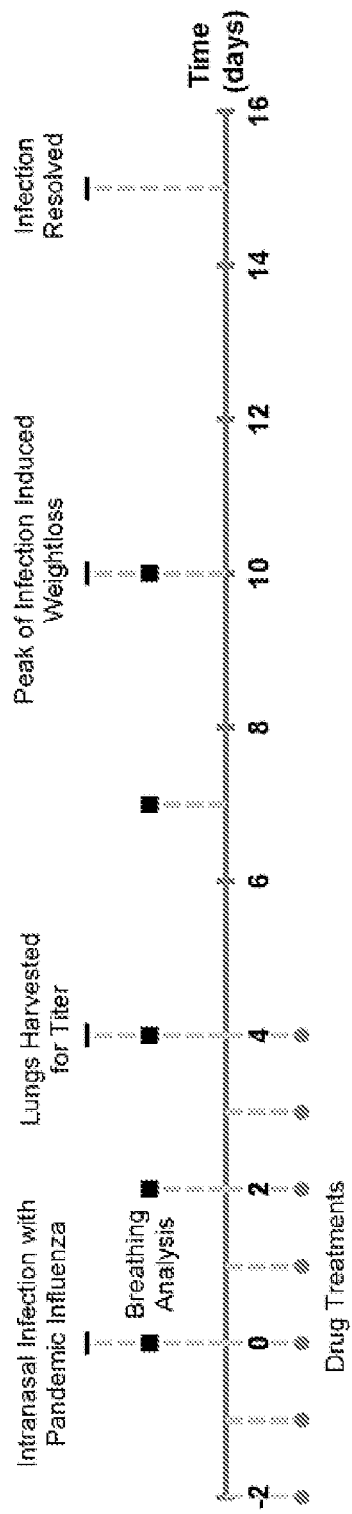
FIG. 8A-D show representative data pertaining to the ability of NVP-BEZ235 treatment to enhance survival in vivo. Specifically, the experimental timeline (8A), effect on weight loss (8B), survival rate (8C), and viral titer (8D) are shown.

Three drugs (NVP-BEZ235, clotrimazole, and α-mangostin) were selected for further investigation that differentially affected cell survival after infection and consistently reduced viral titers (Tables 7 and 9). NVP-BEZ235, a PI3K/mTOR dual inhibitor, induces insulin resistance and alters glucose metabolism in vivo (Smith, G. C., et al. (2012) *The Biochemical Journal* 442: 161-169; Smith, G. C., et al. (2013) *The FEBS Journal* 280: 5337-5349). Clotrimazole, a topical antifungal, disrupts membrane synthesis and is used for common ailments such as vaginal yeast infections, oral thrush, and ringworm. α-Mangostin has antiviral effects on HIV and rotavirus, inhibits respiratory complex IV, and promotes cell cycle arrest in cancers (Chen, S. X., et al. (1996) *Planta medica* 62: 381-382' Johnson, J. J., et al. (2012) *Carcinogenesis* 33, 413-419; Shaneyfelt, M. E., et al. (2006) *Virology journal* 3: 68). To test the efficacy of these drugs in vivo, 10- to 12-week-old C57/B6 mice were administered vehicle or drug daily for 1 week (FIG. 8A). Mice were infected intranasally with CA09 at an infectious dose of $10^3$ $EID_{50}$ and monitored for 15 days.

Referring to FIG. 8A, daily drug treatment was started 48 hours before intranasal infection with CA09 at an infectious dose of 103 ($TCID_{50}$=106.25 per mL) and maintained for 7 days. Weight loss was checked daily, and respiratory parameters were monitored with whole-body plethysmography on days 0, 2, 4, 7, and 10. A subset of mice was euthanized on day 4, and lungs were harvested for viral titers.

Figure 8B:
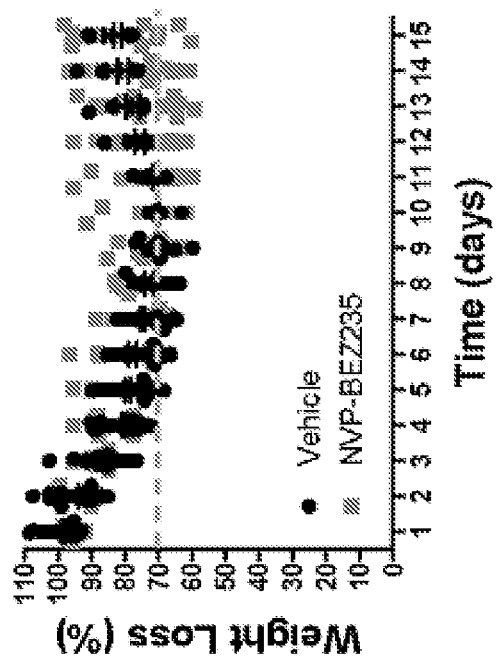
Figure 8C:
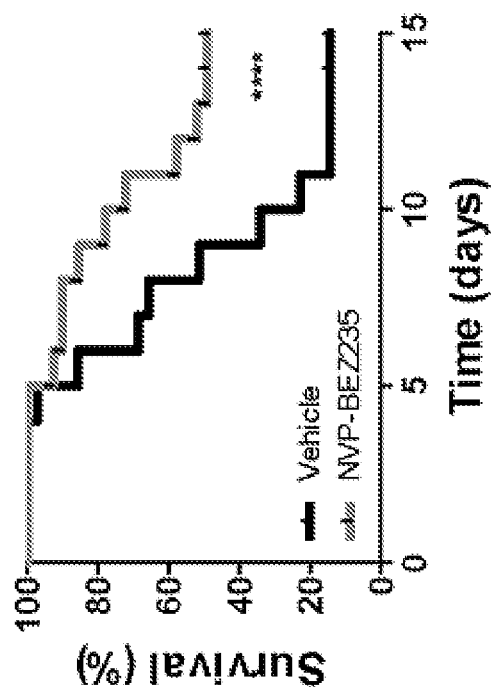

Clotrimazole and α-mangostin had little effect on the course of disease as measured by weight loss or overall survival (data not shown). NVP-BEZ235 had no significant effects on weight loss, but treated mice showed a profound improvement in survival (FIGS. 8B and 8C). Given the reduction in titers after treatment with this compound in NHBE cells in vitro, virus was measured in the infected mouse lungs. Four days following influenza infection a significant reduction in viral titer was observed from the lungs of NVP-BEZ235 treated mice (FIG. 8D).

Referring to FIG. 8B, oral gavage of 200 μL of NVP-BEZ235 (25 mg/kg; red square) or vehicle (black circle) had no effect on weight loss. Error bars reflect standard error of the mean from 45 mice per treatment from 2 independent experiments.

Referring to FIG. 8C, NVP-BEZ235 treatment (red) dramatically improved survival. Error bars reflect standard error of the mean from 57 mice per treatment from 2 independent experiments (p<0.0001 by Mantel-Cox log rank test).

Figure 8D:
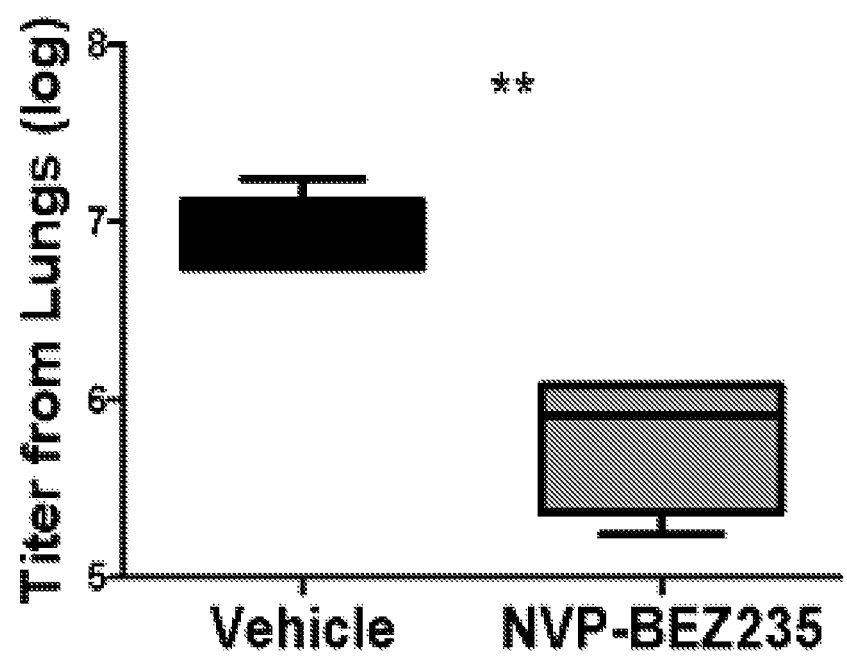

Referring to FIG. 8D, lungs were harvested, homogenized, and titered on MDCK cells, and hemagglutination activity was determined with whole chicken blood. The HA titer was significantly lower in NVP-BEZ235-treated mice (red). Four mice were titered in triplicate from each group (t-test p=0.0027).

Figure 9A:
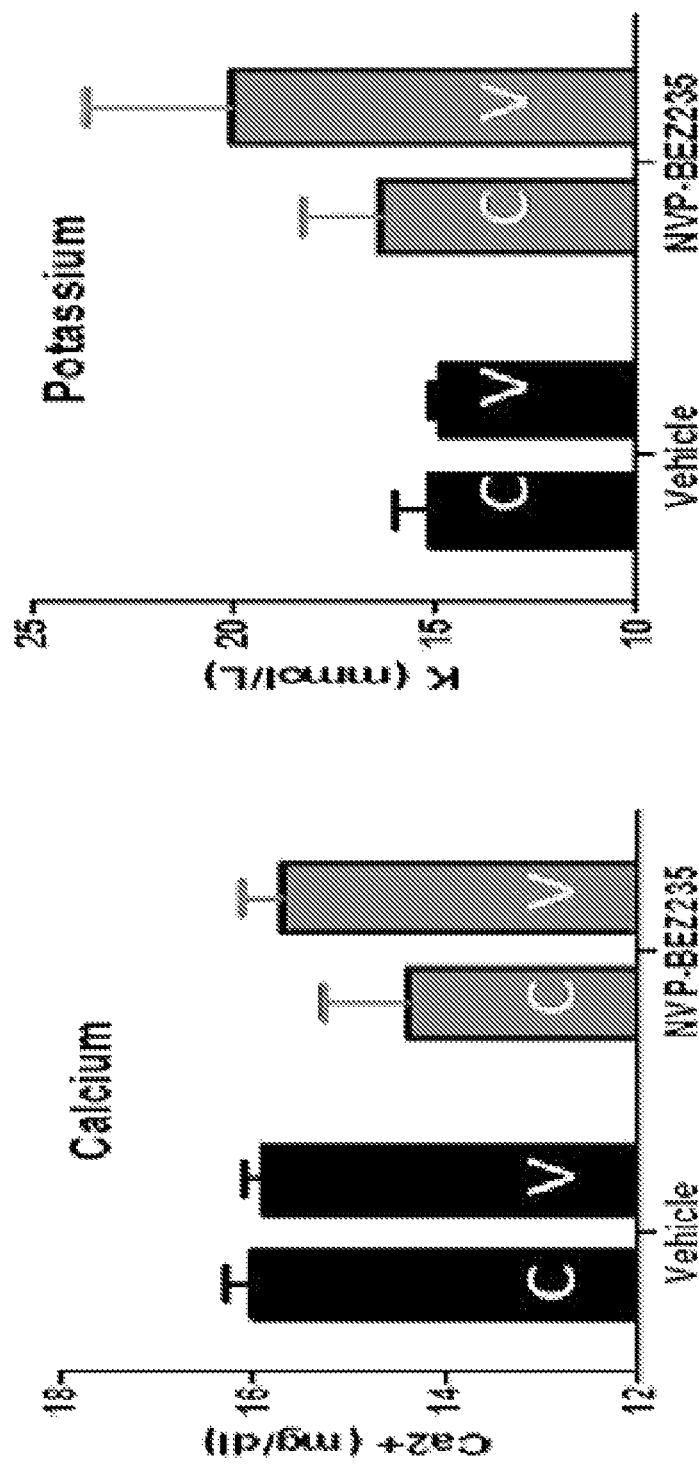
FIG. 9A-E show representative data pertaining to the blood chemistry and cellular analysis in control and influenza virus-infected animals treated with NVP-BEZ235. Specifically, blood electrolytes (9A), kidney and liver markers (9B), protein levels (9C), metabolic markers (9D), and cellular composition (9E) were assessed.
Figure 9A:
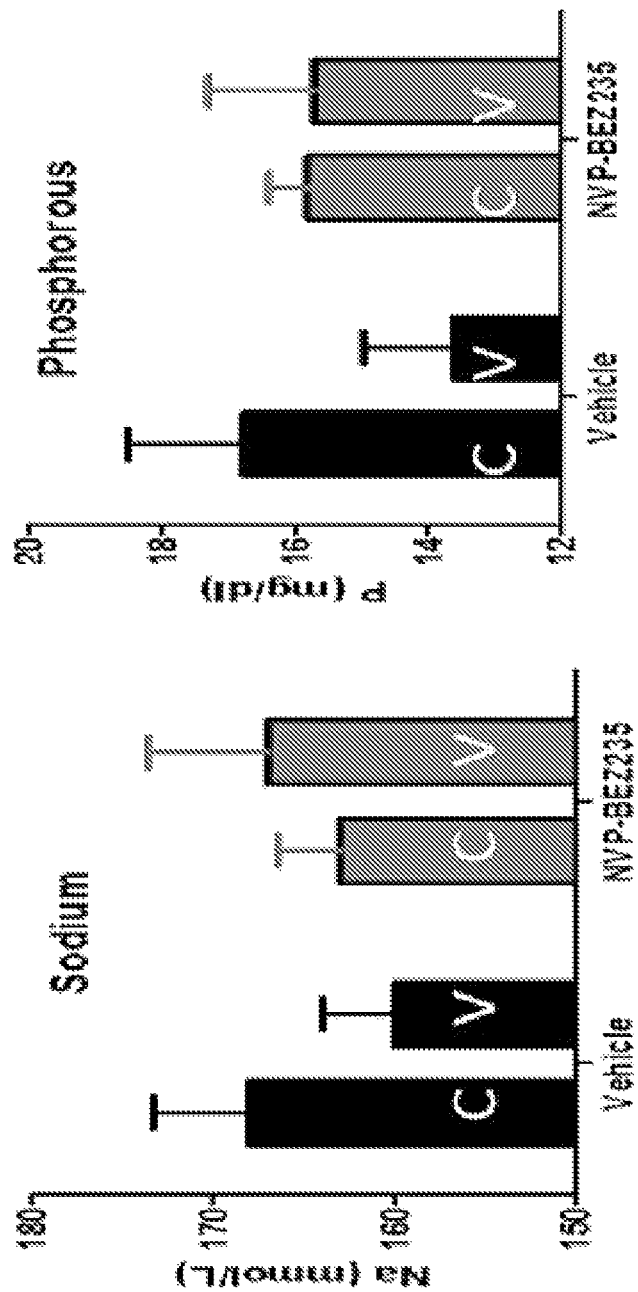
Figure 9B:
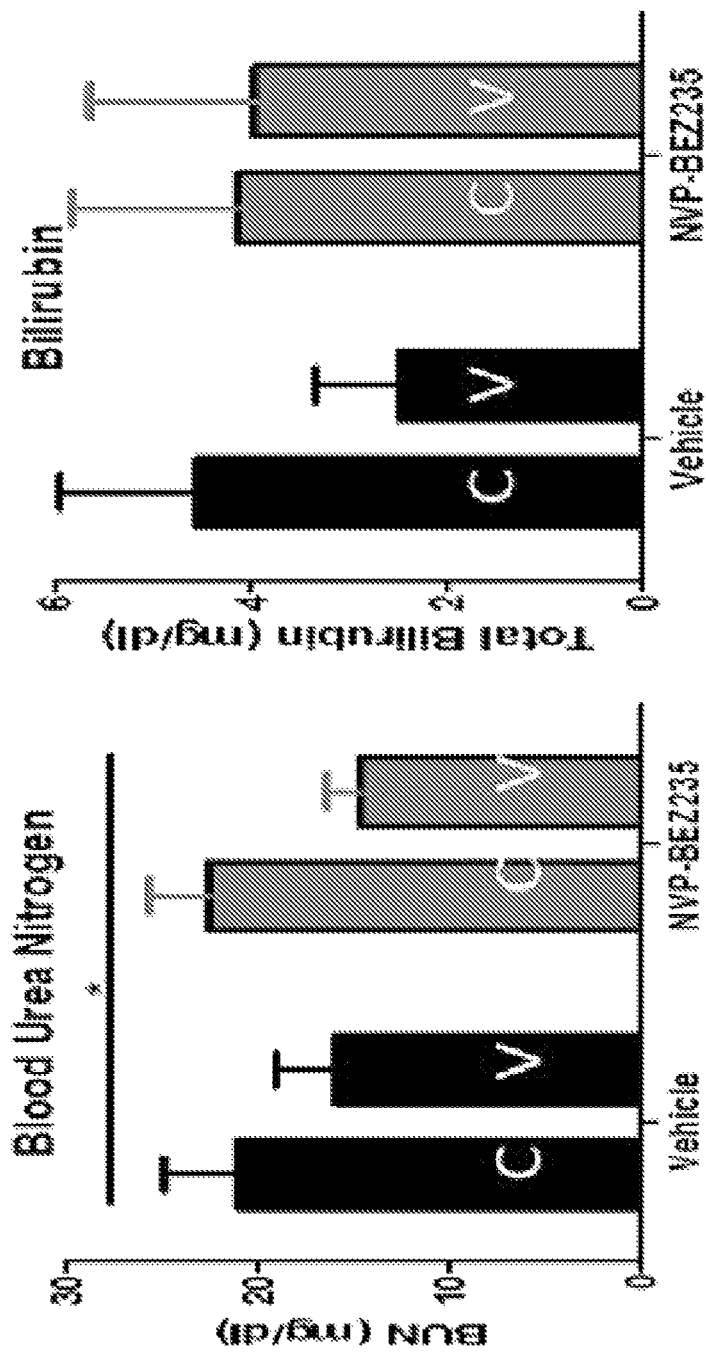
Figure 9B:
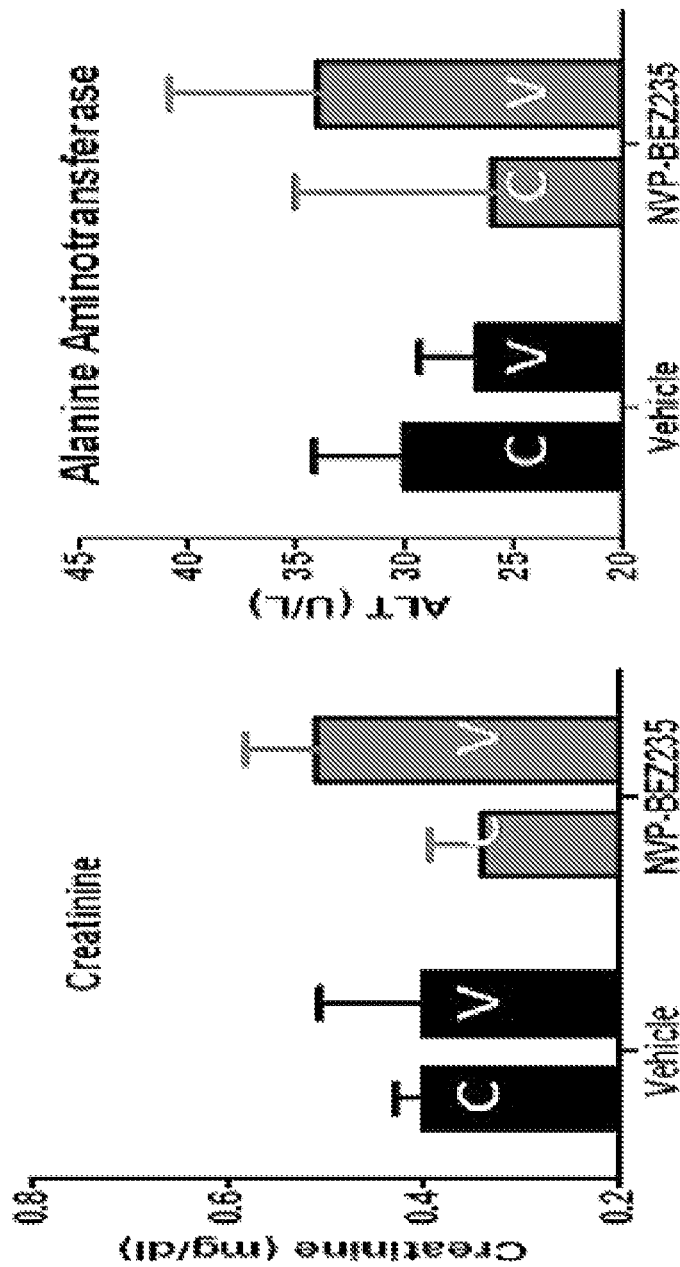
Figure 9C:
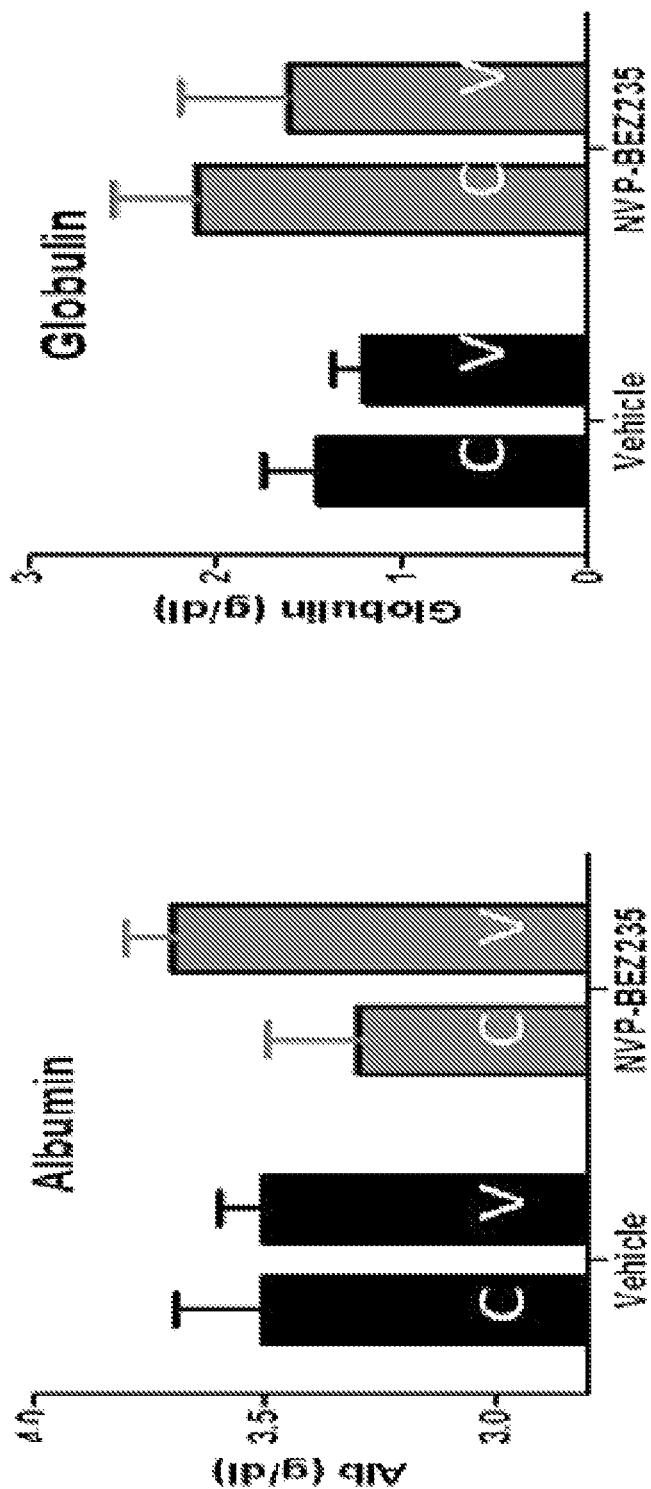
Figure 9C:
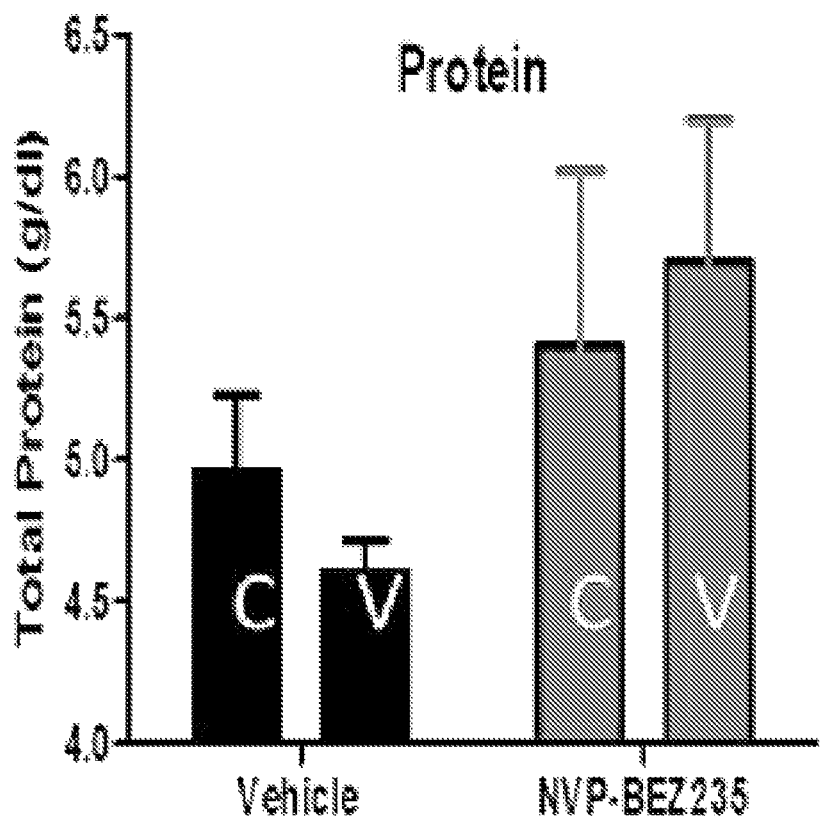
Figure 9D:
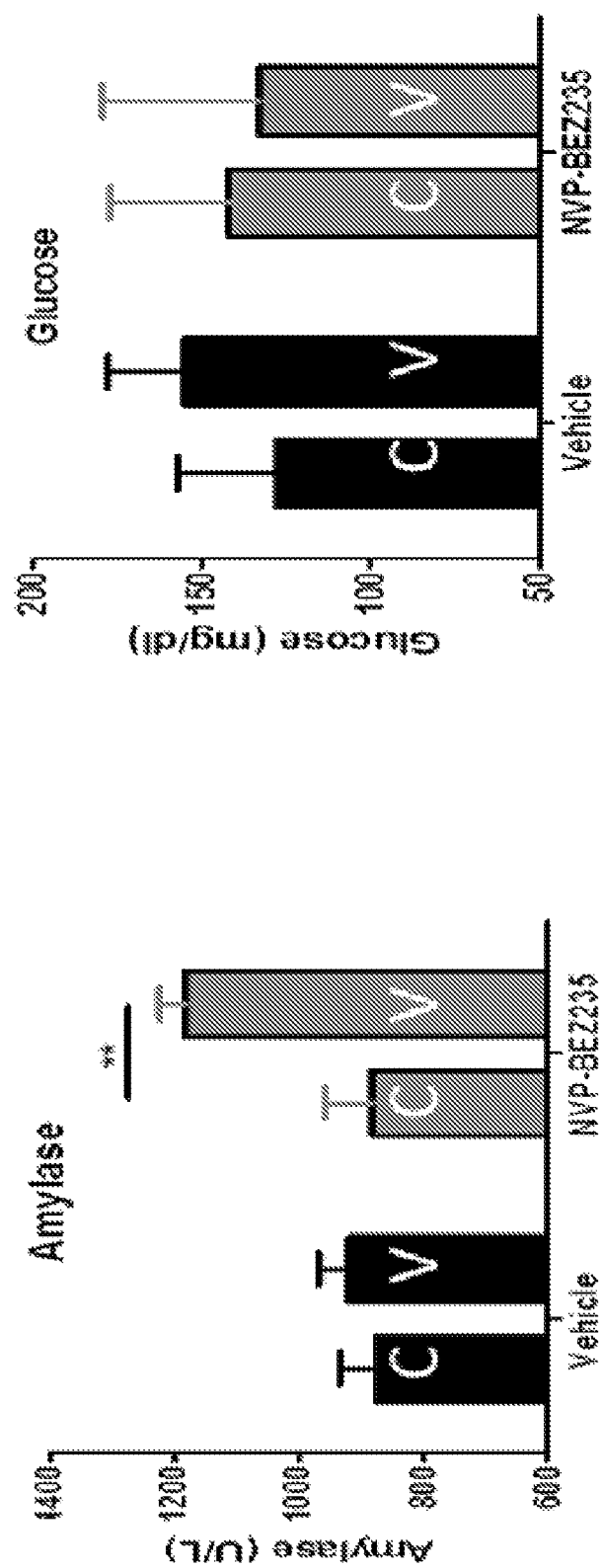
Figure 9E:
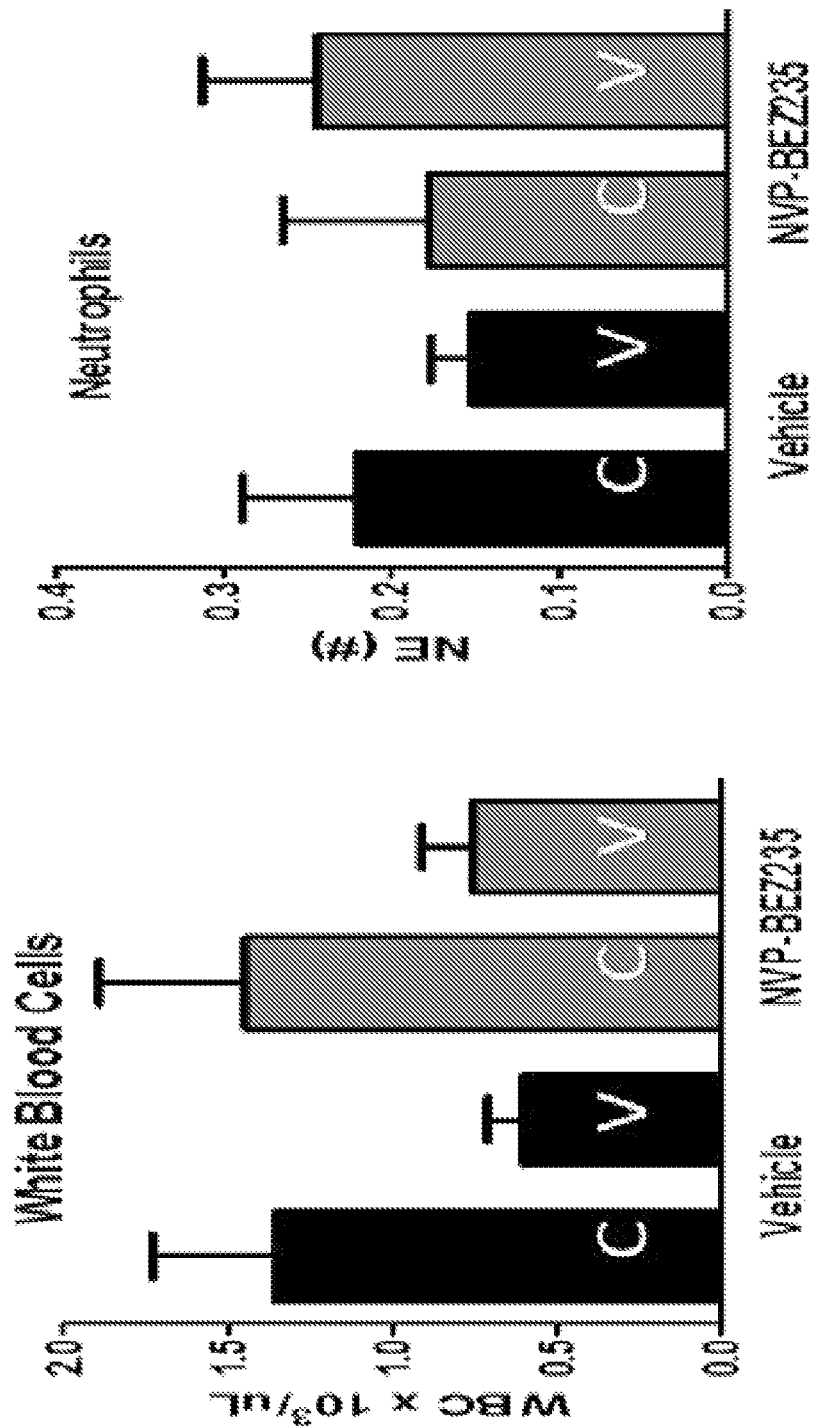
Figure 9E:
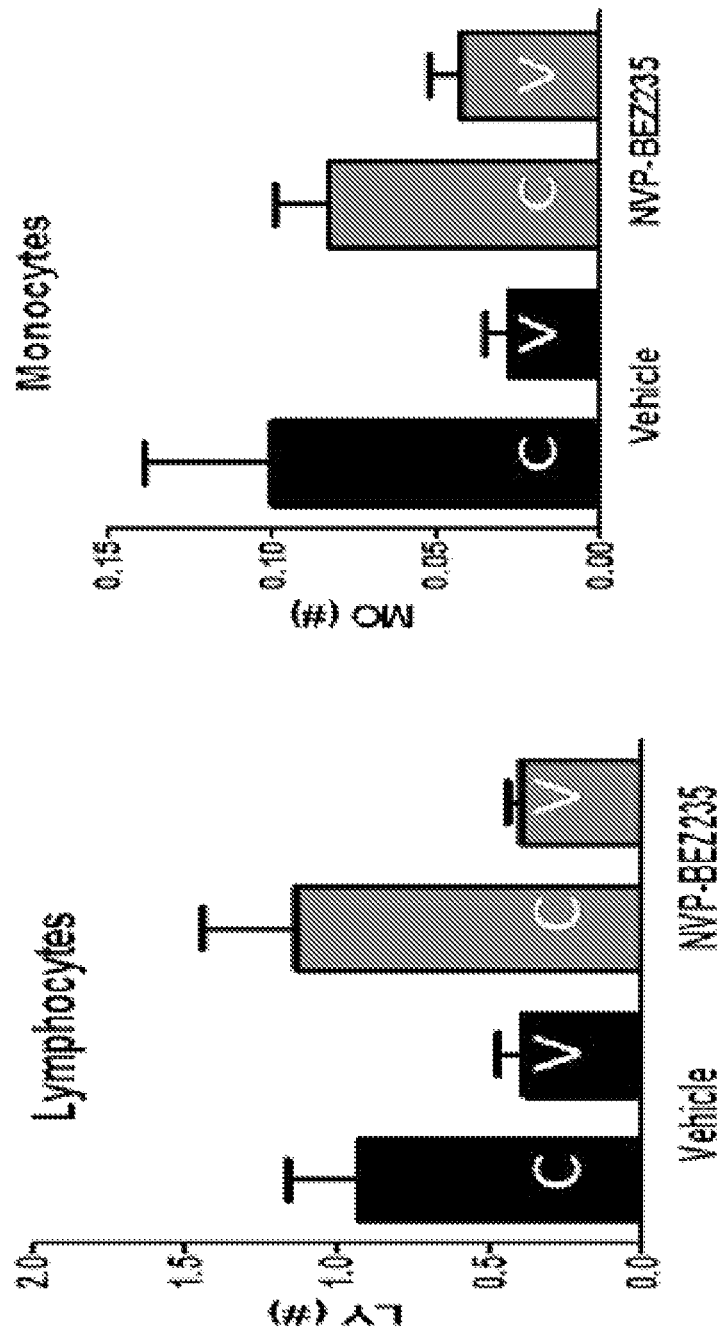
Figure 9E:
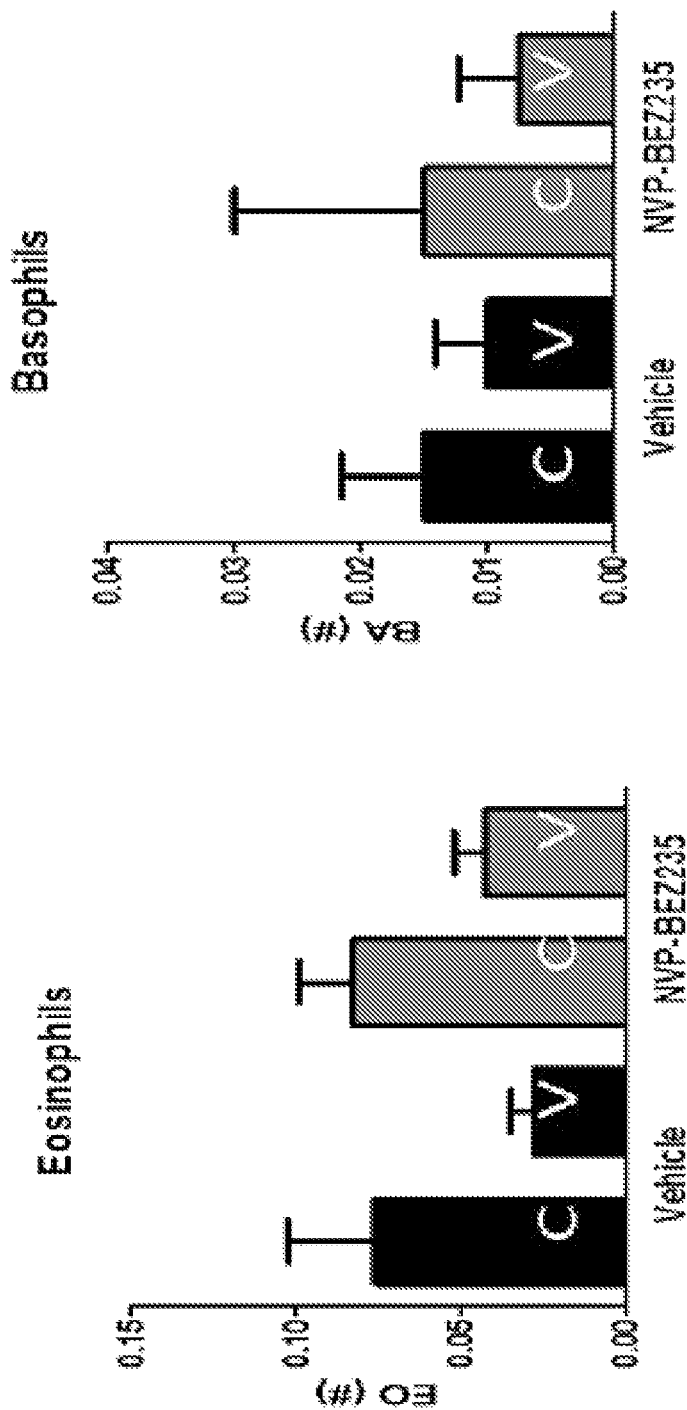

NVP-BEZ235 showed no signs of toxicity in the blood chemistry analysis or in critical blood cell counts (FIG. 9A-G). Dehydration as measured by blood electrolyte levels and renal function was stable with treatment (FIGS. 9A and 9B). Blood protein levels were also unchanged (FIG. 9C). Blood amylase, an enzyme involved in carbohydrate breakdown, was the only parameter significantly altered by NVP-BEZ235 (FIG. 9D). NVP-BEZ235 alters blood insulin and glucose responses, but this had no impact on immune cell proliferation in the blood (FIG. 9E). Thus, without wishing to be bound by theory, it is believed that the drug was well tolerated, given the similarity in weight loss, increased survival, and stable blood chemistry and cell counts.

Referring to FIG. 9A-E, daily drug treatment was started 48 hours before intranasal infection with CA09 at an infectious dose of 103 per mL ($TCID_{50}$=106.25 per mL) and maintained for 7 days. Mice were given daily oral gavage of 200 μL of NVP-BEZ235 (25 mg/kg; red bars) or vehicle (black bars) were bled on day 7 and blood electrolytes (10A), kidney and liver markers (10B), protein levels (10C), metabolic markers (10D), and cellular composition (10E) were assessed by standard clinical assays in the pathology core at St. Jude Children's Research Hospital. Data represent 3 mice per group.

Figure 10E:
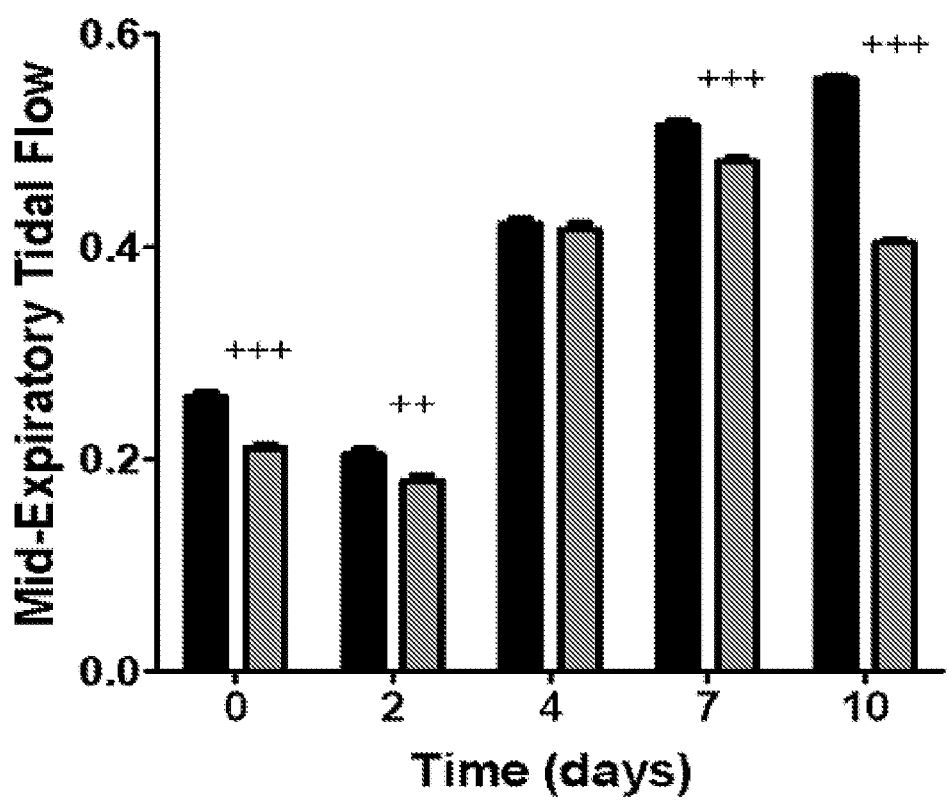
Figure 11:
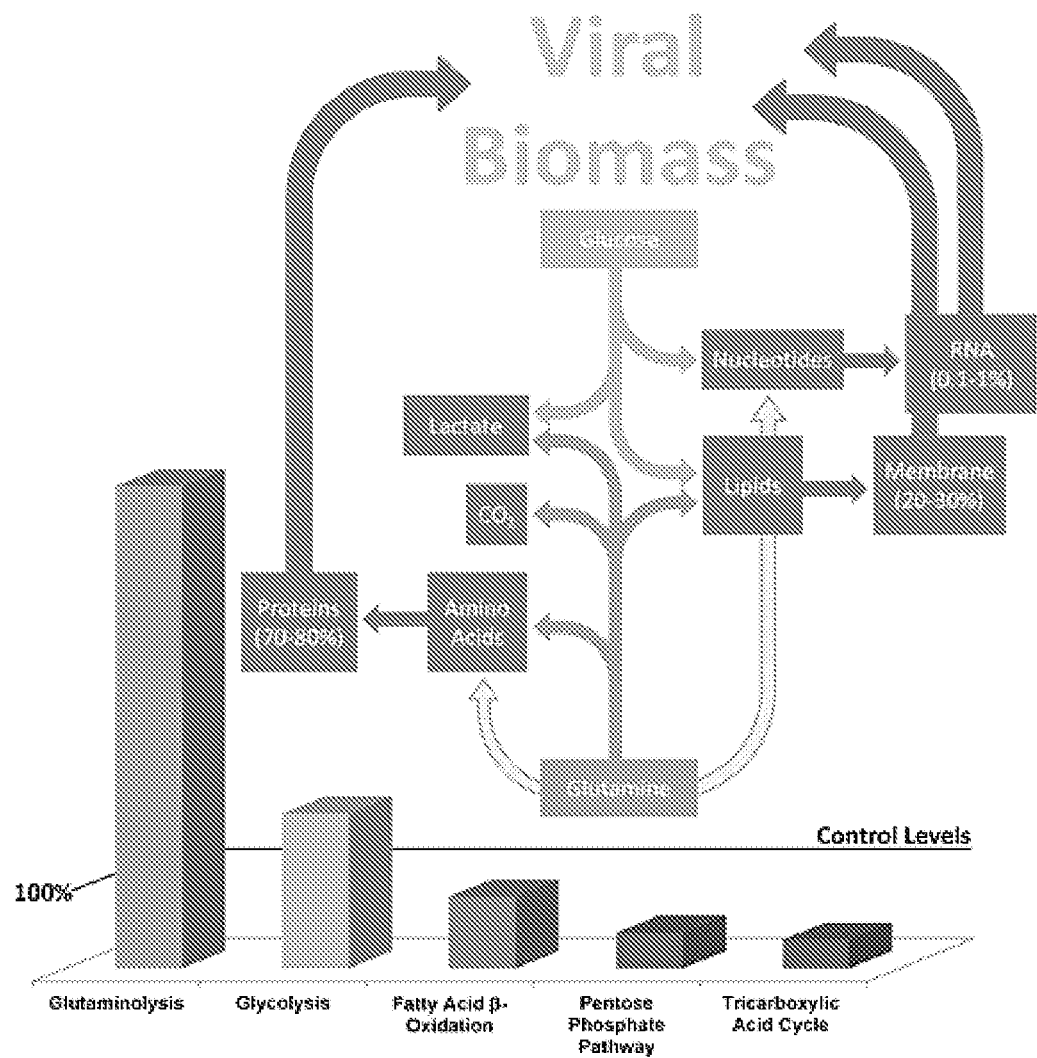
FIG. 11 shows a representative schematic of metabolic alterations following influenza virus infection.

Given that altered lung function is the primary pathologic impairment after infection and $O_2$ and $CO_2$ are the primary substrates and products of aerobic metabolism, respiratory parameters of infected and treated mice were evaluated to determine a possible functional mechanism for the drug-induced improvement in survival (Sanders, C. J., et al. (2013) *American journal of physiology Lung cellular and molecular physiology* 304: L481-488). Whole-body plethysmography has been used to assess the efficacy of antivirals against lung impairment associated with influenza-induced mortality (Julander J. G. et al. (2011) *Antiviral Research* 92: 228-236). NVP-BEZ235 caused decreases in breath frequency, tidal flow, and minute volume and increases in inspiration and expiration time (FIG. 10A-D). Importantly, a reduction in mid-expiratory tidal flow was observed, which is associated with improved outcomes after infection. Thus, NVP-BEZ235 reduces influenza-induced mortality and augments respiratory function in infected adult mice (FIG. 10E).

Referring to FIG. 10A-E, mice were subjected to whole-body plethysmography with an equilibration time of 30 minutes followed by 5 minutes of data collection. All parameters with statistically altered respiratory parameters are represented: inspiration time (10A), expiration time (10B), breath frequency (10C), volume per minute (10D), and the tidal flow of air at the mid-point of expiration (11E). Four mice per treatment were monitored in 2 independent experiment groups, and a t-test was used to determine statistical differences in treatments with p-values indicated by asterisks (* p<0.01,  p<0.001, and * p<0.0001).

Figure 12A:
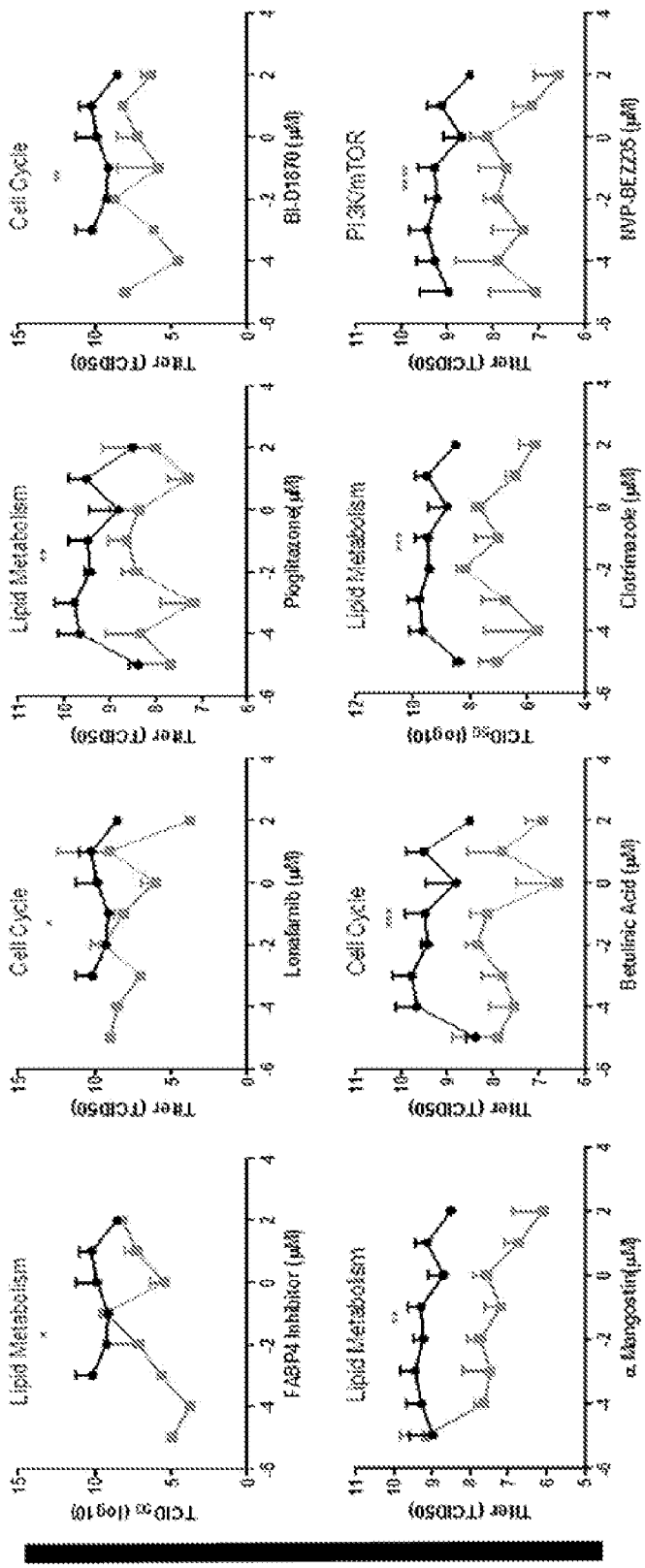
FIG. 12A-E show representative data demonstrating that selective drugs reduce viral titer and restore metabolic flux. Specifically, eight compounds demonstrated an effect with pretreatment (12A) and ten demonstrated an effect following therapeutic treatment (12B). Further, viral infection induced increases in metabolic flux of ECAR (12C), OCR (12D), and PPR (12E), which were reversed by BEZ235.
Figure 12B:
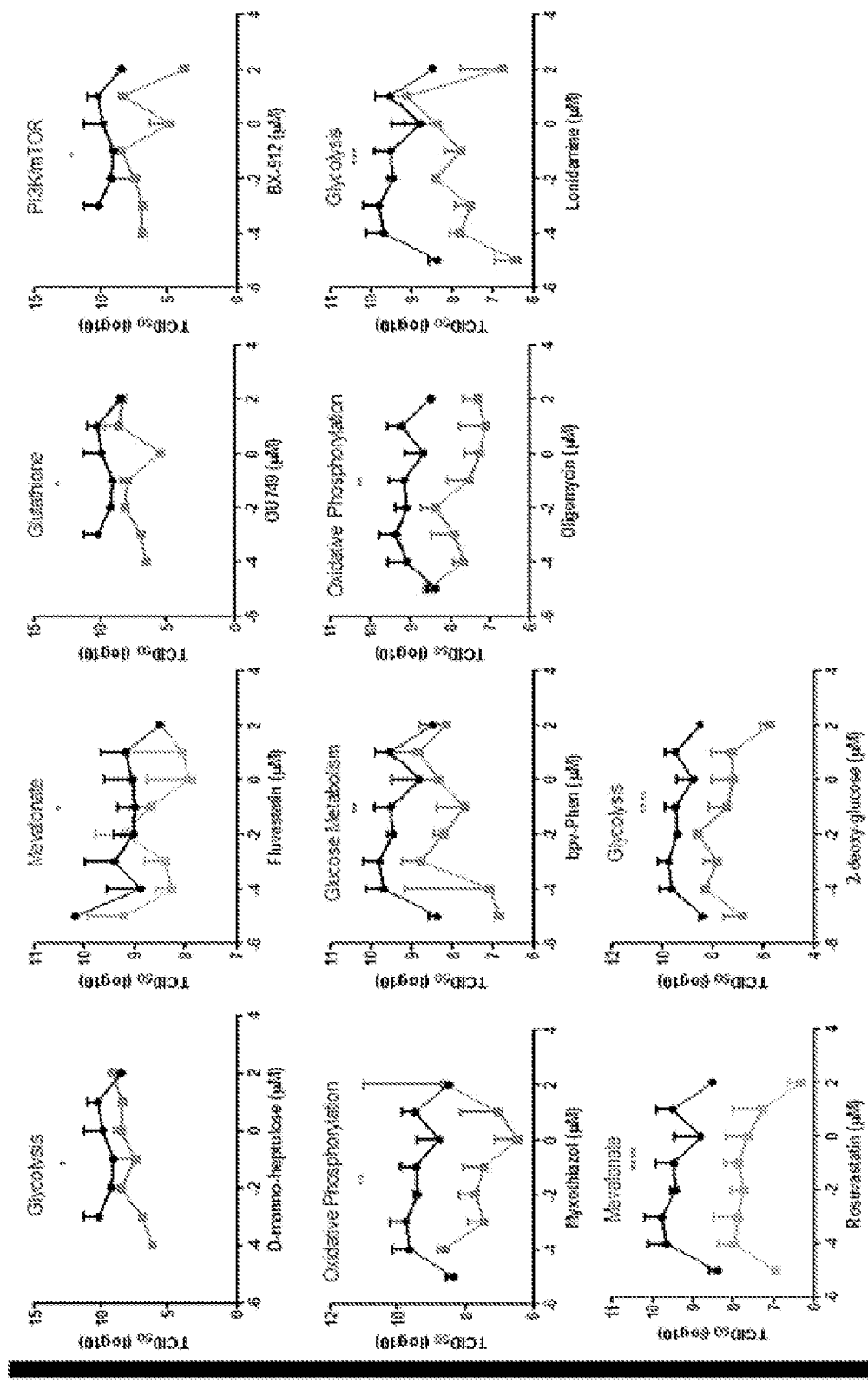

9. Eight Compounds Expose Integral Pathways and Potential Modalities for Therapeutic Intervention of Influenza Infection Eight compounds significantly reduced cytopathic effect with pretreatment; they were primarily impacting lipid metabolism and cell cycle (FIG. 12A). Another ten compounds showed a significant decrease in viral titer following therapeutic treatment (FIG. 12B). Compounds modulating glycolysis were efficient at reducing viral load, including the competitive inhibitor 2-deoxy-glucose.

Referring to FIG. 12A and FIG. 12B, NHBE cells were seeded in BEGM, medium rested, and then infected at −8 or +17 hours with drug treatment at 0 hour and supernatant removed at 72 hours to recapitulate drug screen conditions. The supernatant was then tittered on MDCK cells and the infection was allowed to proceed, in the presence of TPCK trypsin, for 72 hours. Viral titer was then calculated with the Reed Munich method.

Figures 12C, 12D:
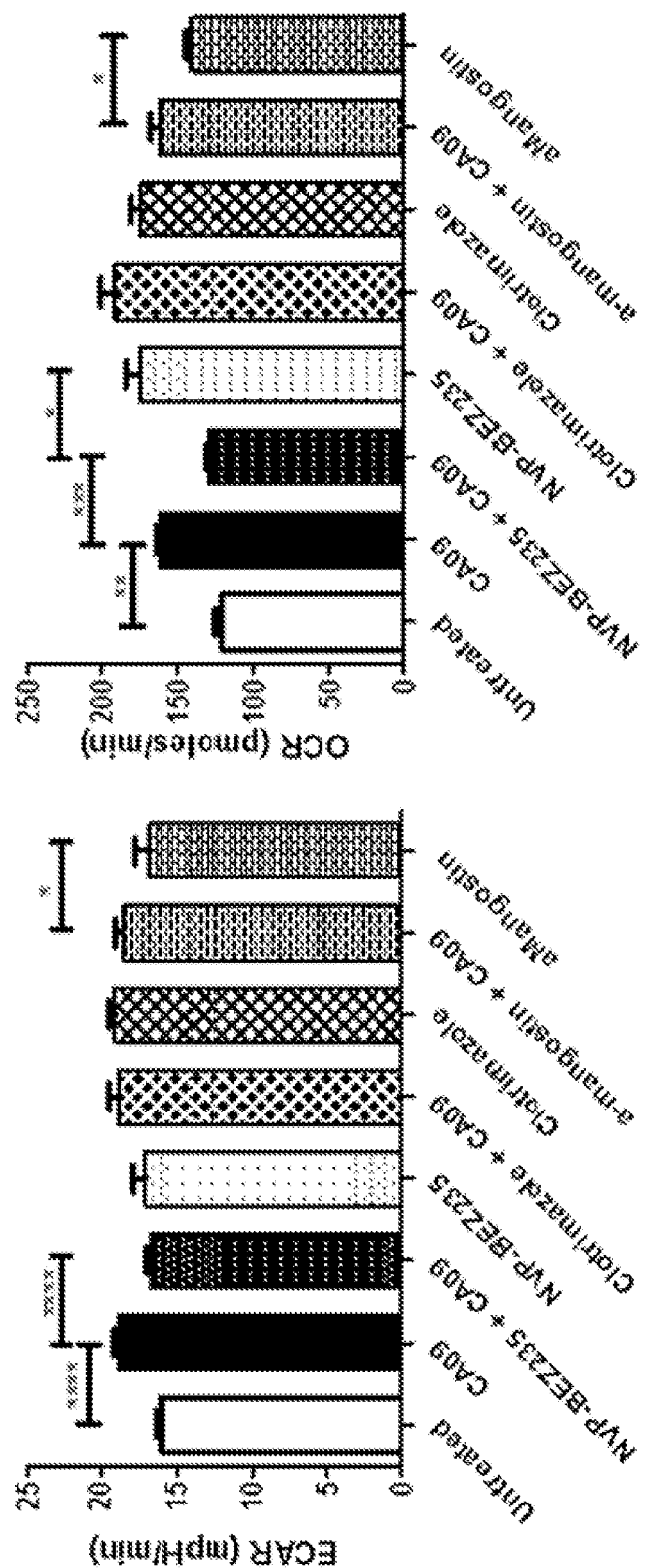
Figure 12E:
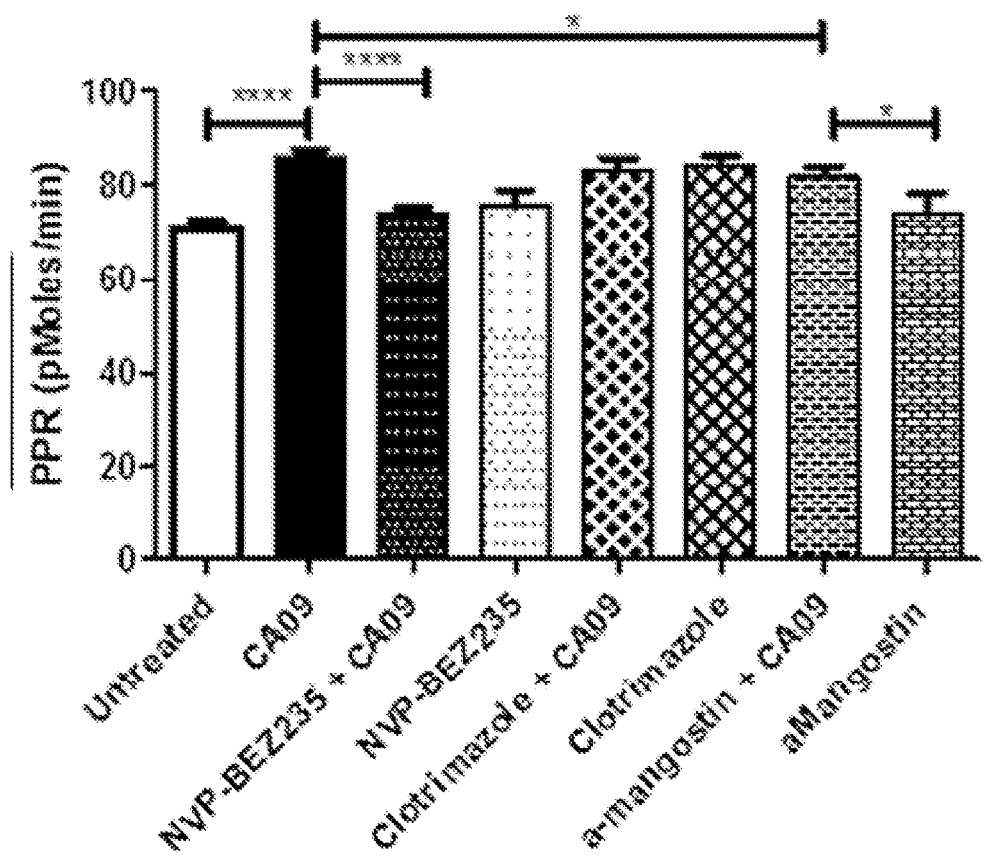

Of the validated drugs hits, BEZ235, Clotrimazole, and α-Mangostin were selected for further study based on their differential effects on NHBE cell survival after infection and consistent reduction in viral titers (FIG. 12A). BEZ235 had one of the most significant drops in titer, baring 2-deoxy-glucose, and is a PI3K/mTOR dual inhibitor known to induce insulin resistance in vivo (FIG. 12A) (Smith et al., 2012). The other two drugs displaying similar profiles were Clotrimazole, a commercially available topical treatment for fungal infections that targets lipid metabolism, and αMangostin, a known anti-viral effective against other RNA viruses (Chen et al., 1996; Choi et al., 2014; Shaneyfelt et al., 2006; Vlietinck et al., 1998). In keeping with the previous results, viral infection induced increases in metabolite flux of ECAR, OCR, and PPR (FIG. 12C-E). Of the three drugs that reliably reduced viral titer, BEZ235 was the only drug to reverse influenza induced metabolic flux to untreated levels (FIG. 12C-E). The dramatic effects of BEZ235 on all three metabolic parameters are consistent with it having the highest efficacy in reducing viral titer of all the compounds tested (FIG. 12A).

Referring to FIG. 12C-E, NHBE cells were seeded in XF24 SEAHORSE cell culture (1:9), peanut oil, or DMSO/PBS (1:10) respectively for 4 hours followed by infection at 1 MOI with CA04. 17 hours later plates were processed and read on Seahorse following manufactures protocol.

10. Mechanism of BEZ235 Efficacy in NHBE Cells

BEZ235 has been extensively characterized as a dual inhibitor of PI3K and mTOR1/2, but the present work was mainly done in transformed cell lines. These model systems were applicable for BEZ235 development as a cancer treatment. However, given the obvious metabolic differences inherent to immortalized cell lines and primary terminally differentiated cell types, the activity of this inhibitor in the primary epithelial cell culture model described herein was determined. 17 hours following influenza infection of NHBE, PI3K and 4E-BP1 are phosphorylated concomitant with the dephosphorylation of 70S6K and S6 (FIG. 13A).

Figure 13A:
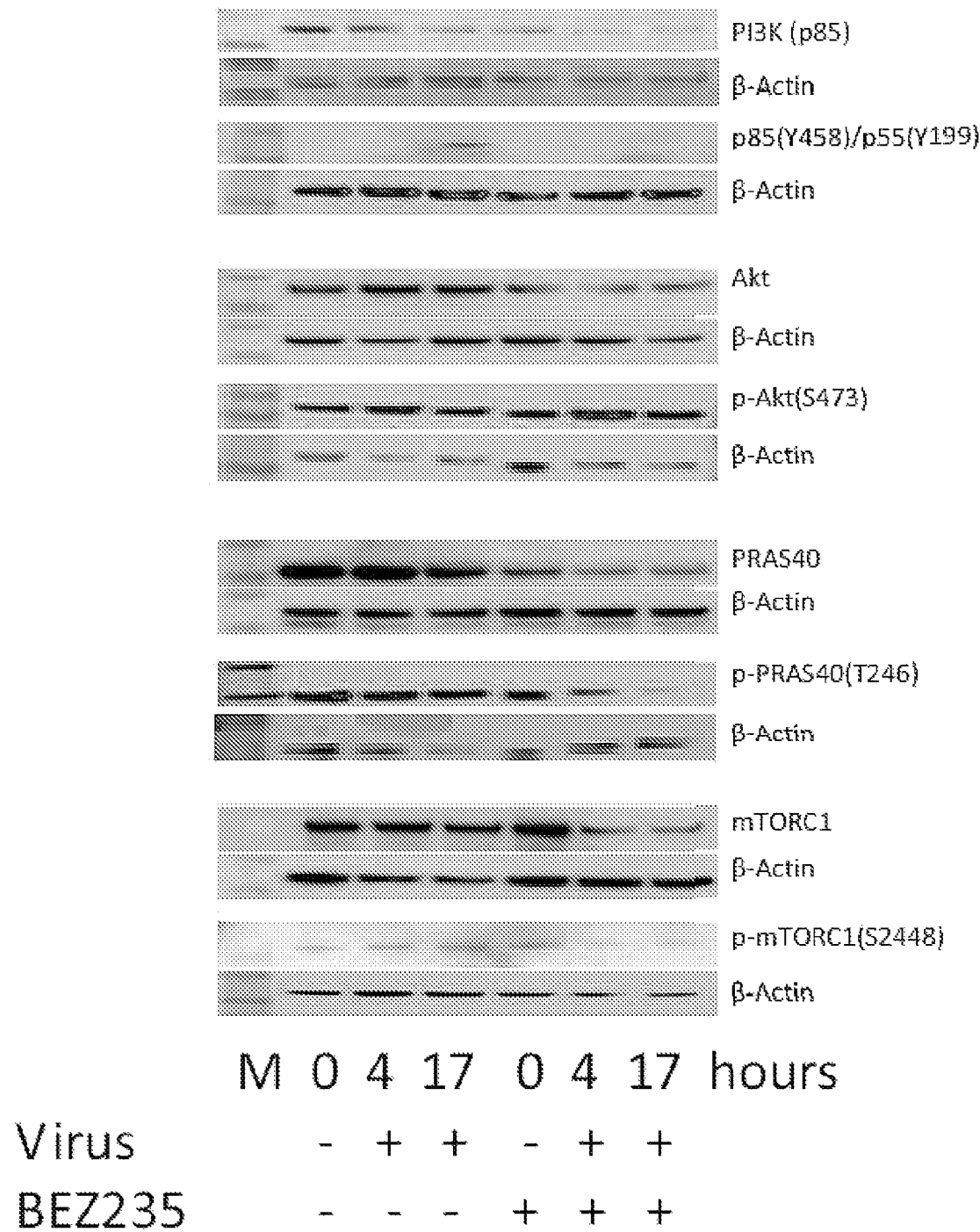
FIG. 13A-D show representative data demonstrating that BEZ235 restricts host metabolic flexibility via constraints on PI3K/mTOR and cMyc pathway activation by the virus. Specifically, BEZ235 reduces mTOR phosphorylation (13A), ablates influenza-induced cMyc expression (13B), restores the spare respiratory capacity of infected NHBE (13C), and slightly reduces the glycolytic capacity (13D).
Figure 13A:
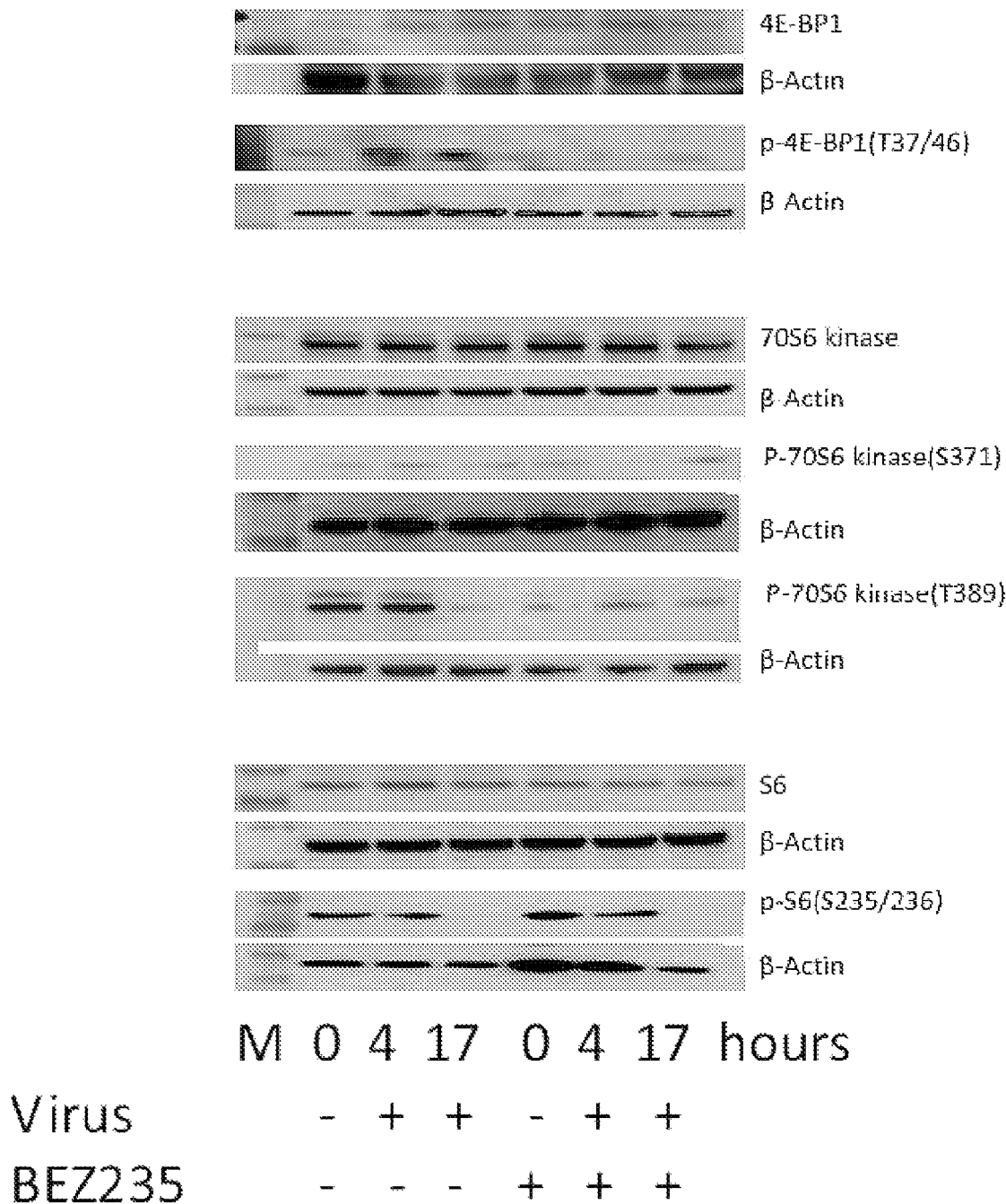

Referring to Figure FIG. 13A, NHBE cells were infected with CA04 for up to 17 hours at MOI1, harvested at indicated time and lysates subjected to immunoblotting with a cMyc protein standard ("ctrl") and probed for cMyc and β-actin.

Figure 13B:
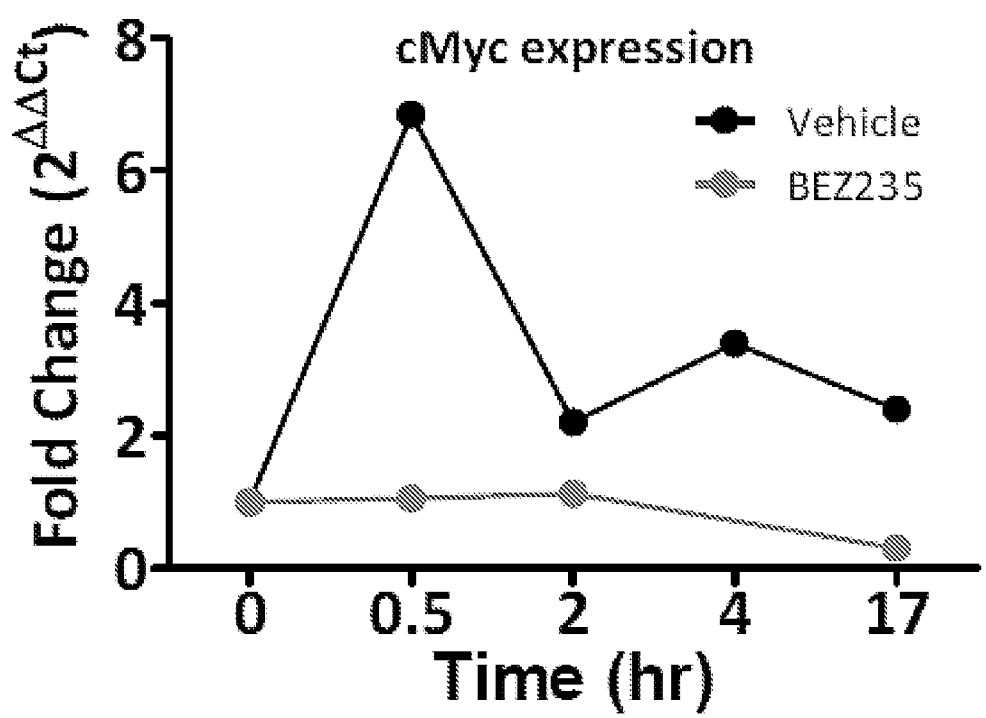
Figure 13C:
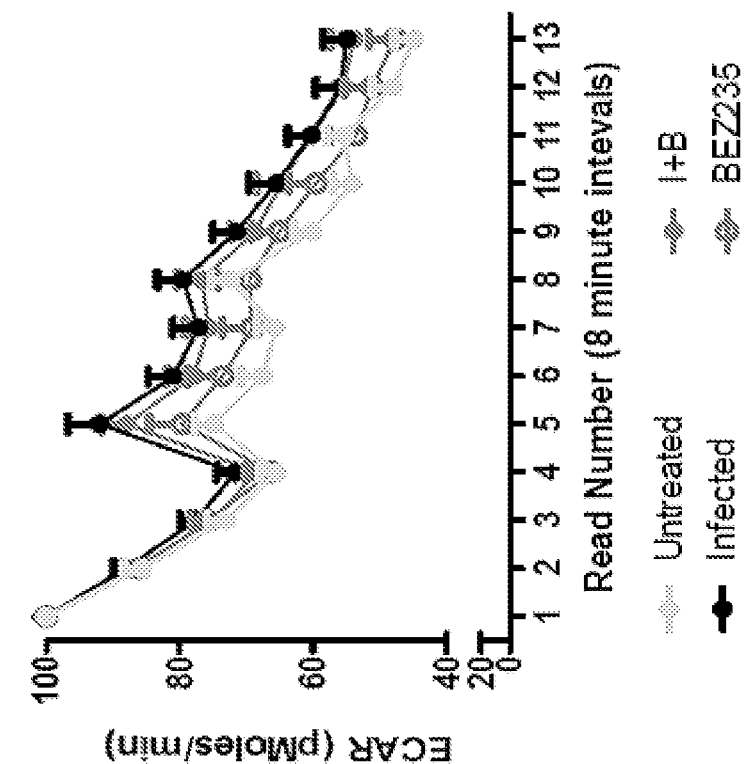

As expected, treatment with PI3K dual mTORC inhibitor BEZ235 prevents viral induction of the mTOR pathway as is demonstrated by blockade of several downstream phosphorylation events. Indeed, BEZ235 reduces mTOR phosphorylation itself concomitant to 70S6K and 4E-BP1 phosphorylation being completely abolished; the latter is indicative of mTORC1 inhibition (FIG. 13A). Consistent with this, BEZ235 treatment leads to a time dependent decrease in phosphorylation of PRAS40 (FIG. 13A). Next, whether these changes were indicative of a fundamental shift in the metabolic state of the infected, treated cell consistent with the observed BEZ235-mediated restoration of metabolic flux was determined (FIG. 13C). It has been previously shown that BEZ235 treatment blocks c-Myc induction via inhibition of p70S6K and its substrate eIF4B (David J. Duffy 2013; Csibi et al. 2014). Likewise, influence-induced cMyc expression was ablated by BEZ235 treatment (FIG. 13B). Further, Csibi and co-workers recently demonstrated that PI3K/mTORC pathway regulates glutamine metabolism and used BEZ235 to strongly inhibit the anaplerotic entry of glutamine to the TCA cycle (Csibi et al. 2014). Indeed, BEZ235 treatment restored the spare respiratory capacity of infected NHBE while slightly reducing the glycolytic capacity as well (FIG. 13C and FIG. 13D).

Referring to FIG. 13B, NHBE cells were infected with CA04 for up to 17 hours at MOI 1, harvested at indicated time and RNA purified from lysates then quantified with 1 PCR.

Figure 13D:
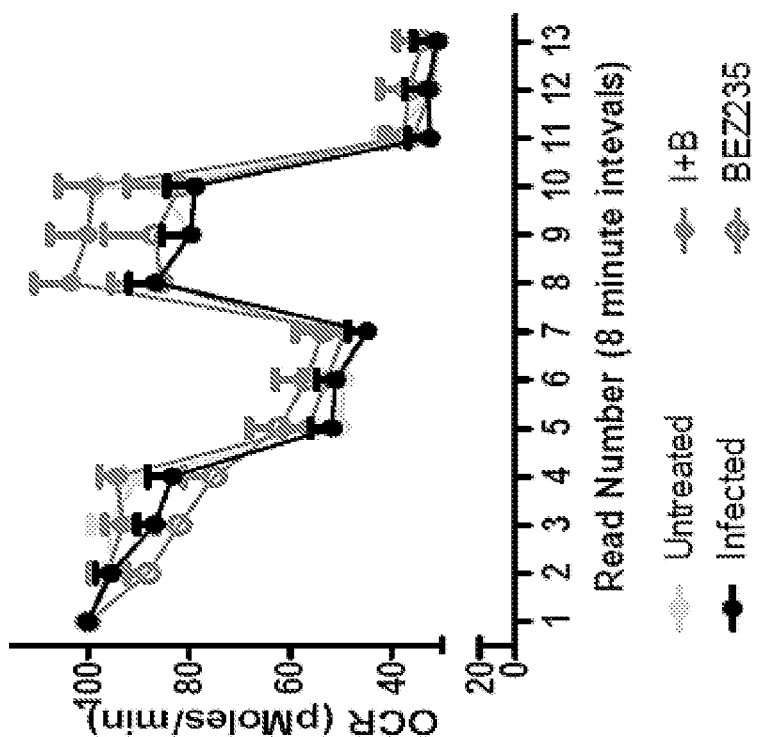

Referring to FIG. 13C and FIG. 13D, NHBE cells were grown and differentiated in 24-well Seahorse plates and left untreated (control), treated with 10 nM BEZ235 for 1 hr, and infected for 17 hours at MOI1 with activate CA04 virus, and subjected to sequential inhibition of mitochondrial function to determine spare glycolytic and respiratory capacity following manufactures protocol (Seahorse) via treatment at 24 minutes with 1 µM Oligomycin, 48 minutes with 0.5 µM FCCP, and 72 minutes 0.5 µM Rotenone to uncouple ATP, accelerate electron transport, and inhibit mitochondrial electron transport via respiratory chain complex I, respectively.

F. REFERENCES

Askovich, P. S., Sanders, C. J., Rosenberger, C. M., Diercks, A. H., Dash, P., Navarro, G., Vogel, P., Doherty, P. C., Thomas, P. G., and Aderem, A. (2013). Differential host response, rather than early viral replication efficiency, correlates with pathogenicity caused by influenza viruses. *PloS one* 8: e74863.

Brand, K., Williams, J. F., and Weidemann, M. J. (1984). Glucose and glutamine metabolism in rat thymocytes. *The Biochemical journal* 221: 471-475.

Buzzai, M., Bauer, D. E., Jones, R. G., Deberardinis, R. J., Hatzivassiliou, G., Elstrom, R. L., and Thompson, C. B. (2005). The glucose dependence of Akt-transformed cells can be reversed by pharmacologic activation of fatty acid beta-oxidation. *Oncogene* 24: 4165-4173.

Chang, C. H., Curtis, J. D., Maggi, L. B., Jr., Faubert, B., Villarino, A. V., O'Sullivan, D., Huang, S. C., van der Windt, G. J., Blagih, J., Qiu, J., et al. (2013). Posttranscriptional control of T-cell effector function by aerobic glycolysis. *Cell* 153: 1239-1251.

Chen, S. X., Wan, M., and Loh, B. N. (1996). Active constituents against HIV-1 protease from Garcinia mangostana. *Planta medica* 62: 381-382.

Cheung, C. Y., Chan, E. Y., Krasnoselsky, A., Purdy, D., Navare, A. T., Bryan, J. T., Leung, C. K., Hui, K. P., Peiris, J. S., and Katze, M. G. (2012). H5N1 virus causes significant perturbations in host proteome very early in influenza virus-infected primary human monocyte-derived macrophages. *The Journal of infectious diseases* 206: 640-645.

Dang, C. V. (1999). c-myc target genes involved in cell growth, apoptosis, and metabolism. *Mol Cell Biol* 19: 1-11.

Daniels, J. B., Eaton, M. D., and Perry, M. E. (1952). Effect of glucose on the growth of influenza virus in deembryonated eggs and tissue cultures. *J Immunol* 69: 321-329.

Dennis, G., Jr., Sherman, B. T., Hosack, D. A., Yang, J., Gao, W., Lane, H. C., and Lempicki, R. A. (2003). DAVID: Database for Annotation, Visualization, and Integrated Discovery. *Genome biology* 4: P3.

Everts, B., Amiel, E., Huang, S. C., Smith, A. M., Chang, C. H., Lam, W. Y., Redmann, V., Freitas, T. C., Blagih, J., van der Windt, G. J., et al. (2014). TLR-driven early glycolytic reprogramming via the kinases TBK1-IKKvarepsilon supports the anabolic demands of dendritic cell activation. *Nature immunology* 15: 323-332.

Filipp, F. V., Ratnikov, B., De Ingeniis, J., Smith, J. W., Osterman, A. L., and Scott, D. A. (2012). Glutamine-fueled mitochondrial metabolism is decoupled from glycolysis in melanoma. *Pigment cell & melanoma research* 25: 732-739.

Fisher, T. N., and Ginsberg, H. S. (1956). The reaction of influenza viruses with guinea pig polymorphonuclear leucocytes. III. Studies on the mechanism by which influenza viruses inhibit phagocytosis. *Virology* 2: 656-664.

Gardner, P. R., Raineri, I., Epstein, L. B., and White, C. W. (1995). Superoxide radical and iron modulate aconitase activity in mammalian cells. *J Biol Chem* 270: 13399-13405.

Henle, G., Deinhardt, F., Bergs, V. V., and Henle, W. (1958). Studies on persistent infections of tissue cultures. I. General aspects of the system. *The Journal of experimental medicine* 108: 537-560.

Hue, L., Sobrino, F., and Bosca, L. (1984). Difference in glucose sensitivity of liver glycolysis and glycogen synthesis. Relationship between lactate production and fructose 2,6-bisphosphate concentration. *The Biochemical journal* 224: 779-786.

Intriago, B., Danus, M., Calvo, N., Escobar, J., Montero, M., Kohan, S., Rebenaque, E., and Milla, L. (2009). Influenza-like infection can result in diffuse fluordeoxyglucose uptake in the lungs. *Clinical nuclear medicine* 34: 737-738.

Isler, J. A., Maguire, T. G., and Alwine, J. C. (2005). Production of infectious human cytomegalovirus virions is inhibited by drugs that disrupt calcium homeostasis in the endoplasmic reticulum. *Journal of virology* 79: 15388-15397.

Johnson, J. J., Petiwala, S. M., Syed, D. N., Rasmussen, J. T., Adhami, V. M., Siddiqui, I. A., Kohl, A. M., and Mukhtar, H. (2012). alpha-Mangostin, a xanthone from mangosteen fruit, promotes cell cycle arrest in prostate cancer and decreases xenograft tumor growth. *Carcinogenesis* 33: 413-419.

Jonges, M., Liu, W. M., van der Vries, E., Jacobi, R., Pronk, I., Boog, C., Koopmans, M., Meijer, A., and Soethout, E. (2010). Influenza virus inactivation for studies of antigenicity and phenotypic neuraminidase inhibitor resistance profiling. *Journal of clinical microbiology* 48: 928-940.

Katz, J., and Wood, H. G. (1963). The use of C1402 yields from glucose-1-and-6-C14 for the evaluation of the pathways of glucose metabolism. *J Biol Chem* 238: 517-523.

Kim, K. H., Rodriguez, A. M., Carrico, P. M., and Melendez, J. A. (2001). Potential mechanisms for the inhibition of tumor cell growth by manganese superoxide dismutase. *Antioxidants & redox signaling* 3: 361-373.

Legge, K. L., and Braciale, T. J. (2003). Accelerated migration of respiratory dendritic cells to the regional lymph nodes is limited to the early phase of pulmonary infection. *Immunity* 18: 265-277.

Moon, A., and Rhead, W. J. (1987). Complementation analysis of fatty acid oxidation disorders. *J Clin Invest* 79: 59-64.

Murphy, M. G., Crocker, J. F., Lee, S. H., Acott, P., and Her, H. (1997). Sequestration of coenzyme A by the industrial surfactant, Toximul MP8. A possible role in the inhibition of fatty-acid beta-oxidation in a surfactant/influenza B virus mouse model for acute hepatic encephalopathy. *Biochimica et biophysica acta* 1361: 103-113.

Newsholme, E. A., Crabtree, B., and Ardawi, M. S. (1985). Glutamine metabolism in lymphocytes: its biochemical, physiological and clinical importance. *J Exp Physiol* 70: 473-489.

Oshansky, C. M., and Thomas, P. G. (2012). The human side of influenza. *Journal of leukocyte biology* 92: 83-96.

Pearce, E. L. (2010). Metabolism in T cell activation and differentiation. *Current opinion in immunology* 22: 314-320.

Pearce, E. L., Walsh, M. C., Cejas, P. J., Harms, G. M., Shen, H., Wang, L. S., Jones, R. G., and Choi, Y. (2009). Enhancing CD8 T-cell memory by modulating fatty acid metabolism. *Nature* 460: 103-107.

Peng, X., Gralinski, L., Ferris, M. T., Frieman, M. B., Thomas, M. J., Proll, S., Korth, M. J., Tisoncik, J. R., Heise, M., Luo, S., et al. (2011). Integrative deep sequencing of the mouse lung transcriptome reveals differential expression of diverse classes of small RNAs in response to respiratory virus infection. *mBio* 2.

Pommerenke, C., Wilk, E., Srivastava, B., Schulze, A., Novoselova, N., Geffers, R., and Schughart, K. (2012). Global transcriptome analysis in influenza-infected mouse lungs reveals the kinetics of innate and adaptive host immune responses. *PloS one* 7: e41169.

Sanders, C. J., Doherty, P. C., and Thomas, P. G. (2011). Respiratory epithelial cells in innate immunity to influenza virus infection. *Cell and tissue research* 343: 13-21.

Sanders, C. J., Vogel, P., McClaren, J. L., Bajracharya, R., Doherty, P. C., and Thomas, P. G. (2013). Compromised respiratory function in lethal influenza infection is characterized by the depletion of type I alveolar epithelial cells beyond threshold levels. *American journal of physiology Lung cellular and molecular physiology* 304: L481-488.

Shaneyfelt, M. E., Burke, A. D., Graff, J. W., Jutila, M. A., and Hardy, M. E. (2006). Natural products that reduce rotavirus infectivity identified by a cell-based moderate-throughput screening assay. *Virology journal* 3: 68.

Smith, G. C., Ong, W. K., Costa, J. L., Watson, M., Cornish, J., Grey, A., Gamble, G. D., Dickinson, M., Leung, S., Rewcastle, G. W., et al. (2013). Extended treatment with selective phosphatidylinositol 3-kinase and mTOR inhibitors has effects on metabolism, growth, behaviour and bone strength. *The FEBS journal* 280: 5337-5349.

Smith, G. C., Ong, W. K., Rewcastle, G. W., Kendall, J. D., Han, W., and Shepherd, P. R. (2012). Effects of acutely inhibiting PI3K isoforms and mTOR on regulation of glucose metabolism in vivo. *The Biochemical journal* 442: 161-169.

Trauner, D. A., Horvath, E., and Davis, L. E. (1988). Inhibition of fatty acid beta oxidation by influenza B virus and salicylic acid in mice: implications for Reye's syndrome. *Neurology* 38: 239-241.

Vastag, L., Koyuncu, E., Grady, S. L., Shenk, T. E., and Rabinowitz, J. D. (2011). Divergent effects of human cytomegalovirus and herpes simplex virus-1 on cellular metabolism. *PLoS pathogens* 7: e1002124.

Willems, H. L., de Kort, T. F., Trijbels, F. J., Monnens, L. A., and Veerkamp, J. H. (1978). Determination of pyruvate oxidation rate and citric acid cycle activity in intact human leukocytes and fibroblasts. *Clinical chemistry* 24: 200-203.

Yao, D., Kuwajima, M., Chen, Y., Shiota, M., Okumura, Y., Yamada, H., and Kido, H. (2007). Impaired long-chain fatty acid metabolism in mitochondria causes brain vascular invasion by a non-neurotropic epidemic influenza A virus in the newborn/suckling period: implications for influenza-associated encephalopathy. *Molecular and cellular biochemistry* 299: 85-92.

Yu, Y., Clippinger, A. J., and Alwine, J. C. (2011a). Viral effects on metabolism: changes in glucose and glutamine utilization during human cytomegalovirus infection. *Trends in microbiology* 19: 360-367.

Yu, Y., Clippinger, A. J., Pierciey, F. J., Jr., and Alwine, J. C. (2011b). Viruses and metabolism: alterations of glucose and glutamine metabolism mediated by human cytomegalovirus. *Advances in virus research* 80: 49-67.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.
What is claimed is:
1. A method for treating an influenza virus in a subject, the method comprising the step of administering to the subject an effective amount of at least one compound having a structure selected from:
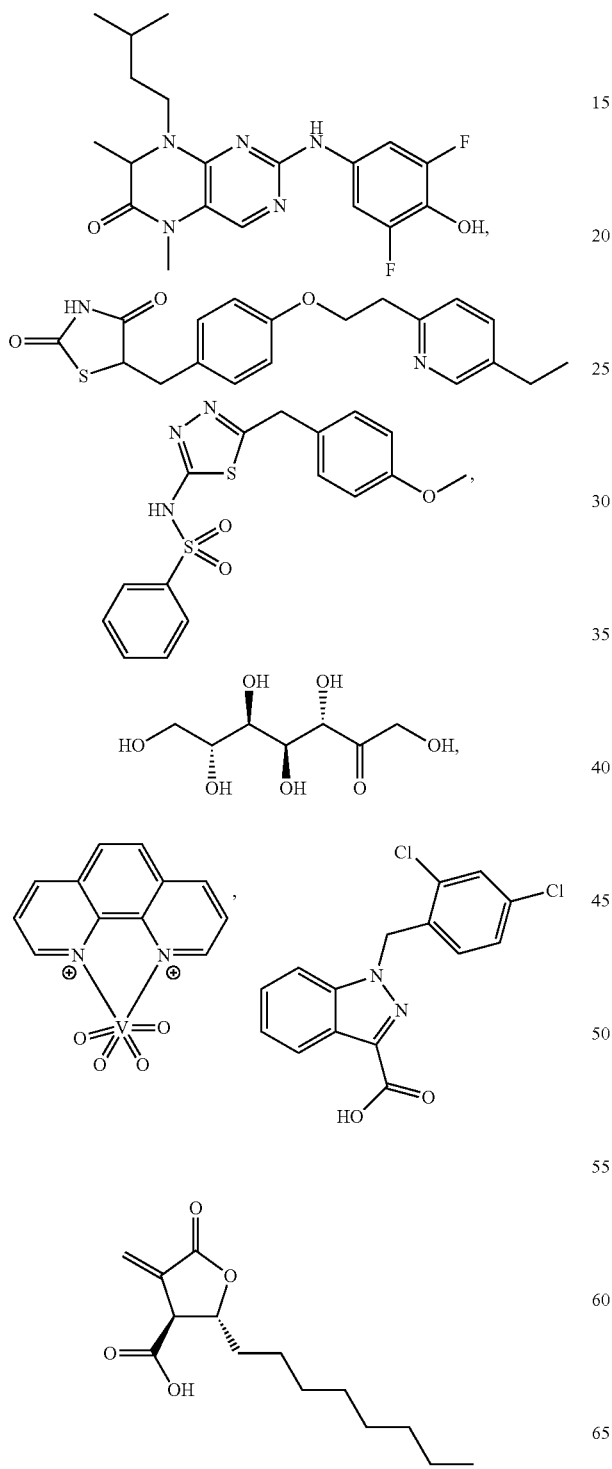
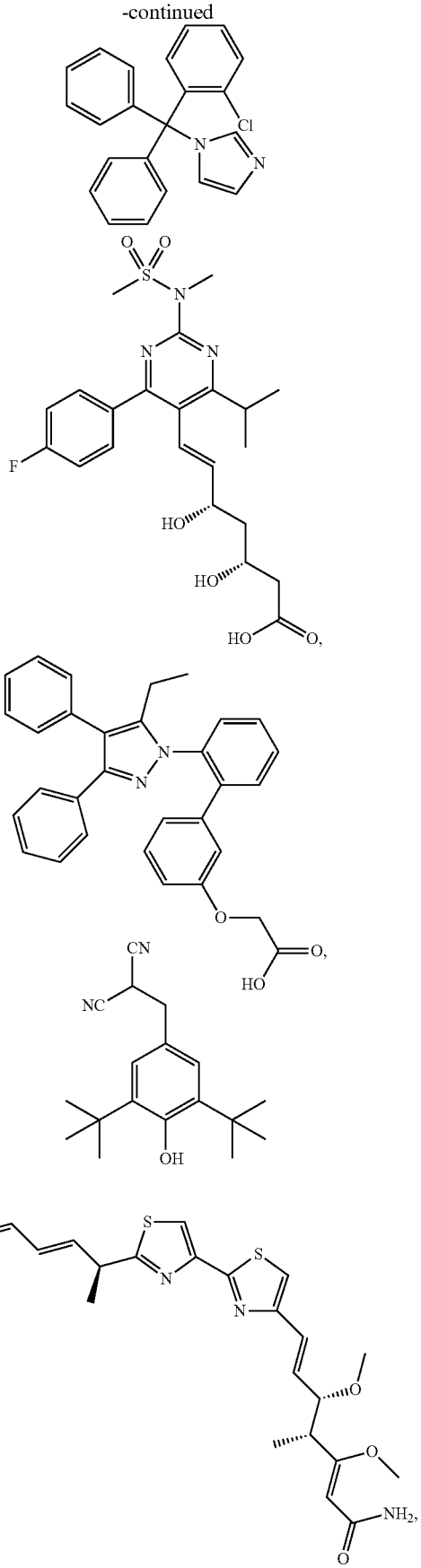

-continued

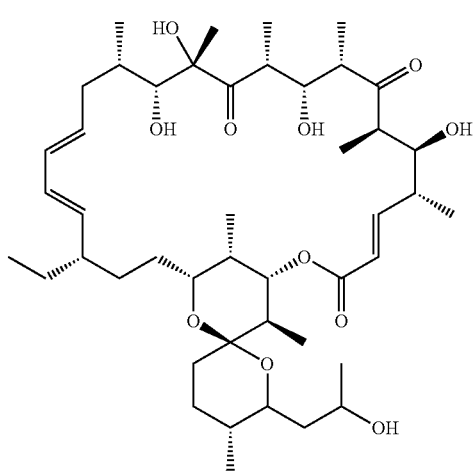 [SMILES: CC[C@@H]1/C=C/C=C/C[C@H](C)[C@@H](O)[C@](C)(O)C(=O)[C@H](C)[C@@H](O)[C@H](C)C(=O)[C@H](C)[C@@H](O)[C@H](C)/C=C/C(=O)O[C@H]2[C@@H](C)[C@@H](CC1)O[C@@]1(CC[C@@H](C)C(CC(C)O)O1)[C@@H]2C]

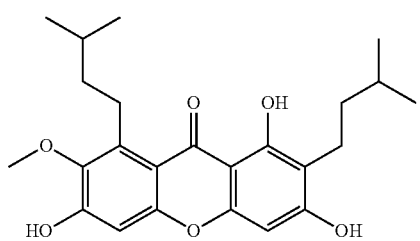 [SMILES: COc1c(O)cc2oc3cc(O)c(CCC(C)C)c(O)c3c(=O)c2c1CCC(C)C]

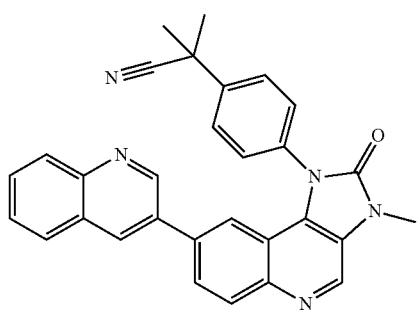 [SMILES: Cn1c(=O)n(-c2ccc(C(C)(C)C#N)cc2)c2c3cc(-c4cnc5ccccc5c4)ccc3ncc21]

or a pharmaceutically acceptable salt thereof, thereby treating the subject for the influenza virus.

2. The method of claim 1, wherein the subject is a mammal.

3. The method of claim 2, wherein the mammal is a human.

4. The method of claim 1, wherein the subject has been diagnosed with a need for treatment of the influenza virus prior to the administering step.

5. The method of claim 1, further comprising the step of identifying a subject in need of treatment of the influenza virus.

6. The method of claim 1, wherein the effective amount is a therapeutically effective amount.

7. The method of claim 1, wherein the effective amount is a prophylactically effective amount.

8. The method of claim 1, wherein the compound is:

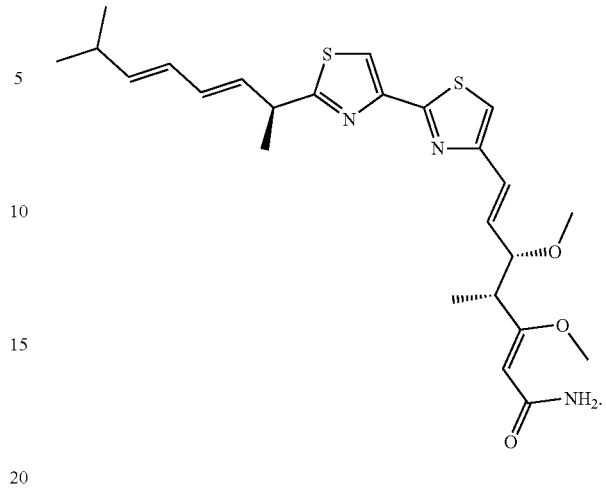

9. The method of claim 1, wherein the compound is:

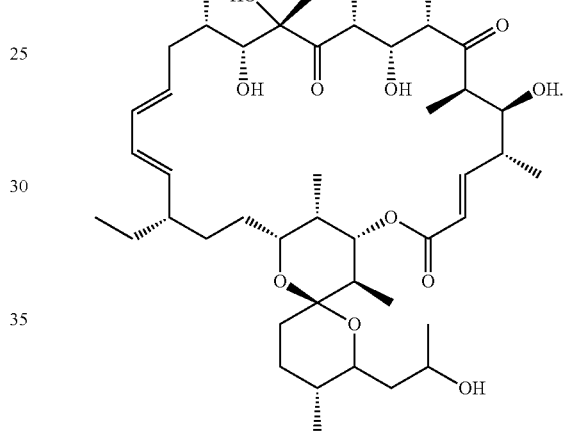

10. The method of claim 1, wherein the compound is:

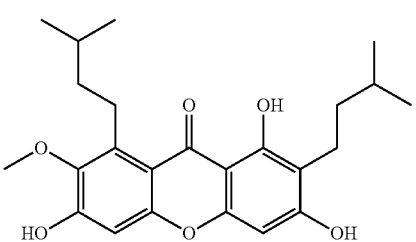

11. The method of claim 1, wherein the compound is:

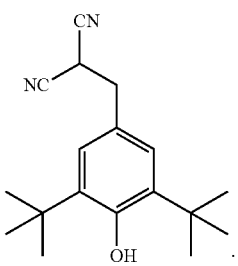 [SMILES: CC(C)(C)c1cc(CC(C#N)C#N)cc(C(C)(C)C)c1O]

12. The method of claim 1, wherein the compound is:

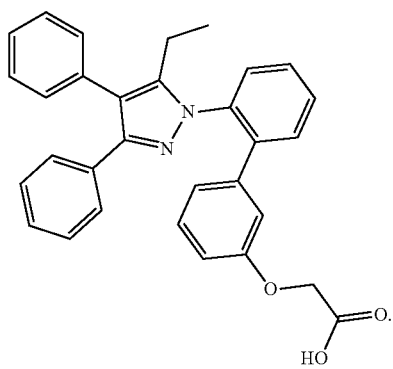 [SMILES: CCc1c(-c2ccccc2)c(-c2ccccc2)nn1-c1ccccc1-c1cccc(OCC(=O)O)c1]

13. The method of claim 1, wherein the compound is:

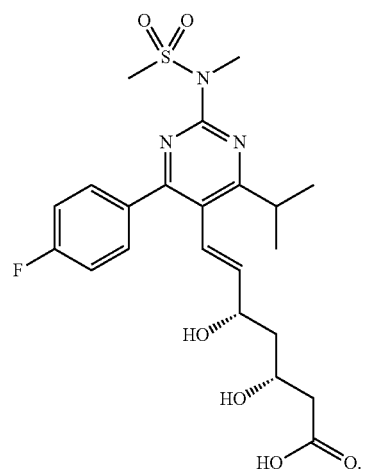 [SMILES: CC(C)c1nc(N(C)S(C)(=O)=O)nc(-c2ccc(F)cc2)c1/C=C/[C@@H](O)C[C@@H](O)CC(=O)O]

14. The method of claim 1, wherein the compound is:

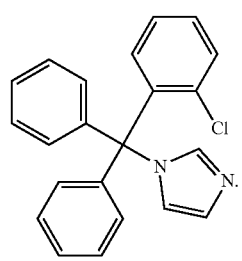 [SMILES: Clc1ccccc1C(c1ccccc1)(c1ccccc1)n1ccnc1]

15. The method of claim 1, wherein the compound is:

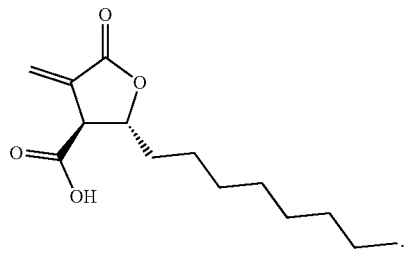 [SMILES: C=C1C(=O)O[C@H](CCCCCCCC)[C@H]1C(=O)O]

16. The method of claim 1, wherein the compound is:

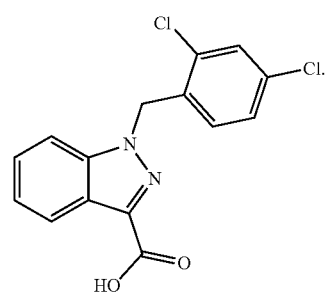 [SMILES: O=C(O)c1nn(Cc2ccc(Cl)cc2Cl)c2ccccc12]

17. The method of claim 1, wherein the compound is:

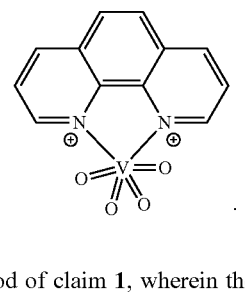

18. The method of claim 1, wherein the compound is:

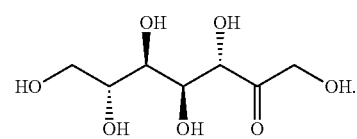 [SMILES: O=C(CO)[C@@H](O)[C@@H](O)[C@H](O)[C@H](O)CO]

19. The method of claim 1, wherein the compound is:

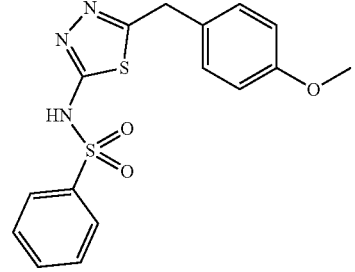

20. The method of claim 1, wherein the compound is:

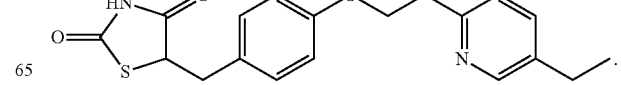

21. The method of claim 1, wherein the compound is:
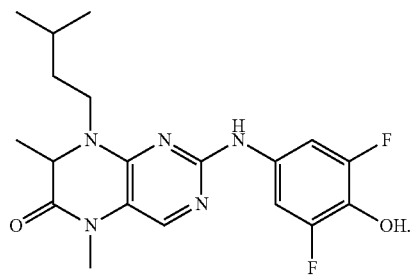 [SMILES: CC(C)CCN1c2nc(Nc3cc(F)c(O)c(F)c3)ncc2N(C)C(=O)C1C]
22. The method of claim 1, wherein the compound is:
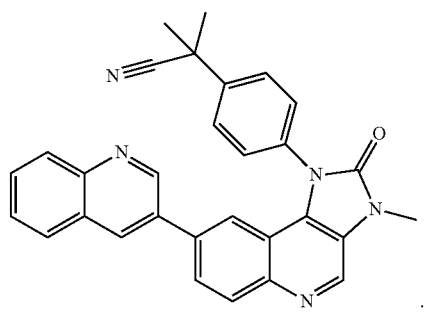 [SMILES: Cn1c(=O)n(-c2ccc(C(C)(C)C#N)cc2)c2c3cc(-c4cnc5ccccc5c4)ccc3ncc21]
* * * * *

UNITED STATES PATENT AND TRADEMARK OFFICE
CERTIFICATE OF CORRECTION

PATENT NO. : 11,083,725 B2
APPLICATION NO. : 15/520756
DATED : August 10, 2021
INVENTOR(S) : Heather S. Smallwood et al.

It is certified that error appears in the above-identified patent and that said Letters Patent is hereby corrected as shown below:

In the Specification

On Column 1, Lines 18-25 please replace:
"This invention was made with U.S. Government support under grant number RR 018522 awarded by the National Institute of Health (NIH), grant numbers CA 096832 and Core Grant CA 021765 awarded by the National Cancer Institute, and grant numbers AI091938 and AI077714 awarded by the National Institute of Allergy and Infectious Diseases. The U.S. government has certain rights in the invention"

With:
-- This invention was made with government support under grant numbers CA 096832, CA 021765, AI091938, and AI077714 awarded by the National Institutes of Health. The government has certain rights in the invention --

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*